US008808997B2

(12) United States Patent
Birse et al.

(10) Patent No.: US 8,808,997 B2
(45) Date of Patent: *Aug. 19, 2014

(54) LUNG CANCER MARKERS, AND USES THEREOF

(75) Inventors: Charles Birse, North Potomac, MD (US); Marcia Lewis, Cohasset, MD (US); Steve Ruben, Brookville, MD (US); Mehdi Mesri, North Potomac, MD (US)

(73) Assignee: Celera Corporation, Alameda, CA (US)

( * ) Notice: Subject to any disclaimer, the term of this patent is extended or adjusted under 35 U.S.C. 154(b) by 711 days.

This patent is subject to a terminal disclaimer.

(21) Appl. No.: 13/005,031

(22) Filed: Jan. 12, 2011

(65) Prior Publication Data

US 2012/0076725 A1 Mar. 29, 2012

Related U.S. Application Data

(62) Division of application No. 12/273,994, filed on Nov. 19, 2008, now Pat. No. 7,892,760.

(60) Provisional application No. 61/003,767, filed on Nov. 19, 2007.

(51) Int. Cl.
*G01N 33/53* (2006.01)

(52) U.S. Cl.
USPC ............................................ 435/7.1

(58) Field of Classification Search
None
See application file for complete search history.

(56) References Cited

U.S. PATENT DOCUMENTS 7,892,760 B2 * 2/2011 Birse et al. .................... 435/7.1

OTHER PUBLICATIONS

Maldonado, F., et al., "Protein Biomarker Panel May Resolve Non-Malignant Nodules Identified Through Low-Dose Helical CT Scanning", 14th World Conference on Lung Cancer, Jul. 2011, Amsterdam, NL.

* cited by examiner

*Primary Examiner* — Sean Aeder
(74) *Attorney, Agent, or Firm* — Celera Corporation

(57) ABSTRACT

Methods and compositions are provided for assessing (e.g., diagnosing), treating, and preventing diseases, especially cancer, and particular lung cancer, using lung cancer markers (LCM). Individual LCM and panels comprising multiple LCM are provided for these and other uses. Methods and compositions are also provided for determining or predicting the effectiveness of a treatment or for selecting a treatment using LCM. Methods and compositions are further provided for modulating cell function using LCM. Also provided are compositions that modulate LCM (e.g., antagonists or agonists), such as antibodies, proteins, small molecule compounds, and nucleic acid agents (e.g., RNAi and antisense agents), as well as pharmaceutical compositions thereof. Further provided are methods of screening for agents that modulate LCM, and agents identified by these screening methods.

38 Claims, 24 Drawing Sheets

FIGURE 1
Lung Cancer Markers

FIGURE 2
Exemplary 8-Marker Panel

Exemplary 8-Marker Panel
(TFPI, SCC, CEA, CA242, MNCAIX, OPN, Cyfra 21-1, and MIF)

FIGURE 4
Examples of Alternative Lung Cancer Biomarkers and Panels Thereof

| | Hist | AS | AS | AS | AS | SC | A | OC | A | AS | AS | AS BA | N | N | N | N | N | N | N | N | N | N | N |
|---|---|---|---|---|---|---|---|---|---|---|---|---|---|---|---|---|---|---|---|---|---|---|---|
| | Stage | III | IV | III | IV | III | III | IV | IV | IIIB | IV | III IV | | | | | | | | | | | |
| SLPI | | 5.3 | 0.0 | 3.9 | 5.3 | 5.3 | 0.0 | 0.0 | 0.0 | 0.0 | 0.0 | 0.0 0.0 | 0.0 | 0.0 | 0.0 | 0.0 | 0.0 | 0.0 | 0.0 | 0.0 | 0.0 | 0.0 | 0.0 |
| TPA | | 10.1 | 0.0 | 2.1 | 0.0 | 2.1 | 1.7 | 0.0 | 0.0 | 0.0 | 0.0 | 0.0 0.0 | 0.0 | 3.2 | 0.0 | 0.0 | 0.0 | 0.0 | 0.0 | 0.0 | 1.7 | 0.0 | 0.0 |
| OPN | | 93.6 | 0.0 | 0.0 | 3.4 | 2.8 | 0.0 | 3.5 | 3.4 | 4.8 | 0.0 | 0.0 0.0 | 0.0 | 0.0 | 2.7 | 0.0 | 0.0 | 0.0 | 0.0 | 0.0 | 0.0 | 0.0 | 0.0 |
| MIF | | 3.9 | 2.2 | 2.2 | 3.4 | 0.0 | 0.0 | 0.0 | 0.0 | 0.0 | 6.5 | 4.8 0.0 | 0.0 | 0.0 | 0.0 | 2.1 | 0.0 | 0.0 | 0.0 | 0.0 | 0.0 | 0.0 | 0.0 |
| TIMP1 | | 1.7 | 1.5 | 1.3 | 0.0 | 0.0 | 0.0 | 1.4 | 1.9 | 0.0 | 0.0 | 1.4 0.0 | 0.0 | 0.0 | 0.0 | 0.0 | 0.0 | 0.0 | 0.0 | 0.0 | 0.0 | 0.0 | 0.0 |
| MMP2 | | 2.8 | 0.0 | 0.0 | 0.0 | 0.0 | 0.0 | 0.0 | 0.0 | 5.2 | 0.0 | 0.0 0.0 | | | | | | | | | | | |
| | | | | | | | | | | | | | | | | | | | | | | | |
| CA242 | | 4.4 | 0.0 | 0.0 | 6.8 | 3.7 | 0.0 | 1.8 | 10.3 | 2.6 | 3.3 | 0.0 0.0 | 0.0 | 0.0 | 0.0 | 0.0 | 0.0 | 0.0 | 0.0 | 0.0 | 0.0 | 0.0 | 0.0 |
| SCC | | 5.6 | 7.7 | 7.5 | 5.5 | 10.6 | 10.7 | 9.4 | 0.0 | 0.0 | 0.0 | 7.4 0.0 | 0.0 | 0.0 | 0.0 | 0.0 | 0.0 | 0.0 | 0.0 | 0.0 | 0.0 | 0.0 | 0.0 |
| CEA | | 16.9 | 16.9 | 0.0 | 16.9 | 2.2 | 0.0 | 16.9 | 15.1 | 0.0 | 3.4 | 0.0 0.0 | | | | | | | | | | | |
| | | | | | | | | | | | | | | | | | | | | | | | |
| NSE | | 3.3 | 7.5 | 3.3 | 4.3 | 0.0 | 0.0 | 0.0 | 0.0 | 0.0 | 4.6 | 0.0 0.0 | 0.0 | 2.9 | 0.0 | 0.0 | 0.0 | 0.0 | 0.0 | 0.0 | 0.0 | 0.0 | 0.0 |
| CA724 | | 20.7 | 0.0 | 0.0 | 0.0 | 22.1 | 0.0 | 0.0 | 162.3 | 0.0 | 0.0 | 0.0 0.0 | 0.0 | 10.2 | 0.0 | 0.0 | 0.0 | 0.0 | 0.0 | 0.0 | 0.0 | 0.0 | 0.0 |
| CA199 | | 10.8 | 0.0 | 0.0 | 5.4 | 0.0 | 0.0 | 10.5 | 10.5 | 0.0 | 0.0 | 0.0 0.0 | 0.0 | 0.0 | 0.0 | 0.0 | 4.2 | 0.0 | 0.0 | 0.0 | 0.0 | 0.0 | 0.0 |
| Cyfra 21-1 | | 7.2 | 0.0 | 12.5 | 2.6 | 8.1 | 0.0 | 0.0 | 0.0 | 31.7 | 0.0 | 5.5 0.0 | 0.0 | 0.0 | 0.0 | 0.0 | 2.8 | 0.0 | 0.0 | 0.0 | 0.0 | 0.0 | 0.0 |
| MNCAIX | | 12.7 | 4.6 | 0.0 | 0.0 | 0.0 | 0.0 | 0.0 | 0.0 | 0.0 | 0.0 | 0.0 0.0 | 0.0 | 0.0 | 0.0 | 0.0 | 0.0 | 0.0 | 0.0 | 0.0 | 0.0 | 0.0 | 3.9 |

6 Markers Assayed in Early Stage Lung Cancer Sera
Scatter Plots of ELISA data

FIGURE 6
Exemplary 11-Marker Panel
*Evaluating Panel Performance Applying Manually Defined Cut-offs for Each ELISA*

FIGURE 11
Autoantibody Analysis
*Autoantibody Markers Can Complement Other Lung Cancer Markers*

FIGURE 12
Examples of Autoantibody Lung Cancer Markers

| Target Name | Symbol |
|---|---|
| kallikrein B, plasma (Fletcher factor) 1 | KLKB1 |
| cofilin 1 (non-muscle) | CFL1 |
| lectin, galactoside-binding, soluble, 1 (galectin 1) | LGALS1 |
| eukaryotic translation elongation factor 1 gamma | EEF1G |
| Reticulon 4 | RTN4 |
| aldolase A, fructose-bisphosphate | ALDOA |
| Heat shock protein HSP 90-alpha | HSPCA |
| poly(A) binding protein, cytoplasmic, 4 (inducible form) | PABPC4 |
| N-acetylglucosamine kinase | NAGK |
| complement factor H-related 1 | CFHL1 |
| colony stimulating factor 1 receptor | CSF1R |
| RAN binding protein 2 | RANBP2 |

\* p53 autoantibody levels were evaluated as a control

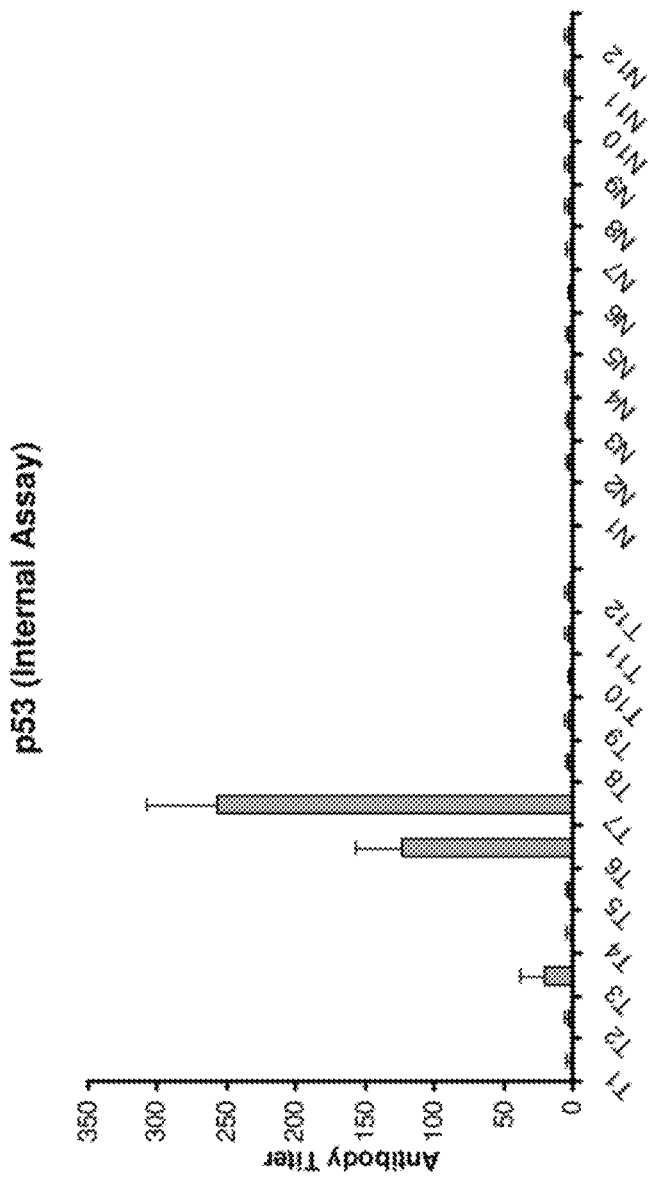

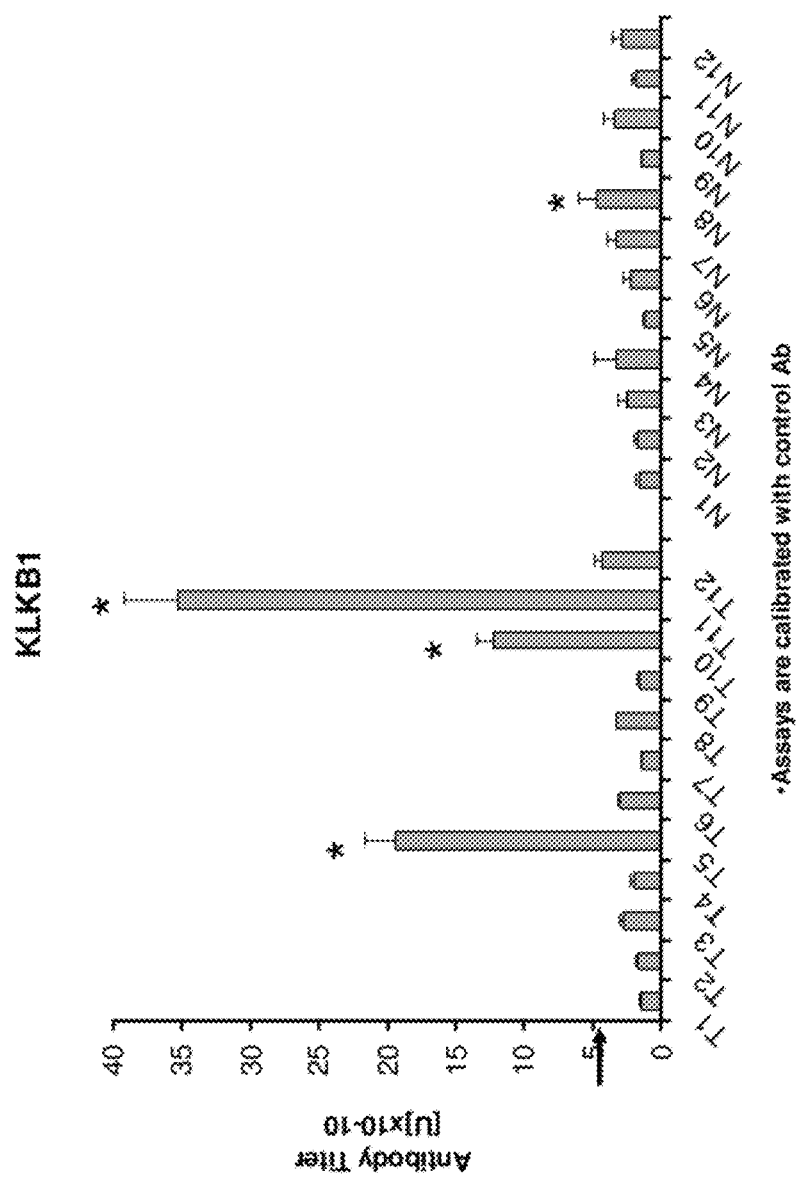

Autoantibody Responses Observed in Lung Cancer Serum Samples

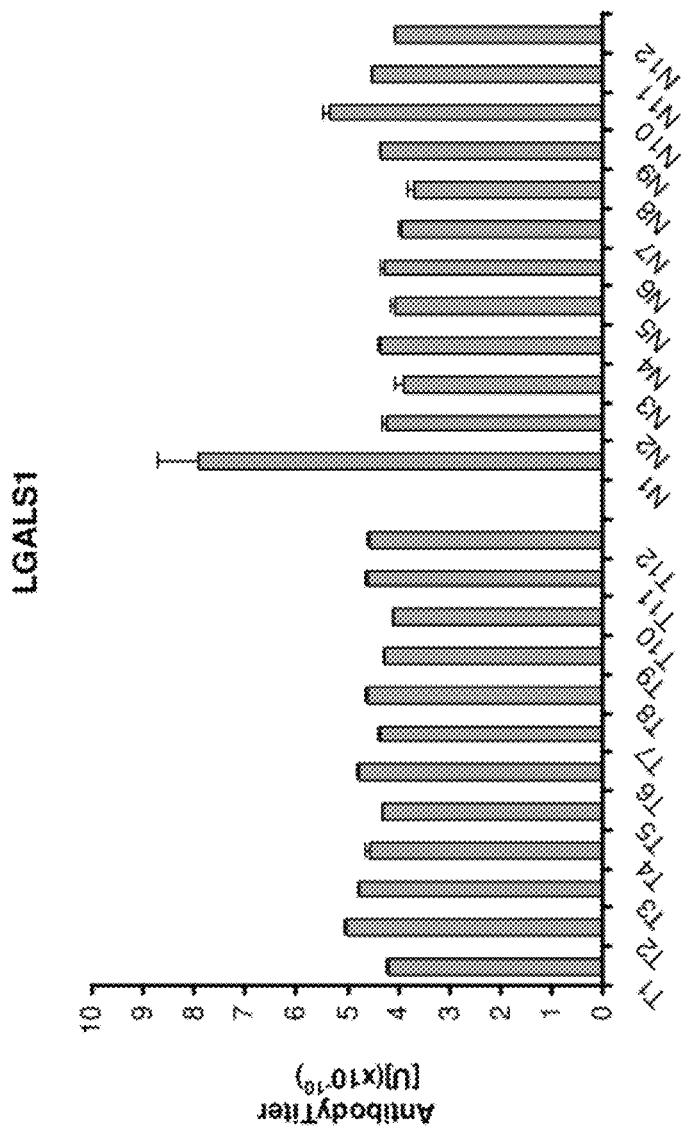

FIGURE 14
Autoantibody Detection in Lung Cancer Sera

| Autoantibody Target | | Histology | Squamous cell carcinoma | Adeno/Squa mous cell carcinoma | Squamous cell carcinoma | Adeno/Squa mous cell carcinoma | Adeno/Squa mous cell carcinoma | Small cell Carcinoma | Adeno/Squa mous cell carcinoma | Adenocarcino ma | Squamous cell carcinoma | Adeno/Squa mous cell carcinoma | Adeno/Squa mous cell carcinoma | Adenocarcino ma |
|---|---|---|---|---|---|---|---|---|---|---|---|---|---|---|
| | | Stage | STAGE III | STAGE III | STAGE III | STAGE III | STAGE IIB | STAGE III | STAGE III | STAGE III | STAGE III | STAGE IIIB | STAGE III | STAGE III |
| p53 | Commercial Assay | Tumor | 0.0 | 0.0 | 2.1 | 0.0 | 0.0 | 46 | 204 | 44 | 0.0 | 0.0 | 0.0 | 52 |
| | | Normal | 0.0 | 0.0 | 0.0 | 0.0 | 0.0 | 0.0 | 0.0 | 0.0 | 0.0 | 0.0 | 0.0 | 0.0 |
| p53 | Internal Assay | Tumor | 0.0 | 0.0 | 2.5 | 0.0 | 0.0 | 124 | 314 | 0.0 | 0.0 | 0.0 | 0.0 | 0.0 |
| | | Normal | 0.0 | 0.0 | 0.0 | 0.0 | 0.0 | 0.0 | 0.0 | 0.0 | 0.0 | 0.0 | 0.0 | 0.0 |
| CA12 | | Tumor | 0.0 | 0.0 | 0.0 | 1.3 | 0.0 | 0.0 | 0.0 | 2.1 | 0.0 | 2.53 | 2.1 | 0.0 |
| | | Normal | 0.0 | 0.0 | 0.0 | 0.0 | 0.0 | 0.0 | 0.0 | 0.0 | 0.0 | 1.4 | 0.0 | 0.0 |
| KLKB1 | | Tumor | 0.0 | 0.0 | 0.0 | 0.0 | 4.3 | 0.0 | 0.0 | 0.0 | 0.0 | 2.7 | 7.8 | 0.0 |
| | | Normal | 0.0 | 0.0 | 0.0 | 0.0 | 0.0 | 0.0 | 0.0 | 1.0 | 0.0 | 0.0 | 0.0 | 0.0 |
| LGALS1 | | Tumor | 0.0 | 0.0 | 0.0 | 0.0 | 2.2 | 0.0 | 0.0 | 0.0 | 0.0 | 0.0 | 0.0 | 0.0 |
| | | Normal | 1.2 | 0.0 | 0.0 | 0.0 | 0.0 | 0.0 | 0.0 | 0.0 | 0.0 | 0.0 | 0.0 | 0.0 |
| CFLN | | Tumor | 0.0 | 0.0 | 0.0 | 1.2 | 0.0 | 0.0 | 0.0 | 0.0 | 0.0 | 1.1 | 2.1 | 0.0 |
| | | Normal | 0.0 | 0.0 | 0.0 | 0.0 | 0.0 | 0.0 | 0.0 | 0.0 | 0.0 | 1.1 | 0.0 | 0.0 |
| EEF1G | | Tumor | 0.0 | 1.2 | 0.0 | 0.0 | 0.0 | 0.0 | 0.0 | 0.0 | 0.0 | 0.0 | 0.0 | 0.0 |
| | | Normal | 1.2 | 0.0 | 0.0 | 0.0 | 0.0 | 0.0 | 0.0 | 0.0 | 0.0 | 0.0 | 0.0 | 0.0 |

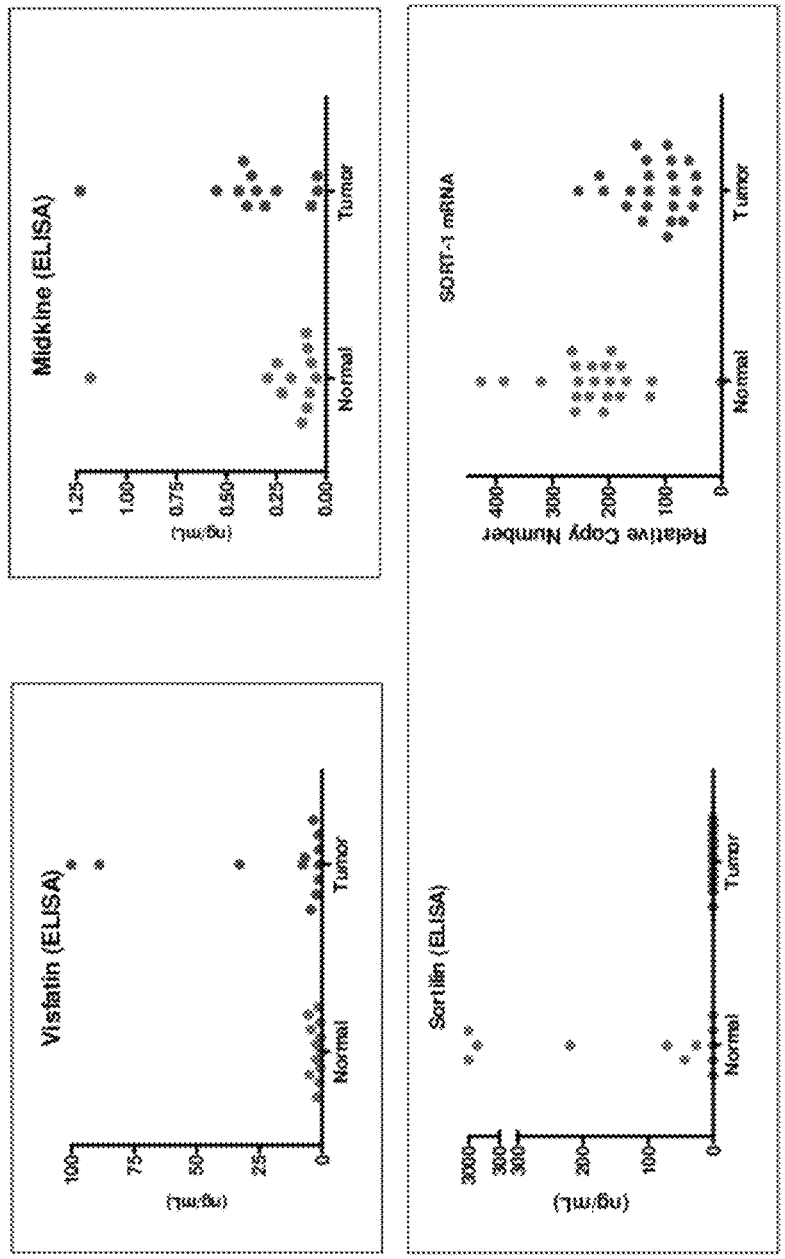

FIGURE 16
Clinicopathological Characteristics of Lung Cancer Serum Samples

| | Screen | | Validation ("44x39" excl. small cell; "44x44" incl. 5 small cell cases) | | Training ("54x53") | | Testing ("50x50") | |
|---|---|---|---|---|---|---|---|---|
| | Controls | Cases | Controls | Cases | Controls | Cases | Controls | Cases |
| | 12 | 12 | 44 | 39 ("44, incl. 5 small cell cases") | 54 | 53 | 50 | 50 |
| Gender | | | | | | | | |
| Male | 8 | 8 | 26 | 23 | 38 | 36 | 31 | 26 |
| Female | 4 | 4 | 18 | 16 | 17 | 16 | 19 | 24 |
| Age | | | | | | | | |
| Mean (SD) | 56.3 (8.1) | 56.9 (9.1) | 65.6 (9.7) | 66.1 (10.2) | 67.2 (12.5) | 70.2 (9.6) | 71.6 | 73.9 |
| Smoking Status | | | | | | | | |
| N | NA | NA | 26 | 2 | | | 5 | |
| Y | NA | NA | 18 | 37 | 54 | 53 | 45 | 50 |
| Pack Years | NA | NA | 22 | 37 | 21.4 | 27.1 | 20.1 | 26.7 |
| Tumor Stage | | | | | | | | |
| I | | | | 32 | | 18 | | 14 |
| II | | | | 7 | | 13 | | 13 |
| III | | | 6 | | | 13 | | 12 |
| IV | | | 6 | | | 9 | | 11 |
| Tumor Histology | | | | | | | | |
| Adenocarcinoma | | 2 | | 19 | | 33 | | 21 |
| Squamous Cell Carcinoma | | | | 12 | | 13 | | 11 |
| Large Cell Carcinoma | | | | 3 | | 7 | | 4 |
| Other NSC | | | | 5 | | | | 7 |
| Bronchioloalveolar Carcinoma | | 1 | | | | | | 5 |
| Neuroendocrine | | 7 | | | | | | 2 |
| Adeno-Squamous | | 1 | | | | | | |
| Oat Cell Carcinoma | | 1 | | | | | | |
| Small Cell Carcinoma | | | | [5] | | | | |

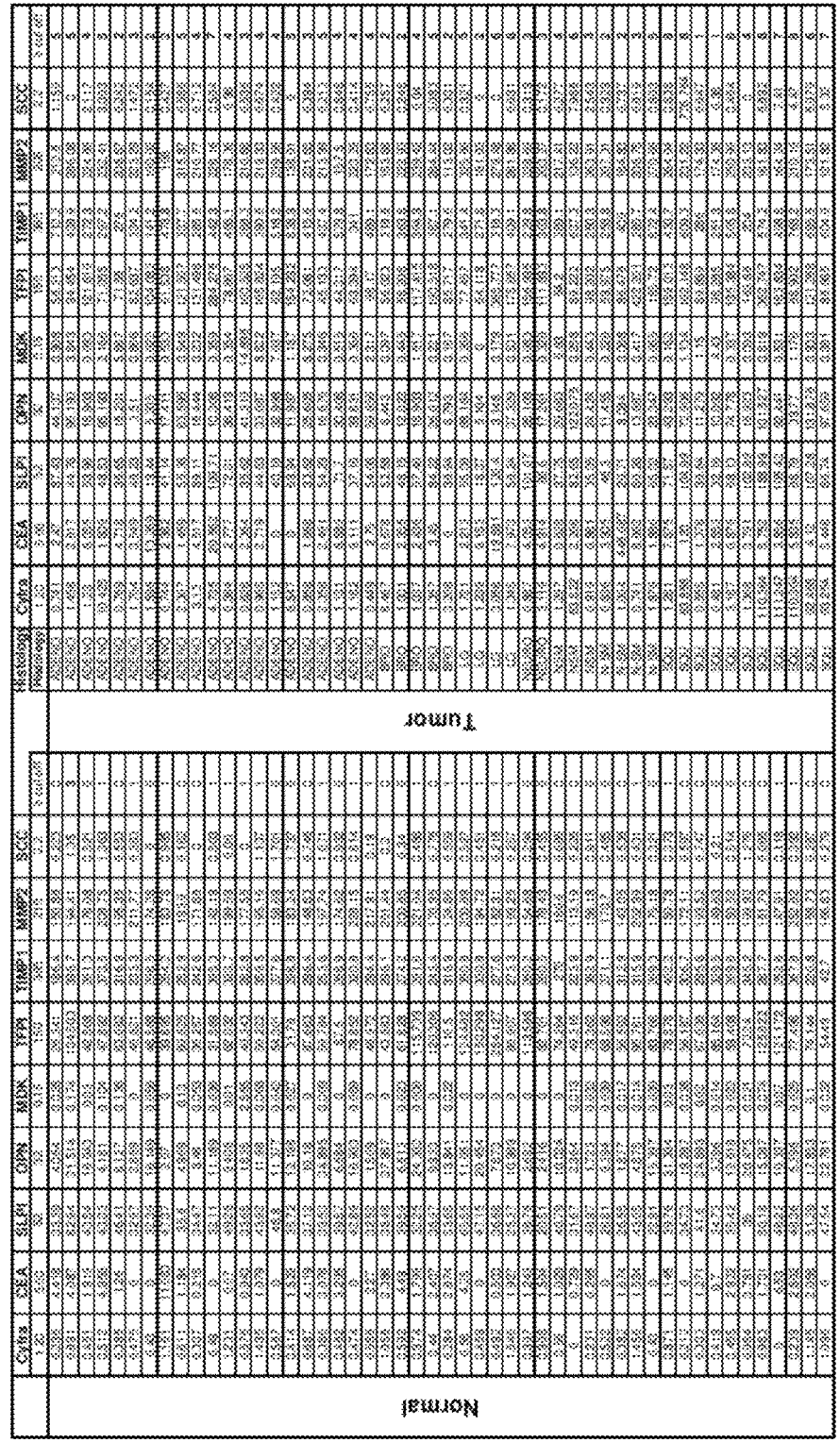

Analysis of Markers to Monitor Lung Tumor Regression/Recurrence

- % change indicates the difference in the pre-surgery to post-surgery levels.

FIGURE 19
Analysis of Markers to Monitor Lung Tumor Regression/Recurrence

Reduced Levels of Markers Following Tumor Resection

| CEA | Cyfra | NSE | TIMP-1 | OPN | TFPI | MDK | SLPI | DEFA1 | SCC | GRP | # of Markers with >50% Drop |
|---|---|---|---|---|---|---|---|---|---|---|---|
| -50.8 | -10.7 | -49.3 | 37.6 | 3.9 | | -78.4 | -1.2 | -2 | -38.5 | 13.7 | 2 |
| | -93.9 | 10.2 | 9.4 | 4.7 | | -70.4 | -8.4 | -9.1 | -66.1 | 56.6 | 3 |
| | | 11.3 | 1.9 | | -10.9 | | -6.3 | 17.7 | | -81.8 | 1 |
| | -81.2 | -14.3 | 31.8 | 8.1 | -6.1 | | 6.4 | -36.3 | | -22.1 | 2 |
| -33.7 | -19.2 | 26.3 | 49.9 | | 18.9 | -84.3 | -2.4 | -21.6 | 29.9 | 149.0 | 0 |
| -75.9 | -98.5 | -32.8 | 71.5 | 61.7 | 23.4 | | 7.1 | 47.9 | | -76.3 | 3 |
| -15.4 | -11.8 | -3.2 | 85.6 | 0.6 | 3.0 | | 21.7 | 6.9 | -19.7 | -43.0 | 0 |
| -40.2 | | -2.0 | 15.4 | -22.6 | 1.2 | | 6.1 | 29.6 | -25.2 | -38.9 | 0 |
| 14.8 | 17.3 | -34.4 | 95.7 | | -0.8 | | 9.0 | -22.4 | | | 0 |
| -35.3 | -62.8 | 3.7 | 62.2 | | 50.8 | | -13.0 | 7.1 | | -13.6 | 1 |
| -39.2 | -32.8 | -30.6 | 24.7 | 32.6 | 42.9 | | -24.9 | -9.8 | -63.1 | -75.0 | 2 |
| -50.8 | | -30.0 | 11.2 | 127.9 | 10.1 | | 12.2 | 6.4 | | 85.5 | 0 |
| -19.4 | -98.2 | -6.0 | 32.5 | 42.2 | -12.1 | -84.0 | -3.6 | -33.5 | -63.4 | 8.4 | 4 |
| -20.7 | -76.6 | -17.9 | 26.1 | -42.2 | -60.0 | -1.0 | 6.4 | -4.6 | -66.1 | 26.9 | 3 |
| | -6.4 | 32.8 | 84.9 | | -58.7 | 2.3 | 48.0 | 85.3 | -66.1 | 49.2 | 1 |
| -11.6 | | -46.1 | 37.6 | 382.5 | 10.7 | 232.1 | 20.9 | 0.8 | -71.4 | -75.1 | 3 |
| -5.2 | 73.3 | 44.1 | 77.5 | 275.6 | -62.8 | 15.4 | 30.0 | 519.4 | -69.6 | 107.1 | 1 |
| -95.9 | -29.2 | -27.9 | 52.3 | 32.6 | 16.0 | 2.9 | 0.1 | 46.3 | -54.2 | -2.1 | 2 |
| -66.4 | | -20.6 | -9.2 | -46.5 | 18.4 | -40.0 | -12.9 | -66.7 | -61.7 | -74.8 | 3 |
| -90.0 | -89.1 | -8.5 | 10.0 | | -0.8 | 2.3 | 13.2 | 85.3 | -66.2 | | 2 |
| -85.1 | 59.2 | 1.0 | 234.1 | 204.4 | 6.8 | -71.1 | 36.3 | -28.7 | -97.4 | | 3 |
| 27.3 | -20.6 | -23.5 | 32.0 | 41.9 | 30.2 | 63.1 | -1.0 | 46.3 | 1.6 | 73.4 | 1 |
| -42.0 | 7.9 | | 12.7 | 103.6 | -19.5 | 97.2 | 3.0 | -66.7 | -19.0 | -5.5 | 2 |
| | 0.6 | | 32.1 | 457.5 | -57.8 | -43.7 | 44.1 | 108.6 | | -34.8 | 0 |
| | | | | 85.7 | 8.3 | 55.8 | 5.7 | 71.4 | -66.6 | | 1 |
| -48.7 | -26.9 | -15.8 | 132.5 | | 5.2 | 142.5 | -2.3 | | -11.2 | 39.9 | 0 |
| | | | 121.7 | | 95.3 | 85.9 | | 462.9 | | | |
| | | | | | | | | Sensitivity | | 73.1% | |

FIGURE 20

Expression of Biomarker Panel in Co-morbid Lung Diseases

| | Cyfra | CEA | SLPI | OPN | MDK | TFPI | TIMP1 | MMP2 | SCC | #> cut-off |
|---|---|---|---|---|---|---|---|---|---|---|
| Cutoff | 3.50 | 5.60 | 55 | 70 | 0.7 | 70 | 440 | 315 | 2.2 | |
| ASTHMA | 0.38 | 3.166 | 44.38 | 53.173 | 0 | 33.127 | 331.8 | 193.38 | 3.839 | 1 |
| | 0.275 | 2.765 | 61.02 | 12.425 | 0.071 | 38.477 | 307.8 | 184.43 | 0.607 | |
| | 0.935 | 3.123 | 33.97 | 2.008 | 0 | 31.089 | 295.7 | 174.05 | 0.449 | 0 |
| | 0.129 | 3.326 | 39.99 | 11.425 | 0.079 | 47.766 | 310.9 | 185.5 | 0.274 | 0 |
| | 0.161 | 3.05 | 50.02 | 9.707 | 0.413 | 42.97 | 305.2 | 222.9 | 0.452 | 0 |
| | 0.737 | 3.865 | 30.26 | 10.858 | 0.19 | 33.236 | 325.9 | 180.14 | 0.189 | 0 |
| | 2.964 | 1.103 | 50.05 | 2.4 | 0.013 | 23.047 | 426.9 | 164.1 | 0.044 | 0 |
| | 0.585 | 0.988 | 41.67 | 7.907 | 0.038 | 21.811 | 332.1 | 134.18 | 0.695 | 0 |
| | 1.278 | 3.888 | 35.71 | 27.186 | 0.096 | 39.674 | 313 | 277.1 | 0.315 | 0 |
| | 0.89 | 2.734 | 40.83 | 11.943 | 0.224 | 36.865 | 408.9 | 180.64 | 0.131 | 0 |
| | 0.523 | 0.786 | 26.58 | 22.188 | 0.898 | 28.654 | 381.9 | 244.93 | 0.191 | 0 |
| | 0.160 | 2.434 | 26.56 | 3.517 | 0.053 | 35.706 | 280.6 | 183.38 | 0.120 | 0 |
| | 0.136 | 2.692 | 34.83 | 12.035 | 0.089 | 32.403 | 336.6 | 183.68 | 0 | 0 |
| | 1.154 | 2.511 | 24.48 | 5.923 | 0 | 40.335 | 352.1 | 157.47 | 0.25 | 0 |
| Benign Lung | 2.306 | 2.695 | 39.45 | 21.897 | 0.128 | 28.486 | 288.2 | 178.85 | 1.086 | 0 |
| | 0.6321 | 31.62 | 27.13 | 2.86 | 0.052 | 23.182 | 306.8 | 193.66 | 0.431 | 0 |
| | 1.147 | 3.375 | 16.22 | 0.406 | 0 | 31.681 | 195.5 | 221.54 | 0.854 | 0 |
| | 0.425 | 4.806 | 21.52 | 0.297 | 0 | 39.045 | 248.1 | 155.7 | 1.32 | 0 |
| | 0.727 | 4.111 | 46.13 | 11.541 | 0.118 | 53.486 | 331.8 | 243.04 | 0.608 | 0 |
| | 1.085 | 2.298 | 32.74 | 3.622 | 0.067 | 42.254 | 249 | 213.56 | 0.697 | 0 |
| | 1.936 | 6.759 | 39.8 | 19.123 | 0 | 53.038 | 248.5 | 203.73 | 0.756 | 0 |
| | 1.93 | 3.421 | 24.02 | 1.693 | 0 | 27.517 | 330.4 | 195.28 | 0.701 | 0 |
| | 0.498 | 30.817 | 24.66 | 2.777 | 0.154 | 24.893 | 347.7 | 209.8 | 0.373 | 0 |
| | 0.767 | 6.49 | 39.05 | 3.137 | 0.007 | 28.45 | 321.3 | 193.38 | 3.865 | 1 |
| | 0.667 | 3.609 | 39.7 | 24.358 | 0.087 | 27.759 | 387.4 | 193.73 | 1.112 | 0 |
| | 0.939 | 2.625 | 26.77 | 27.448 | 0.23 | 28.257 | 262.1 | 237.1 | 0.561 | 0 |
| Bronchitis | 0.812 | 1.44 | 51.8 | 37.672 | 0.308 | 58.738 | 322.7 | 119.71 | 1.08 | 0 |
| | 0.668 | 2.118 | 46.75 | 45.364 | 0.027 | 14.883 | 272.4 | 268.72 | 0 | 0 |
| | 1.89 | 5.379 | 37.67 | 49.749 | 0.23 | 53.606 | 317.1 | 195.38 | 2.091 | 0 |
| | 1.686 | 1.654 | 34.79 | 29.519 | 0.447 | 80.038 | 337.3 | 184.08 | 0.164 | 1 |

Integration of clinical data enhances performance of LCM panel

LUNG CANCER MARKERS, AND USES THEREOF

FIELD OF THE INVENTION

This invention relates to the field of disease assessment and therapy. The invention provides compositions and methods for assessing and treating diseases, especially cancer, and particularly lung cancer.

BACKGROUND OF THE INVENTION

Cancer is one of the leading causes of death worldwide, and cancer, especially lung cancer, is difficult to diagnose and treat effectively. Accordingly, there is a need in the art for new compositions and methods for assessing and treating various cancers, particularly lung cancer.

Lung Cancer

Lung cancer is the second most prevalent type of cancer for both men and women in the United States and is the most common cause of cancer death in both men and women. The five-year survival rate for lung cancer continues to be poor at only about 8-15%. This low survival is because lung cancer is commonly not detected until it has spread beyond the lungs. Only 16% of new lung cancer cases in the United States are detected at the earliest stage, when the cancer is still localized to the lungs. At this early stage, survival is considerably higher, with estimates as high as 70-80%. Therefore, procedures for detecting lung cancer are of critical importance to the outcome of a patient since these procedures have the potential to reduce mortality. Thus, there is a need for new diagnostic compositions and methods that are more sensitive and specific for detecting early lung cancer.

Furthermore, there is also a need for new diagnostic compositions and methods for determining the stage of a patient's disease. Stage determination has potential prognostic value and provides criteria for designing optimal therapy. Biomarkers that are indicative of different stages of lung cancer would be useful to facilitate the staging of lung cancer.

Lung cancer patients are typically monitored following initial therapy and during adjuvant therapy to determine their response to therapy and to detect persistent or recurrent disease or metastasis. Thus, there is clearly a need for lung cancer markers that are more sensitive and specific in detecting lung cancer, its recurrence, and progression.

Although imaging modalities, such as computed tomography (CT) screening, are being studied to aid in the early detection of lung cancer, controversy remains as to the ability of these methods to impact mortality (I-ELCAP Investigators, *NEJM* 2006 (355):1763-71 and Bach et al. 2007. *JAMA* 297:953-961). In addition, the most advanced imaging technologies under study are expensive and not widely available. These CT imaging tests may lead to over-diagnosis of lung cancer, resulting in significant expenses to the health care system to manage patients with pulmonary nodules observed through these CT imaging tests. Furthermore, there is significant morbidity associated with the management of the pulmonary nodules in an effort to ascertain whether the nodules are malignant or benign. It is estimated that 10-50% of smokers in a high risk group have pulmonary nodules upon imaging studies (*CHEST* 2007 Supplement—*Evidence for the Treatment of Patients With Pulmonary Nodules When Is It Lung cancer?: AACP Evidence-Based Clinical Practice Guidelines*). Thus, there is a significant need for novel diagnostics that can be used either independently or with imaging modalities for early diagnosis and improved management of patients with lung cancer. For example, a blood test for biomarkers that has high performance (e.g., high sensitivity and specificity) for detecting lung cancer could provide a low cost complement to CT testing for early detection of cancer. If the performance of a biomarker test were sufficiently high, such a test could serve as a lower cost alternative to CT or X-ray testing. For example, only those patients that tested positive in a biomarker test may then need to undergo more expensive imaging tests. Furthermore, a biomarker test could be used, for example, in a yearly screening regimen for lung cancer.

Although there have been reports of circulating tumor markers and antigens with potential use in lung cancer (see Schneider, J. 2006. *Advances in Clin Chem*, 42: 1-41 for a review), markers currently used generally suffer from low sensitivity and less than desirable specificity, especially among smokers (Schneider, 2006), and are typically only used to monitor for recurrence of lung cancer. Thus, there is a need in the art for a panel of markers with high sensitivity (and varying specificities, depending on the clinical indication), such as for detecting lung cancer. Furthermore, there is also a need for novel markers that are useful individually or as part of a panel for detecting lung cancer. Such markers, and panels of markers, would facilitate management of patients with lung cancer, for example.

For a further review of lung cancer diagnostics, including the use of tumor biomarkers as well as CT screening, see the following citations: Schneider, "Tumor markers in detection of lung cancer", *Adv Clin Chem*. 2006; 42:1-41; Bach et al., "Computed tomography screening and lung cancer outcomes", *JAMA*. 2007 Mar. 7; 297(9):953-61; and International Early Lung Cancer Action Program Investigators et al., "Survival of patients with stage I lung cancer detected on CT screening", *N Engl J. Med*. 2006 Oct. 26; 355(17):1763-71. Also see Pepe et al., "Phases of biomarker development for early detection of cancer", *J Nat'l Cancer Inst*. 2001. 93(14): 1054-1061

Description of Tables 1-2

Tables 1 and 2 provide further information for lung cancer markers ("LCM"), including their names, symbols (alternative symbols are indicated in parentheses), Genbank protein accession numbers, and an exemplary protein sequence for each marker (except for the carbohydrate antigens CA 242, CA 19-9, and CA 72-4, for which representative journal citations are provided for each). Exemplary LCM protein sequences are provided as SEQ ID NOS:1-65 (additionally, the carbohydrate antigens CA 242, CA 19-9, and CA 72-4 are also provided). Nucleic acid sequences (e.g., mRNA transcript sequences and genomic DNA) and alternative protein sequences for each marker are well known in the art and can readily be derived using the information provided in Tables 1-2, for example.

The LCM provided in Table 1 are as follows (alternative names/symbols are indicated in parentheses): SLPI, MIF, TIMP1, TFPI, ENO2 (NSE), CEA (CEACAM5), MMP2, AMBP, Cyfra 21-1 (Cyfra, KRT19), SCC (SERPINB3), OPN, defensin (DEFA1, HNP-1, HNP1-3), CA 242, CA 19-9, CA 72-4, MN/CAIX (CA9), ProGRP (GRP), KRT18 (TPS), ECAD (CDH1), TIMP2, CD44, LGALS3BP, ERBB2 (HER-2), UPA (PLAU), DKK (DKK1), CHGA, VEGF, KITLG, PBEF (visfatin), SORT1 (sortilin), MDK (midkine), IGFBP3, IGFBP4, CTSC, ICAM3, CTGF, LCN2, EGFR, BGN, TIMP3, HGF, MUC16 (CA125), NCAM, CRP, SERPINA1 (ATT), PKM2, RBP, KLK11, KLK13, SAA, and APOC3.

The LCM provided in Table 2 (which are particularly useful as autoantibody markers) are as follows (alternative names/symbols are indicated in parentheses): TP53 (p53), KLKB1, CFL1 (CFLN), EEF1G, HSP90α (HSP90AA1), RTN4, ALDOA, GLG1, PTK7, EFEMP1, SLC3A2 (CD98), CHGB, CEACAM1, ALCAM, HSPB1 (HSP27), LGALS1, and B7H3.

Elevated levels of each of these LCM are indicative of lung cancer, except for sortilin (SORT1), for which low levels are indicative of lung cancer.

Description of Tables 3-12

Table 3 provides 35 different panels of 11 markers (each row of 11 markers represents a panel) that have at least 98% specificity and 82% sensitivity for detecting lung cancer. The total number of occurrences of each marker in these 35 11-marker panels is indicated at the bottom of Table 3. Seven markers (SLPI, TIMP1, TFPI, SCC, OPN, CEA and CA242) appear in all 35 of these panels, GRP appears in 33 of these 35 panels, MIF appears in 29 of these 35 panels, and NSE and HNP-1 each appear in 15 of these 35 panels. AMBP, Cyfra, MMP2, Ca72-4, Ca19-9, and CAIX each appear in 7-9 of these panels, as indicated in Table 3.

Table 4 provides markers the can be included in any of the panels disclosed herein. For example, the markers in Table 4 can be added to any of the panels disclosed herein and/or can replace one or more members of any of the panels disclosed herein. As a specific example, the markers in Table 4 can be added to any of the panels disclosed in Table 5 and/or can replace one or more members of any of the panels disclosed in Table 5. The markers disclosed in Table 4 are also disclosed in Table 2.

Tables 5-12 provide data for the analysis of various panels in various lung cancer uses, such as distinguishing lung cancer samples versus normal samples such as for diagnosing/detecting lung cancer (Tables 5-6 and 11-12, for example), as well as certain specific uses (these specific uses, which may be referred to herein as "indications" or as determining or assessing lung cancer "characteristics", are provided in Tables 7-10, for example). In Tables 5-12, each row represents a panel (a panel may comprise an individual marker). For each panel in Tables 5-12, data are presented based on logistic regression and/or split point analysis (as indicated in each table). Area under the curve (AUC), sensitivity at 95% specificity, and specificity at 95% sensitivity are indicated. "Size" (second column) indicates the number of markers in the given panel. Further information regarding characteristics of the sample sets (the "54×53", "50×50", and "44×44" sample sets) used in each of the analyses is provided in FIG. 16 (the "104×103" sample set used in Table 8 is the "54×53" and "50×50" sample sets combined). In Tables 5-12, and elsewhere herein, "trained" refers to the sample set (which may be referred to as the "training set") which was used to formulate cutoff levels, and "tested" refers to the sample set (which may be referred to as the "testing set") to which these cutoff levels were applied (such as to classify a sample as a lung tumor or normal sample, or other specific use, based on whether marker levels were above or below the cutoff levels established from the training set).

Table 5 provides data for logistic regression and split-point analysis of the 9-marker panel of Cyfra, SLPI, TIMP1, SCC, TFPI, CEACAM5, MMP2, OPN, and MDK, and all subcombinations thereof (including individual markers), in distinguishing lung tumor samples versus normal (i.e., control/healthy) samples, such as for diagnosing/detecting lung cancer. For each panel in Table 5, data are presented based on logistic regression and split point analysis and based on analysis of either training and testing on the same 54×53 (54 controls and 53 cases) sample set, or training on the 54×53 sample set and testing on the 50×50 (50 controls×50 cases) sample set (see FIG. 16 for characteristics of these sample sets). Area under the curve (AUC), sensitivity at 95% speci- ficity, and specificity at 95% sensitivity are indicated. The panels are sorted based on the AUC indicated in the third column. "Size" (second column) indicates the number of markers in the given panel. Thus, Table 5 provides the 9-marker panel of Cyfra, SLPI, TIMP1, SCC, TFPI, CEACAM5, MMP2, OPN, and MDK, and all panel subcombinations thereof, including each of these nine markers individually (each row represents a panel).

Table 6 provides data for split-point analysis of panels (including individual markers) that include any of the nine markers in the panels provided in Table 5 and/or various other markers (which are not in the panels provided in Table 5) in distinguishing lung tumor samples versus normal (i.e., control/healthy) samples, such as for diagnosing/detecting lung cancer.

Table 7 provides data for logistic regression analysis of the 9-marker panel of Cyfra, SLPI, TIMP1, SCC, TFPI, CEACAM5, MMP2, OPN, and MDK, and subcombinations thereof (including individual markers), in distinguishing adenocarcinoma versus squamous cell carcinoma types of lung cancer.

Table 8 provides data for split-point analysis of the 9-marker panel of Cyfra, SLPI, TIMP1, SCC, TFPI, CEACAM5, MMP2, OPN, and MDK, and subcombinations thereof (including individual markers), in distinguishing stage I versus stage III lung cancer. In addition to their utility in distinguishing between early and late stage lung cancer (e.g., stage I or II versus stage III or IV), the panels provided in Table 8 are also useful for distinguishing between any other stages of lung cancer (e.g., any of stages I, II, III, and IV).

Table 9 provides data for split-point analysis of various panels in distinguishing small cell lung cancer (SCLC) versus other types of lung cancer (e.g., non-small cell lung cancer, NSCLC). In the left-side of Table 9, marker levels are higher in NSCLC (as compared to SCLC). In the right-side of Table 9, marker levels are higher in SCLC (as compared to NSCLC).

Table 10 provides data for split-point analysis of the 9-marker panel of Cyfra, SLPI, TIMP1, SCC, TFPI, CEACAM5, MMP2, OPN, and MDK, and subcombinations thereof (including individual markers), in distinguishing malignant lung tumors versus benign lung lesions.

Table 11 provides data for split-point analysis of various panels in distinguishing small cell lung cancer (SCLC) versus normal (i.e., control/healthy) samples.

Table 12 provides data for split-point analysis of various panels in distinguishing lung cancer (including both small cell lung cancer (SCLC) and non-small cell lung cancer (NSCLC)) versus normal (i.e., control/healthy) samples.

BRIEF DESCRIPTION OF THE FIGURES

Figure 1:
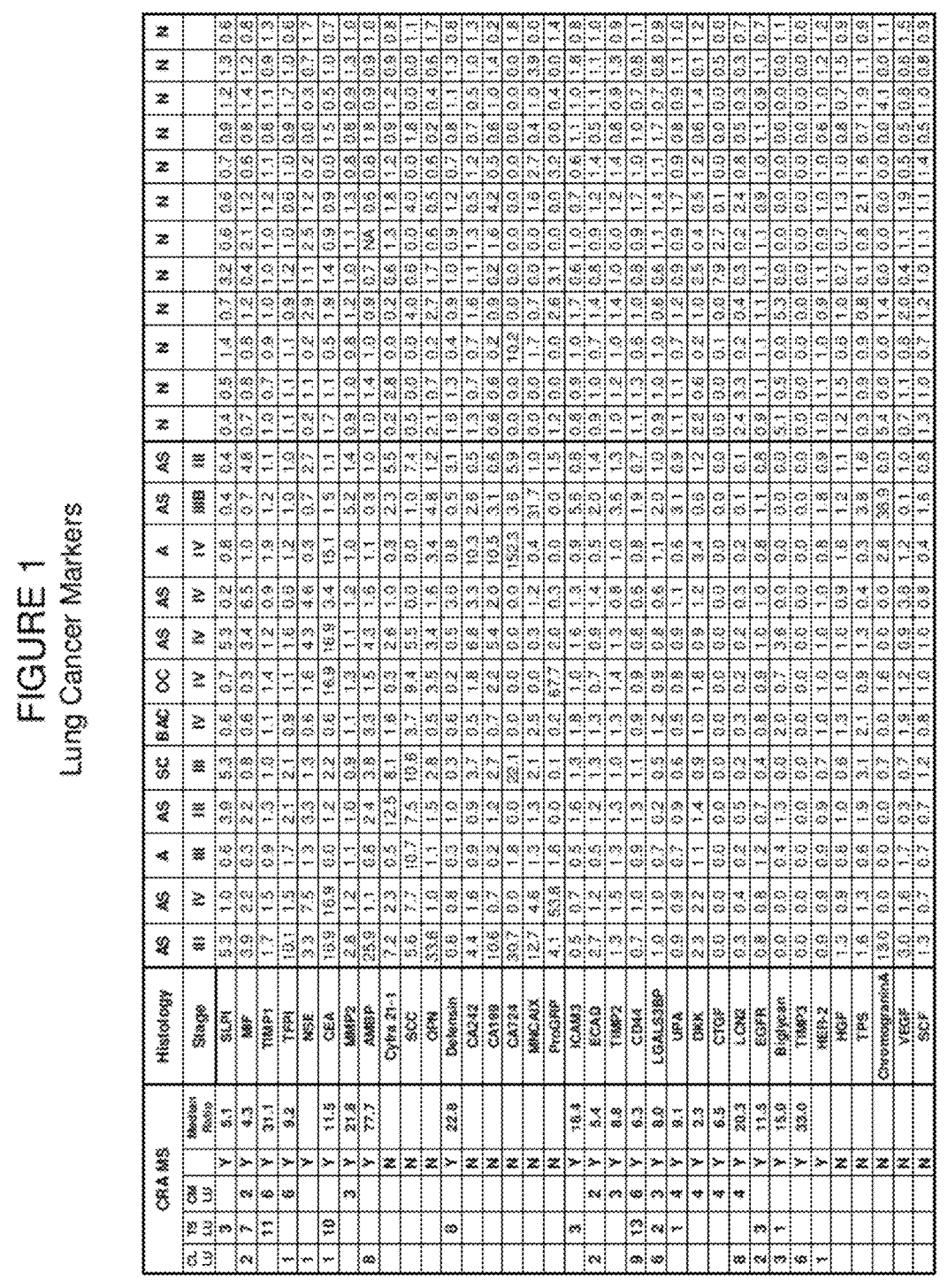

FIG. 1. Shows relative expression levels for exemplary lung cancer markers (LCM) screened by ELISA in a sample set of 12 lung tumor and 12 normal serum samples. The left portion of the table shown in FIG. 1 provides tumor samples identified by histology and tumor state (histology abbreviations for tumor samples are "AS"=adenosquamous, "A"=adenocarcinoma, "SC"=squamous cell carcinoma, and "BAC"=bronchioalveolar carcinoma), and the right portion of the table shows normal samples (identified as "N" for histology). The table is based on mean concentration values of each sample and uses 2 standard deviations (2SD) above normal mean as the cutoff; the value is expressed as fold change from normal mean (thus, any fold change with 2SD above normal mean is above the cutoff). The column labeled "CRA MS" is a summary of mass spectrometry data that indicates the number of differentially expressed lung tumor samples and the median mass spec ratio of these samples (numerical representation of over-expression is indicated by 2.0 or more, whereas numerical representation of under-expression is indicated by 0.5 or less) (lung tumor sample abbreviations for mass spectrometry are "CL LU"=lung cancer cell lines, "TS LU"=lung cancer tissues, and "CM LU"=lung cancer conditioned medium).

FIG. 2. Shows relative expression levels based on ELISA screening of a sample set of 12 lung tumor (upper section) and 12 normal (lower section) serum samples for the eight markers TFPI, SCC (interchangeably referred to as SSC), CEA, CA242, MNCAIX, OPN, Cyfra 21-1, and MIF (as also shown in FIG. 1). The table is based on mean concentration values of each sample and uses 2 standard deviations (2SD) above normal mean as the cutoff; the value is expressed as fold change from normal mean (thus, any fold change with 2SD above normal mean is above the cutoff). Any value below the cut-off is recoded as 0. Any or all of these eight markers may be used in combination as a panel for lung cancer assessment, and the panel may optionally include additional markers.

FIG. 4. Shows relative expression levels based on ELISA screening of a sample set of 12 lung tumor (left portion; histology ("Hist") abbreviations are "AS"=adenosquamous, "A"=adenocarcinoma, "SC"=squamous cell carcinoma, "OC"=oat cell carcinoma, and "BAC"=bronchoalveolar carcinoma) and 12 normal (right portion; identified as "N" for histology) serum samples for alternate panels of LCM, including a panel of the markers SLPI, TFPI, OPN, MIF, TIMP1, and MMP2. Any or all of these markers can also be used in any combination with any or all of the following markers: CA242, SCC, CEA, NSE, CA72-4, CA19-9, Cyfra 21-1, and MN/CAIX, as shown in FIG. 4. The table is based on mean concentration values of each sample and uses two standard deviations (2SD) above normal mean as the cut-off; the value is expressed as fold change from normal mean (thus, any fold change with 2SD above normal mean is above the cutoff). Any value below the cut-off is recoded as 0.

FIG. 6. Shows results of ELISA analysis for the 11 markers Cyfra 21-1, MIF, TIMP1, TFPI, CEA, OPN, SCC, SLPI, HNP-1, GRP, and CA242 in 39 control (normal) samples (left portion, labeled "Control") and 39 lung tumor samples (right portion, labeled "Tumor"). Values shown are concentration (ng/mL). Manually defined cut-offs are indicated immediately below each marker name. The columns labeled "#>cut-off" indicate the total number of markers with elevated expression (i.e., a concentration greater than the manually defined cut-offs) in a given serum sample. "Stage" indicates lung cancer stage, and "Hist Type" indicates histology type. Any or all of these 11 markers may be used in combination as a panel for lung cancer assessment, and the panel may optionally include additional markers.

FIG. 11. Shows results of analysis for certain autoantibody markers (bottom table), as well as certain other lung cancer markers (top table). In the bottom table (autoantibody markers), the column labeled "Lung MS data" indicates a summary of where differential expression has been observed by mass spectrometry (CL=cell lines, TS=tissues, CM=conditioned medium, and IP=immunoprecipitation), the column labeled "SEREX data" indicates autoantibody markers that overlap with the Serological Expression (SEREX) database which identifies markers that elicit a high-titer IgG antibodies, and the column labeled "Rec Protein" indicates the source of recombinant protein used for autoantibody analysis ("vendor" indicates an external commercial source and "CRA" indicates an internal source). Histology abbreviations for tumor samples in the top table are "AS"=adenosquamous, "A"=adenocarcinoma, "SC"=squamous cell carcinoma, and "SM"=small cell carcinoma.

FIG. 12. Shows exemplary autoantibody LCM, which can be used alone or in combination with other LCM. Certain of these autoantibody LCM are also provided in Table 2 along with other autoantibody LCM.

FIG. 14. Shows autoantibody detection in lung cancer and normal serum samples for the autoantibody markers CA12, KLKB1, CFLN, LGALS1, and EEF1G, as well as p53. Autoantibody responses were detected for CA12, KLKB1, and CFLN (cofilin). The table is based on mean concentration values of each sample and uses 2SD above normal mean as the cut-off. Any value below the cutoff is recoded as 0. p53 showed 0 response in normal sera, therefore absolute titers are listed for p53 (positive antibody-dependent values).

FIG. 15. Shows three additional LCM: visfatin (PBEF), sortilin (SORT-1), and midkine (MDK). Any or all of these three LCM can be implemented in a panel of markers for lung cancer diagnosis, for example. FIG. 15 shows abundance levels (in ng/mL) of these three markers in 12 normal lung and 12 lung tumor samples based on ELISA analysis. For sortilin (SORT-1), abundance levels (by relative copy number) of this marker based on mRNA expression analysis of 22 normal lung and 23 lung tumor samples is also provided. For sortilin, lung tumor samples have a decreased abundance level of this marker compared with normal lung samples.

FIG. 16. Shows clinicopathological characteristics of lung cancer serum samples used in various analyses disclosed herein.

FIG. 17. Shows results of ELISA analysis for the 9-marker panel of Cyfra, SLPI, TIMP1, SCC, TFPI, CEACAM5, MMP2, OPN, and MDK in 50 control (normal) samples (left portion, labeled "Normal") and 50 lung tumor samples (right portion, labeled "Tumor"), using split-point analysis applying manually defined cut-offs. The manually defined cut-offs are indicated immediately below each marker name. Values shown are concentration (ng/mL). The columns labeled "≥cut off" indicate the total number of markers with elevated expression (i.e., a concentration greater than or equal to the manually defined cut-offs) in a given serum sample. "Histology" indicates histology type ("adeno"=adenocarcinoma, "squ"=squamous cell carcinoma, "nsm" or "n-sm"=non-small cell carcinoma, "bro"=bronchioloalveolar carcinoma, "LG"=large cell carcinoma, and "neuro"=neuroendocrine). Any or all of these nine markers may be used in combination as a panel for lung cancer assessment, and the panel may optionally include additional markers.

FIG. 19. Shows an analysis of markers to monitor for lung tumor regression/recurrence. Percentage change in levels of biomarkers in patient serum 2-4 weeks post-surgery as compared to pre-surgical levels is indicated.

FIG. 20. Shows an analysis of the expression levels of the 9-marker panel of Cyfra, SLPI, TIMP1, SCC, TFPI, CEACAM5, MMP2, OPN, and MDK in the following co-morbid lung diseases: asthma, bronchitis, and benign lung diseases. Values shown are concentration (ng/mL). The column labeled "#>cut off" indicates the total number of markers with elevated expression (i.e., a concentration greater than the manually defined cut-offs) in a given serum sample. The manually defined cut-offs are indicated immediately below each marker name (in the row labeled "Cut-off").

DETAILED DESCRIPTION OF EXEMPLARY EMBODIMENTS OF THE INVENTION

Figure 3:
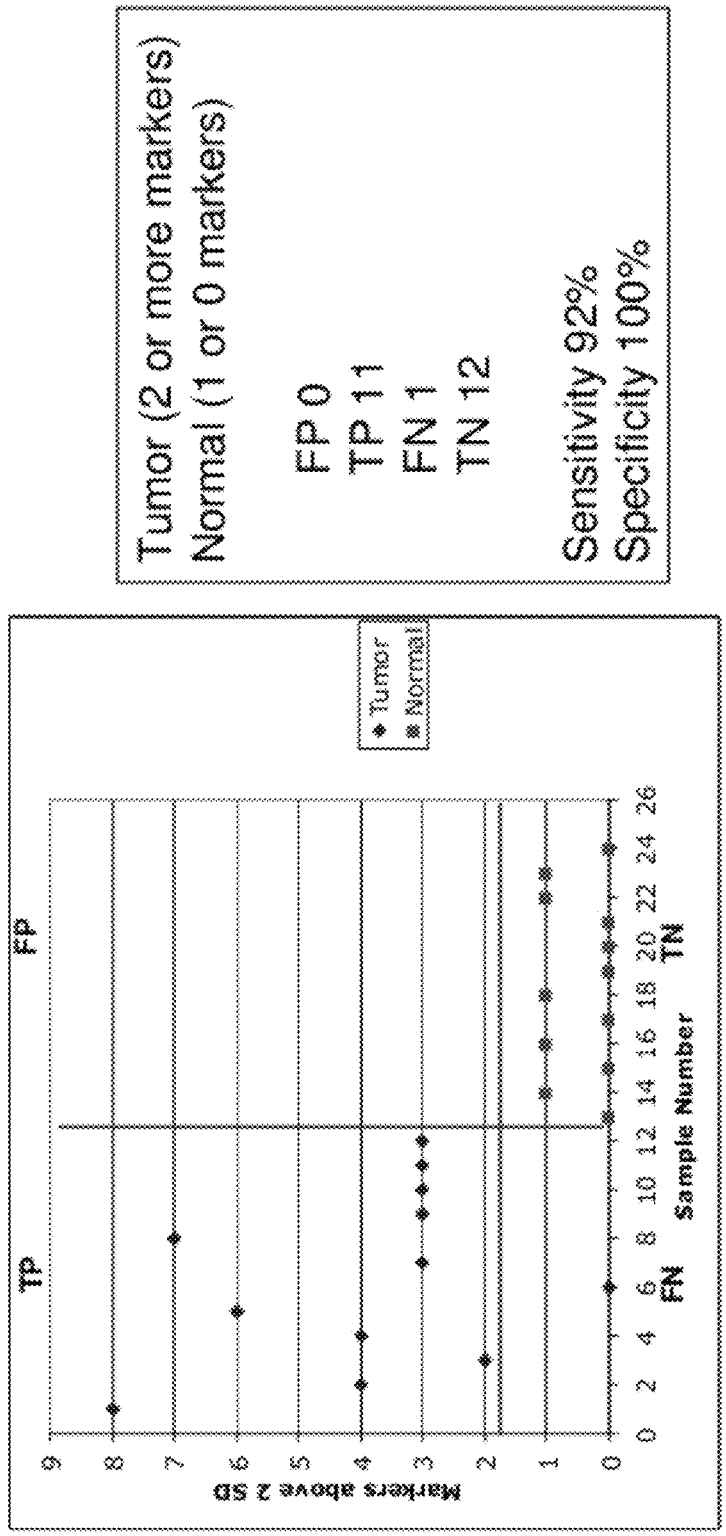
FIG. 3. Shows the performance of the eight marker panel of TFPI, SCC, CEA, CA242, MNCAIX, OPN, Cyfra 21-1, and MIF. Using an algorithm in which markers greater than or equal to two standard deviations were scored "positive", this panel of eight markers had a sensitivity of 92% and specificity of 100% among the 12 sera from lung cancer patients and 12 sera from healthy controls ("FP"=false positives, "TP"=true positives, "FN"=false negatives, and "TN"=true negatives)

The invention will best be understood by reference to the following detailed description of the exemplary embodiments, taken in conjunction with the accompanying table(s) and/or figure(s). The discussion below is exemplary and is not to be taken as limiting the scope defined by the claims.

Exemplary embodiments of the invention provide the following markers (see Tables 1-2), combinations of these markers, and methods of using these markers, particularly for lung cancer-related uses, and especially for lung cancer diagnostics (alternative names/symbols are indicated in parentheses): SLPI, MIF, TIMP1, TFPI, ENO2 (NSE), CEA (CEACAM5), MMP2, AMBP, Cyfra 21-1 (Cyfra, KRT19), SCC (SERPINB3), OPN, defensin (DEFA1, HNP-1, HNP1-3), CA 242, CA 19-9, CA 72-4, MN/CAIX (CA9), ProGRP (GRP), KRT18 (TPS), ECAD (CDH1), TIMP2, CD44, LGALS3BP, ERBB2 (HER-2), UPA (PLAU), DKK (DKK1), CHGA, VEGF, KITLG, PBEF (visfatin), SORT1 (sortilin), MDK (midkine), IGFBP3, IGFBP4, CTSC, ICAM3, CTGF, LCN2, EGFR, BGN, TIMP3, HGF, MUC16 (CA125), NCAM, CRP, SERPINA1 (ATT), PKM2, RBP, KLK11, KLK13, SAA, APOC3, TP53 (p53), KLKB1, CFL1 (CFLN), EEF1G, HSP90α (HSP90AA1), RTN4, ALDOA, GLG1, PTK7, EFEMP1, SLC3A2 (CD98), CHGB, CEACAM1, ALCAM, HSPB1 (HSP27), LGALS1, and B7H3, which are collectively referred to herein as "LCM" ("lung cancer markers"). Elevated levels of each of these LCM are indicative of lung cancer, except for sortilin (SORT1), for which low levels are indicative of lung cancer. Tables 1 and 2 provide further information for each of these LCM, including their names, symbols, Genbank protein accession numbers, and an exemplary protein sequence for each marker (except for the carbohydrate antigens CA 242, CA 19-9, and CA 72-4, for which representative journal citations are provided for each). Exemplary LCM protein sequences are provided as SEQ ID NOS: 1-65 (additionally, the carbohydrate antigens CA 242, CA 19-9, and CA 72-4 are also provided). Nucleic acid sequences (e.g., mRNA transcript sequences and genomic DNA) and alternative protein sequences for each marker are well known in the art and can readily be derived using the information provided in Tables 1-2, for example. The markers provided in Table 2 are particularly useful as autoantibody markers.

Certain embodiments of the invention provide combinations comprising, consisting of, and consisting essentially of the following nine LCM, and subcombinations thereof (these nine LCM may be referred to herein as the "9-marker panel", which is shown in FIG. 17 and Table 5, for example): Cyfra, SLPI, TIMP1, SCC, TFPI, CEACAM5, MMP2, OPN, and MDK. Certain embodiments of the invention provide compositions based on this 9-marker panel and subcombination thereof, and methods of using this 9-marker panel, particularly for uses related to lung cancer (such as detecting lung cancer). In certain embodiments, one or more members of this 9-marker panel is replaced by one or more markers shown in Table 4 and/or one or more markers shown in Table 4 is added to this 9-marker panel. With respect to the nine markers Cyfra, SLPI, TIMP1, SCC, TFPI, CEACAM5, MMP2, OPN, and MDK, elevated levels are indicative of lung cancer (for all of the LCM disclosed herein, elevated levels are indicative of lung cancer, except for sortilin (SORT1), for which low levels are indicative of lung cancer). In certain embodiments, if the levels of two or more markers (i.e., a "plurality") of the 9-marker panel are elevated in a sample (e.g., a serum sample) from an individual, this indicates that the individual has lung cancer. In various other embodiments, if the levels of one or more, three or more, four or more, five or more, six or more, seven or more, eight or more, or all nine markers of the 9-marker panel are elevated in a sample from an individual, this indicates that the individual has lung cancer. In certain embodiments, a marker is classified as being elevated if its level is greater than (or greater than or equal to) a predetermined cutoff level.

Furthermore, certain embodiments of the invention provide combinations comprising, consisting of, and consisting essentially of the following six LCM (each of which is also contained in the above 9-marker panel), and subcombinations thereof (these six LCM may be referred to herein as the "6-marker subset of the 9-marker panel", which is shown in Table 5): Cyfra, SLPI, TIMP1, TFPI, CEACAM5, and MDK. Certain embodiments of the invention provide compositions based on this 6-marker subset of the 9-marker panel and subcombination thereof, and methods of using this 6-marker subset of the 9-marker panel, particularly for uses related to lung cancer (such as detecting lung cancer). In certain embodiments, one or more members of this 6-marker subset of the 9-marker panel is replaced by one or more markers shown in Table 4 and/or one or more markers shown in Table 4 is added to this 6-marker subset of the 9-marker panel. With respect to the six markers Cyfra, SLPI, TIMP1, TFPI, CEACAM5, and MDK, elevated levels are indicative of lung cancer (for all of the LCM disclosed herein, elevated levels are indicative of lung cancer, except for sortilin (SORT1), for which low levels are indicative of lung cancer). In certain embodiments, if the levels of two or more markers (i.e., a "plurality") of the 6-marker subset of the 9-marker panel are elevated in a sample (e.g., a serum sample) from an individual, this indicates that the individual has lung cancer. In various other embodiments, if the levels of one or more, three or more, four or more, five or more, or all six markers of the 6-marker subset of the 9-marker panel are elevated in a sample from an individual, this indicates that the individual has lung cancer. In certain embodiments, a marker is classified as being elevated if its level is greater than (or greater than or equal to) a predetermined cutoff level.

Exemplary embodiments of the invention provide LCM and combinations of LCM (combinations of LCM may be interchangeably referred to herein as panels), and uses thereof, particularly uses related to lung cancer. For example, exemplary embodiments of the invention provide methods and compositions for assessing (e.g., diagnosing/detecting, prognosing, or predicting drug response), treating, and preventing diseases, especially cancer, and particularly lung cancer, using LCM. Furthermore, the compositions and methods of the invention may be suitable for other types of cancer, particularly other epithelial cell-related cancers and solid tumors, as well as other lung diseases.

LCM proteins and fragments thereof (LCM peptides), LCM carbohydrate antigens and fragments thereof, and LCM nucleic acid molecules and fragments thereof encoding LCM proteins and peptides, are collectively referred to as "LCM" or "markers" (which may be interchangeably referred to as "biomarkers", "antigens", or "targets").

The terms "protein" and "polypeptide" are used herein interchangeably. Furthermore, references herein to proteins/polypeptides may also typically encompass carbohydrate antigens ("CA"); for example, references to LCM proteins/polypeptides may also typically encompass the carbohydrate antigens CA 242, CA 19-9, and CA 72-4. Exemplary LCM protein/polypeptide sequences are provided as SEQ ID NOS: 1-65 (additionally, carbohydrate antigens CA 242, CA 19-9, and CA 72-4 are also provided). A "peptide" typically refers to a fragment of a protein/polypeptide. Thus, peptides are interchangeably referred to as fragments. References herein to proteins, peptides, carbohydrate antigens, nucleic acid molecules, and antibodies typically are not limited to the full-size or full-length molecule, but also can encompass fragments of these molecules (unless a particular sequence or structure is explicitly stated).

As used herein, a "lesion" (e.g., a lung lesion) may be interchangeably referred to as a "nodule" (e.g., a lung nodule), and "lung" may be interchangeably referred to as "pulmonary".

As used herein, "subcombinations" (of LCM) may be interchangeably referred to as "subsets" (of LCM).

"Abundance level" may be interchangeably referred to herein as "expression level", or just "level" or "abundance". Determination of LCM levels may be referred to herein as "quantifying" LCM, or "quantification" of LCM.

A "differential" abundance level is a level of a marker (e.g., LCM protein or nucleic acid) in a test sample (e.g., a disease sample) either above or below the normal abundance level of the same marker in a corresponding control or normal sample or group of control/normal samples (e.g., a sample set or population). Thus, for example, a "differential" abundance level can encompass either a "high" (or "increased") or "low" (or "decreased") abundance level. An example of a normal abundance level for a LCM is the mean abundance level of the marker in individuals who do not have lung cancer, which may be the mean abundance of the marker in, for example, a particular control sample set or population of individuals who do not have lung cancer. The normal abundance may also be the typical abundance level of a marker in a normal cell (e.g., a normal lung cell) compared with the typical abundance level of the marker in a corresponding disease cell (e.g., a lung cancer cell).

An example of a "high", "increased", or "elevated" (these terms are used herein interchangeably) abundance level for a LCM is an abundance level that is at least two standard deviations above the normal abundance level of the marker (e.g., the mean abundance level of the marker in individuals who do not have lung cancer). An example of a "low" or "decreased" abundance level for a LCM is an abundance level that is at least two standard deviations below the normal abundance level of the marker (e.g., the mean abundance level of the marker in individuals who do not have lung cancer). Thus, in this particular example, an abundance level that is between 2 standard deviations above and 2 standard deviations below the mean abundance level of the marker in individuals who do not have lung cancer may be considered within a normal abundance level range. These are merely exemplary cut-offs which can be used to label an abundance level of a marker as "high"/"increased" or "low"/"decreased".

In alternative exemplary embodiments, the cut-offs for a "high"/"increased" or "low"/"decreased" abundance can be an abundance level that is greater that one standard deviation above or below the normal abundance level, or greater that three standard deviations above or below the normal abundance level, or any other desired standard deviation. In further alternative exemplary embodiments, the cut-offs for a "high"/"increased" or "low"/"decreased" abundance can be based directly on the expression ratio or fold difference, for example, a 2-fold increase/decrease, 3-fold increase/decrease, or 4-fold increase/decrease, or any other desired degree of increase/decrease. Further, the normal abundance level can be based on, for example, either the mean or median abundance level (e.g., of a given control sample set). Other exemplary methods for developing cut-offs for "high"/"increased" or "low"/"decreased" abundance levels include determining a normal abundance level range (such as by testing a panel of markers in a control sample set of normal lung tissue samples), and classifying any test samples above or below this normal range (or above/below a desired threshold relative to this normal range, such as outside a particular percentage of samples within this normal range such as above or below 95% of samples within the normal range) as "high"/ "increased" or "low"/"decreased", respectively.

A wide variety of further cut-offs for classifying the abundance level of a marker as "high"/"increased" or "low"/"decreased", and methods for formulating these cut-offs, are known in the art and/or can be implemented by one of ordinary skill in the art. For a given marker or panel of markers, various cut-offs can be applied, such as cut-offs that maximize sensitivity while maintaining a desired specificity, for example, or that maximize specificity while maintaining a desired sensitivity. For example, the classification of a sample as a tumor sample or normal sample can be accomplished using a variety of methods that may involve using a set of training data to produce a model that can then be used to classify a test sample (such as to diagnose lung cancer, for example). Tumor/normal cut-offs can be selected by manual inspection of multiple markers from the training data set, and these cut-offs can be applied to classifying test samples (such as to characterize patient samples with respect to lung cancer). Exemplary methods include, but are not limited to, split-point analysis (e.g., Mor et al., "Serum protein markers for early detection of ovarian cancer", *Proc Natl Acad Sci USA*. 2005 May 24; 102(21):7677-82, incorporated herein by reference), logistic regression analysis (e.g., Planque et al., "A multiparametric serum kallikrein panel for diagnosis of non-small cell lung carcinoma", *Clin Cancer Res*. 2008 Mar. 1; 14(5):1355-62, incorporated herein by reference), Naïve Bayes, multivariate analysis, decision tree modeling (e.g., Patz et al., "Panel of serum biomarkers for the diagnosis of lung cancer", *J Clin Oncol* (2007), 25, 5578-5583), and other classification methods (see, for example, Dudoit et al., "Classification in Microarray Experiments", Statistical Analysis of Gene Expression Microarray Data, 2003, Chapman & Hall/ CRC: 93-158, incorporated herein by reference).

The terms "sensitivity" and "specificity" are used herein with respect to the ability of one or more markers to correctly classify a sample as a tumor sample or a non-tumor sample (a non-tumor sample may be interchangeably referred to as a "normal", "control", or "healthy" sample), respectively. "Sensitivity" indicates the performance of the marker(s) with respect to correctly classifying tumor samples. "Specificity" indicates the performance of the marker(s) with respect to correctly classifying non-tumor samples. For example, 98% specificity and 85% sensitivity for a panel of markers used to test a set of control and tumor samples indicates that 98% of the control samples were correctly classified as control samples by the panel, and 85% of the tumor sample were correctly classified as tumor samples by the panel.

Area under the curve (AUC) refers to the area under the curve of a receiver operating characteristic (ROC) curve, which are well known in the art (see, e.g., Planque et al., "A multiparametric serum kallikrein panel for diagnosis of non-small cell lung carcinoma", *Clin Cancer Res*. 2008 Mar. 1; 14(5):1355-62, incorporated herein by reference). AUC measures are useful for comparing the accuracy of a classification algorithm across the complete data range. Classification algorithms with a greater AUC have a greater capacity to classify unknowns correctly between two groups of interest (e.g., lung cancer samples and normal samples). ROC curves are useful for plotting the performance of a particular feature (e.g., an LCM and/or a supplemental biomedical parameter) in distinguishing between two populations (e.g., cases having lung cancer and controls without lung cancer). Typically, the feature data across the entire population (e.g., the cases and controls) are sorted in ascending order based on the value of a single feature. Then, for each value for that feature, the true positive and false positive rates for the data are calculated. The true positive rate is determined by counting the number of cases above the value for that feature and then dividing by the total number of cases. The false positive rate is determined by counting the number of controls above the value for that feature and then dividing by the total number of controls. Although this definition refers to scenarios in which a feature is elevated in cases compared to controls, this definition also applies to scenarios in which a feature is lower in cases compared to the controls (in such a scenario, samples below the value for that feature would be counted). ROC curves can be generated for a single feature as well as for other single outputs, for example, a combination of two or more features can be mathematically combined (e.g., added, subtracted, multiplied, etc.) to provide a single sum value, and this single sum value can be plotted in a ROC curve. Additionally, any combination of multiple features, in which the combination derives a single output value, can be plotted in a ROC curve. These combinations of features may comprise a test. The ROC curve is the plot of the true positive rate (sensitivity) of a test against the false positive rate (specificity) of the test.

Exemplary embodiments of the invention, which are discussed in greater detail below, provide antibodies, proteins, carbohydrate antigens, immunogenic peptides (e.g., peptides which induce a T-cell response), or other biomolecules, as well as small molecules, nucleic acid agents (e.g., RNAi and antisense nucleic acid agents), and other compositions that modulate the markers (e.g., agonists and antagonists), such as by binding to or otherwise interacting with or affecting the markers. These compositions can be used for assessing, treating, and preventing diseases, especially cancer, and particularly lung cancer, as well as other uses. Moreover, the invention provides methods for assessing, treating, and preventing diseases such as lung cancer, particularly by using these compositions. Further provided are methods of screening for agents that modulate LCM, such as by affecting the function, activity, and/or expression level of LCM, and agents identified by these screening methods.

Exemplary embodiments of the invention also provide methods of modulating cell function, especially lung cell function. In particular, the invention provides methods of modulating cell proliferation and/or apoptosis. For example, for cancer/tumor cells, the invention provides methods of inhibiting cell proliferation and/or stimulating apoptosis. Such methods can be applied to the treatment of diseases, especially cancer, and particularly lung cancer. In certain exemplary embodiments, the invention provides methods of treating lung cancer by targeting LCM to thereby inhibit proliferation of lung cancer cells and/or stimulate apoptosis of lung cancer cells.

Exemplary embodiments of the invention further provide methods of determining or predicting effectiveness or response to a particular treatment, and methods of selecting a treatment for an individual, particularly a lung cancer treatment. For example, markers that are differentially expressed by cells (e.g., lung cancer cells) that are more or less responsive (sensitive) or resistant to a particular treatment, such as a cancer treatment, are useful for determining or predicting effectiveness or response to the treatment or for selecting a treatment for an individual.

Exemplary embodiments of the invention also provide methods of selecting individuals for a clinical trial of a therapeutic agent, particularly a clinical trial for lung cancer or other cancer. For example, the markers can be used to identify individuals for inclusion in a clinical trial who are more likely to respond to a particular therapeutic agent. Alternatively, the markers can be used to exclude individuals from a clinical trial who are less likely to respond to a particular therapeutic agent or who are more likely to experience toxic or other undesirable side effects from a particular therapeutic agent. Furthermore, such individuals who are determined to be less likely to respond to a particular therapeutic agent can be selected for inclusion in a clinical trial of a different therapeutic agent that may potentially benefit them.

In certain exemplary embodiments, the various individual LCM and LCM panels described herein are provided as compositions. For example, in certain embodiments, each of the members of an LCM panel, and/or reagents for detecting each of these members, are provided as individual compositions, such as in the form of reagents for detecting each member of an LCM panel by ELISA assays (which may be referred to herein as "ELISA reagents"). Furthermore, in certain embodiments, compositions that comprise multiple members of a panel or an entire panel (and/or reagents for detecting each of these multiple members), are provided, such as in the form of kits that contain reagents (such as ELISA reagents) for detecting multiple members of a panel or an entire panel. Other compositions of the invention include arrays or other platforms that have multiple LCM, or multiple reagents (e.g., antibodies) for detecting multiple LCM, coupled to a substrate. In various compositions of the invention, the LCM, or reagents for detecting LCM (e.g., antibodies), are labeled with a detectable moiety (such as a fluorescent label).

Exemplary LCM Combinations/Panels

For example, using a panel of sera from 12 lung cancer patients and 12 healthy control individuals, a group of 8 markers made up of TFPI, SCC, CEA, CA242, MN/CAIX, OPN, Cyfra 21-1, and MIF (FIG. 2) detected all the cancer samples except a bronchioalveolar cancer sample (which is biologically distinct from other samples in the panel), and only a few of these markers were detected at levels above the threshold in the healthy control samples. When a simple algorithm was applied (i.e., markers greater than or equal to two standard deviations were scored "positive", using the criterion stated above), this group of eight markers had a sensitivity of 92% and specificity of 100% among the 12 sera from lung cancer patients and 12 sera from healthy controls (no false positives, 11 true positives, 1 false negative, and 12 true negatives) (FIG. 3).

An alternate panel was configured that was made up of following markers: SLPI, TFPI, OPN, MIF, TIMP1, and MMP2 (FIG. 4). Any or all of these markers can also be used in any combination with any or all of the following markers: CA242, SCC, CEA, NSE, CA72-4, CA19-9, Cyfra 21-1, and MN/CAIX (FIG. 4).

Figure 5:
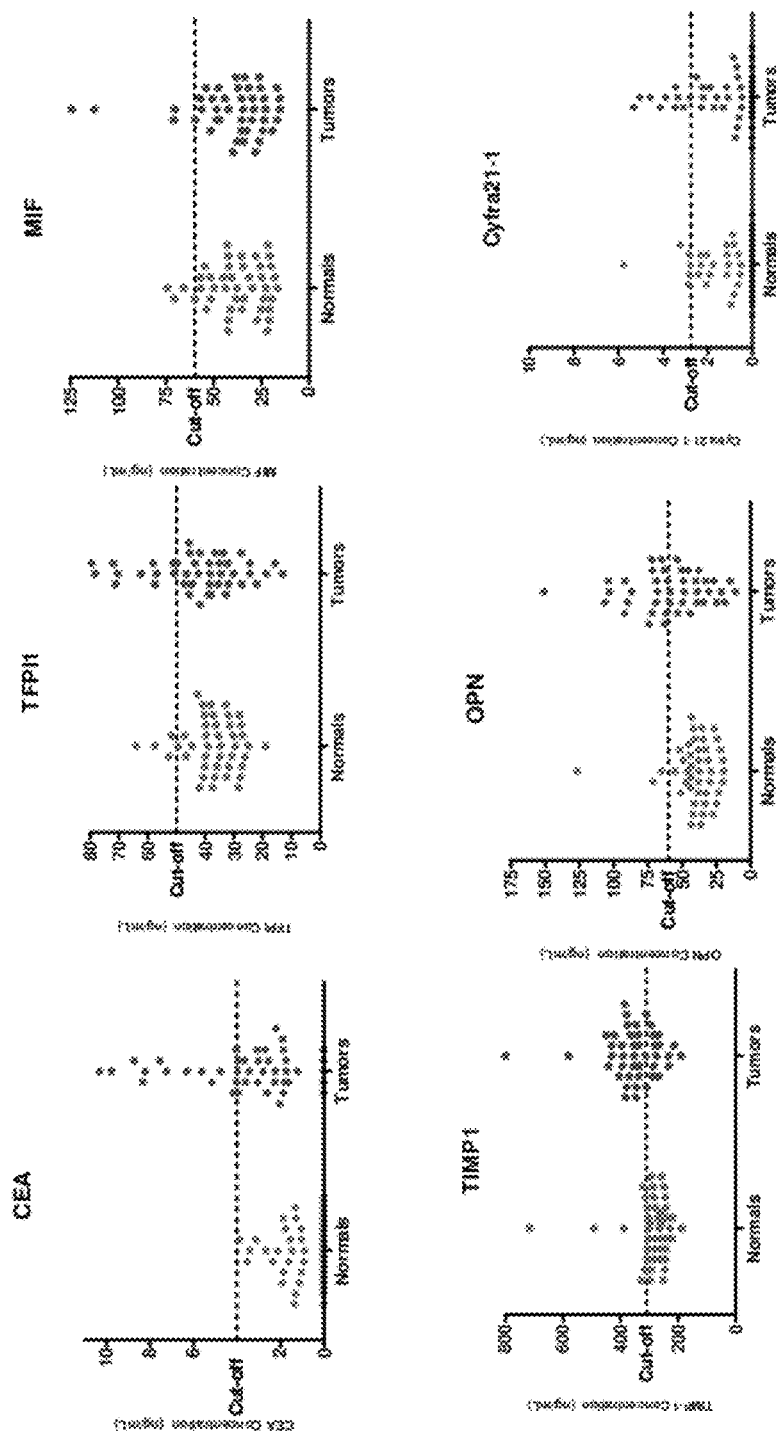
FIG. 5. Shows scatter plots of ELISA data for the six markers CEA, TFPI, MIF, TIMP1, OPN, and Cyfra 21-1 in 44 normal and 44 lung tumor samples, with exemplary cut-offs indicated (dotted lines). Cut-offs can be applied that maximize sensitivity while not compromising specificity of the panel, for example.

Further, a six-marker panel made-up of Cyfra 21-1, TIMP-1, MIF, TFPI, CEA, and OPN was also configured (FIG. 5). This six-marker panel, when tested on a larger group of 44 lung tumor sera and 44 normal sera, resulted in 75% sensitivity at 95% specificity.

Further, an 11-marker panel made-up of Cyfra, MIF, TIMP1, TFPI, CEA, OPN, SCC, SLPI, HNP-1, GRP, and CA242 was also configured (FIG. 6). This 11-marker panel, when tested on a group of 39 lung tumor sera and 39 normal sera, resulted in 98% specificity for controls (38/39 controls) and 85% sensitivity for tumor sera (33/39 tumors) (FIG. 6).

Table 3 shows further examples of various 11-marker panels. Specifically, Table 3 provides 35 different panels of 11 markers (each row of 11 markers represents a panel) that have at least 98% specificity and 82% sensitivity for detecting lung cancer. Seven markers (SLPI, TIMP1, TFPI, SCC, OPN, CEA and CA242) appear in all 35 of these panels, GRP appears in 33 of the 35 panels, MIF appears in 29 of the 35 panels, and NSE and HNP-1 each appear in 15 of the 35 panels. AMBP, Cyfra, MMP2, Ca72-4, Ca19-9, and CAIX each appear in 7-9 of the panels, as indicated in Table 3.

Further, a 9-marker panel made-up of Cyfra, SLPI, TIMP1, SCC, TFPI, CEACAM5, MMP2, OPN, and MDK was also configured (e.g., FIG. 17 and Table 5). This 9-marker panel demonstrated 98% specificity (49/50 controls) and 96% sensitivity (48/50 tumors) (FIG. 17). Additionally, a 6-marker subset of this 9-marker panel was also configured that was made-up of Cyfra, SLPI, TIMP1, TFPI, CEACAM5, and MDK (Table 5).

Other markers, which are also referred to herein as LCM and which may be used either alone or in combination with any of the other LCM described herein in any combination, include a group of antigens to which "self-made" or "autoantibodies" are often found in the circulation of patients with various diseases, particularly cancer (Table 2 and FIGS. 11-14). Examples of these autoantibody markers include the following: KLKB1, CFL1, LGAGS1, EEF1G, RTN4, ALDOA, HSPCA, PABPC4, NAGK, CFHL1, CSF1R, and RANBP2 (FIG. 12), and other autoantibody markers as shown in Table 2. Detection of autoantibody LCM such as these may complement other LCM and enhance the performance of LCM panels, particularly for assessing lung cancer.

The following are exemplary panels of LCM. Various exemplary embodiments of the invention provide, for example, compositions based on these panels and methods of using these panels, particularly for uses related to lung cancer such as diagnosis of lung cancer (e.g., differential levels, such as elevated or low levels as compared to control/normal levels, of a plurality of markers in a panel, or all markers in panel, can indicate the presence of lung cancer). These exemplary panels may consist of, consist essentially of, or comprise the following combinations of markers:

1) Cyfra, SLPI, TIMP1, SCC, TFPI, CEACAM5, MMP2, OPN, and MDK (which may be referred to herein as the "9-marker panel" and is shown in FIG. 17 and Table 5).
2) Cyfra, SLPI, TIMP1, TFPI, CEACAM5, and MDK (which may be referred to herein as the "6-marker subset of the 9-marker panel" and is shown in Table 5).
3) Cyfra, SLPI, TIMP1, SCC, TFPI, CEACAM5, MMP2, OPN, and MDK (the "9-marker panel"), which may optionally be in combination with one or more other markers (which may be added to this 9-marker panel and/or replace one or more members of this 9-marker panel), wherein these other markers may optionally be selected from the group consisting of the markers shown in Tables 1-2 (SEQ ID NOS:1-65 and the carbohydrate antigens CA 242, CA 19-9, and CA 72-4), Table 4, FIG. 1, and FIG. 12, particularly those markers that are shown in Table 4.
4) Cyfra, SLPI, TIMP1, TFPI, CEACAM5, and MDK (the "6-marker subset of the 9-marker panel"), which may optionally be in combination with one or more other markers (which may be added to this 6-marker subset of the 9-marker panel and/or replace one or more members of this 6-marker subset of the 9-marker panel), wherein these other markers may optionally be selected from the group consisting of the markers shown in Tables 1-2 (SEQ ID NOS:1-65 and the carbohydrate antigens CA 242, CA 19-9, and CA 72-4), Table 4, FIG. 1, and FIG. 12, particularly those markers that are shown in Table 4.
5) Any of the panels (which may include single markers) provided in Table 5 (which provides the 9-marker panel and all subcombinations thereof; each row of Table 5 represents a different panel), which may optionally be in combination with one or more other markers (which may be added to any panel in Table 5 and/or replace one or more members of any panel in Table 5), wherein these other markers may optionally be selected from the group consisting of the markers shown in Tables 1-2 (SEQ ID NOS:1-65 and the carbohydrate antigens CA 242, CA 19-9, and CA 72-4), Table 4, FIG. 1, and FIG. 12, particularly those markers that are shown in Table 4.

6) Any of the panels provided in Table 5 or Table 6 (particularly the 9-marker panel of Cyfra, SLPI, TIMP1, SCC, TFPI, CEACAM5, MMP2, OPN, and MDK, as well as subsets thereof, and panels comprising this 9-marker panel or subsets thereof that further include one or more additional markers such as those panels set forth in Table 6), particularly for use in methods for distinguishing lung tumor samples versus normal (i.e., control/healthy) samples. These panels are particularly useful for determining whether an individual has lung cancer (i.e., detecting lung cancer), for example.

7) Any of the panels provided in Table 7 (particularly the 9-marker panel of Cyfra, SLPI, TIMP1, SCC, TFPI, CEACAM5, MMP2, OPN, and MDK, as well as subsets thereof), particularly for use in methods for distinguishing adenocarcinoma versus squamous cell carcinoma. These panels are particularly useful for determining whether an individual's lung cancer is adenocarcinoma or squamous cell carcinoma, for example.

8) Any of the panels provided in Table 8 (particularly the 9-marker panel of Cyfra, SLPI, TIMP1, SCC, TFPI, CEACAM5, MMP2, OPN, and MDK, as well as subsets thereof), particularly for use in methods for distinguishing between any stages of lung cancer (e.g., any of stages I, II, III, and IV), particularly between early stage (stage I or II) and late stage (stage III or IV) lung cancer, and especially between stage I and stage III lung cancer. These panels are particularly useful for determining the stage of an individual's lung cancer, for example.

9) Any of the panels provided in Table 9, particularly for use in methods for distinguishing SCLC versus other types of lung cancer (e.g., NSCLC). These panels are particularly useful for determining whether an individual's lung cancer is SCLC or NSCLC, for example.

10) Any of the panels provided in Table 10 (particularly the 9-marker panel of Cyfra, SLPI, TIMP1, SCC, TFPI, CEACAM5, MMP2, OPN, and MDK, as well as subsets thereof), particularly for use in methods for distinguishing malignant lung tumors versus benign lung lesions. These panels are particularly useful for determining whether a lung lesion identified in an individual (such as by CT screening) is a malignant tumor or a benign lesion, for example.

11) Any of the panels provided in Table 11, particularly for use in methods for distinguishing SCLC versus normal (i.e., control/healthy) samples. These panels are particularly useful for determining whether an individual has SCLC, for example.

12) Any of the panels provided in Table 12, particularly for use in methods for distinguishing lung cancer (including both SCLC and NSCLC) versus normal (i.e., control/healthy) samples. These panels are particularly useful for determining whether an individual has lung cancer such as SCLC or NSCLC, for example.

13) Panels that include any or all of the 11 markers provided in FIG. 19 (and subsets thereof, as well as panels comprising these 11 markers or subsets thereof that further include one or more additional markers), particularly for use in methods of monitoring for lung tumor regression and/or recurrence. These panels are particularly useful for monitoring for lung tumor regression and/or recurrence, for example.

14) Cyfra 21-1, MIF, TIMP1, TFPI, CEA, OPN, SCC, SLPI, HNP-1, GRP, and CA242 (which may be referred to herein as the "11-marker panel" and is shown in FIG. 6).

15) TFPI, CEA, MIF, TIMP1, OPN, and Cyfra 21-1 (which may be referred to herein as the "6-marker panel" and is shown in FIG. 5).

Figure 2:
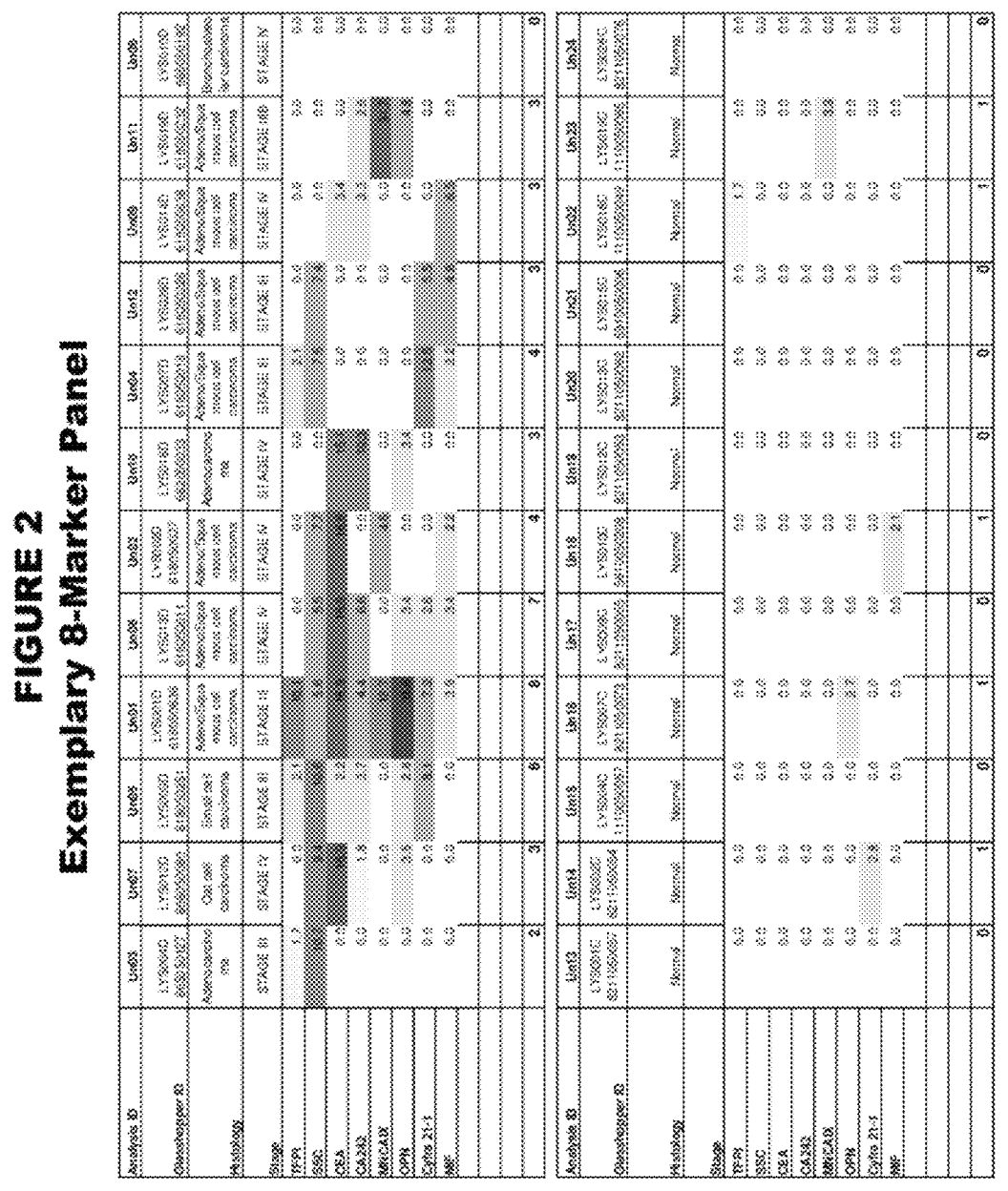

16) TFPI, SCC, CEA, CA242, MN/CAIX, OPN, Cyfra 21-1 and MIF (which may be referred to herein as the "8-marker panel" and is shown in FIGS. 2-3).

17) TFPI, SLPI, OPN, MIF, TIMP1, and MMP2, any or all of which can optionally be used in combination with any or all of the following additional markers: CA242, SCC, CEA, NSE, CA724, CA199, Cyfra 21-1, and MN/CAIX (see FIG. 4).

Figure 7:
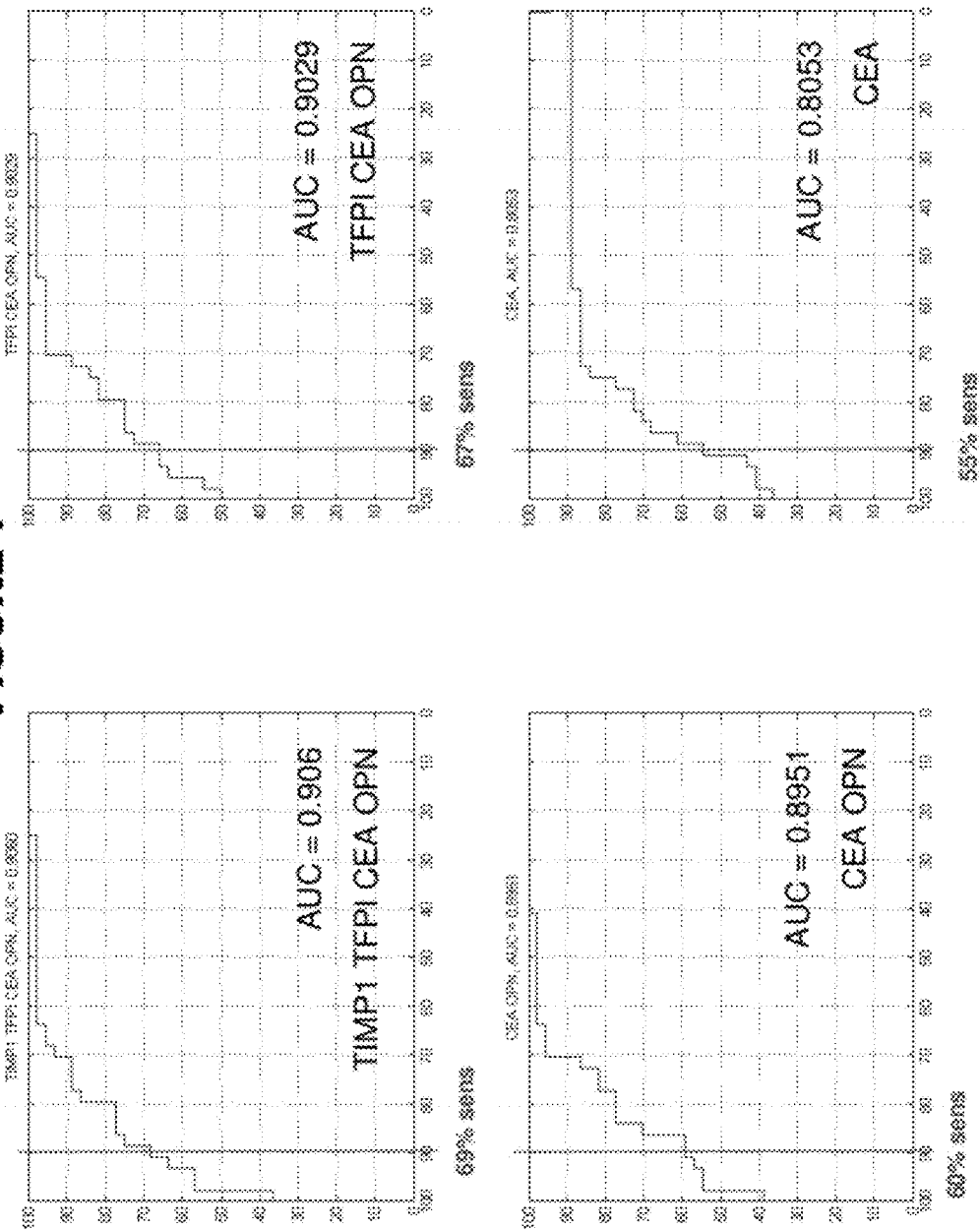
FIG. 7. Shows performance of exemplary panels of markers, demonstrating that increased sensitivity can be achieved by including additional markers. The marker CEA provides 55% sensitivity and 90% specificity, the two markers CEA and OPN provide 60% sensitivity and 90% specificity, the three markers TFPI, CEA, and OPN provide 67% sensitivity and 90% specificity, and the four markers TIMP1, TFPI, CEA, and OPN provide 69% sensitivity and 90% specificity. The score is the sum of the $\log_2$ of the ratios of the tumor concentration to the mean concentration in normal serum. ROC curves can be constructed by varying the cut-off of the score needed to call a sample a tumor.
Figure 8:
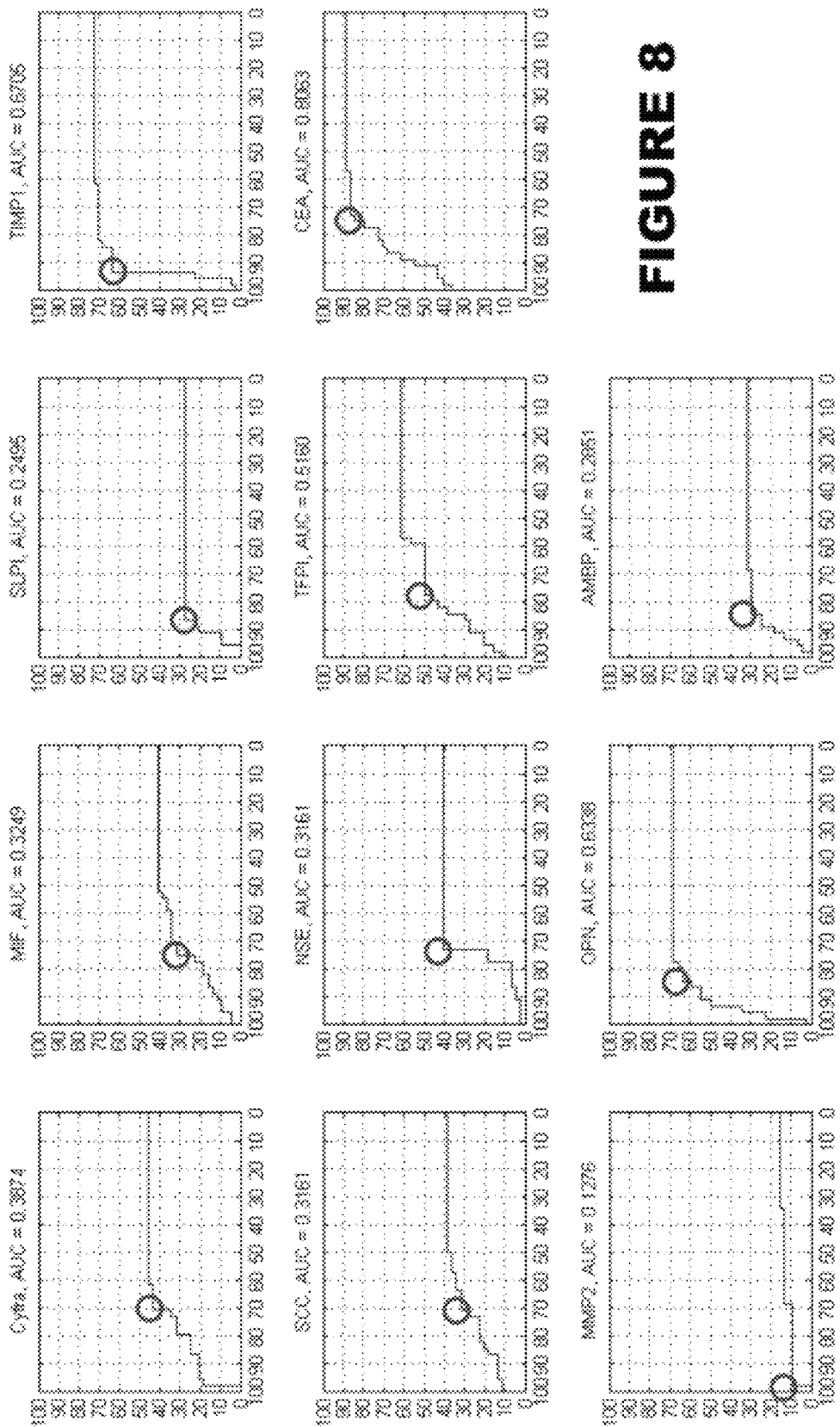
FIG. 8. Shows examples of applying a cut-off for various markers (Cyfra 21-1, MIF, SLPI, TIMP1, SCC, NSE, TFPI, CEA, MMP2, OPN, and AMBP are shown) that provides desirable performance for that marker. The circles show the approximate location of an exemplary cut-off for each marker which is the point on the curve that is closest to the upper-left corner. Different criteria can also be used, for instance false negatives could be weighted more heavily than false positives.

18) TFPI, TIMP1, CEA, and OPN (see FIG. 7).

19) TFPI, CEA, and OPN (see FIG. 7).

20) CEA and OPN (see FIG. 7).

Figure 9:
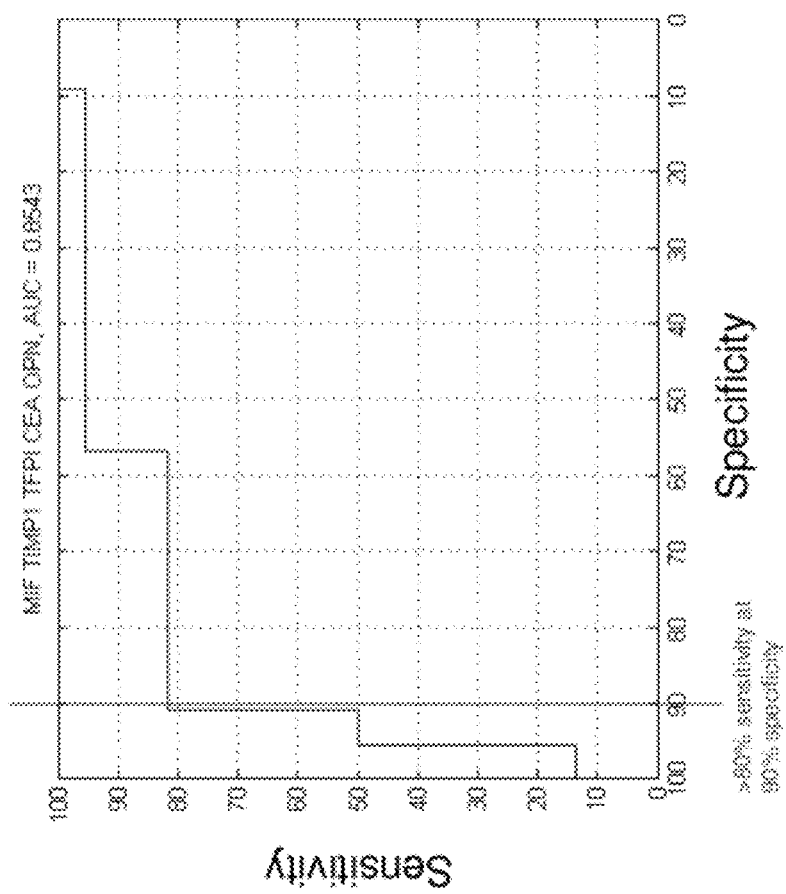
FIGS. 9-10. Shows AUC (area under curve)=0.8543 for markers MIF, TIMP1, TFPI, CEA, and OPN (FIG. 9), and AUC=0.8518 for markers TIMP1, NSE, CEA, and OPN. Score is the number of markers greater than the cutoff that best separates tumor samples from normal samples for each marker. ROC curve can be constructed by varying the cut-off of the score needed to call a sample a tumor.

21) TFPI, MIF, TIMP1, CEA, and OPN (see FIG. 9).

Figure 10:
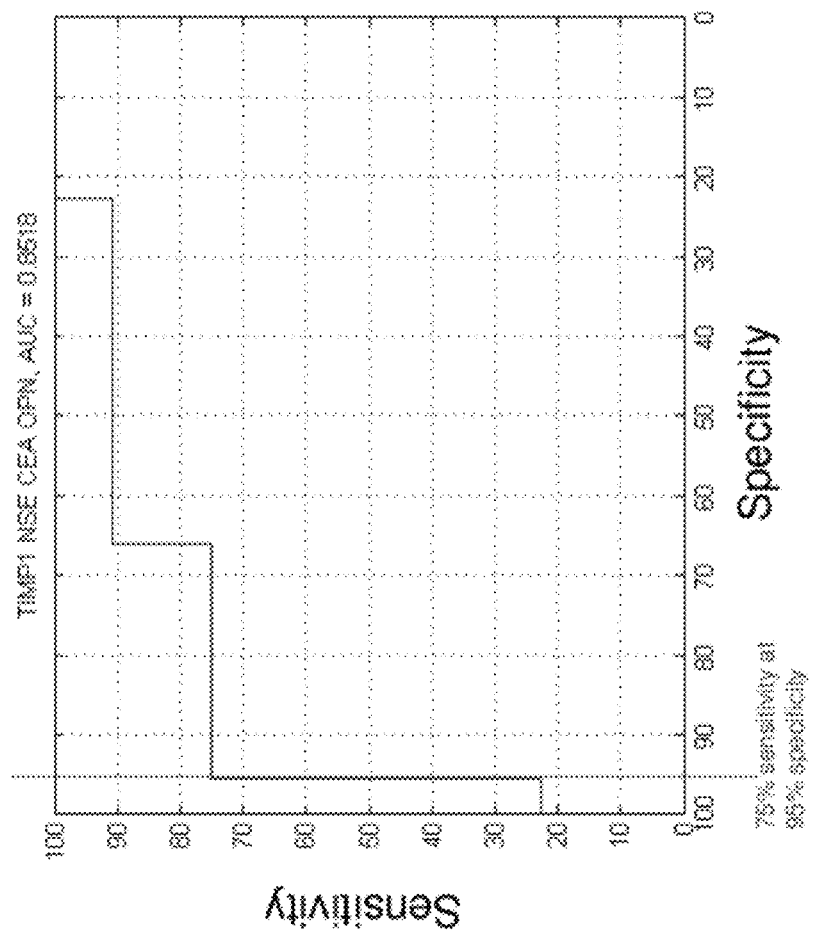

22) TIMP1, NSE, CEA, and OPN (see FIG. 10).

Figure 11:
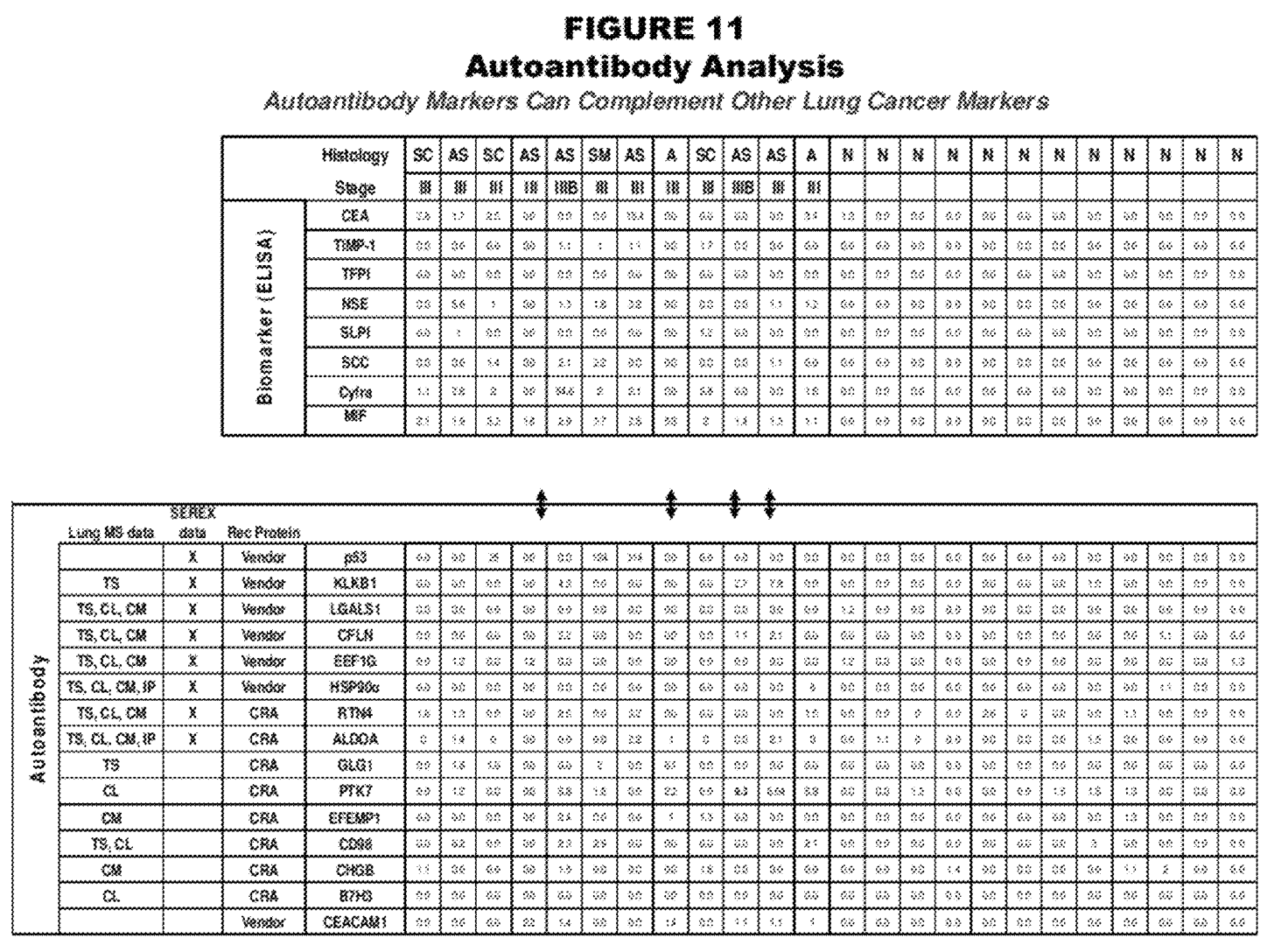

23) TFPI, CEA, TIMP-1, NSE, SLPI, SCC, Cyfra 21-1, and MIF, any or all of which can optionally be in combination with any or all of the following autoantibody markers: p53, KLKB1, LGALS1, CFLN, EEF1G, HSP90α, RTN4, ALDOA, GLG1, PTK7, EFEMP1, CD98, CHGB, B7H3, and CEACAM1 (see FIG. 11).

24) TFPI, SLPI, TFPI2, CEA, and TIMP1.

25) TFPI, SLPI, and TIMP1.

Figure 13C:
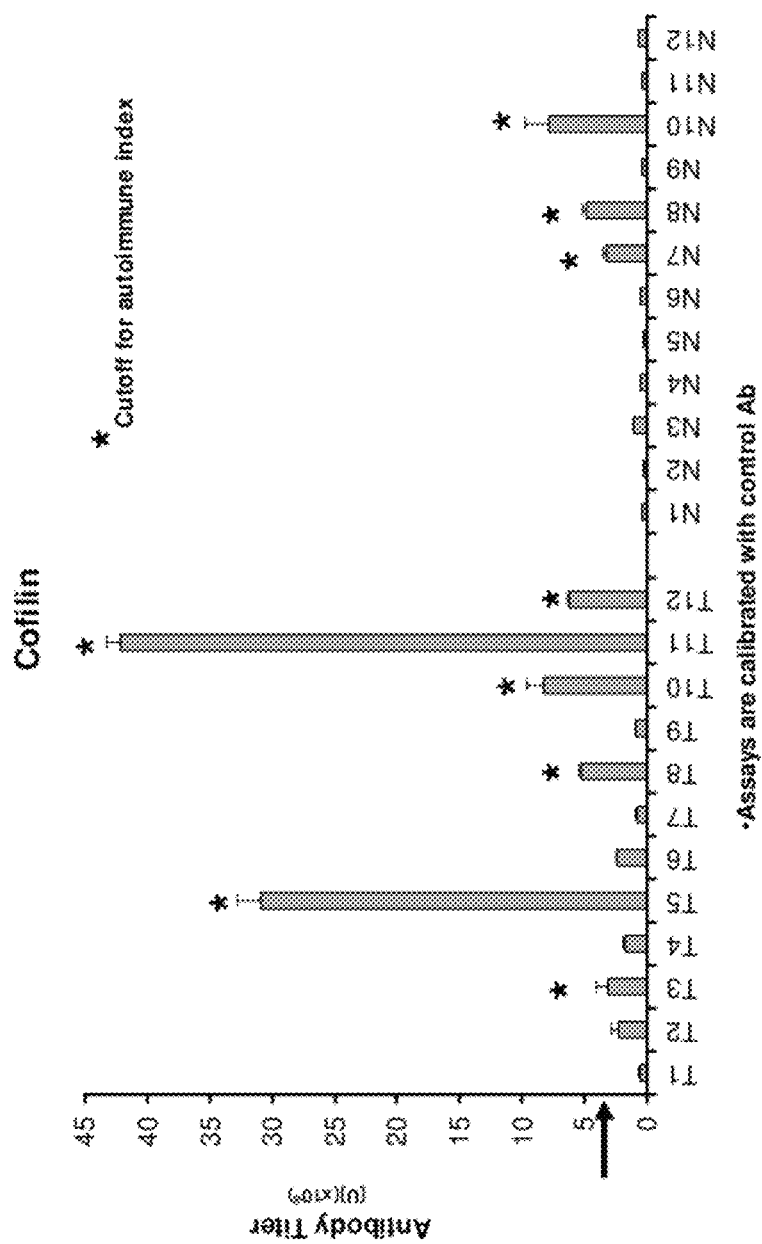
FIG. 13. Shows autoantibody responses observed in lung cancer and normal serum samples for the autoantibody markers KLKB1, cofilin, and LGALS1, as well as p53. Along the horizontal axis, T1 through T12 indicate tumor samples and N1 through N12 indicate normal samples.
Figure 18:
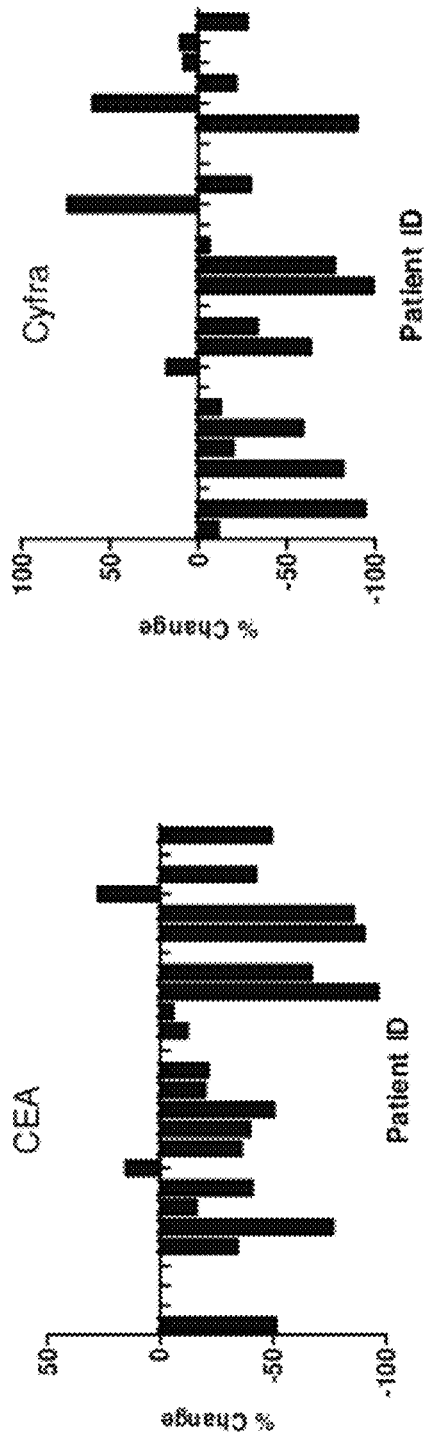
FIG. 18. Describes the analysis of markers to monitor lung tumor regression/recurrence, with CEA and Cyfra as examples. In particular, levels of biomarkers in patient serum 2-4 weeks following surgery were compared to pre-surgical marker levels.

26) KLKB1 and cofilin (CFLN) (see FIG. 13).

27) KLKB1, cofilin (CFLN), and CA12 (see FIG. 14).

28) TFPI, either alone or in combination with one or more other markers, which may optionally be selected from the group consisting of the markers shown in Tables 1-2 (SEQ ID NOS:1-65 and the carbohydrate antigens CA 242, CA 19-9, and CA 72-4), Table 4, FIG. 1, and FIG. 12.

29) One or more markers selected from the group consisting of defensin (DEFA1, HNP-1), ICAM3, CTGF, LCN2, biglycan, and HGF, either alone or in combination with one or more other markers, which may optionally be selected from the group consisting of the markers shown in Tables 1-2 (SEQ ID NOS:1-65 and the carbohydrate antigens CA 242, CA 19-9, and CA 72-4), Table 4, FIG. 1, and FIG. 12.

30) Two or more markers selected from the group consisting of TFPI, defensin, ICAM3, CTGF, LCN2, biglycan, and HGF, either alone or in combination with one or more other markers, which may optionally be selected from the group consisting of the markers shown in Tables 1-2 (SEQ ID NOS:1-65 and the carbohydrate antigens CA 242, CA 19-9, and CA 72-4), Table 4, FIG. 1, and FIG. 12.

31) One or more markers shown in Table 1 (SEQ ID NOS: 1-38 and 56-65 and the carbohydrate antigens CA 242, CA 19-9, and CA 72-4) and/or FIG. 1, in combination with one or more autoantibody markers shown in Table 2 (SEQ ID NOS:39-55) and/or FIG. 12.

32) Any of the 11-marker panels provided in Table 3 (each row of Table 3 represents a different 11-marker panel).

33) SLPI, TIMP1, TFPI, SCC, OPN, CEA, and CA242, which may optionally be in combination with GRP and/or MIF (see Table 3).

34) SLPI, TIMP1, TFPI, SCC, OPN, CEA, and CA242, which may optionally be in combination with GRP and/ or MIF, and which may optionally further be in combination with HNP-1 and/or NSE (see Table 3).

35) SLPI, TIMP1, TFPI, SCC, OPN, CEA, and CA242, which may optionally be in combination with any or all of GRP, MIF, HNP-1, and NSE, and which may optionally further be in combination with any or all of CAIX, Ca19-9, Ca72-4, MMP2, Cyfra 21-1, and AMBP (see Table 3).

36) SLPI, TIMP1, TFPI, SCC, OPN, CEA, and CA242, which may optionally be in combination with any or all of GRP, MIF, HNP-1, NSE, and Cyfra 21-1.

37) One or more markers selected from the group consisting of visfatin, sortilin, and midkine, either alone or in combination with one or more other markers, which may optionally be selected from the group consisting of the markers shown in Tables 1-2 (SEQ ID NOS:1-65 and the carbohydrate antigens CA 242, CA 19-9, and CA 72-4), Table 4, FIG. 1, and FIG. 12.

Exemplary Uses of LCM

Certain exemplary embodiments of the invention relate to methods of detecting the presence of lung cancer in an individual by measuring the amounts of circulating LCM, such as in serum, by immunological methods or other methods. These LCM are, for example, differentially expressed (over- or under-expressed) in individuals with lung cancer as compared to individuals without lung cancer (individuals without lung cancer are interchangeably referred to herein as "normal", "control", or "healthy" individuals). Detection of variation from a "normal" expression level, or differential expression, can be used for, for example, early diagnosis of lung cancer, distinguishing between a benign and malignant lung lesion (such as a lesion observed on a CT scan), monitoring lung cancer recurrence, or other clinical indications.

LCM may be used in a variety of clinical indications for lung cancer, including, but not limited to, detection of lung cancer (such as in a high-risk individual or population), characterizing lung cancer (e.g., determining lung cancer type, sub-type, or stage) such as distinguishing between non-small cell lung cancer (NSCLC) and small cell lung cancer (SCLC) and/or between adenocarcinoma and squamous cell carcinoma (or otherwise facilitating histopathology), determining whether a lung lesion is a benign lesion or a malignant lung tumor, lung cancer prognosis, monitoring lung cancer progression or remission, monitoring for lung cancer recurrence, monitoring metastasis, treatment selection, monitoring response to a therapeutic agent or other treatment, stratification of patients for computed tomography (CT) screening (e.g., identifying those patients at greater risk of lung cancer and thereby most likely to benefit from spiral-CT screening, thus increasing the positive predictive value of CT), combining LCM testing with supplemental biomedical parameters such as smoking history, etc., or with nodule size, morphology, etc. (such as to provide an assay with increased diagnostic performance compared to CT testing or LCM testing alone), facilitating the diagnosis of a pulmonary nodule as malignant or benign, facilitating clinical decision making once a lung cancer lesion is observed on CT (e.g., ordering repeat CT scans if the lesion is deemed to be low risk, such as if an LCM-based test is negative, with or without categorization of lesion size, or considering biopsy if the lesion is deemed medium to high risk, such as if an LCM-based test is positive, with or without categorization of lesion size), and facilitating decisions regarding clinical follow-up (e.g., whether to implement repeat CT scans, fine needle biopsy, or thoracotomy after observing a non-calcified lesion on CT). LCM testing may improve positive predictive value (PPV) over CT screening alone. In addition to their utilities in conjunction with CT screening, LCM can also be used in conjunction with any other imaging modalities used for lung cancer, such as chest X-ray. Furthermore, LCM may also be useful for enabling certain of these uses to be achieved before indications of lung cancer are detected by imaging modalities or other clinical correlates, or before symptoms appear.

As examples of how LCM may be useful for diagnosing lung cancer, a high or low abundance level (i.e., a "differential" abundance level) of one or more LCM in an individual who is not known to have lung cancer may indicate that the individual has lung cancer, thereby enabling early detection of lung cancer at an early stage of the disease when treatment is most effective, perhaps before the lung cancer is detected by other means or before symptoms appear. An increase in the abundance of one or more LCM during the course of lung cancer may be indicative of lung cancer progression, e.g., a lung tumor is growing and/or metastasizing (and thus a poor prognosis), whereas a decrease in the abundance of one or more LCM may be indicative of lung cancer remission, e.g., a lung tumor is shrinking (and thus a good prognosis). Similarly, an increase in the abundance of one or more LCM during the course of lung cancer treatment may indicate that the lung cancer is progressing and therefore indicate that the treatment is ineffective, whereas a decrease in the abundance of one or more LCM during the course of lung cancer treatment may be indicative of lung cancer remission and therefore indicate that the treatment is working successfully. Additionally, an increase or decrease in the abundance of one or more LCM after an individual has apparently been cured of lung cancer may be indicative of lung cancer recurrence. In a situation such as this, for example, the individual can be re-started on therapy (or the therapeutic regimen modified such as to increase dosage amount and/or frequency, if the patient has maintained therapy) at an earlier stage than if the recurrence of lung cancer was not detected until later. Furthermore, a differential abundance level of one or more LCM in an individual may be predictive of the individual's response to a particular therapeutic agent. In monitoring for lung cancer recurrence or progression, changes in LCM levels may indicate the need for repeat imaging (e.g., repeat CT scanning), such as to determine lung cancer activity, or the need for changes in treatment.

Detection of LCM may be particularly useful following, or in conjunction with, lung cancer treatment, such as to evaluate the success of the treatment or to monitor lung cancer remission, recurrence, and/or progression (including metastasis) following treatment. Lung cancer treatment may include, for example, administration of a therapeutic agent to a patient, surgery (e.g., surgical resection of at least a portion of a lung tumor), radiation therapy, or any other type of lung cancer treatment used in the art, and any combination of these treatments. For example, LCM may be detected at least once after treatment or may be detected multiple times after treatment (such as at periodic intervals), or may be detected both before and after treatment. A differential abundance level of LCM, such as an increase or decrease in the abundance level of LCM after treatment compared with the abundance level of LCM before treatment, or an increase or decrease in the abundance level of LCM at a later time point after treatment compared with the abundance level of LCM at an earlier time point after treatment, or a differential abundance level of LCM at a single time point after treatment compared with normal levels of LCM, may be indicative of lung cancer progression, remission, or recurrence.

As a specific example, ELISA analysis of LCM levels in pre-surgery and post-surgery (e.g., 2-4 weeks after surgery) serum samples can be carried out. An increase in the level of LCM in the post-surgery sample compared with the pre-surgery sample can indicate progression of lung cancer (e.g., unsuccessful surgery), whereas a decrease in the level of LCM in the post-surgery sample compared with the pre-surgery sample can indicate regression of lung cancer (e.g., the surgery successfully removed the lung tumor). Similar analyses of LCM levels can be carried out before and after other forms of treatment, such as before and after radiation therapy or administration of a therapeutic agent or cancer vaccine.

In addition to the utilities of testing LCM levels as stand-alone screening tests, testing of LCM levels can also be done in conjunction with CT screening. For example, LCM may facilitate the medical and economic justification for implementing CT screening, such as to screen large asymptomatic populations at risk for lung cancer (e.g., smokers). For example, a "pre-CT" test of LCM levels could be used to stratify high-risk individuals for CT screening, such as to identify those who are at highest risk for lung cancer based on their LCM levels and who should be prioritized for CT screening. If a CT test is implemented, LCM levels (e.g., as determined by immunoassay of serum samples) of one or more LCM can be measured and the scores added to scores for supplemental biomedical parameters (e.g., tumor parameters determined by CT testing) to create a combined score, such as to enhance positive predictive value (PPV) over CT or LCM testing alone. A "post-CT" immunoassay panel for determining LCM levels can be used to determine the likelihood that a pulmonary lesion observed by CT (or other imaging modality) is malignant or benign.

Detection of LCM may be useful for post-CT testing. For example, LCM testing may eliminate a significant number of false positive tests over CT alone. Further, LCM testing may facilitate treatment of patients. As an example, if a lung tumor is less than 5 mm in size, results of LCM testing may move patients from "watch and wait" to biopsy at an earlier time, if a lung tumor is 5-9 mm, LCM testing may eliminate biopsy or thoracotomy on false positive scans, and if a lung tumor is larger than 10 mm, LCM testing may eliminate surgery for sub-population of these patients with benign lesions. Eliminating the need for biopsy in some patients based on LCM testing would be beneficial because there is significant morbidity associated with nodule biopsy and difficulty in obtaining nodule tissue depending on location of nodule. Similarly, eliminating the need for surgery in some patients, such as those whose lesions are actually benign, would avoid unnecessary risks and costs associated with surgery.

In addition to testing LCM levels in conjunction with CT screening (e.g., assessing LCM levels in conjunction with size or other characteristics of a lung nodule observed on a CT scan), information regarding LCM can also be evaluated in conjunction with other types of data, particularly data that indicates an individual's risk for lung cancer (e.g., patient clinical history, symptoms, family history of cancer, risk factors such as whether or not the individual is a smoker, and/or status of other biomarkers, etc.). These various data can be assessed by automated methods, such as a computer program/software, which can be embodied in a computer or other apparatus/device.

The various methods described herein, such as correlating the level of LCM in an individual with an altered (e.g., increased or decreased) risk (or no altered risk) for lung cancer, can be carried out by automated methods such as by using a computer (or other apparatus/devices such as biomedical devices, laboratory instrumentation, or other apparatus/devices having a computer processor) programmed to carry out any of the methods described herein. For example, computer software (which may be interchangeably referred to herein as a computer program) can perform the step of correlating the level of LCM in an individual with an altered (e.g., increased or decreased) risk (or no altered risk) of lung cancer for the individual. Accordingly, certain embodiments of the invention provide a computer (or other apparatus/device) programmed to carry out any of the methods described herein.

LCM may also be used in imaging tests. For example, an imaging agent can be coupled to an LCM, which can be used to aid in lung cancer diagnosis, to monitor disease progression/remission or metastasis, to monitor for disease recurrence, or to monitor response to therapy, among other uses.

LCM can be detected using a variety of platforms. For example, LCM may be detected using singleplex ELISAs, ultrasensitive detection technologies, multiplex formats, and/or automated immuno analyzers.

In addition to detecting LCM in serum, LCM may also be detected in, for example, plasma and bronchial lavage.

LCM may be used for pharmacoproteomic or pharmacogenomic applications; for example, detection of LCM may be used for treatment selection or stratification. Differential expression of LCM in, for example, tumor cells that are resistant to a treatment (e.g., a particular therapeutic agent) and tumor cells that are sensitive to a treatment can be used to predict resistance or sensitivity of an individual's lung cancer to the treatment. As specific examples, CTGF is secreted at elevated levels by cell lines that are resistant to the chemotherapeutic agent Topotecan. In contrast, TIMP1, TFPI, and TIMP2 are secreted at elevated levels by cell lines that are sensitive to the chemotherapeutic agent Iressa. LCM may also be used as treatment response markers for a particular therapeutic agent. For example, certain LCM may be used as surrogate markers of cisplatin or Iressa treatment response.

Thus, the LCM profile of an individual having lung cancer can be used to determine which treatment(s) are best suited for that particular individual. For example, treatments to which an individual's lung cancer is predicted to be sensitive can be selected for the individual rather than treatments to which the individual's lung cancer is predicted to be resistant. As a further example, LCM levels can be used by a medical practitioner to distinguish between types of lung cancer (e.g., non-small cell lung cancer (NSCLC) versus small cell lung cancer (SCLC), adenocarcinoma versus squamous cell carcinoma, different stages of lung cancer, or other lung cancer characteristics) in order to adjust therapy options (e.g., to select a particular therapeutic agent or a particular form of treatment, such as chemotherapy, surgery, or radiation therapy, that is best suited for that particular subtype of lung cancer).

Tables 5-6 and 11-12 provide panels that are particularly well-suited for diagnosing/detecting lung cancer, among other lung cancer-related uses. For example, Tables 5 and 6 provides LCM panels that are particularly well-suited for distinguishing lung tumor samples versus normal (i.e., control/healthy) samples, Table 11 provides LCM panels that are particularly well-suited for distinguishing SCLC versus normal samples, Table 12 provides LCM panels that are particularly well-suited for distinguishing lung cancer (including both SCLC and NSCLC) versus normal samples.

Any of the LCM and the various exemplary LCM panels disclosed herein (such as any of the panels provided in Tables 5-6, such as the 9-marker panel or the 6-marker subset of this 9-marker panel, as well as any LCM provided in Tables 1-2 (SEQ ID NOS:1-65 and the carbohydrate antigens CA 242, CA 19-9, and CA 72-4), Table 4, FIG. 1, and FIG. 12, and any panels that include one or more of these LCM, particularly panels that include one or more markers provided in Table 4) may be used for any of the various lung cancer-related uses disclosed herein. However, certain LCM panels are particularly well-suited for certain specific lung cancer-related uses ("indications"); these specific uses may be referred to herein as determining or assessing various "characteristics" of lung cancer. Examples of such LCM panels that are particularly well-suited for certain specific lung cancer-related uses are provided in Tables 7-10 and FIG. 19. For example, Table 7 provides LCM panels that are particularly well-suited for distinguishing adenocarcinoma versus squamous cell carcinoma types of lung cancer, Table 8 provides LCM panels that are particularly well-suited for distinguishing between different stages of lung cancer (such as between early-stage and late-stage lung cancer such as stage I versus stage III lung cancer, or between any other of stages I, II, III, and IV) such as to determine the stage of lung cancer in a patient, Table 9 provides LCM panels that are particularly well-suited for distinguishing SCLC versus other types of lung cancer (e.g., NSCLC), Table 10 provides LCM panels that are particularly well-suited for distinguishing malignant lung tumors versus benign lung lesions, and FIG. 19 provides LCM that are particularly well-suited for monitoring for lung tumor regression and/or recurrence.

Tables 5-12 provide a variety of exemplary LCM panels, together with performance characterisitics for each panel (AUC, sensitivity, and specificity). In certain embodiments, LCM panels are provided that have at least 70% sensitivity at 95% specificity, or at least 70% specificity at 95% sensitivity. In certain embodiments, LCM panels are provided that have at least 85% sensitivity at 95% specificity, or at least 85% specificity at 95% sensitivity. In further embodiments, LCM panels are provided that have at least 90% sensitivity or at least 90% specificity, or that have at least 95% sensitivity or at least 95% specificity. In yet further embodiments, LCM panels are provided that have at least 70, 75, 80, 85, 90, 91, 92, 93, 94, 95, 96, 97, 98, or 99% (or any other percentage in-between) sensitivity and 70, 75, 80, 85, 90, 91, 92, 93, 94, 95, 96, 97, 98, or 99% (or any other percentage in-between) specificity. In yet further embodiments, LCM panels are provided that have at least 0.7, 0.75, 0.8, 0.85, 0.9, 0.91, 0.92, 0.93, 0.94, 0.95, 0.96, 0.97, 0.98, or 0.99 (or any other value in-between) AUC values. Any of these panels are particularly useful for lung-cancer related uses such as those described herein (e.g., diagnosing lung cancer), such as in clinical practice. However, the desired performance for clinical use of an assay may vary depending on such factors as the particular use, point of implementation, or other factors.

Distinguishing NSCLC and SCLC

The following panels of LCM are particularly useful for distinguishing (which may be interchangeably referred to as "resolving") non-small cell lung carcinoma (NSCLC) and small cell lung carcinoma (SCLC) from each other and/or from normal (i.e., control/healthy) samples. These panels may consist of, consist essentially of, or comprise the following combinations of markers:

1) Any of the panels provided in Table 9, particularly for distinguishing NSCLC versus SCLC.
2) Any of the panels provided in Table 11, particularly for distinguishing SCLC versus normal samples.
3) Any of the panels provided in Table 12, particularly for distinguishing SCLC and NSCLC versus normal samples.
4) OPN (either alone or in combination with one or more other markers), particularly for distinguishing NSCLC from SCLC and for distinguishing SCLC from NSCLC.
5) SCC, OPN, AMBP, and Ca72-4, particularly for distinguishing NSCLC from SCLC (levels of these LCM are higher in NSCLC as compared to SCLC).
6) ENO2, MMP2, Ca19-9, CAIX, and GRP, particularly for distinguishing SCLC from NSCLC (levels of these LCM are higher in SCLC as compared to NSCLC).
7) Cyfra, SLPI, TIMP1, TFPI, CEACAM5, MMP2, and CA242, particularly for distinguishing SCLC from normal samples (particularly by using split-point analysis).
8) SLPI, TIMP1, TFPI, CEACAM5, MMP2, OPN, and CA242, particularly for distinguishing SCLC from normal samples (particularly by using split-point analysis).
9) Cyfra, TIMP1, ENO2, TFPI, CEACAM5, MMP2, OPN, and DEFA1, particularly for distinguishing NSCLC and SCLC from normal samples (particularly by using split-point analysis).
10) Cyfra, MIF, TIMP1, SCC, TFPI, CEACAM5, OPN, and DEFA1, particularly for distinguishing NSCLC and SCLC from normal samples (particularly by using split-point analysis).
11) TIMP1, ENO2, TFPI, CEACAM5, MMP2, OPN, AMBP, and DEFA1, particularly for distinguishing NSCLC and SCLC from normal samples (particularly by using split-point analysis).

Supplemental Biomedical Parameters

The term "supplemental biomedical parameters" refers to one or more assessments of an individual, other than LCM, that are associated with lung cancer risk. "Supplemental biomedical parameters" include, but are not limited to, physical descriptors of a patient, physical descriptors of a pulmonary nodule observed by CT imaging, the height and/or weight of a patient, the gender of a patient, smoking history, occupational history, exposure to carcinogens, exposure to secondhand smoke, family history of lung cancer (or other cancer), the presence of pulmonary nodules, size of nodules, location of nodules, morphology of nodules (e.g., nodules may be observed by CT imaging), etc. Smoking history is usually quantified in terms of "pack years", which refers to the number of years a person has smoked multiplied by the average number of packs smoked per day. For example, a person who has smoked, on average, one pack of cigarettes per day for 35 years is referred to as having 35 pack years of smoking history. Supplemental biomedical parameters can be obtained from an individual using routine techniques known in the art, such as from the individual themselves by use of a routine patient questionnaire or health history questionnaire, etc., or from a medical practitioner, etc. Alternately, supplemental biomedical parameters can be obtained from routine imaging techniques including CT imaging (e.g., low-dose CT imaging) and X-ray.

Testing of LCM in combination with an assessment of supplemental biomedical parameters may, for example, improve sensitivity, specificity, and/or AUC for detecting lung cancer (or other lung cancer-related uses) as compared to LCM testing alone or assessing supplemental biomedical parameters alone (e.g., CT imaging alone).

Accordingly, any of the LCM, and panels of LCM, can be used in combination with supplemental biomedical parameters. Furthermore, supplemental biomedical parameters may serve to replace one or more markers of a panel, such as to enable the use of smaller panels (i.e., panels with fewer biomarkers) while retaining similar performance (e.g., sensitivity, specificity, and/or AUC for detecting lung cancer). Thus, supplemental biomedical parameters can be used in addition to a panel, or in addition to one or more markers of a panel, or as a substitute for one or more markers of a panel. As a specific example, one or more supplemental biomedical parameters can be used in addition to the 9-marker panel of Cyfra, SLPI, TIMP1, SCC, TFPI, CEACAM5, MMP2, OPN, and MDK or the 6-marker subset of this 9-marker panel (Cyfra, SLPI, TIMP1, TFPI, CEACAM5, and MDK). As another specific example, one or more supplemental biomedical parameters can replace one or more members of the 9-marker panel of Cyfra, SLPI, TIMP1, SCC, TFPI, CEACAM5, MMP2, OPN, and MDK or the 6-marker subset of this 9-marker panel (Cyfra, SLPI, TIMP1, TFPI, CEACAM5, and MDK). Furthermore, one or more supplemental biomedical parameters can be used in addition to any of the panels provided in Table 5 and/or can replace one or more members of any of the panels provided in Table 5. Moreover, one or more supplemental biomedical parameters can be used in addition to any of the markers or panels provided herein and/or can replace one or more members of any of the panels provided herein, including the markers provided in Tables 1-2 (SEQ ID NOS:1-65 and the carbohydrate antigens CA 242, CA 19-9, and CA 72-4), Table 4, FIGS. 1, 12, and 19, and the panels provided in Tables 3 and 6-12. Furthermore, supplemental biomedical parameters can be incorporated into algorithms and scoring systems/classifiers, together with biomarker assessments (e.g., biomarker levels), for assessing lung cancer (e.g., diagnosing lung cancer).

Examples of supplemental biomedical parameters include, but are not limited to, any of the following. Any or all of these supplemental biomedical parameters can be used, in any combination, with any of the LCM and LCM panels disclosed herein. For example, any of the LCM and LCM panels disclosed herein can be assessed alone (without considering supplemental biomedical parameters) or can be assessed in combination with CT results (for example), or can be assessed in combination with any other supplemental biomedical parameters, or can be assessed in combination with CT results plus any other supplemental biomedical parameters, or any other combination of supplemental biomedical parameters can be assessed in combination with any of the LCM and LCM panels disclosed herein. Any of these supplemental biomedical parameters can be assessed as part of an algorithm or scoring system/classifier, together with biomarker assessments (e.g., biomarker levels), such as for assessing lung cancer (e.g., diagnosing lung cancer).

1) age, gender, and/or ethnicity;
2) family history of lung cancer or other type of cancer;
3) smoking history (e.g., whether or not an individual previously and/or currently smokes);
4) smoking level (e.g., "pack year": number of cigarettes smoked per day multiplied by number of years of smoking at this rate);
5) size of lesion;
6) location of lesion;
7) lesion morphology (ground glass opacity (GGO), solid, non-solid);
8) edge characteristics of lesion (smooth, lobulated, sharp and smooth, spiculated, infiltrating);
9) any other parameters determined from computed tomography (CT) screening;
10) exposure to second-hand smoke; and
10) any known carcinogen exposure (including, but not limited to, exposure to any of asbestos, radon gas, chemicals, smoke from fires, and air pollution, which can include emissions from stationary or mobile sources such as industrial/factory or auto/marine/aircraft emissions).

Exemplary methods of combining LCM with supplemental biomedical parameters can comprise the steps of obtaining a value for at least one supplemental biomedical parameter (e.g., smoking history) from an individual, comparing the value of each of the supplemental biomedical parameter(s) to one or more predetermined cutoffs, assigning a score for each supplemental biomedical parameter based on said comparison, combining the assigned score for each supplemental biomedical parameter with the assigned score for each LCM to obtain a total score for said individual, comparing the total score with a predetermined total score cutoff, and classifying said individual as having or not having lung cancer (or the likelihood thereof) based on whether the individual's total score is above or below (or equal to) the predetermined total score cutoff. In certain embodiments, if the individual's total score is above (or equal to) the predetermined total score cutoff, then the individual is classified as having lung cancer.

Further exemplary methods can comprise the steps of:
a) obtaining a value for at least one supplemental biomedical parameter of an individual;
b) comparing the value of each supplemental biomedical parameter against one or more predetermined cutoffs and assigning a score for each supplemental biomedical parameter based on said comparison;
c) quantifying in a test sample obtained from the individual, the levels of one or more LCM or LCM panels (e.g., the 9-marker panel of Cyfra, SLPI, TIMP1, SCC, TFPI, CEACAM5, MMP2, OPN, and MDK, or the 6-marker subset of Cyfra, SLPI, TIMP1, TFPI, CEACAM5, and MDK);
d) comparing the amount of each LCM quantified to a predetermined cutoff and assigning a score for each LCM based on said comparison;
e) combining the assigned score for each supplemental biomedical parameter determined in step b with the assigned score for each LCM determined in step d to obtain a total score for said individual;
f) comparing the total score determined in step e with a predetermined total score cutoff; and
g) classifying the individual (or the test sample from the individual) as having or not having lung cancer (or the likelihood thereof) based on whether the individual's total score is above or below (or equal to) the predetermined total score cutoff (in certain embodiments, if the individual's total score is above (or equal to) the predetermined total score cutoff, then the individual is classified as having lung cancer).

In the above exemplary methods, the supplemental biomedical parameter obtained from the individual can be, for example, the individual's smoking history, age, carcinogen exposure, gender, nodule size, nodule morphology, and/or nodule location (nodule characteristics, such as size, morphology, and/or location, may be determined by CT imaging, as well as X-ray or other imaging methods). Preferably, the supplemental biomedical parameter is related to nodule mophology.

Exemplary Scoring Systems and Cutoffs

A variety of methodologies can be used to classify a sample based on assaying one or more LCM disclosed herein. Classifying a sample can be based on a score derived from assessing one or more LCM disclosed herein, optionally in combination with one or more supplemental biomedical parameters (including, but not limited to, the supplemental biomedical parameters disclosed in the preceding section). A score or other classification system can be based on, for example, determining whether the level of one or more LCM is above or below a cutoff level (which may be referred to as a "cutoff value" or just "cutoff"), or is above or below a cutoff value by a certain amount (e.g., by a certain number of standard deviations such as two standard deviations), or the magnitude/extent of how high or low the level of one or more LCM is (which may optionally be in relation to a cutoff value). A wide variety of scoring systems and methodologies for establishing cutoff values are known in the art, and one of ordinary skill in the art would know how to implement a known scoring system or method of establishing cutoff values (or devise a new scoring system or method for establishing cutoff values) that is best suited for the intended use, such as assessing lung cancer based on one or more LCM or LCM panels (optionally in combination with one or more supplemental biomedical parameters). Accordingly, one of ordinary skill in the art could establish and adjust cutoff values to suit the intended use, and could incorporate these cutoff values into any desirable scoring system. For example, cutoff values can be adjusted based on whether increased sensitivity (for detecting tumor samples and avoiding false-negatives) or increased specificity (for avoiding false-positives) is considered more important. For example, cutoffs can be selected such as to achieve at least 70% sensitivity at 95% specificity, or at least 70% specificity at 95% sensitivity, or at least 85% sensitivity at 95% specificity, or at least 85% specificity at 95% sensitivity, or at least 90% or 95% sensitivity, or at least 90% or 95% specificity, or any other desired sensitivity and/or specificity (such as the sensitivity and specificity values described above). As another example, cutoffs can be set lower while requiring more markers in a panel to be above the cutoff levels in order to classify a sample as a tumor sample, or cutoffs can be set higher while requiring fewer markers in a panel to be above the cutoff levels in order to classify a sample as a tumor sample. When a cutoff value is set and applied to testing, it may be interchangeably referred to herein as a "predetermined" or "established" cutoff value. Furthermore, various analysis methods can be applied, including, but not limited to, split-point analysis (such as for setting discrete cutoffs), logistic regression analysis (such as for factoring in the magnitude/extent by which a marker level is elevated or low), Naïve Bayes, multivariate analysis, decision tree modeling, etc.

A representative example is shown in FIG. 17 for the 9-marker panel of Cyfra, SLPI, TIMP1, SCC, TFPI, CEACAM5, MMP2, OPN, and MDK. In FIG. 17, exemplary cutoffs for each of these 9-markers are shown just below each marker symbol, as follows (levels/concentrations, in ng/ml, were determined by ELISA): Cyfra=1.20 ng/ml, CEA=5.00 ng/ml, SLPI=52 ng/ml, OPN=32 ng/ml, MDK=0.15 ng/ml, TFPI=150 ng/ml, TIMP1=385 ng/ml, MMP2=210 ng/ml, and SCC=2.2 ng/ml. These cutoff values were established by examining the levels of these markers in both normal (control) samples and lung tumor samples in the 50×50 sample set and determining appropriate cutoff values that would best distinguish lung tumor versus normal samples (e.g., cutoff values were selected for which the levels of a majority of lung tumor samples are above and the levels of a majority of normal samples are below, so as to maximize sensitivity and specificity). These cutoffs were then applied to the same 50×50 sample set (i.e., the 50×50 sample set was used for both training and testing in this example). In this example, if the levels of two or more of the nine markers was greater than or equal to the established cutoff value for each marker, then the sample was classified as a lung tumor sample (thus, if the levels of none, or only one, of the nine markers was greater than or equal to the established cutoff value for each marker, then the sample was classified as a normal sample). Using this exemplary scoring system in this exemplary sample set, 48 out of 50 tumor samples were correctly classified, whereas the $42^{nd}$ and $43^{rd}$-listed samples were mis-classified as not being tumor samples since the level of only one of the nine markers (rather than the minimum of two or more) in each of these two sample sets was greater than or equal to the cutoff level (96% sensitivity; right-side of FIG. 17). Similarly, using this exemplary scoring system in this exemplary sample set, 49 out of 50 normal (control) samples were correctly classified, whereas the $2^{nd}$-listed sample was mis-classified as being a tumor sample since the levels of three of the nine markers (which meets the minimum of two or more) in this sample set were greater than or equal to the cutoff levels (98% specificity; left-side of FIG. 17). However, one of skill in the art would appreciate that no assay would be expected to correctly classify every single sample; rather, some misclassification is expected in the art. The goal is generally to minimize, rather than eliminate, misclassifications. Further, an assay (such as an assay of LCM levels) can be combined with other types of tests (such as CT screening) to further minimize misclassifications.

In other exemplary scoring systems, if the levels of one or more, three of more, four or more, five of more, six or more, seven or more, eight or more, or all nine markers of the 9-marker panel of Cyfra, SLPI, TIMP1, SCC, TFPI, CEACAM5, MMP2, OPN, and MDK are greater than or equal to the established cutoff value for each marker, then the sample can be classified as a lung tumor sample. In certain exemplary scoring systems, if the level of a marker is greater than or equal to the established cutoff value for that marker, it can be assigned a value of one (for example) and if the level of a marker is below the established cutoff value for that marker, it can be assigned a value of zero (for example). However, any desired values can be assigned to the various outcomes. Furthermore, these values can be added together (or otherwise combined) to determine a total score for a sample, and a classification of the sample as a tumor or normal sample (for example) can be assigned based on this total score. For example, in the example described above and depicted in FIG. 17, a score of two or greater can be used to classify a sample as a tumor sample (and a score below two could be used to classify a sample as a normal sample) if the level of each marker that is greater than or equal to its established cutoff value is assigned a value of one. Any other scoring system can be used, and one of ordinary skill in the art would know how to select or devise a scoring system best suited for the intended use.

A scoring system and cutoff values such as those exemplified in FIG. 17, or any other desirable scoring system and cutoff values, can be applied to any of the other LCM and LCM panels disclosed herein, such as the 6-marker subset of the 9-marker panel (Cyfra, SLPI, TIMP1, TFPI, CEACAM5, and MDK) and any of the other panels provided in Table 5, and can optionally incorporate any supplemental biomedical parameters. For example, any supplemental biomedical parameters can be assigned a value in a scoring system (e.g., a history of smoking can be assigned a value of one or other value, and no smoking history can be assigned a value of zero, negative one, or other value), and such values can be combined with the values assigned to marker levels being above a predetermined cutoff level (for example), such as to generate a total score for classifying a sample as a lung tumor or normal sample. Furthermore, these various scoring systems and cutoff values can be applied to any of the lung cancer-related uses disclosed herein, including specific uses such as those disclosed in Tables 7-10.

Figure 21:
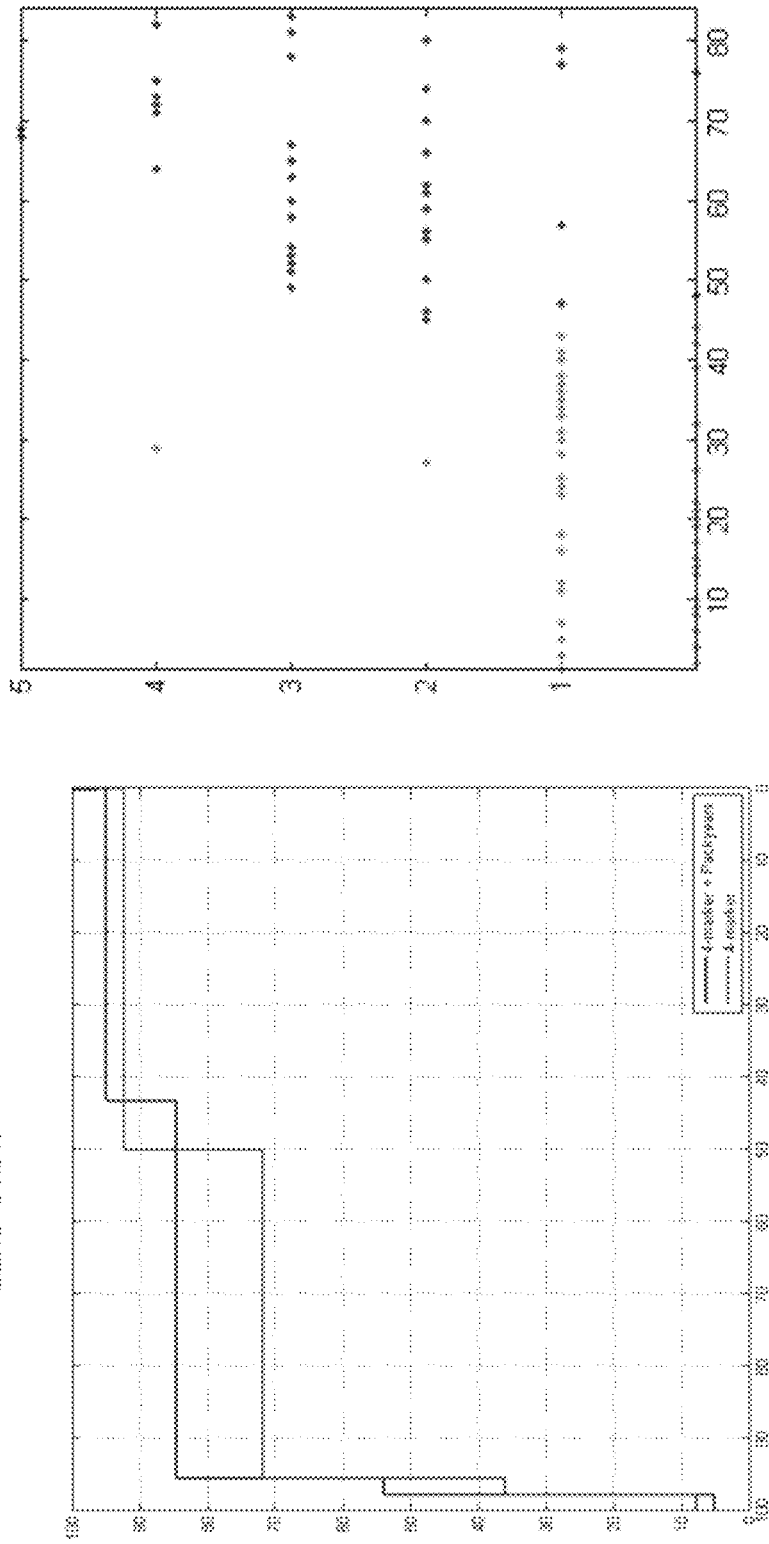
FIG. 21. Shows an analysis of integrating an exemplary supplemental biomedical parameter (smoking history) with an exemplary LCM panel (TIMP1, TFPI, CEACAM5, and Ca72-4) plus pack years ("pack year": number of cigarettes smoked per day multiplied by number of years of smoking at this rate). The left-side graph shows that performance of a 5-marker panel (represented by the line that includes a vertical portion at 50 of the x-axis) is enhanced with addition of smoking history (pack years) (represented by the line that includes a vertical portion at about 43 of the x-axis). Sensitivity increases from 71.5% to 84.6%. The right-side graph shows split-point analysis performed following the addition of smoking history (split at about 45 of the x-axis).

Any of the scoring systems disclosed herein or known in the art, or which may be devised by one of ordinary skill in the art, can be incorporated into a computer program, and such a computer program can be embodied on computer readable medium. For example, a computer program can generate a total score from a sample based on, for example, the number of markers in a panel for which the levels are above predetermined cutoff levels, together with parameters from CT screening (e.g., tumor volume/size, tumor morphology, tumor location, and/or other tumor characteristics, etc.) and/or other supplemental biomedical parameters (e.g., smoking history, age of the individual, etc.), and this total score can be used to classify a sample as a lung tumor or normal sample, for example. A single total score can be generated that represents the combination of multiple different types of assessments (e.g., a combination of LCM levels and supplemental biomedical parameters), or multiple individual scores can be generated for evaluation individually (e.g., a score based on assessment of LCM levels, and one or more separate scores based on supplemental biomedical parameters). An example of this type of integrated approach of combining LCM levels (using the exemplary panel of TIMP1, TFPI, CEACAM5, and Ca72-4) with a supplemental biomedical parameter (smoking history, as indicated by "pack years") is shown in FIG. 21.

Kits

Any combination of LCM and LCM panels (as well as supplemental biomedical parameters) can be provided in the form of kits, such as for use in performing the methods disclosed herein. Furthermore, any kit can contain one or more detectable labels (e.g., detachably labeled reagents such as antibodies), such as a fluorescent moiety, etc.

For example, a kit can comprise (a) reagents comprising at least one antibody for quantifying one or more LCM in a test sample, wherein said LCM comprise: Cyfra, SLPI, TIMP1, SCC, TFPI, CEACAM5, MMP2, OPN, and MDK (or just Cyfra, SLPI, TIMP1, TFPI, CEACAM5, and MDK; or any other LCM or LCM panels disclosed herein, such as the panels disclosed in Tables 5-12), and optionally (b) one or more algorithms or computer programs for performing the steps of comparing the amount of each LCM quantified in the test sample to one or more predetermined cutoffs and assigning a score for each LCM quantified based on said comparison, combining the assigned score for each LCM quantified to obtain a total score, comparing the total score with a predetermined total score, and using said comparison to determine whether an individual has lung cancer. Alternatively, rather than one or more algorithms or computer programs, one or more instructions for manually performing the above steps by a human can be provided.

In certain embodiments, a kit can contain: (a) reagents comprising at least one antibody for quantifying one or more LCM in a test sample, wherein said LCM are Cyfra, SLPI, TIMP1, SCC, TFPI, CEACAM5, MMP2, OPN, and MDK, and (b) reagents containing one or more LCM for quantifying at least one antibody in a test sample; wherein said antibodies are: TP53 (p53), KLKB1, CFL1 (CFLN), EEF1G, HSP90α (HSP90AA1), RTN4, ALDOA, GLG1, PTK7, EFEMP1, SLC3A2 (CD98), CHGB, CEACAM1, ALCAM, HSPB1 (HSP27), LGALS1, and B7H3, and optionally (c) one or more algorithms or computer programs for performing the steps of comparing the amount of each LCM and antibody quantified in the test sample to one or more predetermined cutoffs and assigning a score for each LCM and antibody quantified based on said comparison, combining the assigned score for each LCM and antibody quantified to obtain a total score, comparing the total score with a predetermined total score, and using said comparison to determine whether an individual has lung cancer. Alternatively, rather than one or more algorithms or computer programs, one or more instructions for manually performing the above steps by a human can be provided.

Translating LCM Assessments to Lung Cancer Assessments, and Systems Therefor

An assessment of LCM in an individual, such as LCM levels determined by assaying a serum sample (or other sample) from the individual, can be translated to an assessment of lung cancer for the individual. For example, the levels of multiple LCM (such as each of the LCM in the 9-marker panel of Cyfra, SLPI, TIMP1, SCC, TFPI, CEACAM5, MMP2, OPN, and MDK) can be translated to a score or other identifier that indicates whether an individual has lung cancer (or that indicates the likelihood that the individual has lung cancer), for example. Similarly, the score or other identifier may indicate a specific type of lung cancer assessment, such as the assessments of various lung cancer characteristics described herein, including (but not limited to), determination of whether an individual's lung cancer is adenocarcinoma or squamous cell carcinoma, determination of the stage of an individual's lung cancer (such as distinguishing between stage I and stage III lung cancer), determination of whether an individual's lung cancer is SCLC or NSCLC, determining whether a lung lesion identified in an individual (such as by CT screening) is a malignant tumor or a benign lesion, and determining lung tumor regression and/or recurrence. Any of these determinations may be expressed in a discrete (e.g., absolute) or continuous (e.g., likelihood) manner, for example.

Furthermore, the assessment of LCM in an individual, such as LCM levels, can be translated to a tangible report. Thus, a score or other identifier that indicates the lung cancer assessment can be provided in the form of a tangible report.

Additionally, the translation, such as the translation of LCM levels to a lung cancer assessment (such as a score or other identifier), can be performed by a computer. Furthermore, certain embodiments provide computer readable medium having a computer program code embodied thereon for translating LCM levels to a lung cancer assessment.

In certain embodiments, the invention provides systems for assessing one or more LCM, particularly the levels of multiple LCM, and translating this LCM assessment to an assessment of lung cancer, such as a determination of whether an individual has (or is likely to have) lung cancer (which may be indicated by a score or other identifier). In certain embodiments, these systems include one or more computers to receive an LCM assessment, translate the LCM assessment to a lung cancer assessment, and output the lung cancer assessment (e.g., as a score or other identifier). These systems may optionally comprise multiple computers that communicate via the internet (or any other mode of communication used in the art for inter-computer communication).

Accordingly, certain embodiments of the invention provide methods of translating an assessment of LCM (e.g., LCM levels) to an assessment of lung cancer (e.g., a score or other indication of whether an individual has lung cancer, or their likelihood of having lung cancer, or other specific lung cancer assessment). In certain embodiments, this assessment of lung cancer is provided in the form of a tangible report. In certain embodiments, the translation is performed by a computer. Furthermore, certain embodiments of the invention provide computers programmed to translate an LCM assessment to a lung cancer assessment. Certain embodiments provide computer readable medium having a computer program code embodied thereon for translating LCM levels to a lung cancer assessment. In certain embodiments, a system is provided for receiving an LCM assessment, translating the LCM assessment to a lung cancer assessment, and outputting the lung cancer assessment (e.g., as a score or other identifier). In various embodiments, the system comprises one or more computers (which may optionally communicate via the internet or other mode of communication).

Reports, Transmission of Reports, and Programmed Computers

The results of a test (e.g., a diagnosis of lung cancer for an individual based on the level, or other assay, of one or more LCM disclosed herein, or assessment of tumor progression/regression/recurrence, lung cancer stage, type of lung cancer such as NSCLC versus SCLC or adenocarcinoma versus squamous cell carcinoma, malignant tumor versus benign lung lesion, etc.), and/or any other information pertaining to a test (e.g., the levels of one or more LCM disclosed herein in a sample from an individual, which may optionally be provided in the absence of explicit disease or diagnostic information), may be referred to herein as a "report". A tangible report can optionally be generated as part of a testing process (which may be interchangeably referred to herein as "reporting", or as "providing" a report, "producing" a report, or "generating" a report).

Examples of tangible reports may include, but are not limited to, reports in paper (such as computer-generated printouts of test results) or equivalent formats and reports stored on computer readable medium (such as a CD, USB flash drive or other removable storage device, computer hard drive, or computer network server, etc.). Reports, particularly those stored on computer readable medium, can be part of a database, which may optionally be accessible via the internet (such as a database of patient records or biomedical information stored on a computer network server, which may be a "secure database" that has security features that limit access to the report, such as to allow only the patient and the patient's medical practioners to view the report while preventing other unauthorized individuals from viewing the report, for example). In addition to, or as an alternative to, generating a tangible report, reports can also be displayed on a computer screen (or the display of another electronic device or instrument).

A report can further be "transmitted" or "communicated" (these terms may be used herein interchangeably), such as to the individual who was tested, a medical practitioner (e.g., a doctor, nurse, clinical laboratory practitioner, etc.), a healthcare organization, a clinical laboratory, and/or any other party or requester intended to view or possess the report. The act of "transmitting" or "communicating" a report can be by any means known in the art, based on the format of the report. Furthermore, "transmitting" or "communicating" a report can include delivering a report ("pushing") and/or retrieving ("pulling") a report. For example, reports can be transmitted/communicated by various means, including being physically transferred between parties (such as for reports in paper format) such as by being physically delivered from one party to another, or by being transmitted electronically or in signal form (e.g., via e-mail or over the internet, by facsimile, and/or by any wired or wireless communication methods known in the art) such as by being retrieved from a database stored on a computer network server, etc.

In certain exemplary embodiments, the invention provides computers (or other apparatus/devices such as biomedical devices or laboratory instrumentation) programmed to carry out the methods described herein. For example, in certain embodiments, the invention provides a computer programmed to receive (i.e., as input) the levels of one or more LCM disclosed herein and provide (i.e., as output) a lung cancer diagnosis or other result (e.g., assessment of tumor progression/regression/recurrence, lung cancer stage, type of lung cancer such as NSCLC versus SCLC or adenocarcinoma versus squamous cell carcinoma, malignant tumor versus benign lung lesion, etc.) based on the levels of one or more LCM. Such output (e.g., communication of lung cancer diagnosis, etc.) may be, for example, in the form of a report on computer readable medium, printed in paper form, and/or displayed on a computer screen or other display.

Further exemplary embodiments of the invention are described in greater detail below.

1. LCM Proteins

Exemplary embodiments of the invention provide LCM proteins that consist of, consist essentially of, or comprise the amino acid sequences of SEQ ID NOS:1-65 (additionally, carbohydrate antigens CA 242, CA 19-9, and CA 72-4 are also provided, which may also be encompassed by references herein to proteins/polypeptides), as well as all known variants and fragments of these proteins, and nucleic acid molecules that are within the art to make and use. Examples of such obvious variants include, but are not limited to, naturally-occurring allelic variants, pre-processed or mature processed forms of a protein, non-naturally occurring recombinantly-derived variants, orthologs, and paralogs. Such variants can readily be generated using art-known techniques in the fields of recombinant nucleic acid technology and protein biochemistry.

A protein is said to be "isolated" or "purified" when it is substantially free of cellular material or free of chemical precursors or other chemicals. LCM proteins can be purified to homogeneity or other degrees of purity. The level of purification can be based on the intended use. The primary consideration is that the preparation allows for the desired function of the protein, even if in the presence of considerable amounts of other components.

In some uses, "substantially free of cellular material" includes preparations of a protein having less than about 30% (by dry weight) other proteins (i.e., contaminating protein), less than about 20% other proteins, less than about 10% other proteins, or less than about 5% other proteins. When the protein is recombinantly produced, it can also be substantially free of culture medium, i.e., culture medium represents less than about 20% of the volume of the protein preparation.

The language "substantially free of chemical precursors or other chemicals" includes preparations of a protein in which the protein is separated from chemical precursors or other chemicals that are involved in the protein's synthesis. In one embodiment, the language "substantially free of chemical precursors or other chemicals" includes preparations of a LCM protein having less than about 30% (by dry weight) chemical precursors or other chemicals, less than about 20% chemical precursors or other chemicals, less than about 10% chemical precursors or other chemicals, or less than about 5% chemical precursors or other chemicals.

Isolated LCM proteins can be purified from cells that naturally express it, purified from cells that have been altered to express it (recombinant), or synthesized using known protein synthesis methods (e.g., Sambrook et al., Molecular Cloning: A Laboratory Manual. 3rd. ed., Cold Spring Harbor Laboratory Press, Cold Spring Harbor, N.Y., (2001)). For example, a nucleic acid molecule encoding a LCM protein can be cloned into an expression vector, the expression vector introduced into a host cell, and the protein expressed in the host cell. The protein can then be isolated from the cells by an appropriate purification scheme using standard protein purification techniques.

A LCM protein or fragment thereof can be attached to heterologous sequences to form chimeric or fusion proteins. Such chimeric and fusion proteins comprise a protein operatively linked to a heterologous protein having an amino acid sequence not substantially homologous to the protein.

"Operatively linked" indicates that the protein and the heterologous protein are fused in-frame. The heterologous protein can be fused to the N-terminus or C-terminus of the protein.

In some uses, the fusion protein does not affect the activity of the protein per se. For example, the fusion protein can include, but is not limited to, beta-galactosidase fusions, yeast two-hybrid GAL fusions, poly-His fusions, MYC-tagged, HI-tagged, and Ig fusions. Such fusion proteins, particularly poly-His fusions, can facilitate the purification of recombinant LCM proteins. In certain host cells (e.g., mammalian host cells), expression and/or secretion of a protein can be increased by using a heterologous signal sequence.

A chimeric or fusion LCM protein can be produced by standard recombinant DNA techniques. For example, DNA fragments coding for different protein sequences can be ligated together in-frame in accordance with conventional techniques. In another embodiment, a fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and re-amplified to generate a chimeric gene sequence (Ausubel et al., Current Protocols in Molecular Biology, 1992-2006). Moreover, many expression vectors are commercially available that already encode a fusion moiety (e.g., a GST protein). A LCM-encoding nucleic acid can be cloned into such an expression vector such that the fusion moiety is linked in-frame to the LCM protein.

To determine the percent identity of two amino acid sequences or two nucleic acid sequences, the sequences can be aligned for optimal comparison purposes (e.g., gaps can be introduced in one or both of a first and a second amino acid or nucleic acid sequence for optimal alignment and non-homologous sequences can be disregarded for comparison purposes). In an exemplary embodiment, at least 30%, 40%, 50%, 60%, 70%, 80%, or 90% or more of the length of a reference sequence can be aligned for comparison purposes. The amino acid residues or nucleotides at corresponding amino acid positions or nucleotide positions can then be compared. When a position in the first sequence is occupied by the same amino acid residue or nucleotide as the corresponding position in the second sequence, then the molecules are identical at that position (as used herein, amino acid or nucleic acid "identity" is equivalent to amino acid or nucleic acid "homology"). The percent identity between the two sequences is a function of the number of identical positions shared by the sequences, taking into account the number of gaps, and the length of each gap, that are introduced for optimal alignment of the two sequences.

The comparison of sequences and determination of percent identity and similarity between two sequences can be accomplished using a mathematical algorithm. (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., Stockton Press, New York, 1991). In an exemplary embodiment, the percent identity between two amino acid sequences is determined using the Needleman and Wunsch (*J. Mol. Biol.* (48):444-453 (1970)) algorithm which has been incorporated into the GAP program in the GCG software package, using either a Blossom 62 matrix or a PAM250 matrix, a gap weight of 16, 14, 12, 10, 8, 6, or 4, and a length weight of 1, 2, 3, 4, 5, or 6. In another exemplary embodiment, the percent identity between two nucleotide sequences can be determined using the GAP program in the GCG software package (Devereux et al., *Nucleic Acids Res.* 12(1):387 (1984)) using a NWSgapdna.CMP matrix and a gap weight of 40, 50, 60, 70, or 80, and a length weight of 1, 2, 3, 4, 5, or 6. In another exemplary embodiment, the percent identity between two amino acid or nucleotide sequences is determined using the algorithm of E. Myers and W. Miller (CABIOS, 4:11-17 (1989)) which has been incorporated into the ALIGN program (version 2.0), using a PAM120 weight residue table, a gap length penalty of 12, and a gap penalty of 4.

The sequences of the proteins and nucleic acid molecules of the invention can further be used as a "query sequence" to perform a search against sequence databases to, for example, identify other protein family members or related sequences. Such searches can be performed using the NBLAST and XBLAST programs (version 2.0) of Altschul et al. (*J. Mol. Biol.* 215:403-10 (1990)). BLAST nucleotide searches can be performed with the NBLAST program, score=100, wordlength=12, to obtain nucleotide sequences homologous to the query nucleic acid molecule. BLAST protein searches can be performed with the XBLAST program, score=50, wordlength=3, to obtain amino acid sequences homologous to the query proteins. To obtain gapped alignments for comparison purposes, Gapped BLAST can be utilized as described in Altschul et al. (*Nucleic Acids Res.* 25(17):3389-3402 (1997)). When utilizing BLAST and gapped BLAST programs, the default parameters of the respective programs (e.g., XBLAST and NBLAST) can be used.

As used herein, two proteins (or a region or domain of the proteins) have significant homology/identity (also referred to as substantial homology/identity) when the amino acid sequences are typically at least about 70-80%, 80-90%, 90-95%, 96%, 97%, 98%, or 99% identical A significantly homologous amino acid sequence can be encoded by a nucleic acid molecule that hybridizes to a LCM protein-encoding nucleic acid molecule under stringent conditions, as more fully described below.

Orthologs of a LCM protein typically have some degree of significant sequence homology to at least a portion of a LCM protein and are encoded by a gene from another organism. Preferred orthologs are isolated from mammals, preferably non-human primates, for the development of human therapeutic markers and agents. Such orthologs can be encoded by a nucleic acid molecule that hybridizes to a LCM protein-encoding nucleic acid molecule under moderate to stringent conditions, as more fully described below, depending on the degree of relatedness of the two organisms yielding the proteins.

Non-naturally occurring variants of the LCM proteins can readily be generated using recombinant techniques. Such variants include, but are not limited to, deletions, additions, and substitutions in the amino acid sequence of the LCM protein. For example, one class of substitutions is conserved amino acid substitutions. Such substitutions are those that substitute a given amino acid in a LCM protein by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., *Science* 247:1306-1310 (1990).

Variant LCM proteins can be fully functional or can lack function in one or more activities, e.g., ability to bind substrate, ability to phosphorylate substrate, ability to mediate signaling, etc. Fully functional variants typically contain only conservative variations or variation in non-critical residues or in non-critical regions.

Non-functional variants typically contain one or more non-conservative amino acid substitutions, deletions, insertions, inversions, or truncations, or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081-1085 (1989)). The latter procedure introduces single alanine mutations at every residue in the molecule. The resulting mutant molecules are then tested for biological activity or in assays such as in vitro proliferative activity. Sites that are critical for binding partner/substrate binding can also be determined by structural analysis such as crystallization, nuclear magnetic resonance, or photoaffinity labeling (Smith et al., *J. Mol. Biol.* 224:899-904 (1992); de Vos et al., *Science* 255:306-312 (1992)).

LCM of the invention include fragments of LCM, and peptides that comprise and consist of such fragments. Such fragments of LCM may be naturally-occurring in the human body. An exemplary fragment typically comprises at least about 5, 6, 8, 10, 12, 14, 16, 18, 20 or more contiguous amino acid residues of a LCM protein. Such fragments can be chosen based on the ability to retain one or more of the biological activities of LCM or can be chosen for the ability to perform a function, e.g., bind a substrate or act as an immunogen. Particularly important fragments are biologically active fragments, such as peptides that are, for example, about 8 or more amino acids in length. Such fragments can include a domain or motif of a LCM, e.g., an active site, a transmembrane domain, or a binding domain. Further, possible fragments include, but are not limited to, soluble peptide fragments and fragments containing immunogenic structures. Domains and functional sites can readily be identified, for example, by computer programs well known and readily available to those of skill in the art (e.g., PROSITE analysis).

Proteins can contain amino acids other than the 20 amino acids commonly referred to as the 20 naturally-occurring amino acids. Further, many amino acids, including the terminal amino acids, can be modified by natural processes, such as processing and other post-translational modifications, or by chemical modification techniques well known in the art. Common modifications that occur naturally in proteins are well known to those of skill in the art.

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cros slinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, tRNA-mediated addition of amino acids to proteins such as arginylation, and ubiquitination.

Such modifications are well known to those of skill in the art and have been described in the scientific literature. Several particularly common modifications, glycosylation, lipid attachment, sulfation, gamma-carboxylation of glutamic acid residues, hydroxylation and ADP-ribosylation, for instance, are described in most basic texts, such as Proteins-Structure and Molecular Properties, 2nd Ed., T. E. Creighton, W. H. Freeman and Company, New York (1993). Many detailed reviews are available on this individual, such as by Wold (Posttranslational Covalent Modification of Proteins, B. C. Johnson, Ed., Academic Press, New York 1-12 (1983)); Seifter et al. (Meth. Enzymol. 182: 626-646 (1990)); and Rattan et al. (Ann. N.Y. Acad. Sci. 663:48-62 (1992)).

Accordingly, exemplary LCM proteins and fragments thereof of the invention can also encompasses derivatives or analogs in which, for example, a substituted amino acid residue is not one encoded by the genetic code, in which a substituent group is included, in which a mature LCM is fused with another composition, such as a composition to increase the half-life of a LCM (e.g., polyethylene glycol or albumin), or in which additional amino acids are fused to a mature LCM, such as a leader or secretory sequence or a sequence for purification of a mature LCM or a pro-protein sequence.

2. Antibodies to LCM Proteins

Exemplary embodiments of the invention provide antibodies to LCM proteins, including, for example, monoclonal and polyclonal antibodies; chimeric, humanized, and fully human antibodies; and antigen-binding fragments and variants thereof, as well as other embodiments.

Antibodies that selectively bind to a LCM protein can be made using standard procedures known to those of ordinary skills in the art. The term "antibody" is used in the broadest sense, and specifically covers, for example, monoclonal antibodies, polyclonal antibodies, multispecific antibodies (e.g., bispecific antibodies), chimeric antibodies, humanized antibodies, fully human antibodies, and antibody fragments (e.g., Fab, F(ab')$_2$, Fv and Fv-containing binding proteins), so long as they exhibit LCM-binding activity. Antibodies (Ab's) and immunoglobulins (Ig's) are glycoproteins typically having the same structural characteristics. Antibodies can be of the IgG, IgE, IgM, IgD, and IgA class or subclass thereof (e.g., IgG1, IgG2, IgG3, IgG4, IgA1 and IgA2). Antibodies may be interchangeably referred to as "LCM-binding molecules".

The term "monoclonal antibody", as used herein, refers to an antibody obtained from a population of substantially homogeneous antibodies, i.e., the individual antibodies comprising the population are substantially identical except for possible naturally occurring mutations that may be present in minor amounts. Monoclonal antibodies are highly specific and are typically directed against a single antigenic site. Furthermore, in contrast to polyclonal antibody preparations, which typically include different antibodies directed against different determinants (epitopes), each monoclonal antibody is typically directed against a single determinant on an antigen. In addition to their specificity, monoclonal antibodies are advantageous in that substantially homogenous antibodies can be produced by a hybridoma culture which is uncontaminated by other immunoglobulins or antibodies. The modifier "monoclonal" antibody indicates the character of the antibody as being obtained from a substantially homogeneous population of antibodies, and is not to be construed as requiring production of the antibody by any particular method. For example, monoclonal antibodies can be made by hybridoma methods such as described by Kohler and Milstein, *Nature* 256: 495-497 (1975), by recombinant methods (e.g., as described in U.S. Pat. No. 4,816,567), or can be isolated from phage antibody libraries such as by using the techniques described in Clackson et al., *Nature* 352: 624-628 (1991) or Marks et al., *J. Mol. Biol.* 222: 581-597 (1991).

"Humanized" forms of non-human (e.g., murine or rabbit) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Typically, humanized antibodies are human immunoglobulins (a recipient antibody) in which residues from a complementarity determining regions ("CDR") of the recipient are replaced by residues from a CDR of a non-human species (a donor antibody) such as mouse, rat, or rabbit having the desired specificity, affinity, and capacity. In some instances, Fv framework residues of the human immunoglobulin are replaced by corresponding non-human residues. Furthermore, a humanized antibody may comprise residues which are found neither in the recipient antibody nor in the imported CDR or framework region (FR) sequences. These modifications can be made to further refine and optimize antibody performance. In general, a humanized antibody can comprise substantially all of at least one, and typically two, variable domains, in which all or substantially all of the CDRs correspond to those of a non-human immunoglobulin and all or substantially all of the FRs are those of a human immunoglobulin consensus sequence. A humanized antibody can also comprise at least a portion of an immunoglobulin constant region (Fc), typically that of a human immunoglobulin. For further details concerning humanized antibodies, see: Jones et al., *Nature* 321:522-525 (1986); Reichmann et al., *Nature* 332:323-327 (1988); Presta, *Curr. Op. Struct. Biol.* 2:593-596 (1992); Queen et al., U.S. Pat. Nos. 5,530,101; 5,585,089; 5,693,762; and 6,180,370; and Winter, U.S. Pat. No. 5,225,539.

Antibodies, as used herein, include antibody fragments, particularly antigen-binding fragments, as well as other modified antibody structures and antigen-binding scaffolds (such as modified antibody structures that are smaller or have less than all domains or chains compared with a typical naturally occurring, full-size human antibody). Examples of antibody fragments and other modified antibody structures and antigen-binding scaffolds are known in the art by such terms as minibodies (e.g., U.S. Pat. No. 5,837,821), Nanobodies (llama heavy chain antibodies; Ablynx, Ghent, Belgium), Adnectins (fibronectin domains; Adnexus Therapeutics, Waltham, Mass.), Affibodies (protein-binding domain of *Staphylococcus aureus* protein A; Affibody, Stockholm, Sweden), peptide aptamers (synthetic peptides; Aptanomics, Lyon, France), Avimers (A-domains derived from cell surface receptors; Avidia, Mountain View, Calif. (acquired by Amgen)), Transbodies (transferrin; BioRexis Pharmaceuticals, King of Prussia, Pa. (acquired by Pfizer)), trimerized tetranectin domains (Borean Pharma, Aarhus, Denmark), Domain antibodies (heavy or light chain antibodies; Domantis, Cambridge, UK (acquired by GlaxoSmithKline)), Evibodies (derived from V-like domains of T-cell receptors CTLA-4, CD28 and inducible T-cell costimulator; EvoGenix Therapeutics, Sydney, Australia), scFV fragments (stable single chain antibody fragments; ESBATech, Zurich, Switzerland), Unibodies (monovalent IgG4 mAbs fragments; Genmab, Copenhagen, Denmark), BiTEs (bispecific, T-cell activating single-chain antibody fragments; Micromet, Munich, Germany), DARPins (designed ankyrin repeat proteins; Molecular Partners, Zurich, Switzerland), Anticalins (derived from lipocalins; Pieris, Freising-Weihenstephan, Germany), Affilins (derived from human lens protein gamma crystalline; Scil Proteins, Halle, Germany), and SMIPs (small modular immunopharmaceuticals; Trubion Pharmaceuticals, Seattle, Wash.) (Sheridan, *Nature Biotechnology*, 2007 April; 25(4):365-6).

An "isolated" or "purified" antibody is one that has been identified and separated and/or recovered from a component of the environment in which it is produced. Contaminant components of its production environment are materials that would interfere with diagnostic or therapeutic uses for the antibody, and may include enzymes, hormones, and other proteinaceous or nonproteinaceous solutes. In exemplary embodiments, the antibody can be purified as measurable by any of at least three different methods: 1) to greater than 95% by weight of antibody as determined by the Lowry method, preferably more than 99% by weight; 2) to a degree sufficient to obtain at least 15 residues of N-terminal or internal amino acid sequence by use of a spinning cup sequenator; or 3) to homogeneity by SDS-PAGE under reducing or non-reducing conditions using Coomasie blue or silver stain. Isolated antibody can include an antibody in situ within recombinant cells since at least one component of the antibody's natural environment will not be present. Ordinarily, however, an isolated antibody can be prepared by at least one purification step.

An "antigenic region", "antigenic determinant", or "epitope" includes any protein determinant capable of specific binding to an antibody. This is the site on an antigen to which each distinct antibody molecule binds. Epitopic determinants can be active surface groupings of molecules such as amino acids or sugar side chains and may have specific three-dimensional structural characteristics or charge characteristics.

"Antibody specificity" refers to an antibody that has a stronger binding affinity for an antigen from a first individual species than it has for a homologue of that antigen from a second individual species. Typically, an antibody "binds specifically" to a human antigen (e.g., has a binding affinity (Kd) value of no more than about $1 \times 10^{-7}$ M, preferably no more than about $1 \times 10^{-8}$ M, and most preferably no more than about $1 \times 10^{-9}$ M) but has a binding affinity for a homologue of the antigen from a second individual species which is at least about 50-fold, or at least about 500-fold, or at least about 1000-fold, weaker than its binding affinity for the human antigen. The antibodies can be of any of the various types of antibodies as described herein, such as humanized or fully human antibodies.

An antibody "selectively" or "specifically" binds a marker protein when the antibody binds the marker protein and does not significantly bind to unrelated proteins. An antibody can still be considered to selectively or specifically bind a marker protein even if it also binds to other proteins that are not substantially homologous with the marker protein as long as such proteins share homology with a fragment or domain of the marker protein. In this case, it would be understood that antibody binding to the marker protein is still selective despite some degree of cross-reactivity.

Exemplary embodiments of the invention provide an "antibody variant", which refers to an amino acid sequence variant of an antibody wherein one or more of the amino acid residues have been modified. Such variants necessarily have less than 100% sequence identity with the amino acid sequence of the antibody, and have at least 75%, 80%, 85%, 90%, 95%, 96%, 97%, 98%, or 99% amino acid sequence identity with the amino acid sequence of either the heavy or light chain variable domain of the antibody.

The term "antibody fragment" refers to a portion of a full-length antibody, including the antigen binding or variable region or the antigen-binding portion thereof. Examples of antibody fragments include Fab, Fab', F(ab')$_2$ and Fv fragments. Papain digestion of antibodies typically produces two identical antigen binding fragments, called the Fab fragment, each with a single antigen binding site, and a residual "Fc"

fragment. Pepsin treatment typically yields an F(ab')$_2$ fragment that has two antigen binding fragments which are capable of crosslinking antigen, and a residual other fragment (which is termed pFc'). Examples of additional antigen-binding fragments can include diabodies, triabodies, tetrabodies, single-chain Fv, single-chain Fv-Fc, SMIPs, and multispecific antibodies formed from antibody fragments. A "functional fragment", with respect to antibodies, typically refers to an Fv, F(ab), F(ab')$_2$ or other antigen-binding fragments comprising one or more CDRs that has substantially the same antigen-binding specificity as an antibody.

An "Fv" fragment is an example of an antibody fragment that contains a complete antigen recognition and binding site. This region typically consists of a dimer of one heavy and one light chain variable domain in a tight, non-covalent association ($V_H$-$V_L$ dimer). It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen.

An "Fab" fragment (also designated as "F(ab)") also contains the constant domain of the light chain and the first constant domain (CH1) of the heavy chain. Fab' fragments differ from Fab fragments by the addition of a few residues at the carboxyl terminus of the heavy chain CH1 domain, including one or more cysteines from the antibody hinge region. Fab'-SH is the designation for Fab' in which the cysteine residue(s) of the constant domains have a free thiol group. F(ab') fragments are produced by cleavage of the disulfide bond at the hinge cysteines of the F(ab')$_2$ pepsin digestion product. Additional chemical couplings of antibody fragments are known to those of ordinary skill in the art.

A "single-chain Fv" or "scFv" antibody fragment contains $V_H$ and $V_L$ domains, wherein these domains are present in a single polypeptide chain. Typically, the Fv polypeptide further comprises a polypeptide linker between the $V_H$ and $V_L$ domains that enables the scFv to form the desired structure for antigen binding. For a review of scFv, see Plückthun in The Pharmacology of Monoclonal Antibodies, vol. 113, Rosenburg and Moore eds., Springer-Verlag, New York, pp. 269-315 (1994). A single chain Fv-Fc is an scFv linked to a Fc region.

A "diabody" is a small antibody fragment with two antigen-binding sites, which fragments comprise a variable heavy domain ($V_H$) connected to a variable light domain ($V_L$) in the same polypeptide chain. By using a linker that is too short to allow pairing between the two domains on the same chain, the domains are forced to pair with the complementary domains of another chain and create two antigen-binding sites. Diabodies are described more fully in, for example, EP 0 404 097; WO 93/11161; and Hollinger et al., Proc. Natl. Acad. Sci. USA 90:6444-6448 (1993). Triabodies, tetrabodies and other antigen-binding antibody fragments have been described by Hollinger and Hudson, 2005, Nature Biotechnology 23:1126.

A "small modular immunopharmaceutical" (or "SMIP") is a single-chain polypeptide including a binding domain (e.g., an scFv or an antigen binding portion of an antibody), a hinge region, and an effector domain (e.g., an antibody Fc region or a portion thereof). SMIPs are described in published U.S. Patent Application No. 20050238646.

Many methods are known for generating and/or identifying antibodies to a given marker protein. Several such methods are described by Kohler et al., 1975, Nature 256: 495-497; Lane, 1985, J. Immunol. Meth. 81:223-228; Harlow et al., 1988, Antibodies: A Laboratory Manual. Cold Spring Harbor Laboratory Press; Harlow et al., 1998, Using Antibodies, Cold Spring Harbor Press; Zhong et al., 1997, J. Indust. Microbiol. Biotech. 19(1):71-76; and Berry et al., 2003, Hybridoma and Hybridomics 22(1): 23-31.

Polyclonal antibodies can be prepared by any known method or modifications of these methods, including obtaining antibodies from patients. In certain exemplary methods for generating antibodies such as polyclonal antibodies, an isolated protein can be used as an immunogen which is administered to a mammalian organism, such as a rat, rabbit, or mouse. For example, a complex of an immunogen such as a LCM protein (or fragment thereof) and a carrier protein can be prepared and an animal immunized by the complex. Serum or plasma containing antibodies against the protein can be recovered from the immunized animal and the antibodies separated and purified (in the same manner as for monoclonal antibodies, for example). The gamma globulin fraction or the IgG antibodies can be obtained, for example, by use of saturated ammonium sulfate or DEAE SEPHADEX, or other techniques known to those skilled in the art. The antibody titer in the antiserum can be measured in the same manner as in the supernatant of a hybridoma culture.

A marker such as a full-length LCM protein, an antigenic peptide fragment, a fusion protein thereof, or a carbohydrate antigen or fragment thereof, can be used as an immunogen. A marker used as an immunogen is not limited to any particular type of immunogen. In one aspect, antibodies can be prepared from regions or discrete fragments (e.g., functional domains, extracellular domains, or portions thereof) of a LCM. Antibodies can be prepared from any region of a marker as described herein. In particular, the markers can be selected from the group consisting of SEQ ID NOS:1-65, the carbohydrate antigens CA 242, CA 19-9, and CA 72-4, and fragments thereof. An antigenic fragment can typically comprise at least 8, 10, 12, 14, 16, or more contiguous amino acid residues, for example. Such fragments can be selected based on a physical property, such as fragments that correspond to regions located on the surface of a marker (e.g., hydrophilic regions) or can be selected based on sequence uniqueness.

Antibodies can also be produced by inducing production in a lymphocyte population or by screening antibody libraries or panels of highly specific binding reagents, such as disclosed in Orlandi et al. (Proc. Natl. Acad. Sci. 86:3833-3837 (1989)) or Winter et al. (Nature 349:293-299 (1991)). A protein can be used in screening assays of phagemid or B-lymphocyte immunoglobulin libraries to identify antibodies having a desired specificity. Numerous protocols for competitive binding or immunoassays using either polyclonal or monoclonal antibodies with established specificities are well known in the art (e.g., Smith, Curr. Opin. Biotechnol. 2: 668-673 (1991)).

Antibodies can also be generated using various phage display methods known in the art. In representative phage display methods, functional antibody domains are displayed on the surface of phage particles which carry nucleic acid molecules that encode the antibody domains. In particular, such phage can be utilized to display antigen-binding domains expressed from a repertoire or combinatorial antibody library (e.g., human or murine). Phage expressing an antigen binding domain that binds an antigen of interest can be selected or identified with the antigen, e.g., using labeled antigen or antigen bound or captured to a solid surface or bead. Phage used in methods such as these can typically be filamentous phage including fd and M13 binding domains expressed from phage with Fab, Fv, or disulfide stabilized Fv antibody domains recombinantly fused to either the phage gene III or gene VIII protein. Examples of phage display methods that can be used to make antibodies include methods described in Brinkman et al., *J. Immunol. Methods* 182:41-50 (1995); Ames et al., *J. Immunol. Methods* 184:177-186 (1995); Kettleborough et al., *Eur. J. Immunol.* 24:952-958 (1994); Persic et al., *Gene* 187:9-18 (1997); Burton et al., *Advances in Immunology* 57:191-280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

Antibodies, antigen binding fragments, and/or antibody variants can be produced by recombinant and genetic engineering methods well known in the art. For example, methods of expressing heavy and light chain genes in *E. coli* are described in PCT publication numbers WO901443, WO901443, and WO9014424, and in Huse et al., 1989 *Science* 246:1275-1281. When using recombinant techniques, such as to produce an antibody variant, the antibody variant can be produced intracellularly, in the periplasmic space, or directly secreted into the medium. If an antibody variant is produced intracellularly, as a first step, the particulate debris, either host cells or lysed fragments, can be removed, for example, by centrifugation or ultrafiltration. Carter et al. (*Bio/Technology* 10: 163-167 (1992)) describe a procedure for isolating antibodies that are secreted to the periplasmic space of *E. coli*. Briefly, cell paste can be thawed in the presence of sodium acetate (pH 3.5), EDTA, and phenylmethylsulfonylfluoride (PMSF) over about 30 minutes. Cell debris can be removed by centrifugation. Where an antibody variant is secreted into the medium, supernatants from such expression systems can first be concentrated using a commercially available protein concentration filter (e.g., an Amicon or Millipore PELLICON ultrafiltration unit). A protease inhibitor such as PMSF can be included in any of the foregoing steps to inhibit proteolysis, and antibiotics can be included to prevent the growth of contaminating microorganisms.

An antibody composition prepared from cells can be purified using, for example, affinity chromatography, hydroxylapatite chromatography, gel electrophoresis, and/or dialysis. The suitability of protein A as an affinity ligand typically depends on the species and isotype of the immunoglobulin Fc domain of an antibody. Protein A can be used to purify antibodies that are based on human delta1, delta2, or delta4 heavy chains (Lindmark et al., *J. Immunol. Meth.* 62: 1-13 (1983)). Protein G can be used for all mouse isotypes and for human delta3 (Guss et al., *EMBO J.* 5: 1567-1575 (1986)). The matrix to which the affinity ligand is attached can be, for example, agarose or mechanically stable matrices such as controlled pore glass or poly(styrenedivinyl)benzene. Where the antibody comprises a CH3 domain, the BAKERBOND ABX™ resin (J. T. Baker, Phillipsburg, N.J.) can be used for purification. Other exemplary techniques for antibody purification include, but are not limited to, fractionation on an ion-exchange column, ethanol precipitation, reverse phase HPLC, chromatography on silica, chromatography on heparin hepharos, chromatography on an anion or cation exchange resin (such as a polyaspartic acid column), chromatofocusing, SDS-PAGE, and ammonium sulfate precipitation.

Following any preliminary purification step(s), contaminants in a mixture containing an antibody of interest can be removed by low pH hydrophobic interaction chromatography using an elution buffer at a pH between about 2.5-4.5, preferably performed at low salt concentrations (e.g., from about 0-0.25M salt).

Full-length antibodies, as well as antibody fragments, can also be expressed and isolated from bacteria such as *E. coli*, such as described in Mazor et al., "Isolation of engineered, full-length antibodies from libraries expressed in *Escherichia coli*", *Nat Biotechnol.* 2007 May; 25(5):563-5 and Sidhu, "Full-length antibodies on display", *Nat. Biotechnol.* 2007 May; 25(5):537-8.

Further details regarding antibodies are set forth in the following U.S. Pat. No. 6,248,516 (Winter et al.); U.S. Pat. No. 6,291,158 (Winter et al.); U.S. Pat. No. 5,885,793 (Griffiths et al.); U.S. Pat. No. 5,969,108 (McCafferty et al.); U.S. Pat. No. 5,939,598 (Kucherlapati et al.); U.S. Pat. No. 4,816,397 (Boss et al.); U.S. Pat. No. 4,816,567 (Cabilly et al.); U.S. Pat. No. 6,331,415 (Cabilly et al.); U.S. Pat. No. 5,770,429 (Lonberg et al.); U.S. Pat. No. 5,639,947 (Hiatt et al.); and U.S. Pat. No. 5,260,203 (Ladner et al.), each of which is incorporated herein by reference, and in the following published U.S. patent applications: US20040132101 (Lazar et al.), US20050064514 (Stavenhagen et al.), US20040261148 (Dickey et al.), and US20050014934 (Hinton et al.), each of which is incorporated herein by reference. Antibody engineering is further described in Jain et al., "Engineering antibodies for clinical applications", *Trends Biotechnol.* 2007 July; 25(7):307-16.

3. Antibody-Drug Conjugates to LCM Proteins

An antibody against LCM can be coupled (e.g., covalently bonded) to a suitable therapeutic agent (as further discussed herein) either directly or indirectly (e.g., via a linker group). A direct reaction between an antibody and a therapeutic agent is possible when each possesses a substituent capable of reacting with the other. For example, a nucleophilic group, such as an amino or sulfhydryl group, on one molecule may be capable of reacting with a carbonyl-containing group, such as an anhydride or an acid halide, or with an alkyl group containing a good leaving group (e.g., a halide) on the other molecule.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

A variety of bifunctional or polyfunctional reagents, both homo- and hetero-functional (such as those described in the catalog of the Pierce Chemical Co., Rockford, Ill.), can be employed as the linker group. Coupling can be effected, for example, through amino groups, carboxyl groups, sulfhydryl groups, or oxidized carbohydrate residues (e.g., U.S. Pat. No. 4,671,958).

Where a therapeutic agent is more potent when free from the antibody portion of an immunoconjugate, it may be desirable to use a linker group that is cleavable during or upon internalization into a cell. A number of different cleavable linker groups have been described. Mechanisms for the intracellular release of an agent from these linker groups include cleavage by reduction of a disulfide bond (e.g., U.S. Pat. No. 4,489,710), by irradiation of a photolabile bond (e.g., U.S. Pat. No. 4,625,014), by hydrolysis of derivatized amino acid side chains (e.g., U.S. Pat. No. 4,638,045), by serum complement-mediated hydrolysis (e.g., U.S. Pat. No. 4,671,958), by protease cleavable linker (e.g., U.S. Pat. No. 6,214,345), and by acid-catalyzed hydrolysis (e.g., U.S. Pat. No. 4,569,789).

It may be desirable to couple more than one agent to an antibody. Multiple molecules of an agent can be coupled to one antibody molecule, and more than one type of agent can be coupled to the same antibody. For example, about 1, 2, 4, 6, 8, 10, 12, 14, 16, 18, 20, or 22 (or any other number in-between) molecules of therapeutic agents can be coupled to an antibody. The average number or quantitative distribution of therapeutic agent molecules per antibody molecule in a preparation of conjugation reactions can be determined by conventional means such as mass spectroscopy, ELISA, or HPLC. Separation, purification, and characterization of homogeneous antibody-drug conjugates having a certain number of therapeutic agents conjugated thereto can be achieved by means such as reverse phase HPLC or electrophoresis (see, e.g., Hamblett et al., *Clinical Cancer Res.* 10:7063-70 (2004).

Examples of suitable therapeutic agents that can be conjugated to an antibody include, but are not limited to, chemotherapeutic agents (e.g., cytotoxic or cytostatic agents or immunomodulatory agents), radiotherapeutic agents, therapeutic antibodies, small molecule drugs, peptide drugs, immunomodulatory agents, differentiation inducers, and toxins.

Examples of useful classes of cytotoxic or immunomodulatory agents include, but are not limited to, antitubulin agents, auristatins, DNA minor groove binders, DNA replication inhibitors, alkylating agents (e.g., platinum complexes such as cis-platin, mono(platinum), bis(platinum) and tri-nuclear platinum complexes and carboplatin), anthracyclines, antibiotics, antifolates, antimetabolites, chemotherapy sensitizers, duocarmycins, etoposides, fluorinated pyrimidines, ionophores, lexitropsins, nitrosoureas, platinols, pre-forming compounds, purine antimetabolites, puromycins, radiation sensitizers, steroids, taxanes, topoisomerase inhibitors, vinca alkaloids, and the like.

Examples of individual cytotoxic or immunomodulatory agents include, but are not limited to, androgen, anthramycin (AMC), asparaginase, 5-azacytidine, azathioprine, bleomycin, busulfan, buthionine sulfoximine, calicheamicin or calicheamicin derivatives, camptothecin or camptothecins derivatives, carboplatin, carmustine (BSNU), CC-1065, chlorambucil, cisplatin, colchicine, cyclophosphamide, cytidine arabinoside (cytarabine), cytochalasin B, dacarbazine, dactinomycin (formerly actinomycin), daunorubicin, decarbazine, docetaxel, doxorubicin, etoposide, estrogen, 5-fluordeoxyuridine, 5-fluorouracil, gemcitabine, gramicidin D, hydroxyurea, idarubicin, ifosfamide, irinotecan, lomustine (CCNU), maytansine, mechlorethamine, melphalan, 6-mercaptopurine, methotrexate, mithramycin, mitomycin C, mitoxantrone, nitroimidazole, paclitaxel, palytoxin, plicamycin, procarbizine, rhizoxin, streptozotocin, tenoposide, 6-thioguanine, thioTEPA, topotecan, vinblastine, vincristine, vinorelbine, VP-16, and VM-26.

Examples of other suitable cytotoxic agents include, but are not limited to, DNA minor groove binders (e.g., enediynes and lexitropsins, a CBI compound; see also U.S. Pat. No. 6,130,237), duocarmycins, taxanes (e.g., paclitaxel and docetaxel), puromycins, vinca alkaloids, CC-1065, SN-38, topotecan, morpholino-doxorubicin, rhizoxin, cyanomorpholino-doxorubicin, echinomycin, combretastatin, netropsin, epothilone A and B, estramustine, cryptophysins, cemadotin, a maytansinoid, discodermolide, eleutherobin, and mitoxantrone.

Examples of other suitable agents include, but are not limited to, radionuclides, differentiation inducers, drugs, toxins, and derivatives thereof. Exemplary radionuclides include $^{90}$Y, $^{123}$I, $^{125}$I, $^{131}$I, $^{186}$Re, $^{188}$Re, $^{211}$At, and $^{212}$Bi. Exemplary drugs include methotrexate, and pyrimidine and purine analogs. Exemplary differentiation inducers include phorbol esters and butyric acid. Exemplary toxins include ricin, abrin, diptheria toxin, cholera toxin, gelonin, *Pseudomonas* exotoxin, *Shigella* toxin, and pokeweed antiviral protein.

In some embodiments, the therapeutic agent used in an antibody-drug conjugate is an anti-tubulin agent. Examples of anti-tubulin agents include, but are not limited to, taxanes (e.g., Taxol® (paclitaxel), Taxotere® (docetaxel)), T67 (Tularik) and vinca alkyloids (e.g., vincristine, vinblastine, vindesine, and vinorelbine). Other antitubulin agents include, for example, baccatin derivatives, taxane analogs (e.g., epothilone A and B), nocodazole, colchicine and colcimid, estramustine, cryptophysins, cemadotin, maytansinoid, combretastatins, discodermolide, and eleutherobin.

In certain embodiments, the cytotoxic agent is a maytansinoid, another group of anti-tubulin agents. For example, in specific embodiments, the maytansinoid is maytansine, DM-1 (ImmunoGen, Inc.; see also Chari et al., *Cancer Res.* 52:127-131 (1992)) or DM-4. In some embodiments, the therapeutic agent is an auristatin, such as auristatin E (also known in the art as dolastatin-10) or a derivative thereof. Typically, an auristatin E derivative is, e.g., an ester formed between auristatin E and a keto acid. For example, auristatin E can be reacted with paraacetyl benzoic acid or benzoylvaleric acid to produce AEB and AEVB, respectively. Other typical auristatin derivatives include AFP, MMAF, and MMAE. The synthesis and structure of auristatin derivatives are described in U.S. Patent Application Publication Nos. 2003-0083263, 2005-0238649 and 2005-0009751; PCT Publication Nos WO 04/010957 and WO 02/088172, and U.S. Pat. Nos. 6,323,315; 6,239,104; 6,034,065; 5,780,588; 5,665,860; 5,663,149; 5,635,483; 5,599,902; 5,554,725; 5,530,097; 5,521,284; 5,504,191; 5,410,024; 5,138,036; 5,076,973; 4,986,988; 4,978,744; 4,879,278; 4,816,444; and 4,486,414.

4. LCM Nucleic Acid Molecules

Exemplary isolated LCM nucleic acid molecules of the invention consist of, consist essentially of, or comprise a nucleotide sequence that encodes a LCM protein of the invention, an allelic variant thereof, or an ortholog or paralog thereof, for example. As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about kilobases (KB), 4 KB, 3 KB, 2 KB, or 1 KB or less, particularly contiguous protein-encoding sequences and protein-encoding sequences within the same gene but separated by introns in the genomic sequence, and flanking nucleotide sequences that contain regulatory elements. The primary consideration is that the nucleic acid is isolated from remote and unimportant flanking sequences such that it can be individualed to the specific manipulations described herein such as recombinant expression, preparation of probes and primers, and other uses specific to the nucleic acid molecules. Moreover, an "isolated" nucleic acid molecule, such as a transcript/cDNA molecule, can be substantially free of other cellular material, or culture medium when produced by recombinant techniques, or chemical precursors or other chemicals when chemically synthesized.

A nucleic acid molecule can be fused to other coding or regulatory sequences and still be considered isolated. Isolated nucleic acid molecules can include heterologous nucleotide sequences, such as heterologous nucleotide sequences that are fused to a nucleic acid molecule by recombinant techniques. For example, recombinant DNA molecules contained in a vector are considered isolated. Further examples of isolated DNA molecules include recombinant DNA molecules maintained in heterologous host cells, or purified (partially or substantially) DNA molecules in solution. Isolated RNA molecules include in vivo or in vitro RNA transcripts of isolated DNA molecules. Isolated nucleic acid molecules further include such molecules produced synthetically.

Isolated nucleic acid molecules can encode a mature protein plus additional amino or carboxyl-terminal amino acids, or amino acids interior to the mature protein (when the mature form has more than one peptide chain, for instance). Such sequences may play a role in processing of a protein from precursor to a mature form, facilitate protein trafficking, prolong or shorten protein half-life, or facilitate manipulation of a protein for assay or production, among other things. As generally is the case in situ, additional amino acids may be processed away from the mature protein by cellular enzymes.

Isolated nucleic acid molecules include, but are not limited to, sequences encoding a LCM protein alone, sequences encoding a mature protein with additional coding sequences (such as a leader or secretory sequence (e.g., a pre-pro or pro-protein sequence)), and sequences encoding a mature protein (with or without additional coding sequences) plus additional non-coding sequences (e.g., introns and non-coding 5' and 3' sequences such as transcribed but non-translated sequences that play a role in transcription, mRNA processing (including splicing and polyadenylation signals), ribosome binding, and/or stability of mRNA). In addition, nucleic acid molecules can be fused to a marker sequence encoding, for example, a peptide that facilitates purification.

Isolated nucleic acid molecules can be in the form of RNA, such as mRNA, or in the form of DNA, including cDNA and genomic DNA obtained by cloning or produced by chemical synthetic techniques or by a combination thereof. Nucleic acid molecules, especially DNA, can be double-stranded or single-stranded. Single-stranded nucleic acid can be the coding strand (sense strand) or the non-coding strand (anti-sense strand).

Exemplary embodiments of the invention further provide isolated nucleic acid molecules that encode fragments of a LCM protein as well as nucleic acid molecules that encode obvious variants of a LCM protein. Such nucleic acid molecules may be naturally occurring, such as allelic variants (same locus), paralogs (different locus), and orthologs (different organism), or can be constructed by recombinant DNA methods or by chemical synthesis. Such non-naturally occurring variants can be made by mutagenesis techniques, including those applied to nucleic acid molecules, cells, or organisms. Accordingly, nucleic acid molecule variants can contain nucleotide substitutions, deletions, inversions, and/or insertions. Variations can occur in either or both the coding and non-coding regions, and variations can produce conservative and/or non-conservative amino acid substitutions.

A fragment of a nucleic acid molecule typically comprises a contiguous nucleotide sequence at least 8, 10, 12, 15, 16, 18, 20, 22, 25, 30, 40, 50, 100, 150, 200, 250, 500 (or any other number in-between) or more nucleotides in length. The length of a fragment can be based on its intended use. For example, a fragment can encode epitope bearing regions of a protein, or can be used as DNA probes and primers. Isolated fragments can be produced by synthesizing an oligonucleotide probe using known techniques, for example, and can optionally be labeled and used to screen a cDNA library, genomic DNA, or mRNA, for example. Primers can be used in PCR reactions to clone specific regions of a gene.

A probe/primer typically comprises substantially a purified oligonucleotide or oligonucleotide pair. An oligonucleotide typically comprises a nucleotide sequence that hybridizes under stringent conditions to at least about 8, 10, 12, 14, 15, 16, 17, 18, 19, 20, 21, 22, 23, 24, 25, 30, 40, 50 (or any other number in-between) or more contiguous nucleotides.

Allelic variants, orthologs, and homologs can be identified using methods well known in the art. These variants can comprise a nucleotide sequence encoding a protein that is typically 60-70%, 70-80%, 80-90%, 90-95%, 96%, 97%, 98%, or 99% homologous to the nucleotide sequence. Such nucleic acid molecules can readily be identified as being able to hybridize under moderate to stringent conditions, to a nucleotide sequence shown in the Sequence Listing or a fragment thereof.

As used herein, the term "hybridizes under stringent conditions" is intended to describe conditions for hybridization and washing under which nucleotide sequences encoding a protein at least 60-70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in, for example, Current Protocols in Molecular Biology, John Wiley & Sons, N.Y. (1989-2006), 6.3.1-6.3.6. One example of stringent hybridization conditions is hybridization in 6× sodium chloride/sodium citrate (SSC) at about 45° C., followed by one or more washes in 0.2×SSC, 0.1% SDS at 50-65° C. Examples of moderate to low stringency hybridization conditions are well known in the art.

Exemplary embodiments of the invention also include kits for detecting the presence of LCM nucleic acid (e.g., DNA or mRNA) in a biological sample. For example, a kit can comprise reagents such as a labeled or labelable nucleic acid and/or other agents capable of detecting LCM nucleic acid in a biological sample; means for determining the amount of LCM nucleic acid in the sample; and means for comparing the amount of LCM nucleic acid in the sample with a standard. The nucleic acid and/or other agent can be packaged in one or more suitable containers. The kit can further comprise instructions for using the kit to detect LCM nucleic acid.

5. Vectors and Host Cells

Exemplary embodiments of the invention also provide vectors containing LCM nucleic acid molecules. The term "vector" refers to a vehicle, such as a nucleic acid molecule, which can transport the LCM nucleic acid molecules. When the vector is a nucleic acid molecule, the LCM nucleic acid molecules are covalently linked to the vector nucleic acid. A vector can be, for example, a plasmid, single or double stranded phage, a single or double stranded RNA or DNA viral vector, or artificial chromosome, such as a BAC, PAC, YAC, OR MAC.

A vector can be maintained in a host cell as an extrachromosomal element where it replicates and produces additional copies of the LCM nucleic acid molecules. Alternatively, a vector can integrate into a host cell genome and produce additional copies of the LCM nucleic acid molecules when the host cell replicates.

Exemplary embodiments of the invention provide vectors for maintenance (cloning vectors) and vectors for expression (expression vectors) of the nucleic acid molecules, for example. Expression vectors can express a portion of, or all of, a protein sequence. Vectors can function in prokaryotic or eukaryotic cells or in both (shuttle vectors). Vectors also include insertion vectors, which integrate a nucleic acid molecule into another nucleic acid molecule, such as into the cellular genome (such as to alter in situ expression of a gene and/or gene product). For example, an endogenous protein-coding sequence can be entirely or partially replaced via homologous recombination with a protein-coding sequence containing one or more specifically introduced mutations.

Expression vectors can contain cis-acting regulatory regions that are operably-linked in the vector to the nucleic acid molecules such that transcription of the nucleic acid molecules is allowed in a host cell. The nucleic acid molecules can be introduced into the host cell with a separate nucleic acid molecule capable of affecting transcription. The separate nucleic acid molecule may provide, for example, a trans-acting factor interacting with the cis-regulatory control region to allow transcription of the nucleic acid molecules from the vector. Alternatively, a trans-acting factor may be supplied by a host cell. Additionally, a trans-acting factor can be produced from a vector itself. It is understood, however, that transcription and/or translation of nucleic acid molecules can occur in cell-free systems.

Regulatory sequences to which LCM nucleic acid molecules can be operably linked include, for example, promoters for directing mRNA transcription. These include, but are not limited to, the left promoter from bacteriophage, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors can also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region, a ribosome binding site for translation. Other regulatory control elements for expression include initiation and termination codons as well as polyadenylation signals. Numerous regulatory sequences useful in expression vectors are well known in the art (e.g., Sambrook et al., Molecular Cloning: A Laboratory Manual. 3rd. ed., Cold Spring Harbor Laboratory Press, Cold Spring Harbor, N.Y. (2001)).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., Molecular Cloning: A Laboratory Manual. 3rd. ed., Cold Spring Harbor Laboratory Press, Cold Spring Harbor, N.Y. (2001).

A regulatory sequence can provide constitutive expression in one or more host cells (e.g., tissue specific) or can provide for inducible expression in one or more cell types such as by temperature, nutrient additive, or exogenous factors such as a hormone or other ligand. A variety of vectors providing for constitutive and inducible expression in prokaryotic and eukaryotic hosts are well known in the art.

Nucleic acid molecules can be inserted into vector nucleic acid by well-known methodology. For example, the DNA sequence that will ultimately be expressed can be joined to an expression vector by cleaving the DNA sequence and the expression vector with one or more restriction enzymes and then ligating the fragments together. Procedures for restriction enzyme digestion and ligation are well known in the art.

A vector containing a nucleic acid molecule of interest can be introduced into an appropriate host cell for propagation or expression using well-known techniques. Bacterial cells include, but are not limited to, *E. coli, Streptomyces*, and *Salmonella typhimurium*. Eukaryotic cells include, but are not limited to, yeast, insect cells such as *Drosophila*, animal cells such as COS and CHO cells (e.g., DG44 or CHO-s), and plant cells.

As described herein, it may be desirable to express a protein as a fusion protein. Accordingly, exemplary embodiments of the invention provide fusion vectors that allow for the production of fusion proteins. Fusion vectors can, for example, increase the expression of a recombinant protein; increase the solubility of a recombinant protein, and/or aid in the purification of a protein such as by acting as a ligand for affinity purification. A proteolytic cleavage site can be introduced at the junction of the fusion moiety so that the desired protein can ultimately be separated from the fusion moiety. Proteolytic enzymes include, but are not limited to, factor Xa, thrombin, and enteroenzyme. Typical fusion expression vectors include pGEX (Smith et al., Gene 67:31-40 (1988)), pMAL (New England Biolabs, Beverly, Mass.) and pRIT5 (Pharmacia, Piscataway, N.J.), which fuse glutathione S-transferase (GST), maltose E binding protein, or protein A, respectively, to a recombinant marker protein. Examples of suitable inducible non-fusion *E. coli* expression vectors include pTrc (Amann et al., Gene 69:301-315 (1988)) and pET 11d (Studier et al., Gene Expression Technology: Methods in Enzymology 185:60-89 (1990)).

Recombinant protein expression can be maximized in host bacteria by providing a genetic background wherein the host cell has an impaired capacity to proteolytically cleave the recombinant protein (Gottesman, S., Gene Expression Technology: Methods in Enzymology 185, Academic Press, San Diego, Calif. (1990), pp. 119-128). Alternatively, the sequence of a nucleic acid molecule of interest can be altered to provide preferential codon usage for a specific host cell, such as *E. coli* (Wada et al., Nucleic Acids Res. 20:2111-2118 (1992)).

LCM nucleic acid molecules can, for example, be expressed by expression vectors in a yeast host. Examples of vectors for expression in yeast (e.g., *S. cerevisiae*) include pYepSec1 (Baldari, et al., EMBO J. 6:229-234 (1987)), pMFa (Kurjan et al., Cell 30:933-943 (1982)), pJRY88 (Schultz et al., Gene 54:113-123 (1987)), and pYES2 (Invitrogen Corporation, San Diego, Calif.). Nucleic acid molecules can also be expressed in insect cells using, for example, baculovirus expression vectors. Baculovirus vectors available for expression of proteins in cultured insect cells (e.g., Sf 9 cells) include the pAc series (Smith et al., Mol. Cell. Biol. 3:2156-2165 (1983)) and the pVL series (Lucklow et al., Virology 170:31-39 (1989)). Nucleic acid molecules can also be expressed in mammalian cells using mammalian expression vectors. Examples of mammalian expression vectors include pCDM8 (Seed, B. Nature 329:840 (1987)), pMT2PC (Kaufman et al., EMBO J. 6:187-195 (1987)), and CHEF (U.S. Pat. No. 5,888,809).

The expression vectors listed herein are provided by way of example only of well-known vectors available to those of ordinary skill in the art that would be useful to express LCM nucleic acid molecules. The person of ordinary skill in the art would be aware of other vectors suitable for maintenance, propagation, and/or expression of LCM nucleic acid molecules (e.g., Sambrook et al. Molecular Cloning: A Laboratory Manual. 3rd. ed., Cold Spring Harbor Laboratory Press, Cold Spring Harbor, N.Y. (2001).

Exemplary embodiments of the invention also encompasses vectors in which LCM nucleic acid molecules are cloned into a vector in reverse orientation, but operably linked to a regulatory sequence that permits transcription of antisense RNA. Thus, an antisense transcript can be produced to all, or to a portion, of a LCM nucleic acid molecule, including coding and non-coding regions. Expression of this antisense RNA may be individual to each of the parameters described above in relation to expression of the sense RNA (e.g., regulatory sequences, constitutive or inducible expression, tissue-specific expression).

Exemplary embodiments of the invention provide recombinant host cells containing the vectors described herein. Host cells include, for example, prokaryotic cells, lower eukaryotic cells such as yeast, other eukaryotic cells such as insect cells, and higher eukaryotic cells such as mammalian cells.

Recombinant host cells can be prepared by introducing vector constructs, such as described herein, into cells by techniques readily available to a person of ordinary skill in the art. These techniques include, but are not limited to, calcium phosphate transfection, DEAE-dextran-mediated transfection, cationic lipid-mediated transfection, electroporation, transduction, infection, lipofection, microinjection, and other techniques such as those found in Sambrook, et al. (Molecular Cloning: A Laboratory Manual. 3rd. ed., Cold Spring Harbor Laboratory Press, Cold Spring Harbor, N.Y. (2001).

For example, using techniques such as these, a retroviral or other viral vector can be introduced into mammalian cells. Examples of mammalian cells into which a retroviral vector can be introduced include, but are not limited to, primary mammalian cultures or continuous mammalian cultures, COS cells, NIH3T3, 293 cells (ATCC #CRL 1573), and dendritic cells.

Host cells can contain more than one vector. Thus, different nucleotide sequences can be introduced on different vectors of the same cell. Similarly, nucleic acid molecules of interest can be introduced either alone or with other unrelated nucleic acid molecules such as those providing trans-acting factors for expression vectors. When more than one vector is introduced into a cell, the vectors can be introduced independently, co-introduced, or joined to the nucleic acid molecule vector.

Bacteriophage and viral vectors can be introduced into cells as packaged or encapsulated virus by standard procedures for infection and transduction. Viral vectors can be replication-competent or replication-defective. If viral replication is defective, replication can occur in host cells that provide functions that complement the defects.

Vectors can include selectable markers that enable the selection of a subpopulation of cells that contain the recombinant vector constructs. Markers can be contained in the same vector that contains the nucleic acid molecules of interest or can be on a separate vector. Exemplary markers include tetracycline or ampicillin-resistance genes for prokaryotic host cells, and dihydrofolate reductase or neomycin resistance for eukaryotic host cells. However, any marker that provides selection for a phenotypic trait can be used.

While mature proteins can be produced in bacteria, yeast, mammalian cells, and other cells under the control of appropriate regulatory sequences, cell-free transcription and translation systems can also be used to produce these proteins using RNA derived from the DNA constructs described herein.

If secretion of a protein is desired, appropriate secretion signals can be incorporated into a vector. The signal sequence can be endogenous or heterologous to the protein.

If a protein is not secreted into a medium, the protein can be isolated from a host cell by standard disruption procedures, including freeze/thaw, sonication, mechanical disruption, use of lysing agents, and the like. A protein can then be recovered and purified by well-known purification methods including, for example, ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that, depending upon the host cell used in recombinant production of a protein, proteins can have various glycosylation patterns or can be non-glycosylated, such as when produced in bacteria. In addition, proteins can include an initial modified methionine in some instances as a result of a host-mediated process.

Recombinant host cells that express a LCM protein have a variety of uses. For example, such host cells are useful for producing LCM proteins, which can be further purified to produce desired amounts of the protein or fragments thereof. Thus, host cells containing expression vectors are useful for protein production.

Host cells are also useful for conducting cell-based assays involving a LCM protein or fragments thereof. For example, a recombinant host cell expressing a LCM protein can be used to assay compounds that stimulate or inhibit the protein's function.

Host cells are also useful for identifying mutant LCM proteins in which the protein's function is affected. Host cells expressing mutant proteins are useful for assaying compounds that have a desired effect on the mutant proteins (e.g., stimulating or inhibiting function), particularly if the mutant proteins naturally occur and give rise to a pathology.

6. Diagnosis and Treatment in General

The following terms, as used in the present specification and claims, are intended to have the meaning as defined below, unless indicated otherwise.

As used herein, a "biological sample" (or just "sample") can comprise, for example, tissue, blood, sera, cells, cell lines, or biological fluids such as plasma, interstitial fluid, urine, cerebrospinal fluid, and the like. A biological sample is typically, although not necessarily, obtained from an individual by a medical practitioner.

As used herein, a "individual" can be a mammalian individual or non-mammalian individual, preferably a mammalian individual. A mammalian individual can be a human or non-human, preferably a human. The terms "individual", "individual", and "patient" are used herein interchangeably.

A "healthy" or "normal" individual or biological sample is a individual or biological sample in which the disease of interest (e.g., lung cancer) is not detectable, as ascertained by using conventional diagnostic methods (such a biological sample can interchangeably be referred to as a "control" sample).

As used herein, "disease(s)" include cancer, especially aerodigestive cancers, and particularly lung cancer, as well as associated diseases and pathologies, such as other lung diseases.

The term "diagnose" (or "diagnosing", etc.) refers to determining the current state or status (e.g., the presence/absence or characteristics) of a disease condition, such as initially detecting the presence of a disease, characterizing/classifying a disease, or detecting disease progression, remission, or recurrence.

The term "prognose" (or "prognosing", etc.) refers to predicting the future course of a disease in a patient who has the disease (e.g., predicting patient survival).

The term "assess" (or "assessing", etc.) can encompass "diagnose" and "prognose" but can also encompass making future determinations/predictions about the disease in an individual who does not have the disease or determining/predicting the likelihood that a disease will recur in an individual who apparently has been cured of the disease. The term "assess" can also encompass making assessments of an individual's response to a therapy, such as predicting whether an individual is likely to respond favorably to a therapeutic agent or is unlikely to respond to a therapeutic agent (or will experience toxic or other undesirable side effects, for example), selecting a therapeutic agent for administration to an individual, or monitoring or determining an individual's response to a therapy that has been administered to the individual.

Thus, "assessing" lung cancer can include, for example, prognosing the future course of lung cancer; predicting recurrence of lung cancer in an individual who apparently has been cured of lung cancer; and/or determining or predicting an individual's response to a lung cancer treatment or selecting a lung cancer treatment to administer to an individual based on the individual's LCM profile (i.e., the differential abundance level of one or more LCM in the individual).

The following examples may be referred to as either "diagnosing" or "assessing" lung cancer: initially detecting the presence of lung cancer; determining a specific stage, type or sub-type, or other classification or characteristic of lung cancer; determining whether a lung lesion is a benign lesion or a malignant lung tumor; and/or detecting/monitoring lung cancer progression (e.g., monitoring lung tumor growth or metastatic spread), remission, or recurrence.

LCM are therefore useful as "prognostic markers" (e.g., predicting disease progression) and "predictive markers" (e.g., predicting drug response), among other uses.

"Treat", "treating", or "treatment" of a disease includes: (1) inhibiting the disease, i.e., arresting or reducing the development of the disease or its clinical symptoms, or (2) relieving the disease, i.e., causing regression of the disease or its clinical symptom(s).

The term "prophylaxis" is used to distinguish from "treatment," and to encompass both "preventing" and "suppressing." It is not always possible to distinguish between "preventing" and "suppressing," as the ultimate inductive event or events may be unknown, latent, or the patient is not ascertained until well after the occurrence of the event or events. Therefore, the term "protection", as used herein, is meant to include "prophylaxis."

A "therapeutically effective amount" means the amount of an agent that, when administered to a individual for treating a disease, is sufficient to effect such treatment for the disease. The "therapeutically effective amount" can vary depending on such factors as the agent, the disease and its severity, and the age, weight, etc., of the individual to be treated.

Exemplary embodiments of the invention provide methods for treating diseases, especially cancer, and particularly lung cancer, comprising administering to a patient a therapeutically effective amount of an antagonist, agonist, or a pharmaceutical composition thereof. Exemplary embodiments of the invention further provide agonists and antagonists to LCM proteins, as well as pharmaceutical compositions that comprise an agonist or antagonist with a suitable carrier such as a pharmaceutically acceptable excipient.

Exemplary agonists or antagonists include antibodies that specifically bind to a LCM protein. Antibodies can be used alone or in combination with one or more other therapeutic agents (e.g., as an antibody-drug conjugate or a combination therapy). Further examples of molecules that can be used as antagonists include, but are not limited to, small molecules that inhibit the function or abundance level of LCM, and inhibitory nucleic acid molecules such as RNAi or antisense nucleic acid molecules that specifically hybridize to LCM nucleic acid.

Exemplary embodiments of the invention further encompass novel agents identified by screening assays using LCM, such as the screening assays described herein, as well as methods of using these agents, such as for treatment or diagnostic purposes. For example, an agent identified as described herein (e.g., a LCM-modulating agent, a LCM-specific nucleic acid molecule such as an RNAi or antisense molecule, a LCM-specific antibody, a LCM-specific antibody-drug conjugate, or a LCM-binding partner) can be used in an animal or other model, such as to determine efficacy, toxicity, or side effects of treatment with the agent.

Modulators of LCM protein activity, such as modulators identified according to the drug screening assays described herein, can be used to treat a individual with a disorder mediated by a LCM, e.g., by treating cells or tissues that express LCM at a differential level. Methods of treatment can include the step of administering a modulator of LCM activity in a pharmaceutical composition to a individual in need of such treatment.

In certain exemplary embodiments, if decreased expression or activity of a protein is desired, an antibody to the protein or an inhibitor/antagonist and the like, or a pharmaceutical agent containing one or more of these molecules, can be administered to an individual. In other exemplary embodiments, if increased expression or activity of a protein is desired, the protein itself or an agonist/enhancer and the like, or a pharmaceutical agent containing one or more of these molecules, can be administered. Administration can be effected by methods well known in the art and may include delivery by an antibody specifically targeted to the protein. Neutralizing antibodies, which inhibit dimer formation, can be used when decreased expression or activity of a protein is desired.

Although modulating agents can be administered in a pure or substantially pure form, modulating agents can also be administered as pharmaceutical compositions, formulations, or preparations with a carrier. Exemplary formulations of the invention, such as for human or veterinary use, comprise a suitable active LCM-modulating agent, together with one or more pharmaceutically acceptable carriers and, optionally, other therapeutic ingredients. The carrier(s) are "acceptable" in the sense of being compatible with other ingredients of a formulation and not deleterious to the recipient thereof. The formulations can be presented in unit dosage form and can be prepared by any method known to the skilled artisan.

Examples of suitable pharmaceutical carriers include proteins such as albumins (e.g., U.S. Pat. No. 4,507,234), peptides and polysaccharides such as aminodextran (e.g., U.S. Pat. No. 4,699,784), and water. A carrier can also bear an agent by noncovalent bonding or by encapsulation, such as within a liposome vesicle (e.g., U.S. Pat. Nos. 4,429,008 and 4,873,088). Carriers specific for radionuclide agents include radiohalogenated small molecules and chelating compounds. For example, U.S. Pat. No. 4,735,792 discloses representative radiohalogenated small molecules and their synthesis. A radionuclide chelate can be formed from chelating compounds that include those containing nitrogen and sulfur atoms as the donor atoms for binding the metal, metal oxide, radionuclide. For example, U.S. Pat. No. 4,673,562 discloses representative chelating compounds and their synthesis.

Methods of preparing pharmaceutical formulations typically include the step of bringing into association the active ingredient with the carrier, which constitutes one or more accessory ingredients. Formulations can be prepared by uniformly and intimately bringing into association the active ingredient with liquid carriers or finely divided solid carriers, or both, and then, if necessary, shaping the product into the desired formulation.

Formulations suitable for intravenous, intramuscular, subcutaneous, or intraperitoneal administration can comprise sterile aqueous solutions of the active ingredient with solutions, which can be isotonic with the blood of the recipient. Such formulations can be prepared by dissolving solid active ingredient in water containing physiologically compatible substances such as sodium chloride (e.g., 0.1-2.0 M), glycine, and the like, and having a buffered pH compatible with physiological conditions to produce an aqueous solution, and rendering the solution sterile. These may be present in unit or multi-dose containers, for example, sealed ampoules or vials.

Exemplary formulations of the invention can incorporate a stabilizer. Exemplary stabilizers include polyethylene glycol, proteins, saccharides, amino acids, inorganic acids, detergents, and organic acids, which can be used either alone or as admixtures. These stabilizers can be incorporated in an amount of, for example, 0.11-10,000 parts by weight per part by weight of an agent. If two or more stabilizers are to be used, their total amount can be within the range specified above. These stabilizers can be used in aqueous solutions at an appropriate concentration and pH. The specific osmotic pressure of such aqueous solutions can be in the range of 0.1-3.0 osmoles, preferably in the range of 0.8-1.2. The pH of the aqueous solution can be adjusted to be within the range of 5.0-9.0, preferably within the range of 6-8. In formulating an antibody or antibody-drug conjugate, an anti-adsorption agent can be used.

Additional pharmaceutical methods can be employed to control duration of action. Controlled release can be achieved through the use of polymer to complex or absorb the proteins or their derivatives. Controlled delivery can be achieved by selecting appropriate macromolecules (e.g., polyester, polyamino acids, polyvinyl, pyrrolidone, ethylenevinylacetate, methylcellulose, carboxymethylcellulose, or protamine sulfate) and the concentration of macromolecules as well as the methods of incorporation in order to control release. Another possible method to control the duration of action by controlled-release preparations is to incorporate an anti-LCM antibody into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, by coacervation techniques or by interfacial polymerization, for example, hydroxymethylcellulose or gelatin-microcapsules and poly(methylmethacylate) microcapsules, respectively, or in colloidal drug delivery systems, for example, liposomes, albumin microspheres, microemulsions, nanoparticles, and nanocapsules or in macroemulsions.

When oral preparations are desired, the compositions can be combined with typical carriers, such as lactose, sucrose, starch, talc magnesium stearate, crystalline cellulose, methyl cellulose, carboxymethyl cellulose, glycerin, sodium alginate or gum arabic, among others.

Any of the therapeutic agents provided herein may be administered in combination with other therapeutic agents. Selection of agents for use in combination therapy can be made by one of ordinary skill in the art according to conventional pharmaceutical principles. A combination of therapeutic agents may act synergistically to affect treatment of a particular disorder at a lower dosage of each agent.

7. Methods of Detection and Diagnosis Based on LCM Proteins

LCM proteins are useful for diagnosing a disease, particularly diseases in which the protein is over- or under-expressed, especially cancer, and particularly lung cancer. The diagnostic methods may be further suitable for monitoring disease progression in patients undergoing treatment, or for testing for reoccurrence of disease in patients who were previously treated for a disease, for example. Accordingly, exemplary embodiments of the invention provide methods for detecting the presence of, or abundance levels of, a LCM protein in a biological sample.

In vitro techniques for detection of proteins include, but are not limited to, enzyme linked immunosorbent assays (ELISAs), Western blots, immunoprecipitations, and immunofluorescence using a detection reagent, such as an antibody or protein binding agent. Alternatively, a protein can be detected in vivo in a individual by introducing into the individual a labeled antibody (or other types of detection agent) specific for the protein marker. For example, an antibody can be labeled with a radioactive marker whose presence and location in a individual can be detected by standard imaging techniques. Also useful are methods that detect variants of a protein (e.g., allelic variants or mutations) and methods that detect fragments of a protein in a sample.

Examples of immunoassays that can be used in accordance with exemplary embodiments of the invention include, but are not limited to, competitive and non-competitive assays using techniques such as Western blots, radioimmunoassays, ELISA, "sandwich" immunoassays, immunoprecipitation assays, precipitation reactions, gel diffusion precipitin reactions, immunodiffusion assays, agglutination assays, complement-fixation assays, immunoradiometric assays, fluorescent immunoassays, and protein A immunoassays, as well as fluorescence polarization immunoassay (FPIA), fluorescence immunoassay (FIA), enzyme immunoassay (EIA), and nephelometric inhibition immunoassay (NIA). Immunoassays such as these are well known in the art and are described in, for example, Ausubel et al., Current Protocols in Molecular Biology, 1992-2006.

For example, ELISA can be used to detect or quantify one or more LCM. For example, ELISA (or other types of LCM assays) can be used to detect LCM in, for example, a high-risk individual or population, in an individual suspected of having lung cancer, or in an individual with no suspicion of having lung cancer (e.g., an individual undergoing routine screening for lung cancer).

In certain exemplary ELISA methods, an antibody that specifically binds to an LCM antigen may be coated to the well of a suitable container (e.g., a 96 well microtiter plate), a patient sample (e.g., a serum sample) can be added to the well and incubated for a period of time, and the presence of the LCM antigen in the patient sample can be detected upon binding of the LCM antigen in the patient sample to the antibody that is coated to the well. In this instance, a second antibody conjugated to a detectable moeity may optionally be added following the addition of the patient sample to the coated well. ELISA methods such as these may be modified or optimized as desired.

Further, instead of coating the well with an antibody to an LCM antigen, the LCM antigen itself may be coated to the well. Thus, in certain exemplary ELISA methods, an LCM antigen can be coated to the well of a suitable container (e.g., a 96 well microtiter plate), an antibody (which may optionally be conjugated to a detectable moiety such as an enzymatic substrate like horseradish peroxidase or alkaline phosphatase) to the LCM antigen can be added to the well and incubated for a period of time, and the presence of the LCM antigen can be detected. The antibody to the LCM antigen does not have to be conjugated to a detectable moiety; for example, a second antibody (which recognizes the antibody to the LCM antigen) conjugated to a detectable moeity may be added to the well. ELISA methods such as these may be modified or optimized as desired.

Proteins can be isolated from a biological sample (such as from a patient having a disease) and assayed for the presence of a mutation. A mutation can include, for example, one or more amino acid substitutions, deletions, insertions, rearrangements (such as from aberrant splicing events), or inappropriate post-translational modifications. Examples of analytic methods useful for detecting mutations in a protein include, but are not limited to, altered electrophoretic mobility, altered tryptic peptide digest, altered protein activity in cell-based or cell-free assays, alteration in substrate or antibody-binding patterns, altered isoelectric point, and direct amino acid sequencing.

Information obtained by detecting a protein can be used, for example, to determine prognosis and appropriate course of treatment for a disease. For example, individuals with a particular LCM expression level or stage of disease may respond differently to a given treatment that individuals lacking LCM expression, or individuals over- or under-expressing LCM. Information obtained from diagnostic methods of the invention can provide for the personalization of diagnosis and treatment.

In exemplary embodiments, the invention provides methods for diagnosing disease (including, for example, monitoring treatment response or recurrence of disease following treatment) in a individual comprising: determining the abundance level of LCM (e.g., LCM protein or nucleic acid, or protein or nucleic acid fragments thereof) in a test sample from the individual; wherein a difference in the abundance level of LCM relative to the abundance level of LCM in a test sample from a healthy individual, or the level established for a healthy individual, is indicative of disease.

Exemplary embodiments of the invention provide methods for diagnosing diseases having differential protein expression. For example, normal, control, or standard values (e.g., that represent typical expression levels of a protein in healthy individuals) can be established, such as by combining body fluids, tissues, or cell extracts taken from a normal healthy mammalian or human individual with specific antibodies to a protein under conditions for complex formation. Standard values for complex formation in normal and disease tissues can be established by various methods, such as photometric means. Complex formation, as it is expressed in a test sample, can be compared with the standard values. Deviation from a normal standard and toward a disease standard can provide parameters for disease diagnosis or prognosis while deviation away from a disease standard and toward a normal standard can be used to evaluate treatment efficacy, for example.

Immunological methods for detecting and measuring complex formation as a measure of protein expression using either specific polyclonal or monoclonal antibodies are known in the art. Examples of such techniques include ELISAs, radioimmunoassays (RIAs), flow cytometry (also referred to as fluorescence-activated cell sorting, or FACS), and antibody arrays. Such immunoassays typically involve the measurement of complex formation between a protein and its specific antibody. These assays and their quantitation against purified, labeled standards are well known in the art (Ausubel, supra, unit 10.1-10.6). For example, a two-site, monoclonal-based immunoassay utilizing antibodies reactive to two non-interfering epitopes can be utilized, and competitive binding assay can also be utilized (Pound (1998) Immunochemical Protocols, Humana Press, Totowa N.J.).

For diagnostic applications, an antibody can be labeled with a detectable moiety (interchangeably referred to as a "label" or "detectable substance"), such as to facilitate detection by various imaging methods. Methods for detection of labels include, but are not limited to, fluorescence, light, confocal, and electron microscopy; magnetic resonance imaging and spectroscopy; fluoroscopy, computed tomography and positron emission tomography. Examples of suitable labels include, but are not limited to, fluorescein, rhodamine, eosin and other fluorophores, radioisotopes, gold, gadolinium and other lanthanides, paramagnetic iron, fluorine-18 and other positron-emitting radionuclides. Additionally, labels may be bi- or multi-functional and be detectable by more than one of the methods listed. Antibodies may be directly or indirectly labeled. Attachment of labels to antibodies includes covalent attachment of a label, incorporation of a label into an antibody, and covalent attachment of a chelating compound for binding of a label, among others well known in the art.

Numerous detectable moieties are available for labeling antibodies, including, but not limited to, those in the following categories:

(a) Radioisotopes, such as $^{36}$S, $^{14}$C, $^{125}$I, $^{3}$H, and $^{131}$I. An antibody can be labeled with a radioisotope using the techniques described in Current Protocols in Immunology, vol 1-2, Coligen et al., Ed., Wiley-Interscience, New York, Pubs. (1991-2006), for example, and radioactivity can be measured using scintillation counting.

(b) Fluorescent labels such as rare earth chelates (europium chelates) or fluorescein and its derivatives, rhodamine and its derivatives, dansyl, Lissamine, phycoerythrin and Texas Red are available. Fluorescent labels can be conjugated to an antibody using the techniques disclosed in Current Protocols in Immunology, supra, for example. Fluorescence can be quantified using a fluorometer.

(c) Various enzyme-substrate labels are available (e.g., U.S. Pat. Nos. 4,275,149 and 4,318,980). An enzyme generally catalyzes a chemical alteration of a chromogenic substrate which can be measured using various techniques. For example, an enzyme may catalyze a color change in a substrate, which can be measured spectrophotometrically. Alternatively, an enzyme may alter the fluorescence or chemiluminescence of a substrate. Techniques for quantifying a change in fluorescence are described herein and well known in the art A chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al., Methods for the Preparation of Enzyme-Antibody Conjugates for Use in Enzyme Immunoassay, in Methods in Enzyme. (Ed. J. Langone & H. Van Vunakis), Academic press, New York, 73: 147-166 (1981).

A label can be indirectly conjugated with an antibody. The skilled artisan will be aware of various techniques for achieving this. For example, an antibody can be conjugated with biotin and any of the three broad categories of labels mentioned above can be conjugated with avidin, or vice versa. Biotin binds selectively to avidin and thus, the label can be conjugated with the antibody in this indirect manner. Alternatively, to achieve indirect conjugation of a label with an antibody, an antibody can be conjugated with a small hapten (e.g., digoxin) and one of the different types of labels mentioned above can be conjugated with an anti-hapten antibody (e.g., anti-digoxin antibody). Thus, indirect conjugation of a label with an antibody can be achieved.

Antibodies can be used to isolate LCM proteins by standard techniques, such as affinity chromatography or immunoprecipitation, and antibodies can facilitate the purification of the natural protein from cells and recombinantly-produced protein expressed in host cells. Biological samples can be tested directly for the presence of a LCM protein by assays (e.g., ELISA or radioimmunoassay) and format (e.g., microwells, dipstick, etc., as described in International Patent Publication WO 93/03367). Alternatively, proteins in a sample can be size separated (e.g., by polyacrylamide gel electrophoresis (PAGE)), in the presence or absence of sodium dodecyl sulfate (SDS), and the presence of a LCM detected by immunoblotting (e.g., Western blotting).

Antibody binding can also be detected by "sandwich" immunoassays, immunoradiometric assays, gel diffusion precipitation reactions, immunodiffusion assays, in situ immunoassays (e.g., using colloidal gold, enzyme or radio-isotope labels, for example), precipitation reactions, agglutination assays (e.g., gel agglutination assays, hemagglutination assays, etc.), complement fixation assays, immunofluorescence assays, protein A assays, and immunoelectrophoresis assays, etc.

In certain exemplary embodiments, antibody binding can be detected by detecting a label on the primary antibody. In other exemplary embodiments, a primary antibody can be detected by detecting binding of a secondary antibody or reagent to the primary antibody. In further exemplary embodiments, the secondary antibody is labeled. Numerous means are known in the art for detecting binding in an immunoassay and are within the scope of the invention. In some embodiments, an automated detection assay is utilized. Methods for the automation of immunoassays are well known in the art (e.g., U.S. Pat. Nos. 5,885,530: 4,981,785: 6,159,750: and 5,358,691, each of which is herein incorporated by reference). In some embodiments, the analysis and presentation of results are also automated. For example, in some embodiments, software that generates a prognosis based on the presence or absence of one or more antigens can be implemented.

Competitive binding assays typically rely on the ability of a labeled standard to compete with a test sample for binding with a limited amount of antibody. The amount of antigen in the test sample is inversely proportional to the amount of standard that becomes bound to the antibodies. To facilitate determining the amount of standard that becomes bound, the antibodies generally are insolubilized before or after the competition. As a result, the standard and test sample that are bound to the antibodies can be separated from the standard and test sample that remain unbound.

Sandwich assays typically involve the use of two antibodies, each capable of binding to a different immunogenic portion, or epitope, of the protein to be detected. In typical sandwich assays, the test sample to be analyzed is bound by a first antibody, which is immobilized on a solid support, and thereafter a second antibody binds to the test sample, thus forming an insoluble three-part complex (e.g., U.S. Pat. No. 4,376,110). The second antibody can itself be labeled with a detectable moiety (direct sandwich assays) or can be measured using an anti-immunoglobulin antibody that is labeled with a detectable moiety (indirect sandwich assay). For example, one type of sandwich assay is an ELISA assay, in which case the detectable moiety is an enzyme.

Antibodies can also be used for in vivo diagnostic assays. Generally, an antibody can be labeled with a radionuclide (such as $^{111}$In, $^{99}$Tc, $^{14}$C, $^{131}$I, $^{3}$H, $^{32}$P or $^{35}$S), so that disease cells or tissues can be localized using immunoscintiography, for example. In certain embodiment, antibodies or fragments thereof bind to the extracellular domains of two or more LCM proteins and the affinity value (Kd) is less than $1 \times 10^8$ M.

For immunohistochemistry, a disease tissue sample may be, for example, fresh or frozen or may be embedded in paraffin and fixed with a preservative such as formalin. A fixed or embedded section can be contacted with a labeled primary antibody and secondary antibody, wherein the antibody is used to detect LCM protein expression in situ.

Antibodies can be used to detect a marker protein in situ, in vitro, or in a cell lysate or supernatant in order to evaluate the abundance and pattern of expression. Also, antibodies can be used to assess abnormal tissue distribution or abnormal expression during development or progression of a biological condition. Antibodies against LCM proteins are useful for detecting the presence of the proteins in cells or tissues to determine the pattern of expression of the proteins among various tissues in an organism and over the course of the organism's development.

Further, antibodies can be used to assess expression in disease states such as in active stages of a disease or in an individual with a predisposition toward disease related to the protein's function. When a disorder is caused by inappropriate tissue distribution, developmental expression, or level of expression of a protein, or expressed/processed form, for example, an antibody can be prepared against the normal protein. If a disorder is characterized by a specific mutation in a protein, antibodies specific for the mutant protein can be used to assay for the presence of the specific mutant protein and to target the mutant protein for therapeutic purposes. Antibodies are also useful as diagnostic tools, as immunological markers for aberrant protein analyzed by electrophoretic mobility, isoelectric point, tryptic peptide digest, and other physical assays known in the art.

Certain exemplary diagnostic methods of the invention can also include monitoring a treatment modality. Accordingly, where treatment is ultimately aimed at correcting, for example, the function, activity, expression level, tissue distribution, or developmental expression of a protein, antibodies directed against the protein can be used to monitor therapeutic efficacy and to modify a treatment regimen as necessary.

Additionally, antibodies to a marker protein are useful in pharmacogenomic analysis. For example, antibodies prepared against polymorphic proteins can be used to identify individuals that require modified treatment modalities. Moreover, the marker proteins and antibodies thereto can be used for clinical trials, such as to identify individuals that should be included (e.g., individuals more likely to respond to a therapy) or excluded (e.g., individuals less likely to respond to a therapy, or individuals more likely to experience harmful side effects from a therapy) from a clinical trial.

The invention also encompasses kits for using antibodies to detect the presence of a marker protein in a biological sample. An exemplary kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be configured to detect a single marker protein or epitope or can be configured to detect one of a multitude of epitopes, such as in an antibody detection array.

LC/MS and ICAT

In certain exemplary embodiments, the invention provides detection or diagnostic methods of a LCM by using LC/MS. Proteins can be prepared from cells by methods known in the art (e.g., Zhang et al., *Nature Biotechnology* 21(6):660-666 (2003)). The differential expression of proteins in disease and healthy (or drug-resistant and drug-sensitive, for example) samples can be quantitated using mass spectrometry and ICAT (Isotope Coded Affinity Tag) labeling, which is known in the art. ICAT is an isotope label technique that allows for discrimination between two populations of proteins, such as a healthy and a disease sample. Over-expression or under-expression of a LCM protein, as measured by ICAT, can indicate, for example, the likelihood of having or developing a disease or an associated pathology.

LC/MS spectra can be collected for labeled samples and processed as follows. The raw scans from the LC/MS instrument can be individualed to peak detection and noise reduction software. Filtered peak lists can then be used to detect 'features' corresponding to specific peptides from the original sample(s). Features are characterized by their mass/charge ratio, charge, retention time, isotope pattern, and/or intensity, for example.

The intensity of a peptide present in both healthy and disease samples can be used to calculate the differential expression, or relative abundance, of the peptide. The intensity of a peptide found exclusively in one sample can be used to calculate a theoretical expression ratio for that peptide (singleton). Expression ratios can be calculated for each peptide in an assay or experiment.

Statistical tests can be performed to assess the robustness of the data and select statistically significant differentials. To ensure the accuracy of data, the following steps can be taken: a) ensure that similar features are detected in all replicates of an experiment; b) assess the distribution of the log ratios of all peptides (a Gaussian is expected); c) calculate the overall pair wise correlations between ICAT LC/MS maps to ensure that the expression ratios for peptides are reproducible across multiple replicates; and d) aggregate multiple experiments in order to compare the expression ratio of a peptide in multiple diseases or disease samples.

8. Methods of Treatment Based on LCM Proteins a. Antibody Therapy

Antibodies of the invention can be used for therapeutic purposes. It is contemplated that antibodies of the invention may be used to treat a mammal, preferably a human, with a disease, especially cancer, and particularly lung cancer. The antibodies can be delivered alone, in a pharmaceutical composition (such as with a carrier), or conjugated to one or more therapeutic agents, for example.

Antibodies can be useful for modulating (e.g., agonizing or antagonizing) protein function, such as for therapeutic purposes. Antibodies can also be useful for inhibiting protein function by, for example, blocking the binding of a LCM protein to a binding partner such as a substrate, which can be useful therapeutically. Antibodies can be prepared against, for example, specific portions of a protein that contain domains required for protein function, or against intact protein that is associated with a cell membrane.

Antibodies of the invention can also be used for enhancing the immune response. The antibodies can be administered in amounts similar to those used for other therapeutic administrations of antibodies. For example, pooled gamma globulin can be administered at a range of about 1 mg to about 100 mg per patient.

Antibodies reactive with LCM proteins can be administered alone or in conjunction with other therapies, such as anti-cancer therapies, to a mammal afflicted with cancer or other disease. Examples of anti-cancer therapies include, but are not limited to, chemotherapy, radiation therapy, and adoptive immunotherapy therapy with TIL (tumor infiltrating lymphocytes).

The selection of an antibody subclass for therapy may depend upon the nature of the antigen to be acted upon. For example, an IgM may be preferred in situations where the antigen is highly specific for the disease marker and rarely occurs on normal cells. However, where the disease-associated antigen is also expressed in normal tissues, although at lower levels, the IgG subclass may be preferred. The IgG subclass may be preferred in these instances because the binding of at least two IgG molecules in close proximity is typically required to activate complement, and therefore less complement-mediated damage may occur in normal tissues that express smaller amounts of the antigen and thus bind fewer IgG antibody molecules. Furthermore, IgG molecules, by being smaller, may be more able than IgM molecules to localize to a diseased tissue.

A mechanism for antibody therapy can be that a therapeutic antibody recognizes a soluble or cell surface marker protein that is expressed (preferably, over-expressed) in a disease cell. By NK cell or complement activation, or conjugation of the antibody with an immunotoxin or radiolabel, the interaction of the antibody with the marker protein can abrogate ligand/receptor interaction or activation of apoptosis, for example.

Potential mechanisms of antibody-mediated cytotoxicity of diseased cells include phagocyte (antibody-dependent cellular cytotoxicity (ADCC)), complement (complement-dependent cytotoxicity (CDC)), naked antibody (receptor cross-linking apoptosis and growth factor inhibition), or targeted payload labeled with a therapeutic agent, such as a radionuclide, immunotoxin, or immunochemotherapeutic or other therapeutic agent.

In certain exemplary embodiments, an antibody is administered to a nonhuman mammal for the purposes of obtaining preclinical data, for example. Exemplary nonhuman mammals to be treated include nonhuman primates, dogs, cats, rodents, and other mammals in which preclinical studies are performed. Such mammals may be established animal models for a disease or may be used to study toxicity of an antibody of interest, for example. Dose escalation studies may be performed in the mammal, for example.

An antibody can be administered to an individual by any suitable means, including parenteral, subcutaneous, intraperitoneal, intrapulmonary, and intranasal, and, if desired for local immunomodulatory treatment, intralesional administration. Parenteral infusions include intramuscular, intravenous, intraarterial, intraperitoneal, or subcutaneous administration. In addition, an antibody can be administered by pulse infusion, particularly with declining doses of the antibody. The dosing can be given by injections, such as intravenous or subcutaneous injections, which may depend in part on whether the administration is brief or chronic.

For the prevention or treatment of a disease, the appropriate dosage of an antibody may depend on the type of disease to be treated, the severity and the course of the disease, whether the antibody is administered for preventive or therapeutic purposes, previous therapy, the patient's clinical history and response to the antibody, and the discretion of the attending physician.

Depending on the type and severity of disease, about 1 μg/kg to 150 mg/kg (e.g., 0.1-20 mg/kg) of antibody can be an initial candidate dosage for administration to a patient, whether, for example, by one or more separate administrations, or by continuous infusion. A typical daily dosage may range from about 1 μg/kg to 100 mg/kg or more, depending on such factors as those mentioned above. An antibody-drug conjugate can be administered from about 1 μg/kg to 50 mg/kg, typically from about 0.1-20 mg/kg, whether, for example, by one or more separate administrations, or by continuous infusion. A typical daily dosage may range from about 0.1 mg/kg to 10 mg/kg, or from about 0.3 mg/kg to about 7.5 mg/kg, depending on such factors as those mentioned above. For repeated administrations over several days or longer, depending on the condition, the treatment can be sustained until a desired suppression of disease symptoms occurs. However, other dosage regimens may be useful. Therapy progress can be monitored by conventional techniques and assays.

Antibody composition can be formulated, dosed, and administered in a manner consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

An antibody may optionally be formulated with, or administered with, one or more therapeutic agents used to prevent or treat the disorder in question. For example, an antibody can be administered as a co-therapy with a standard of care therapeutic for the specific disease being treated.

b. Other Immunotherapy

An "immunogenic peptide" is a peptide that comprises an allele-specific motif such that the peptide typically will bind an MHC allele (HLA in human) and be capable of inducing a CTL (cytotoxic T-lymphocytes) response. Thus, immunogenic peptides typically are capable of binding to an appropriate class I or II MHC molecule and inducing a cytotoxic T cell or T helper cell response against the antigen from which the immunogenic peptide is derived.

Peptides derived from a LCM protein can be modified to increase their immunogenicity, such as by enhancing the binding of the peptide to the MHC molecules in which the peptide is presented. The peptide or modified peptide can be conjugated to a carrier molecule to enhance the antigenicity of the peptide. Examples of carrier molecules, include, but are not limited to, human albumin, bovine albumin, lipoprotein and keyhole limpet hemo-cyanin ("Basic and Clinical Immunology" (1991) Stites and Terr (eds) Appleton and Lange, Norwalk Conn., San Mateo, Calif.).

Further, amino acid sequence variants of a peptide can be prepared, such as by altering the nucleic acid sequence of the DNA which encodes the peptide, or by peptide synthesis. At the genetic level, these variants can be prepared by, for example, site-directed mutagenesis of nucleotides in the DNA encoding the peptide, thereby producing DNA encoding the variant, and thereafter expressing the DNA in recombinant cell culture. The variants can exhibit the same qualitative biological activity as the nonvariant peptide.

Exemplary embodiments of the invention provide peptides or modified peptides derived from a LCM protein that are differentially expressed in disease. Examples of peptide modifications include, but are not limited to, substitutions, deletions, or additions of one or more amino acids in a given immunogenic peptide sequence, or mutation of existing amino acids within a given immunogenic peptide sequence, or derivatization of existing amino acids within a given immunogenic peptide sequence. Any amino acid in an immunogenic peptide sequence may be modified. In some embodiments, at least one amino acid can be substituted or replaced within the given immunogenic peptide sequence. Any amino acid may be used to substitute or replace a given amino acid within the immunogenic peptide sequence. Modified peptides can include any immunogenic peptide obtained from differentially expressed proteins, which has been modified and exhibits enhanced binding to the MHC molecule with which it associates when presented to a T-cell. These modified peptides can be synthetically or recombinantly produced by conventional methods, for example.

In certain exemplary embodiments of the invention, the peptides comprise, or consist of, sequences of about 5-30 amino acids in length which are immunogenic (i.e., capable of inducing an immune response when injected into a individual).

In certain exemplary embodiments, the peptides may be used, for example, to treat T cell-mediated pathologies. The term "T cell-mediated pathologies" refers to any condition in which an inappropriate T cell response is a component of the pathology. The term is intended to encompass both T cell mediated diseases and diseases resulting from unregulated clonal T cell replication.

Modified (e.g., recombinant) or natural LCM proteins, or fragments thereof, can be used as a vaccine either prophylactically or therapeutically. When provided prophylactically, a vaccine can be provided in advance of any evidence of disease. The prophylactic administration of a disease vaccine may serve to prevent or attenuate a disease in a mammal such as a human.

An exemplary vaccine formulation can comprise an immunogen that induces an immune response directed against a disease-associated antigen such as a LCM protein. For example, a substantially or partially purified LCM protein or fragments thereof can be administered as a vaccine in a pharmaceutically acceptable carrier. An immunogen can be administered in a pure or substantially pure form, or can be administered as a pharmaceutical composition, formulation, or preparation. Exemplary doses of protein that can be administered are about 0.001 to about 100 mg per patient, or about 0.01 to about 100 mg per patient. Immunization can be repeated as necessary until a sufficient titer of anti-immunogen antibody or immune cells has been obtained.

Vaccine can be prepared using, for example, recombinant protein or expression vectors comprising a nucleic acid sequence encoding all or part of a LCM protein. Examples of vectors that can be used in vaccines include, but are not limited to, defective retroviral vectors, adenoviral vectors vaccinia viral vectors, fowl pox viral vectors, or other viral vectors (Mulligan, R. C., (1993) *Science* 260:926-932). The vectors can be introduced into a mammal (e.g., a human) either prior to any evidence of a disease or to mediate regression of a disease in a mammal afflicted with the disease. Examples of methods for administering a viral vector into mammals include, but are not limited to, exposure of cells to the virus ex vivo, or injection of the retrovirus or a producer cell line of the virus into the affected tissue, or intravenous administration of the virus. Alternatively, the vector can be administered locally by direct injection into a disease lesion or topical application in a pharmaceutically acceptable carrier. The quantity of viral vector to be administered can be based on the titer of virus particles. An exemplary range can be about $10^6$ to about $10^{11}$ virus particles per mammal.

After immunization, the efficacy of the vaccine can be assessed by, for example, the production of antibodies or immune cells that recognize the antigen, as assessed by specific lytic activity, specific cytokine production, or disease regression, which can be measured using conventional methods. If the mammal to be immunized is already afflicted with a disease, the vaccine can be administered in conjunction with other therapeutic treatments. Examples of other therapeutic treatments include, but are not limited to, adoptive T cell immunotherapy and coadministration of cytokines or other therapeutic drugs.

In certain embodiments, mammals, preferably humans, at high risk for disease, especially cancer, are prophylactically treated with vaccines of the invention. Examples include, but are not limited to, individuals with a family history of a disease, individuals who themselves have a history of disease (e.g., cancer that has been previously resected and at risk for reoccurrence), or individuals already afflicted with a disease. When provided therapeutically, a vaccine can be provided to enhance the patient's own immune response to a disease antigen. An exemplary vaccine, which acts as an immunogen, can be a cell, cell lysate from cells transfected with a recombinant expression vector, or a culture supernatant containing the expressed protein, for example. Alternatively, an immunogen can be, for example, a partially or substantially purified recombinant protein, peptide, or analog thereof, or a modified protein, peptide, or analog thereof. The proteins or peptides can be, for example, conjugated with lipoprotein or administered in liposomal form or with adjuvant.

Vaccination can be carried out using conventional methods. For example, an immunogen can be used in a suitable diluent such as saline or water, or complete or incomplete adjuvants. Further, an immunogen may or may not be bound to a carrier, including carriers to increase the immunogenicity of the immunogen. Examples of carrier molecules include, but are not limited to, bovine serum albumin (BSA), keyhole limpet hemocyanin (KLH), tetanus toxoid, and the like. An immunogen also may be coupled with lipoproteins or administered in liposomal form or with adjuvants. An immunogen can be administered by any route appropriate for antibody production such as intravenous, intraperitoneal, intramuscular, subcutaneous, and the like. An immunogen can be administered once or at periodic intervals until a significant titer of anti-LCM immune cells or anti-LCM antibody is produced. The presence of anti-LCM immune cells can be assessed by measuring the frequency of precursor CTL (cytotoxic T-lymphocytes) against LCM antigen prior to and after immunization by a CTL precursor analysis assay (Coulie et al., 1992, *International Journal Of Cancer* 50:289-297). An immunoassay can be used to detect antibody in serum.

The safety of a vaccine can be determined by examining the effect of immunization on the general health of an immunized animal (e.g., weight change, fever, change in appetite or behavior, etc.) and looking for pathological changes during autopsies. After initial testing in animals, a vaccine can be tested in patients having a disease of interest. Conventional methods can be used to evaluate the immune response of a patient to determine the efficiency of the vaccine.

In certain exemplary embodiments of the invention, a LCM protein or fragments thereof, or a modified LCM protein, can be exposed to dendritic cells cultured in vitro. The cultured dendritic cells provide a means of producing T-cell dependent antigens comprised of dendritic cell-modified antigen or dendritic cells pulsed with antigen, in which the antigen is processed and expressed on the antigen-activated dendritic cell. The antigen-activated dendritic cells or processed dendritic cell antigens can be used as immunogens for vaccines or for the treatment of diseases. The dendritic cells can be exposed to the antigen for sufficient time to allow the antigens to be internalized and presented on the surface of dendritic cells. The resulting dendritic cells or the dendritic cell-processed antigens can then be administered to an individual in need of therapy. Such methods are described in Steinman et al. (WO93/208185) and in Banchereau et al. (EPO Application 0563485A1).

In certain exemplary embodiments of the invention, T-cells isolated from individuals can be exposed to a LCM protein or fragment thereof, or a modified LCM protein, in vitro and then administered in a therapeutically effective amount to a patient in need of such treatment. Examples of where T-lymphocytes can be isolated include, but are not limited to, peripheral blood cells lymphocytes (PBL), lymph nodes, or tumor infiltrating lymphocytes (TIL). Such lymphocytes can be isolated from the individual to be treated or from a donor by methods known in the art and cultured in vitro (Kawakami et al., 1989, *J. Immunol.* 142: 2453-3461). Lymphocytes can be cultured in media such as RPMI or RPMI 1640 or AIM V for 1-10 weeks. Viability can be assessed by trypan blue dye exclusion assay. Examples of how these sensitized T-cells can be administered to a mammal include, but are not limited to, intravenously, intraperitoneally, or intralesionally. Parameters that can be assessed to determine the efficacy of these sensitized T-lymphocytes include, but are not limited to, production of immune cells in the mammal being treated or tumor regression. Conventional methods can be used to assess these parameters. Such treatment can be given in conjunction with cytokines or gene-modified cells, for example (Rosenberg et al., 1992, *Human Gene Therapy*, 3: 75-90; Rosenberg et al., 1992, *Human Gene Therapy*, 3: 57-73).

9. Screening Methods Using LCM Proteins

Exemplary embodiments of the invention provide methods of screening for agents (interchangeably referred to by such terms as candidate agents, compounds, or candidate compounds) that modulate LCM protein activity (interchangeably referred to as protein function). Examples of candidate agents include, but are not limited to, proteins, peptides, antibodies, nucleic acids (such as antisense and RNAi nucleic acid molecules), and small molecules. Exemplary embodiments of the invention further provide agents identified by these screening methods, and methods of using these agents, such as for treating diseases, especially cancer, and particularly lung cancer.

Exemplary screening methods can typically comprise the steps of (i) contacting a LCM protein with a candidate agent, and (ii) assaying for LCM protein activity, wherein a change in protein activity in the presence of the agent relative to protein activity in the absence of the agent indicates that the agent modulates LCM protein activity.

Other exemplary screening methods can determine a candidate agent's ability to modulate LCM expression. Exemplary methods can typically comprise the steps of (i) contacting a candidate agent with a system that is capable of expressing LCM protein or LCM mRNA, and (ii) assaying for the level of LCM protein or LCM mRNA, wherein a change in the level in the presence of the agent relative to the level in the absence of the agent indicates that the agent modulates LCM expression levels.

Exemplary embodiments of the invention further provide methods to screen for agents that bind to LCM proteins. Exemplary methods can typically comprise the steps of contacting a LCM protein with a test agent and measuring the extent of binding of the agent to the LCM protein.

LCM proteins can be used to identify agents that modulate activity of a protein in its natural state or an altered form that causes a specific disease or pathology. LCM proteins and appropriate variants and fragments can be used in high-throughput screens to assay candidate compounds for their ability to bind to LCM. These compounds can be further screened against functional LCM proteins to determine the effect of the compound on the protein's activity. Further, these compounds can be tested in animal or invertebrate systems to determine activity/effectiveness. Compounds can be identified that activate (agonist) or inactivate (antagonist) LCM proteins to a desired degree.

LCM proteins can be used to screen agents for their ability to stimulate or inhibit interaction between a LCM protein and a target molecule that normally interacts with the LCM protein (e.g., a substrate, an extracellular binding ligand, or a component of a signal pathway that a LCM protein normally interacts with such as a cytosolic signal protein). Exemplary assays can include the steps of combining a LCM protein or fragment thereof with a candidate compound under conditions that allow the LCM protein (or fragment thereof) to interact with a target molecule, and detecting the formation of a complex between the LCM protein and the target molecule or detecting the biochemical consequence of the interaction between the LCM protein and the target molecule, such as any of the associated effects of signal transduction (e.g., protein phosphorylation, cAMP turnover, adenylate cyclase activation, etc.). Any of the biological or biochemical functions mediated by a LCM protein can be used as an endpoint assay to identify an agent that modulates LCM activity.

Candidate compounds or agents include, but are not limited to, 1) peptides such as soluble peptides, including Ig-tailed fusion peptides and members of random peptide libraries (see, e.g., Lam et al., Nature 354:82-84 (1991); Houghten et al., Nature 354:84-86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., Cell 72:767-778 (1993)); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries).

An exemplary candidate compound or agent is a soluble fragment of a LCM that competes for substrate binding. Other exemplary candidate compounds include mutant LCM proteins or appropriate fragments containing mutations that affect LCM function and thus compete for substrate. Accordingly, a fragment that competes for substrate, for example with a higher affinity, or a fragment that binds substrate but does not allow release, is encompassed by the invention.

Compounds can also be screened by using chimeric proteins in which any portion of a protein such as an amino terminal extracellular domain, a transmembrane domain (e.g., transmembrane segments or intracellular or extracellular loops), or a carboxy terminal intracellular domain can be replaced in whole or part by heterologous domains or subregions. For example, a substrate-binding region can be used that interacts with a different substrate than the substrate that is recognized by a native marker protein. Accordingly, a different set of signal transduction components can be available as an end-point assay for activation, thereby allowing assays to be performed in other than the specific host cell from which a marker is derived.

Competition binding assays can also be used to screen for compounds that interact with a marker protein (e.g., binding partners and/or ligands). For example, a test compound can be exposed to a marker protein under conditions that allow the test compound to bind or otherwise interact with the marker protein. Soluble marker protein can also be added to the mixture. If the test compound interacts with the soluble marker protein, it can decrease the amount of complex formed or activity of the marker protein. This type of assay is particularly useful in instances in which compounds are sought that interact with specific regions of a marker protein. Thus, the soluble marker protein that competes with the marker protein can contain peptide sequences corresponding to the marker region of interest.

To perform cell-free drug screening assays, it may be desirable to immobilize either a LCM protein (or fragment thereof) or a molecule that binds the LCM protein (referred to herein as a "binding partner") to facilitate separation of complexes from uncomplexed forms, as well as to facilitate automation of the assays.

Techniques for immobilizing proteins on matrices can be utilized in exemplary drug screening assays. In exemplary embodiments, a fusion protein can be provided which adds a domain that allows a protein to be bound to a matrix. For example, glutathione-S-transferase fusion proteins can be adsorbed onto glutathione SEPHAROSE beads (Sigma Chemical, St. Louis, Mo.) or glutathione derivatized microtitre plates, which are then combined with cell lysates (e.g., $^{35}$S-labeled) and a candidate compound, and the mixture incubated under conditions conducive to complex formation (e.g., at physiological conditions for salt and pH). Following incubation, the beads can be washed to remove any unbound label, and the matrix immobilized and radiolabel determined directly, or in the supernatant after the complexes are dissociated. Alternatively, the complexes can be dissociated from the matrix, separated by SDS-PAGE, and the level of a binding partner found in the bead fraction quantitated from the gel using standard electrophoretic techniques. For example, either a marker protein or a binding partner can be immobilized by conjugation of biotin and streptavidin using techniques well known in the art. Alternatively, antibodies that are reactive with a marker protein but do not interfere with binding of the marker protein to its binding partner can be derivatized to the wells of a plate, and the marker protein trapped in the wells by antibody conjugation. Preparations of a binding partner and a candidate compound can be incubated in marker protein-presenting wells and the amount of complex trapped in the well can be quantitated. Methods for detecting such complexes, in addition to those described for GST-immobilized complexes, include immunodetection of complexes using antibodies reactive with a binding partner, or which are reactive with a marker protein and compete with the binding partner, as well as marker protein-linked assays which rely on detecting an enzymatic activity associated with a binding partner.

In exemplary embodiments of the invention, a LCM protein can be used as a "bait protein" in a two-hybrid assay or three-hybrid assay (see, e.g., U.S. Pat. No. 5,283,317; Zervos et al. (1993) Cell 72:223-232; Madura et al. (1993) J. Biol. Chem. 268:12046-12054; Bartel et al. (1993) Biotechniques 14:920-924; Iwabuchi et al. (1993) Oncogene 8:1693-1696; and Brent WO94/10300), to identify other proteins, which bind to or interact with a LCM protein and are involved in the protein's activity. The two-hybrid system is based on the modular nature of most transcription factors, which typically consist of separable DNA-binding and activation domains. In exemplary embodiments, the two-hybrid assay can utilize two different DNA constructs. In one construct, a gene that encodes a LCM protein can be fused to a gene encoding the DNA binding domain of a known transcription factor (e.g., GAL-4). In the other construct, a DNA sequence from a library of DNA sequences that encode an unidentified protein ("prey" or "sample") can be fused to a gene that encodes the activation domain of the known transcription factor. If the "bait" and the "prey" proteins are able to interact in vivo, forming a LCM-dependent complex, the DNA-binding and activation domains of the transcription factor are brought into close proximity. This proximity allows transcription of a reporter gene (e.g., LacZ), which can be operably linked to a transcriptional regulatory site responsive to the transcription factor. Expression of the reporter gene can be detected and cell colonies containing the functional transcription factor can be isolated and used to obtain the cloned gene that encodes the protein that interacts with the LCM protein.

Agents that modulate a LCM protein can be identified using one or more of the above assays, alone or in combination. For example, a cell-based or cell free system can be used for initial identification of agents, and then activity of the agents can be confirmed in an animal or other model system. Such model systems are well known in the art and can readily be employed in this context.

10. Diagnosis, Treatment, and Screening Methods Using LCM Nucleic Acid Molecules The nucleic acid molecules of the invention are useful, for example, as probes, primers, chemical intermediates, and in biological assays. The nucleic acid molecules are useful as hybridization probes for messenger RNA, transcript/cDNA, and genomic DNA to detect or isolate full-length cDNA and genomic clones encoding a LCM protein, or variants thereof. The nucleic acid molecules are also useful as primers for PCR to amplify any given region of a nucleic acid molecule and are useful to synthesize antisense molecules of desired length and sequence. The nucleic acid molecules are also useful for producing ribozymes corresponding to all, or a part, of the mRNA produced from the nucleic acid molecules described herein.

The nucleic acid molecules are also useful for constructing recombinant vectors. Exemplary vectors include expression vectors that express a portion of, or all of, a LCM protein. The nucleic acid molecules are also useful for expressing antigenic portions of the proteins. The nucleic acid molecules are also useful for constructing host cells expressing a part, or all, of the proteins. The nucleic acid molecules are also useful for constructing transgenic animals expressing all, or a part, of the proteins.

A primer or probe can correspond to any sequence along the entire length of a LCM-encoding nucleic acid molecule. Accordingly, a primer or probe can be derived from 5' non-coding regions, coding regions, or 3' noncoding regions, for example.

Exemplary in vitro techniques for detection of mRNA include Northern hybridizations and in situ hybridizations. Exemplary in vitro techniques for detecting DNA include Southern hybridizations and in situ hybridization. Reverse transcriptase PCR amplification (RT-PCR) and the like can also be used for detecting RNA expression. A specific exemplary method of detection comprises using TaqMan technology (Applied Biosystems, Foster City, Calif.).

a. Methods of Diagnosis Using Nucleic Acids

Nucleic acid molecules of the invention are useful, for example, as hybridization probes for determining the presence, level, form, and/or distribution of nucleic acid expression. Exemplary probes can be used to detect the presence of, or to determine levels of, a specific nucleic acid molecule in cells, tissues, and in organisms. Accordingly, probes corresponding to a LCM described herein can be used to assess expression and/or gene copy number in a given cell, tissue, or organism, which can be applied to, for example, diagnosis of disorders involving an increase or decrease in LCM protein expression relative to normal LCM protein expression levels.

Probes can be used as part of a diagnostic test kit for identifying cells or tissues that express LCM protein differentially, such as by measuring a level of a LCM-encoding nucleic acid (e.g., mRNA or genomic DNA) in a sample of cells from a individual, or determining if a LCM-encoding nucleic acid is mutated.

Exemplary embodiments of the invention encompass kits for detecting the presence of LCM-encoding nucleic acid (e.g., mRNA or genomic DNA) in a biological sample. For example, an exemplary kit can comprise reagents such as a labeled or labelable nucleic acid or agent capable of detecting LCM nucleic acid in a biological sample; means for determining the amount of LCM nucleic acid in the sample; and means for comparing the amount of LCM nucleic acid in the sample with a standard. The compound or agent can be packaged in a suitable container. The kit can further comprise instructions for using the kit to detect LCM nucleic acid.

The nucleic acid molecules are useful in diagnostic assays for qualitative changes in LCM nucleic acid expression, and particularly in qualitative changes that lead to pathology. The nucleic acid molecules can be used to detect mutations in LCM genes and gene expression products such as mRNA. The nucleic acid molecules can be used as hybridization probes to detect naturally occurring genetic mutations in a LCM gene and to determine whether a individual with the mutation is at risk for a disorder caused by the mutation. Examples of mutations include deletions, additions, or substitutions of one or more nucleotides in a gene, chromosomal rearrangements (such as inversions or transpositions), and modification of genomic DNA such as aberrant methylation patterns or changes in gene copy number (such as amplification). Detection of a mutated form of a LCM gene associated with a dysfunction can provide a diagnostic tool for an active disease or susceptibility to disease in instances in which the disease results from overexpression, underexpression, or altered expression of a LCM protein, for example.

Mutations in a LCM gene can be detected at the nucleic acid level by a variety of techniques. For example, genomic DNA, RNA, or cDNA can be analyzed directly or can be amplified (e.g., using PCR) prior to analysis. In certain exemplary embodiments, detection of a mutation involves the use of a probe/primer in a PCR reaction (see, e.g. U.S. Pat. Nos. 4,683,195 and 4,683,202), such as anchor PCR or RACE PCR, or, alternatively, in a ligation chain reaction (LCR) (see, e.g., Landegran et al., *Science* 241:1077-1080 (1988) and Nakazawa et al., *PNAS* 91:360-364 (1994)), the latter of which can be particularly useful for detecting point mutations in a gene (see Abravaya et al., *Nucleic Acids Res.* 23:675-682 (1995)). Exemplary methods such as these can include the steps of collecting a sample of cells from a patient, isolating nucleic acid (e.g., genomic, mRNA, or both) from the cells of the sample, contacting the nucleic acid with one or more primers which specifically hybridize to a marker nucleic acid under conditions such that hybridization and amplification of the marker nucleic acid (if present) occurs, and detecting the presence or absence of an amplification product, or detecting the size of the amplification product and comparing the length to a control sample. Deletions and insertions can be detected by a change in size of the amplified product compared to a normal genotype. Point mutations can be identified by hybridizing amplified DNA to normal RNA or antisense DNA sequences, for example.

Alternatively, mutations in a LCM gene can be identified, for example, by alterations in restriction enzyme digestion patterns as determined by gel electrophoresis. Further, sequence-specific ribozymes (U.S. Pat. No. 5,498,531) can be used to identify the presence of specific mutations by development or loss of a ribozyme cleavage site. Perfectly matched sequences can be distinguished from mismatched sequences by nuclease cleavage digestion assays or by differences in melting temperature.

Sequence changes at specific locations can be assessed by nuclease protection assays such as RNase and S1 protection, or chemical cleavage methods. Furthermore, sequence differences between a mutant LCM gene and a corresponding wild-type gene can be determined by direct DNA sequencing. A variety of automated sequencing procedures can be utilized when performing diagnostic assays (Naeve, C. W., (1995) Biotechniques 19:448), including sequencing by mass spectrometry (e.g., PCT International Publication No. WO 94/16101; Cohen et al., Adv. Chromatogr. 36:127-162 (1996); and Griffin et al., Appl. Biochem. Biotechnol. 38:147-159 (1993)).

Other methods for detecting mutations in a nucleic acid include methods in which protection from cleavage agents is used to detect mismatched bases in RNA/RNA or RNA/DNA duplexes (Myers et al., Science 230:1242 (1985)); Cotton et al., PNAS 85:4397 (1988); Saleeba et al., Meth. Enzymol. 217:286-295 (1992)), electrophoretic mobility of mutant and wild type nucleic acid is compared (Orita et al., PNAS 86:2766 (1989); Cotton et al., Mutat. Res. 285:125-144 (1993); and Hayashi et al., Genet. Anal. Tech. Appl. 9:73-79 (1992)), and movement of mutant or wild-type fragments in polyacrylamide gels containing a gradient of denaturant is assayed using denaturing gradient gel electrophoresis (DGGE) (Myers et al., Nature 313:495 (1985)). Examples of other techniques for detecting point mutations include selective oligonucleotide hybridization, selective amplification, and selective primer extension.

b. Methods of Monitoring Treatment and Pharmacogenomic Methods Using Nucleic Acids Nucleic acid molecules of the invention are also useful for monitoring the effectiveness of modulating agents on the expression or activity of a LCM gene, such as in clinical trials or in a treatment regimen. For example, the gene expression pattern of a LCM gene can serve as a barometer for the continuing effectiveness of treatment with a compound, particularly with compounds to which a patient can develop resistance. The gene expression pattern can also serve as a marker indicative of a physiological response of the affected cells to the compound. For example, based on monitoring nucleic acid expression, the administration of a compound can be increased or alternative compounds to which the patient has not become resistant can be administered instead. Similarly, if the level of nucleic acid expression falls below a desirable level, administration of the compound can be commensurately decreased.

The nucleic acid molecules are also useful for testing an individual for a genotype that, while not necessarily causing a disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules provided herein can be used to assess the mutation content of a marker gene in an individual in order to select an appropriate compound or dosage regimen for treatment. For example, marker nucleic acid molecules having genetic variations that affect treatment can provide diagnostic markers that can be used to tailor treatment to an individual. Accordingly, the production of recombinant cells and animals having these genetic variations allows effective clinical design of treatment compounds and dosage regimens, for example.

c. Methods of Treatment Using Nucleic Acids

Nucleic acid molecules of the invention are useful to design antisense constructs to control LCM gene expression in cells, tissues, and organisms. An antisense nucleic acid molecule typically blocks translation of mRNA into LCM protein by hybridizing to marker mRNA in a sequence-specific manner. Nucleic acid molecules of the invention can also be used to specifically suppress gene expression by methods such as RNA interference (RNAi). RNAi and antisense-based gene suppression are well known in the art (e.g., Science 288:1370-1372, 2000). RNAi typically operates on a post-transcriptional level and is sequence specific. RNAi and antisense nucleic acid molecules are useful for treating diseases, especially cancer. RNAi fragments, particularly double-stranded (ds) RNAi, as well as antisense nucleic acid molecules can also be used to generate loss-of-function phenotypes by suppressing gene expression. Accordingly, exemplary embodiments of the invention provide RNAi and antisense nucleic acid molecules, and methods of using these RNAi and antisense nucleic acid molecules, such as for therapy or for modulating cell function. Nucleic acid molecules may also be produced that are complementary to a region of a gene involved in transcription, such as to hybridize to the gene to prevent transcription.

Exemplary embodiments of the invention relate to isolated RNA molecules (double-stranded; single-stranded) that are about 17 to about 29 nucleotides (nt) in length, and more particularly about 21 to about 25 nt in length, which mediate RNAi (e.g., degradation of mRNA, and such mRNA may be referred to herein as mRNA to be degraded). With respect to RNAi, the terms RNA, RNA molecule(s), RNA segment(s), and RNA fragment(s) are used interchangeably to refer to RNA that mediates RNAi. These terms include double-stranded RNA, single-stranded RNA, isolated RNA (e.g., partially purified RNA, essentially pure RNA, synthetic RNA, recombinantly produced RNA), as well as altered RNA that differs from naturally occurring RNA by the addition, deletion, substitution, and/or alteration of one or more nucleotides. Such alterations can include, for example, addition of non-nucleotide material, such as to the end(s) of a 21-25 nt RNA or internally (at one or more nucleotides of the RNA). Nucleotides in exemplary RNA molecules of the invention can also comprise non-standard nucleotides, including non-naturally occurring nucleotides or deoxyribonucleotides. Collectively, all such altered RNAs are referred to as analogs or analogs of naturally-occurring RNA. RNA of 21-25 nt typically need only be sufficiently similar to natural RNA that it has the ability to mediate RNAi. As used herein, the phrase "mediates RNAi" refers to the ability to distinguish which RNAs are to be degraded by RNAi processes. RNA that mediates RNAi directs degradation of particular mRNAs by RNAi processes. Such RNA may include RNAs of various structures, including short hairpin RNA.

In certain exemplary embodiments, the invention relates to RNA molecules of about 21 to about 25 nt that direct cleavage of specific mRNA to which their sequence corresponds. It is not necessary that there be a perfect correspondence (i.e., match) of the sequences, but the correspondence must be sufficient to enable the RNA to direct RNAi cleavage of the marker mRNA (Holen et al., *Nucleic Acids Res.* 33:4704-4710 (2005)). In an exemplary embodiment, the 21-25 nt RNA molecules of the invention comprise a 3' hydroxyl group.

Certain exemplary embodiments of the invention relate to 21-25 nt RNAs of specific genes, produced by chemical synthesis or recombinant DNA techniques, that mediate RNAi. As used herein, the term "isolated RNA" includes RNA obtained by any means, including processing or cleavage of dsRNA, production by chemical synthetic methods, and production by recombinant DNA techniques, for example. Exemplary embodiments of the invention further relate to uses of the 21-25 nt RNAs, such as for therapeutic or prophylactic treatment and compositions comprising 21-25 nt RNAs that mediate RNAi, such as pharmaceutical compositions comprising 21-25 nt RNAs and an appropriate carrier.

Further exemplary embodiments of the invention relate to methods of mediating RNAi of genes of a patient. For example, RNA of about 21 to about 25 nt which targets a specific mRNA to be degraded can be introduced into a patient's cells. The cells can be maintained under conditions allowing degradation of the mRNA, resulting in RNA-mediated interference of the mRNA of the gene in the cells of the patient. Treatment of cancer patients, for example, with RNAi may inhibit the growth and spread of the cancer and reduce tumor size. Treatment of patients using RNAi can also be in combination with other therapies. For example, RNAi can be used in combination with other treatment modalities, such as chemotherapy, radiation therapy, and other treatments. In an exemplary embodiment, a chemotherapy agent is used in combination with RNAi. In a further exemplary embodiment, GEMZAR (gemcitabine HCl) chemotherapy is used with RNAi.

Treatment of certain diseases by RNAi may require introduction of the RNA into the disease cells. RNA can be directly introduced into a cell, or introduced extracellularly into a cavity, interstitial space, into the circulation of a patient, or introduced orally, for example. Physical methods of introducing nucleic acids, such as injection directly into a cell or extracellular injection into a patient, may also be used. RNA may be introduced into vascular or extravascular circulation, the blood or lymph system, or the cerebrospinal fluid, for example. RNA may be introduced into an embryonic stem cell or another multipotent cell, which may be derived from a patient. Physical methods of introducing nucleic acids include injection of a solution containing the RNA, bombardment by particles covered by the RNA, soaking cells or tissue in a solution of the RNA, or electroporation of cell membranes in the presence of the RNA. A viral construct packaged into a viral particle may be used to introduce an expression construct into a cell, with the construct expressing the RNA. Other methods known in the art for introducing nucleic acids to cells may be used, such as lipid-mediated carrier transport, chemical-mediated transport, and the like. The RNA may be introduced along with components that perform one or more of the following activities: enhance RNA uptake by the cell, promote annealing of the duplex strands, stabilize the annealed strands, or otherwise increase inhibition of the marker gene.

Exemplary RNA of the invention can be used alone or as a component of a kit having at least one reagent for carrying out in vitro or in vivo introduction of the RNA to a cell, tissue/fluid, or patient. Exemplary components of a kit include dsRNA and a vehicle that promotes introduction of the dsRNA. A kit may also include instructions for using the kit.

Certain exemplary embodiments of the invention provide compositions and methods for cleavage of mRNA by ribozymes having nucleotide sequences complementary to one or more regions in the mRNA, thereby attenuating the translation of the mRNA. Examples of regions in mRNA that can be targeted by ribozymes include coding regions, particularly coding regions corresponding to catalytic or other functional activities of a marker protein, such as substrate binding. These compositions and methods may be used to treat a disorder characterized by abnormal or undesired marker nucleic acid expression.

In certain exemplary embodiments, nucleic acid molecules of the invention may be used for gene therapy in individuals having cells that are aberrant in gene expression of a marker. For example, recombinant cells that have been engineered ex vivo (which can include an individual's own cells) can be introduced into an individual where the cells produce the desired marker protein to thereby treat the individual.

d. Methods of Screening Using Nucleic Acids

Nucleic acid expression assays are useful for drug screening to identify compounds that modulate LCM nucleic acid expression.

Exemplary embodiments of the invention thus provide methods for identifying a compound that can be used to treat a disease associated with differential expression of a LCM gene, especially cancer. Exemplary methods can typically include assaying the ability of a compound to modulate the expression of a marker nucleic acid to thereby identify a compound that can be used to treat a disorder characterized by undesired marker nucleic acid expression. The assays can be performed in cell-based or cell-free systems. Examples of cell-based assays include cells naturally expressing marker nucleic acid or recombinant cells genetically engineered to express specific marker nucleic acid sequences.

Assays for marker nucleic acid expression can involve direct assay of marker nucleic acid levels, such as mRNA levels, or on collateral compounds involved in a signal pathway. Further, the expression of genes that are up- or down-regulated in response to a signal pathway can also be assayed. In these embodiments, the regulatory regions of these genes can be operably linked to a reporter gene such as luciferase.

Thus, in exemplary embodiments, modulators of gene expression of a marker can be identified in methods wherein a cell is contacted with a candidate agent and the expression of marker mRNA determined. The level of expression of marker mRNA in the presence of the candidate agent is compared to the level of expression of marker mRNA in the absence of the candidate agent. The candidate agent can then be identified as a modulator of marker nucleic acid expression based on this comparison and may be used, for example, to treat a disorder characterized by aberrant marker nucleic acid expression. When expression of marker mRNA is statistically significantly greater in the presence of the candidate agent than in its absence, the candidate agent is identified as a stimulator (agonist) of nucleic acid expression. When nucleic acid expression is statistically significantly less in the presence of the candidate agent than in its absence, the candidate compound is identified as an inhibitor (antagonist) of nucleic acid expression.

11. Arrays and Expression Analysis

"Array" (interchangeably referred to as "microarray") typically refers to an arrangement of at least one, but more typically at least two, nucleic acid molecules, proteins, or antibodies on a substrate. In certain exemplary arrangements, at least one of the nucleic acid molecules, proteins, or antibodies typically represents a control or standard, and other nucleic acid molecules, proteins, or antibodies are of diagnostic or therapeutic interest. In exemplary embodiments, the arrangement of nucleic acid molecules, proteins, or antibodies on the substrate is such that the size and signal intensity of each labeled complex (e.g., formed between each nucleic acid molecule and a complementary nucleic acid, or between each protein and a ligand or antibody, or between each antibody and a protein to which the antibody specifically binds) is individually distinguishable.

An "expression profile" is a representation of marker expression in a sample. A nucleic acid expression profile can be produced using, for example, arrays, sequencing, hybridization, or amplification technologies for nucleic acids from a sample. A protein expression profile can be produced using, for example, arrays, gel electrophoresis, mass spectrometry, or antibodies (and, optionally, labeling moieties) which specifically bind proteins. Nucleic acids, proteins, or antibodies can be attached to a substrate or provided in solution, and their detection can be based on methods well known in the art.

A substrate includes, but is not limited to, glass, paper, nylon or other type of membrane, filter, chip, metal, or any other suitable solid or semi-solid (e.g., gel) support.

Exemplary arrays can be prepared and used according to the methods described in U.S. Pat. No. 5,837,832; PCT application WO95/11995; Lockhart et al., 1996, *Nat. Biotech.* 14: 1675-1680; Schena et al., 1996; *Proc. Natl. Acad. Sci.* 93: 10614-10619; and U.S. Pat. No. 5,807,522. Exemplary embodiments of the invention also provide antibody arrays (see, e.g., de Wildt et al. (2000) *Nat. Biotechnol.* 18:989-94).

Certain exemplary embodiments of the invention provide a nucleic acid array for assaying marker expression, which can be composed of single-stranded nucleic acid molecules, usually either synthetic antisense oligonucleotides or fragments of cDNAs, fixed to a solid support. The oligonucleotides can be, for example, about 6-60 nucleotides in length, about 15-30 nucleotides in length, or about 20-25 nucleotides in length.

To produce oligonucleotides to a marker nucleic acid molecule for an array, the marker nucleic acid molecule of interest is typically examined using a computer algorithm to identify oligonucleotides of defined length that are unique to the nucleic acid molecule, have a GC content within a range suitable for hybridization, and lack predicted secondary structure that may interfere with hybridization. In certain instances, it may be desirable to use pairs of oligonucleotides on an array. In exemplary embodiments, the "pairs" can be identical, except for one nucleotide (which can be located in the center of the sequence, for example). The second oligonucleotide in the pair (mismatched by one) serves as a control. Any number of oligonucleotide pairs may be utilized.

Oligonucleotides can be synthesized on the surface of a substrate, such as by using a light-directed chemical process or by using a chemical coupling procedure and an ink jet application apparatus (e.g., PCT application W095/251116).

In some exemplary embodiments, an array can be used to diagnose or monitor the progression of disease, for example, by assaying marker expression.

For example, an oligonucleotide probe specific for a marker can be labeled by standard methods and added to a biological sample from a patient under conditions that allow for the formation of hybridization complexes. After an incubation period, the sample can be washed and the amount of label (or signal) associated with hybridization complexes can be quantified and compared with a standard value. If complex formation in the patient sample is significantly altered (higher or lower) in comparison to a normal (e.g., healthy) standard, or is similar to a disease standard, this differential expression can be diagnostic of a disorder.

By analyzing changes in patterns of marker expression, disease may be diagnosed at earlier stages before a patient is symptomatic. In exemplary embodiments of the invention, arrays or marker expression analysis methods can be used to formulate a diagnosis or prognosis, to design a treatment regimen, and/or to monitor the efficacy of treatment. For example, a treatment dosage can be established that causes a change in marker expression patterns indicative of successful treatment, and marker expression patterns associated with the onset of undesirable side effects can be avoided. In further exemplary embodiments, assays of marker expression can be repeated on a regular basis to determine if the level of marker expression in a patient begins to approximate that which is observed in a normal individual. The results obtained from successive assays may be used to show the efficacy of treatment over a period ranging from several days to years, for example.

Exemplary arrays of the invention can also be used to screen candidate agents, such as to identify agents that produce a marker expression profile similar to that caused by known therapeutic agents, with the expectation that agents that cause a similar expression profile of a marker may have similar therapeutic effects and/or modes of action on the marker.

EXAMPLES

Exemplary embodiments of the invention are further described in the following examples, which do not limit the scope of the invention.

1. Tissue Samples and Cell Lines

Tissue Processing and Preparation of Single Cell Suspensions from Tissue Tissue samples (e.g., normal tissues or disease tissues such as surgically resected neoplastic or metastatic lesions) can be procured from clinical sites and transported in transport buffer. Tissues can be collected as remnant tissues following surgical resection of cancer (or other disease) tissues. Remnant tissues are supplied following processing for pathological diagnosis according to proper standards of patient care. Normal tissue specimens can be normal tissue adjacent to tumors (or other disease tissue) that is collected during tumor resection. Normal tissue from healthy patients not having cancer (or other disease of interest) can also be included, such as to reduce the contribution from pre-neoplastic changes that may exist in normal adjacent tissue. Procurement of tissue samples is carried out in an anonymous manner in compliance with federally mandated ethical and legal guidelines (HIPAA) and in accordance with clinical institution ethical review board and internal institutional review board guidelines.

Tissue can be crudely minced and incubated for 20-30 minutes with periodic agitation at 37° C. in Enzyme Combination #1 (200 units collagenase, cat# C5894 Sigma; 126 µg DNAse I, cat#D4513 Sigma (in 10 mM Tris/HCl pH7.5); 50 mM NaCl; 10 mM MgCl2; 0.05% elastase, cat# E7885 Sigma) (additionally, hyaluronidase enzyme may also be utilized). D-PBS is added at 3× the volume of the enzyme combination, the tissue finely minced, and disassociated cells passed through a 200 µm filter. The cells are washed twice with D-PBS. Red blood cells are lysed with PharMLyse (BD Biosciences) when necessary. Cell number and viability are determined by PI exclusion (GUAVA). Cells at a total cell number greater than $20\times10^6$ are sorted using a high-speed sorter (MoFlo Cytomation) for epithelial cells (EpCAM positive).

The remaining undigested tissue is incubated for 20-30 minutes with periodic agitation at 37° C. in Enzyme Combination #2 (1× Liberase Blendzyme 1, cat#988-417 Roche; 1× Liberase Blendzyme 3, cat#814-184 Roche; 0.05% elastase, cat# E7885 Sigma). D-PBS is added at 3× the volume of the enzyme combination, and the tissue finely minced until tissue is completely disassociated. The cells are passed through a 200 µm filter, washed twice with D-PBS, and pooled with cells from the Enzyme Combination #1 digestion.

Cells are passed through a 70 µm filter for single cell suspension, and cell number and viability are determined by PI exclusion (GUAVA). When needed, red blood cells are lysed with PharMLyse (BD Biosciences). Cells are incubated in 20 ml of 1× PharMLyse in D-PBS for 30 seconds with gentle agitation and cells pelleted at 300×g for 5 minutes at 4° C. Cells are washed once in D-PBS and cell number and viability are recalculated by PI exclusion using the GUAVA. Cells at a total cell number greater than $20 \times 10^6$ are sorted using a high-speed sorter (MoFlo Cytomation) for epithelial cells (EpCAM positive).

Single cell suspensions can also be prepared from tissue samples as follows: specimens are washed in DTT for 15 min, digested with Dispase (30-60 min), then filtered twice (380 µm/74 µm) before red blood cells are removed through addition of ACK lysis buffer. Epithelial (EpCAM) and leukocyte (CD45) content and cellular viability (PI exclusion) can be determined through flow cytometry analysis (LSR I, BD Biosciences, San Jose, Calif.).

The epithelial content of both disease and normal specimens can be enriched through depletion of immune CD45-positive cells by flow cytometry or purification of Epithelial Cell Surface Antigen (ECSA/EpCam)-positive cells by bead capture.

Bead capture of epithelial cells can be performed using a Dynal CELLection Epithelial Enrich kit (Invitrogen, Carlsbad, Calif.) as follows. Dynal CELLection beads at a concentration of $2 \times 10^8$ beads are incubated with $1 \times 10^8$ cells in HBSS with 10% fetal calf serum for 30 minutes at 4° C. Cells and beads are placed in a magnet system Dynal MPC for 2 minutes. Bead/cell complexes are washed in RPMI 1640 media with 1% fetal calf serum. Cells are released from the bead complex with 15 minute incubation with DNase with agitation in RPMI with 1% fetal calf serum.

DynalBead cell depletion of CD45 cells can be carried out as follows. DynalBead M-450 CD45 beads and cells are incubated at a concentration of 250 µl beads per $2 \times 10^7$ cells for 30 minutes at 4° C. Bead/cell complexes are washed in DPBS buffer with 2% fetal bovine serum. Cells and beads are placed in a magnet system Dynal MPC for 2 minutes. The supernatant contains EpCAM enriched cells.

Cell Line Culture

Cell lines can be obtained from the American Type Culture Collection (ATCC, Manassas, Va.). For example, lung cancer cell lines and normal control lung cell lines (e.g., Beas2B cells can be used as a normal control lung cell line) can be used, such as to determine the expression levels of markers (e.g., proteins or encoding mRNA transcripts) in lung cancer cells compared with normal lung cells. Cell lines can be grown in a culturing medium that is supplemented as necessary with growth factors and serum, in accordance with the ATCC guidelines for each particular cell line. Cultures are established from frozen stocks in which the cells are suspended in a freezing medium (cell culture medium with 10% DMSO [v/v]) and flash frozen in liquid nitrogen. Frozen stocks prepared in this way are stored in liquid nitrogen vapor. Cell cultures are established by rapidly thawing frozen stocks at 37° C. Thawed stock cultures are slowly transferred to a culture vessel containing a large volume of supplemented culture medium. For maintenance of culture, cells are seeded at $1 \times 10^5$ cells/per ml in medium and incubated at 37° C. until confluence of cells in the culture vessel exceeds 50% by area. At this time, cells are harvested from the culture vessel using enzymes or EDTA where necessary. The density of harvested, viable cells is estimated by hemocytometry and the culture reseeded as above. A passage of this nature is repeated no more than 25 times, at which point the culture is destroyed and reestablished from frozen stocks as described above.

Alternatively, for secreted protein analysis, cells can be grown under routine tissue culture conditions in 490 cm² roller bottles at an initial seeding density of approximately 15 million cells per roller bottle. When the cells reach ~70-80% confluence, the culturing media is removed, the cells are washed 3 times with D-PBS and once with CD293 protein-free media (Invitrogen cat#11913-019), and the culturing media is replaced with CD293 for generating conditioned media. Cells are incubated for 72 hours in CD293 and the media is collected for analysis, such as mass spectrometry analysis of secreted proteins (30-300 ml). Cell debris is removed from the conditioned media by centrifugation at 300 g for 5 minutes and filtering through a 0.2 micron filter prior to analysis.

2. Cloning and Expression of Marker Proteins cDNA Retrieval

Peptide sequences can be searched using the BLAST algorithm against relevant protein sequence databases to identify the corresponding full-length protein (reference sequence). Each full-length protein sequence can then be searched using the BLAST algorithm against a human cDNA clone collection. For each sequence of interest, clones can be pulled and streaked onto LB/Ampicillin (100 µg/ml) plates. Plasmid DNA is isolated using Qiagen spin mini-prep kit and verified by restriction digest. Subsequently, the isolated plasmid DNA is sequence verified against the reference full-length protein sequence. Sequencing reactions are carried out using Applied Biosystems BigDye Terminator kit followed by ethanol precipitation. Sequence data is collected using the Applied Biosystems 3700 Genetic Analyzer and analyzed by alignment to the reference full-length protein sequence using the Clone Manager alignment tool.

PCR

PCR primers are designed to amplify the region encoding the full-length protein and/or any regions of the protein that are of interest for expression (e.g., antigenic or hydrophilic regions as determined by the Clone Manager sequence analysis tool). Primers also contain 5' and 3' overhangs to facilitate cloning (see below). PCR reactions contain 2.5 units Platinum Taq DNA Polymerase High Fidelity (Invitrogen), 50 ng cDNA plasmid template, 1 µM forward and reverse primers, 800 µM dNTP cocktail (Applied Biosystems), and 2 mM MgSO$_4$. After 20-30 cycles (94° C. for 30 seconds, 55° C. for 1 minute, and 73° C. for 2 minutes), the resulting product is verified by sequence analysis and quantitated by agarose gel electrophoresis.

Construction of Entry Clones

PCR products are cloned into an entry vector for use with the Gateway recombination based cloning system (Invitrogen). These vectors include pDonr221, pDonr201, pEntr/D-TOPO, or pEntr/SD/D-TOPO and are used as described in the cloning methods below.

TOPO Cloning into pEntr/D-TOPO or pEntr/SD/D-TOPO

For cloning using this method, the forward PCR primer contains a 5' overhang containing the sequence "CACC". PCR products are generated as described above and cloned into the entry vector using the Invitrogen TOPO® cloning kit.

Reactions are typically carried out at room temperature for 10 minutes and subsequently transformed into TOP10 chemically competent cells (Invitrogen, CA). Candidate clones are picked, and plasmid DNA is prepared using a Qiagen spin mini-prep kit and screened by restriction enzyme digestion. Inserts are subsequently sequence-verified as described above.

Gateway Cloning into pDonr201 or pDonr221

For cloning using this method, PCR primers contain forward and reverse 5' overhangs. PCR products are generated as described above. Protein-encoding nucleic acid molecules are recombined into the entry vector using the Invitrogen Gateway BP Clonase enzyme mix. Reactions are typically carried out at 25° C. for 1 hour, treated with Proteinase K at 37° C. for 10 minutes, and transformed into Library Efficiency DH5αc chemically competent cells (Invitrogen, CA). Candidate clones are picked, plasmid DNA is prepared using a Qiagen spin mini-prep kit, and screened by restriction enzyme digestion. Inserts are subsequently sequence-verified as described above.

Construction of Expression Clones

Protein-encoding nucleic acid molecules are transferred from the entry construct into a series of expression vectors using the Gateway LR Clonase enzyme mix. Reactions are typically carried out for 1 hour at 25° C., treated with Proteinase K at 37° C. for 10 minutes, and subsequently transformed into Library Efficiency DH5a chemically competent cells (Invitrogen). Candidate clones are picked, plasmid DNA is prepared using a Qiagen spin mini-prep kit, and screened by restriction enzyme digestion. Expression vectors include, but are not limited to, pDest14, pDest15, pDest17, pDest8, pDest10 and pDest20. These vectors allow expression in systems such as E. coli and recombinant baculovirus. Other vectors not listed here allow expression in yeast, mammalian cells, or in vitro.

Expression of Recombinant Proteins in E. coli

Constructs are transformed into one or more of the following host strains: BL21 SI, BL21 AI, (Invitrogen), Origami B (DE3), Origami B (DE3) pLysS, Rosetta (DE3), Rosetta (DE3) pLysS, Rosetta-Gami (DE3), Rosetta-Gami (DE3) pLysS, or Rosetta-Gami B (DE3) pLysS (Novagen). The transformants are grown in LB with or without NaCl and with appropriate antibiotics, at temperatures in the range of 20-37° C., with aeration. Expression is induced with the addition of IPTG (0.03-0.30 mM) or NaCl (75-300 mM) when the cells are in mid-log growth. Growth is continued for one to 24 hours post-induction. Cells are harvested by centrifugation in a Sorvall RC-3C centrifuge in a H6000A rotor for 10 minutes at 3000 rpm at 4° C. Cell pellets are stored at −80° C.

Expression of Recombinant Proteins using Baculovirus

Recombinant proteins are expressed using baculovirus in Sf21 fall army worm ovarian cells. Recombinant baculoviruses are prepared using the Bac-to-Bac system (Invitrogen) per the manufacturer's instructions. Proteins are expressed on the large scale in Sf900 μl serum-free medium (Invitrogen) in a 10 L bioreactor tank (27° C., 130 rpm, 50% dissolved oxygen for 48 hours).

3. Recombinant Protein Purification

Recombinant proteins can be purified from E. coli and/or insect cells using a variety of standard chromatography methods. Briefly, cells are lysed using sonication or detergents. The insoluble material is pelleted by centrifugation at 10,000×g for 15 minutes. The supernatant is applied to an appropriate affinity column. For example, His-tagged proteins are separated using a pre-packed chelating sepharose column (Pharmacia) or GST-tagged proteins are separated using a glutathione sepharose column (Pharmacia). After using the affinity column, proteins are further separated using various techniques, such as ion exchange chromatography (columns from Pharmacia) to separate on the basis of electrical charge or size exclusion chromatography (columns from Tosohaas) to separate on the basis of molecular weight, size, and shape.

Expression and purification of the protein can also be achieved using either a mammalian cell expression system or an insect cell expression system. The pUB6/V5-His vector system (Invitrogen, CA) can be used to express cDNA in CHO cells. The vector contains the selectable bsd gene, multiple cloning sites, the promoter/enhancer sequence from the human ubiquitin C gene, a C-terminal V5 epitope for antibody detection with anti-V5 antibodies, and a C-terminal polyhistidine (6×His) sequence for rapid purification on PROBOND resin (Invitrogen, CA). Transformed cells are selected on media containing blasticidin.

*Spodoptera frugiperda* (Sf9) insect cells are infected with recombinant *Autographica californica* nuclear polyhedrosis virus (baculovirus). The polyhedrin gene is replaced with the cDNA by homologous recombination and the polyhedrin promoter drives cDNA transcription. The protein is synthesized as a fusion protein with 6×His which enables purification as described above. Purified proteins can be used to produce antibodies.

4. Chemical Synthesis of Proteins

Proteins or portions thereof can be produced not only by recombinant methods (such as described above), but also by using chemical methods well known in the art. Solid phase peptide synthesis can be carried out in a batchwise or continuous flow process which sequentially adds α-amino- and side chain-protected amino acid residues to an insoluble polymeric support via a linker group. A linker group such as methylamine-derivatized polyethylene glycol is attached to poly(styrene-co-divinylbenzene) to form the support resin. The amino acid residues are N-a-protected by acid labile Boc (t-butyloxycarbonyl) or base-labile Fmoc (9-fluorenylmethoxycarbonyl) groups. The carboxyl group of the protected amino acid is coupled to the amine of the linker group to anchor the residue to the solid phase support resin. Trifluoroacetic acid or piperidine are used to remove the protecting group in the case of Boc or Fmoc, respectively. Each additional amino acid is added to the anchored residue using a coupling agent or pre-activated amino acid derivative, and the resin is washed. The full-length peptide is synthesized by sequential deprotection, coupling of derivitized amino acids, and washing with dichloromethane and/or N,N-dimethylformamide. The peptide is cleaved between the peptide carboxy terminus and the linker group to yield a peptide acid or amide. (Novabiochem 1997/98 Catalog and Peptide Synthesis Handbook, San Diego Calif. pp. S1-S20).

Automated synthesis can also be carried out on machines such as the 431A peptide synthesizer (Applied Bio systems, Foster City, Calif.). A protein or portion thereof can be purified by preparative high performance liquid chromatography and its composition confirmed by amino acid analysis or by sequencing (Creighton, 1984, Proteins, Structures and Molecular Properties, W H Freeman, New York N.Y.).

5. Antibody Production

Polyclonal Antibodies

Polyclonal antibodies against recombinant proteins can be raised in rabbits (Green Mountain Antibodies, Burlington, Vt.). Briefly, two New Zealand rabbits are immunized with 0.1 mg of antigen in complete Freund's adjuvant. Subsequent immunizations are carried out using 0.05 mg of antigen in incomplete Freund's adjuvant at days 14, 21, and 49. Bleeds are collected and screened for recognition of the antigen by solid phase ELISA and Western blot analysis. The IgG fraction is separated by centrifugation at 20,000×g for 20 minutes followed by a 50% ammonium sulfate cut. The pelleted protein is resuspended in 5 mM Tris and separated by ion exchange chromatography. Fractions are pooled based on IgG content. Antigen-specific antibody is affinity purified using Pierce AminoLink resin coupled to the appropriate antigen.

Isolation of Antibody Fragments Directed Against a Marker Protein from a Library of scFvs Naturally occurring V-genes isolated from human PBLs can be constructed into a library of antibody fragments which contain reactivities against a marker protein to which the donor may or may not have been exposed (see, for example, U.S. Pat. No. 5,885,793, incorporated herein by reference in its entirety).

Rescue of the library: A library of scFvs is constructed from the RNA of human PBLs, as described in PCT publication WO 92/01047. To rescue phage displaying antibody fragments, approximately $10^9$ E. coli harboring the phagemid are used to inoculate 50 ml of 2×TY containing 1% glucose and 100 μg/ml of ampicillin (2×TY-AMP-GLU) and grown to an O.D. of 0.8 with shaking. Five ml of this culture is used to innoculate 50 ml of 2×TY-AMP-GLU, 2×$10^8$ TU of delta gene 3 helper (M13 delta gene III, see PCT publication WO 92/01047) are added and the culture incubated at 37° C. for 45 minutes without shaking and then at 37° C. for 45 minutes with shaking. The culture is centrifuged at 4000 rpm. for 10 min. and the pellet resuspended in 2 liters of 2×TY containing 100 μg/ml ampicillin and 50 μg/ml kanamycin and grown overnight. Phage are prepared as described in PCT publication WO 92/01047.

Preparation of M13 delta gene III: M13 delta gene III helper phage does not encode gene III protein, hence the phage(mid) displaying antibody fragments have a greater avidity of binding to antigen. Infectious M13 delta gene III particles are made by growing the helper phage in cells harboring a pUC19 derivative supplying the wild type gene III protein during phage morphogenesis. The culture is incubated for 1 hour at 37° C. without shaking and then for a further hour at 37° C. with shaking. Cells are spun down (IEC-Centra 8,400 rpm for 10 min), resuspended in 300 ml 2×TY broth containing 100 μg ampicillin/ml and 25 μg kanamycin/ml (2×TY-AMP-KAN) and grown overnight, shaking at 37° C. Phage particles are purified and concentrated from the culture medium by two PEG-precipitations (Sambrook et al., 2001, Molecular Cloning: A Laboratory Manual. 3rd. ed., Cold Spring Harbor Laboratory Press, Cold Spring Harbor, N.Y.), resuspended in 2 ml PBS and passed through a 0.45 μm filter (Minisart NML; Sartorius) to give a final concentration of approximately $10^{13}$ transducing units/ml (ampicillin-resistant clones).

Panning of the library: Immunotubes (Nunc) are coated overnight in PBS with 4 ml of either 100 μg/ml or 10 μg/ml of a marker protein of interest. Tubes are blocked with 2% Marvel-PBS for 2 hours at 37° C. and then washed 3 times in PBS. Approximately $10^{13}$ TU of phage is applied to the tube and incubated for 30 minutes at room temperature tumbling on an over-and-under turntable and then left to stand for another 1.5 hours. Tubes are washed 10 times with PBS 0.1% Tween-20 and 10 times with PBS. Phage are eluted by adding 1 ml of 100 mM triethylamine and rotating 15 minutes on an under-and-over turntable after which the solution is immediately neutralized with 0.5 ml of 1.0 M Tris-HCl, pH 7.4. Phages are then used to infect 10 ml of mid-log E. coli TG1 by incubating eluted phage with bacteria for 30 minutes at 37° C. The E. coli are then plated on TYE plates containing 1% glucose and 100 μg/ml ampicillin. The resulting bacterial library is then rescued with delta gene 3 helper phage as described above to prepare phage for a subsequent round of selection. This process is then repeated for a total of 4 rounds of affinity purification with tube-washing increased to 20 times with PBS, 0.1% Tween-20 and 20 times with PBS for rounds 3 and 4.

Characterization of binders: Eluted phage from the 3rd and 4th rounds of selection are used to infect E. coli HB 2151 and soluble scFv is produced (Marks et al., 1991, J. Mol. Biol. 222: 581-597) from single colonies for assay. ELISAs are performed with microtitre plates coated with either 10 μg/ml of the marker protein of interest in 50 mM bicarbonate pH 9.6. Clones positive in ELISA are further characterized by PCR fingerprinting (see, e.g., PCT publication WO 92/01047) and then by sequence analysis.

Monoclonal Antibodies a) Materials:

1. Complete Media No Sera (CMNS) for washing of the myeloma and spleen cells; Hybridoma medium CM-HAT (Cell Mab (BD), 10% FBS (or HS); 5% Origen HCF (hybridoma cloning factor) containing 4 mM L-glutamine and antibiotics) to be used for plating hybridomas after the fusion.

2. Hybridoma medium CM-HT (no aminopterin) (Cell Mab (BD), 10% FBS 5% Origen HCF containing 4 mM L-glutamine and antibiotics) to be used for fusion maintenance is stored in the refrigerator at 4-6° C. The fusions are fed on days 4, 8, and 12, and subsequent passages. Inactivated and pre-filtered commercial fetal bovine serum (FBS) or horse serum (HS) are thawed and stored in the refrigerator at 4° C. and is pretested for myeloma growth from single cells prior to use.

3. The L-glutamine (200 mM, 100× solution), which is stored at −20° C., is thawed and warmed until completely in solution. The L-glutamine is dispensed into media to supplement growth. L-glutamine is added to 2 mM for myelomas and 4 mM for hybridoma media. Further, the penicillin, streptomycin, amphotericin (antibacterial-antifungal stored at −20° C.) is thawed and added to Cell Mab Media to 1%.

4. Myeloma growth media is Cell Mab Media (Cell Mab Media, Quantum Yield, from BD, which is stored in the refrigerator at 4° C. in the dark), to which is added L-glutamine to 2 mM and antibiotic/antimycotic solution to 1% and is called CMNS.

5. One bottle of PEG 1500 in Hepes (Roche, N.J.) is prepared.

6. 8-Azaguanine is stored as the dried powder supplied by SIGMA at −700° C. until needed. One vial/500 ml of media is reconstituted and the entire contents are added to 500 ml media (e.g., 2 vials/liter).

7. Myeloma Media is CM which has 10% FBS (or HS) and 8-Aza (1×) stored in the refrigerator at 4° C.

8. Clonal cell medium D (Stemcell, Vancouver) contains HAT and methyl cellulose for semi-solid direct cloning from the fusion. This comes in 90 ml bottles with a CoA and is melted at 37° C. in a waterbath in the morning of the day of the fusion. The cap is loosened and the bottle is left in a $CO_2$ incubator to sufficiently gas the medium D and bring the pH down.

9. Hybridoma supplements HT [hypoxanthine, thymidine] to be used in medium for the section of hybridomas and maintenance of hybridomas through the cloning stages, respectively.

10. Origen HCF can be obtained directly from Igen and is a cell supernatant produced from a macrophage-like cell-line. It can be thawed and aliquoted to 15 ml tubes at 5 ml per tube and stored frozen at −20° C. Positive hybridomas are fed HCF through the first subcloning and are gradually weaned (individual hybridomas can continue to be supplemented, as needed). This and other additives are typically more effective in promoting new hybridoma growth than conventional feeder layers.

b) Procedure:

To generate monoclonal antibodies, mice are immunized with 5-50 μg of antigen, either intra-peritoneally (i.p.) or by intravenous injection in the tail vein (i.v.). The antigen used can be a recombinant marker protein of interest, for example. The primary immunization takes place two months prior to the harvesting of splenocytes from the mouse, and the immunization is typically boosted by i.v. injection of 5-50 μg of antigen every two weeks. At least one week prior to the expected fusion date, a fresh vial of myeloma cells is thawed and cultured. Several flasks of different densities can be maintained so that a culture at the optimum density is ensured at the time of fusion. An optimum density can be $3-6 \times 10^5$ cells/ml, for example. 2-5 days before the scheduled fusion, a final immunization of approximately 5 μg of antigen in PBS is administered (either i.p. or i.v).

Myeloma cells are washed with 30 ml serum free media by centrifugation at 500 g at 4° C. for 5 minutes. Viable cell density is determined in resuspended cells using hemocytometry and vital stains. Cells resuspended in complete growth medium are stored at 37° C. during the preparation of splenocytes. Meanwhile, to test aminopterin sensitivity, $1 \times 10^6$ myeloma cells are transferred to a 15 ml conical tube and centrifuged at 500 g at 4° C. for 5 minutes. The resulting pellet is resuspended in 15 ml of HAT media and cells plated at 2 drops/well on a 96-well plate.

To prepare splenocytes from immunized mice, the animals are euthanised and submerged in 70% ethanol. Under sterile conditions, the spleen is surgically removed and placed in 10 ml of RPMI medium supplemented with 20% fetal calf serum in a petri dish. Cells are extricated from the spleen by infusing the organ with medium >50 times using a 21 g syringe.

Cells are harvested and washed by centrifugation (at 500 g at 4° C. for 5 minutes) with 30 ml of medium. Cells are resuspended in 10 ml of medium and the density of viable cells determined by hemocytometry using vital stains. The splenocytes are mixed with myeloma cells at a ratio of 5:1 (spleen cells: myeloma cells). Both the myeloma and spleen cells are washed twice more with 30 ml of RPMI-CMNS, and the cells are spun at 800 rpm for 12 minutes.

Supernatant is removed and cells are resuspended in 5 ml of RPMI-CMNS and are pooled to fill volume to 30 ml and spun down as before. Then, the pellet is broken up by gently tapping on the flow hood surface and resuspending in 1 ml of BMB REG1500 (prewarmed to 37° C.) dropwise with a 1 cc needle over 1 minute.

RPMI-CMNS to the PEG cells and RPMI-CMNS are added to slowly dilute out the PEG. Cells are centrifuged and diluted in 5 ml of Complete media and 95 ml of Clonacell Medium D (HAT) media (with 5 ml of HCF). The cells are plated out 10 ml per small petri plate.

Myeloma/HAT control is prepared as follows: dilute about 1000 P3X63 Ag8.653 myeloma cells into 1 ml of medium D and transfer into a single well of a 24-well plate. Plates are placed in an incubator, with two plates inside of a large petri plate, with an additional petri plate full of distilled water, for 10-18 days under 5% $CO_2$ overlay at 37° C. Clones are picked from semisolid agarose into 96-well plates containing 150-200 μl of CM-HT. Supernatants are screened 4 days later in ELISA, and positive clones are moved up to 24-well plates. Heavy growth requires changing of the media at day 8 (+/− 150 ml). The HCF can be further decreased to 0.5% (gradually—2%, then 1%, then 0.5%) in the cloning plates.

6. Liquid Chromatography and Mass Spectrometry (LC/MS)

For LC/MS analysis, proteins are reduced in 2.5 mM DTT for 1 hour at 37° C., and alkylated with ICAT™ reagent according to the procedures recommended by the manufacturer (Applied Biosystems, Framingham, Mass.). The reaction is quenched by adding excess DTT. Proteins are digested using sequencing grade modified trypsin overnight at 37° C. followed by desalting using 3 cc Oasis HLB solid phase extraction columns (Waters, Milford, Mass.) and vacuum drying. Cysteine-containing peptides are purified by avidin column (Applied Biosystems, Framingham, Mass.). The peptides are reconstituted in buffer A (0.1% formic acid in water) and separated over a C18 monomeric column (150 mm, 150 μm i.d., Grace Vydac 238EV5, 5 μm) at a flow rate of 1.5 μl/min with a trap column. Peptides are eluted from the column using a gradient, 3%-30% buffer B (0.1% formic acid in 90% acetonitrile) in 215 min, 30%-90% buffer B in 30 min. Eluted peptides are analyzed using an online QSTAR XL system (MDS/Sciex, Toronto, ON). Peptide ion peaks from the map are automatically detected with RESPEC™ (PPL Inc., UK).

The sequence-composition of peptides detected, for example, at higher levels in disease samples (or drug-resistant samples) relative to adjacent normal tissue (or drug-sensitive samples) can be resolved through tandem mass spectrometry and database analysis. For data analysis, peptide ion peaks of LC/MS maps from normal and disease samples can be aligned based on mass to charge ratio (m/z), retention time (Rt), and charge state (z). The list of aligned peptide ions is loaded into Spotfire (Spotfire Inc. Somerville, Mass.). Intensities can be normalized before further differential analysis between disease and normal samples. Differentially expressed ions are manually verified before LC-MS/MS-based peptide sequencing and database searching for protein/protein identification.

For intensity normalization and expression analysis, a heat map can be constructed by sorting the rows by the ratio of the mean intensity in the disease samples to the mean intensity of the normal samples. Rows are included if there is at least one MS/MS identification of an ion in the row. The display colors are determined for each row separately by assigning black to the median intensity in the row, green to the lowest intensity in the row, and red to the highest intensity.

Using a mass spectrometry procedure such as this, a comprehensive analysis of proteins differentially expressed by disease cells (or drug resistant cells, for example) compared with normal cells (or cells responsive/sensitive to a drug, for example) can be carried out.

7. mRNA Expression Analysis

Expression of marker mRNA can be quantitated by RT-PCR using TaqMan® technology. The Taqman® system couples a 5' fluorogenic nuclease assay with PCR for real-time quantitation. A probe is used to monitor the formation of the amplification product.

Total RNA can be isolated from disease model cell lines using an RNEasy Kit® (Qiagen, Valencia, Calif.) with DNase treatment (per the manufacturer's instructions). Normal human tissue RNAs can be acquired from commercial vendors (e.g., Ambion, Austin, Tex.; Stratagene, La Jolla, Calif.; BioChain Institute, Newington, N.H.), as well as RNAs from matched disease/normal tissues.

Marker transcript sequences can be identified for differentially expressed peptides by database searching using a search algorithm such as BLAST. TaqMan® assays (PCR primer/ probe sets) specific for those transcripts can be obtained from Applied Biosystems (AB) as part of the Assays on Demand™ product line or by custom design through the AB Assays by Design$^{SM}$ service. If desired, the assays can be designed to span exon-exon borders so as not to amplify genomic DNA.

RT-PCR can be accomplished using AmpliTaq Gold® and MultiScribe™ reverse transcriptase in the One Step RT-PCR Master Mix reagent kit (AB) (according to the manufacturer's instructions). Probe and primer concentrations are 250 nM and 900 nM, respectively, in a 15 µl reaction. For each experiment, a master mix of the above components is made and aliquoted into each optical reaction well. Eight nanograms of total RNA is used as template. Quantitative RT-PCR can be performed using the ABI Prism® 7900HT Sequence Detection System (SDS). The following cycling parameters are used: 48° C. for 30 min. for one cycle; 95° C. for 10 min for one cycle; and 95° C. for 15 sec, 60° C. for 1 min. for 40 cycles.

SDS software can be utilized to calculate the threshold cycle ($C_T$) for each reaction, and $C_T$ values are used to quantitate the relative amount of starting template in the reaction. The $C_T$ values for each set of reactions can be averaged for all subsequent calculations Data can be analyzed to determine estimated copy number per cell. Gene expression can be quantitated relative to 18S rRNA expression and copy number estimated assuming $5 \times 10^6$ copies of 18S rRNA per cell. Alternatively, data can be analyzed for fold difference in expression using an endogenous control for normalization and expressed relative to a normal tissue or normal cell line reference. The choice of endogenous control can be determined empirically by testing various candidates against the cell line and tissue RNA panels and selecting the one with the least variation in expression. Relative changes in expression can be quantitated using the $2^{-\Delta\Delta C_T}$ method (Livak et al., 2001, Methods 25: 402-408; User bulletin #2: ABI Prism 7700 Sequence Detection System). Alternatively, total RNA can be quantitated using a RiboGreen RNA Quantitation Kit according to manufacturer's instructions and the percentage mRNA expression calculated using total RNA for normalization. Percentage knockdown can then be calculated relative to a no addition control.

8. Flow Cytometry (FACS) Analysis

Flow cytometry is interchangeably referred to as fluorescence-activated cell sorting (FACS). Quantitative flow cytometry can be used to compare the level of expression of a protein on disease cells to the level found on normal cells, for example.

Expression levels of a marker protein on primary tissue samples can be quantified using the Quantum Simply Cellular System (Bangs Laboratories, Fishers, Ind.) and a marker-specific antibody. Normal adjacent and disease tissues can be processed into single cell suspensions, as described above, which can be stained for various markers (e.g., the epithelial marker EpCam) and the marker-specific antibody. At least $0.5 \times 10^6$ cells are typically used for each analysis. Cells are washed once with Flow Staining Buffer (0.5% BSA, 0.05% NaN3 in D-PBS). To the cells, 20 µl of each marker-specific antibody are added. An additional 5 µl of anti-EpCam antibody conjugated to APC can be added when unsorted cells are used. Cells are incubated with antibodies for 30 minutes at 4° C. Cells are washed once with Flow Staining Buffer and either analyzed immediately on an LSR flow cytometry apparatus or fixed in 1% formaldehyde and stored at 4° C. until LSR analysis. Antibodies used to detect a marker can be PE-conjugated. PE-conjugated mouse IgG1k can used as an isotype control antibody. Cells are analyzed by flow cytometry and epitope copy number and the percentage of viable epithelial cells positive for marker expression can be measured. Cell numbers and viability can be determined by PI exclusion (GUAVA) for cells isolated from both normal and disease tissue. Standard curve and samples can be analyzed on a LSR I (BDBiosciences, San Jose Calif.) flow cytometer. Antibody binding capacity for each lineage population can be calculated using geometric means and linear regression.

Expression levels of a marker protein can be quantified in cell lines with QIFIKIT flow cytometric indirect immunofluorescence assay (Dako A/S) using a primary antibody to the marker. Briefly, cells are detached with versene or trypsin and washed once with complete media and then PBS. $5 \times 10^5$ cells/sample are incubated with saturating concentration (10 µg/ml) of primary antibody for 60 minutes at 4° C. After washes, a FITC-conjugated secondary antibody (1:50 dilution) is added for 45 minutes at 4° C. QIFIKIT standard beads are simultaneously labeled with the secondary antibody. Binding of antibodies is analyzed by flow cytometry and specific antigen density is calculated by subtracting background antibody equivalent from antibody-binding capacity based on a standard curve of log mean fluorescence intensity versus log antigen binding capacity.

Cells can also be prepared for flow cytometry analysis (as well as other types of analysis) as follows: cells are incubated with 1:100 dilution of BrdU in culturing media for 2-4 hours (BrdU Flow Kit, cat#559619 BD Biosciences). Cells are washed 3 times with D-PBS and disassociated from the flask with versene. Cell numbers and viability can be determined by PI exclusion (GUAVA). Cells are washed once with Flow Staining Buffer (0.5% BSA, 0.05% NaN$_3$ in D-PBS). Cells are incubated with 400 µl of Cytofix/Cytoperm Buffer (BrdU Flow Kit, BD Biosciences) for 15-30 minutes at 4° C. Cells are washed once with Flow Staining Buffer and resuspended in 400 µl Cytoperm Plus Buffer (BrdU Flow Kit BD Biosciences). Cells are incubated for 10 minutes at 4° C. and washed once with 1× Perm/Wash Buffer (BrdU Flow Kit, BD Biosciences). Cells are incubated for 1 hour at 37° C. protected from light in DNAse solution (BrdU Flow Kit, BD Biosciences). Cells are washed once with 1× Perm/Wash Buffer and incubated for 20 min at room temperature with anti-BrdU FITC-conjugated antibody (BrdU Flow Kit, BD Biosciences), PE-conjugated active caspase 3 (BD Biosciences cat#550821), and PE mouse IgG2B isotype control. Cells are washed once with 1× Perm/Wash Buffer and resuspended in DAPI for LSR flow cytometry analysis.

9. Immunohistochemistry (IHC)

IHC of Tissue Sections

Paraffin embedded, fixed tissue sections (e.g., from disease tissue samples such as solid tumors or other cancer tissues) can be obtained from a panel of normal tissues as well as tumor (or other disease) samples with matched normal adjacent tissues, along with replicate sections (if desired). For example, for an initial survey of marker expression, a panel of common cancer formalin-fixed paraffin-embedded (FFPE) tissue microarrays (TMAs) can be used for analysis, and such TMAs can be obtained from commercial sources (TriStar, Rockville, Md.; USBiomax, Rockville, Md.; Imgenex, San Diego, Calif.; Petagen/Abxis, Seoul, Korea). Sections can be stained with hemotoxylin and eosin and histologically examined to ensure adequate representation of cell types in each tissue section.

An identical set of tissues can be obtained from frozen sections for use in those instances where it is not possible to generate antibodies that are suitable for fixed sections. Frozen tissues do not require an antigen retrieval step.

Paraffin Fixed Tissue Sections

An exemplary protocol for hemotoxylin and eosin staining of paraffin embedded, fixed tissue sections is as follows. Sections are deparaffinized in three changes of xylene or xylene substitute for 2-5 minutes each. Sections are rinsed in two changes of absolute alcohol for 1-2 minutes each, in 95% alcohol for 1 minute, followed by 80% alcohol for 1 minute. Slides are washed in running water and stained in Gill solution 3 hemotoxylin for 3-5 minutes. Following a vigorous wash in running water for 1 minute, sections are stained in Scott's solution for 2 minutes. Sections are washed for 1 minute in running water and then counterstained in eosin solution for 2-3 minutes, depending upon the desired staining intensity. Following a brief wash in 95% alcohol, sections are dehydrated in three changes of absolute alcohol for 1 minute each and three changes of xylene or xylene substitute for 1-2 minutes each. Slides are coverslipped and stored for analysis.

Optimization of Antibody Staining

For each antibody, a positive and negative control sample can be generated using data from ICAT analysis of disease cell lines or tissues. Cells can be selected that are known to express low levels of a particular marker as determined from the ICAT data, and this cell line can be used as a reference normal control. Similarly, a disease cell line that is determined to over-express the marker can also be selected.

Antigen Retrieval

Sections are deparaffinized and rehydrated by washing 3 times for 5 minutes in xylene, two times for 5 minutes in 100% ethanol, two times for 5 minutes in 95% ethanol, and once for 5 minutes in 80% ethanol. Sections are then placed in endogenous blocking solution (methanol+2% hydrogen peroxide) and incubated for 20 minutes at room temperature. Sections are rinsed twice for 5 minutes each in deionized water and twice for 5 minutes in phosphate buffered saline (PBS), pH 7.4.

Alternatively, where necessary, sections are de-parrafinized by High Energy Antigen Retrieval as follows: sections are washed three times for 5 minutes in xylene, two times for 5 minutes in 100% ethanol, two times for 5 minutes in 95% ethanol, and once for 5 minutes in 80% ethanol. Sections are placed in a Coplin jar with dilute antigen retrieval solution (10 mM citrate acid, pH 6). The Coplin jar containing slides is placed in a vessel filled with water and microwaved on high for 2-3 minutes (700 watt oven). Following cooling for 2-3 minutes, steps 3 and 4 are repeated four times (depending on the tissue), followed by cooling for 20 minutes at room temperature. Sections are then rinsed in deionized water (two times for 5 minutes), placed in modified endogenous oxidation blocking solution (PBS+2% hydrogen peroxide), and rinsed for 5 minutes in PBS.

Alternatively, formalin fixed paraffin embedded tissues can be deparaffinized and processed for antigen retrieval using the EZ-retriever system (BioGenex, San Ramon, Calif.). EZ-antigen Retrieval common solution is used for deparaffinization and EZ-retrieval citrate-based buffer used for antigen retrieval. Samples are pre-blocked with non-serum protein block (Dako A/S, Glostrup, Denmark) for 15 min. Primary antibodies (at 2.5-5.0 µg/ml, for example) are incubated overnight at room temperature. Envision Plus system HRP (Dako A/S) is used for detection with diaminobenzidine (DAB) as substrate for horseradish peroxidase.

Blocking and Staining

Sections are blocked with PBS/1% bovine serum albumin (PBA) for 1 hour at room temperature followed by incubation in normal serum diluted in PBA (2%) for 30 minutes at room temperature to reduce non-specific binding of antibody. Incubations are performed in a sealed humidity chamber to prevent air-drying of the tissue sections. The choice of blocking serum is typically the same as the species of the biotinylated secondary antibody. Excess antibody is gently removed by shaking and sections covered with primary antibody diluted in PBA and incubated either at room temperature for 1 hour or overnight at 4° C. (care is taken that the sections do not touch during incubation). Sections are rinsed twice for 5 minutes in PBS, shaking gently. Excess PBS is removed by gently shaking. The sections are covered with diluted biotinylated secondary antibody in PBA and incubated for 30 minutes to 1 hour at room temperature in the humidity chamber. If using a monoclonal primary antibody, addition of 2% rat serum can be used to decrease the background on rat tissue sections. Following incubation, sections are rinsed twice for 5 minutes in PBS, shaking gently. Excess PBS is removed and sections incubated for 1 hour at room temperature in Vectastain ABC reagent (as per kit instructions). The lid of the humidity chamber is secured during all incubations to ensure a moist environment. Sections are rinsed twice for 5 minutes in PBS, shaking gently.

Developing and Counterstaining

Sections are incubated for 2 minutes in peroxidase substrate solution that is made up immediately prior to use as follows: 10 mg diaminobenzidine (DAB) dissolved in 10 ml of 50 mM sodium phosphate buffer, pH 7.4; 12.5 microliters 3% $CoCl_2/NiCl_2$ in deionized water; and 1.25 microliters hydrogen peroxide.

Slides are rinsed well three times for 10 minutes in deionized water and counterstained with 0.01% Light Green acidified with 0.01% acetic acid for 1-2 minutes, depending on the desired intensity of counterstain.

Slides are rinsed three times for 5 minutes with deionized water and dehydrated two times for 2 minutes in 95% ethanol; two times for 2 minutes in 100% ethanol; and two times for 2 minutes in xylene. Stained slides are mounted for visualization by microscopy.

Slides are scored manually using a microscope such as the Zeiss Axiovert 200M microscope (Carl Zeiss Microimaging, Thornwood, N.Y.). Representative images are acquired using 40× objective (400× magnification).

IHC Staining of Frozen Tissue Sections

For IHC staining of frozen tissue sections, fresh tissues are embedded in OCT in plastic mold, without trapping air bubbles surrounding the tissue. Tissues are frozen by setting the mold on top of liquid nitrogen until 70-80% of the block turns white at which point the mold is placed on dry ice. The frozen blocks are stored at −80° C. Blocks are sectioned with a cryostat with care taken to avoid warming to greater than −10° C. Initially, the block is equilibrated in the cryostat for about 5 minutes and 6-10 mm sections are cut sequentially. Sections are allowed to dry for at least 30 minutes at room temperature. Following drying, tissues are stored at 4° C. for short term and −80° C. for long term storage.

Sections are fixed by immersing in an acetone jar for 1-2 minutes at room temperature, followed by drying at room temperature. Primary antibody is added (diluted in 0.05 M Tris-saline [0.05 M Tris, 0.15 M NaCl, pH 7.4], 2.5% serum) directly to the sections by covering the section dropwise to cover the tissue entirely. Binding is carried out by incubation in a chamber for 1 hour at room temperature. Without letting the sections dry out, the secondary antibody (diluted in Tris-saline/2.5% serum) is added in a similar manner to the primary antibody and incubated as before (at least 45 minutes).

Following incubation, the sections are washed gently in Tris-saline for 3-5 minutes and then in Tris-saline/2.5% serum for another 3-5 minutes. If a biotinylated primary antibody is used, in place of the secondary antibody incubation, slides are covered with 100 µl of diluted alkaline phosphatase conjugated streptavidin, incubated for 30 minutes at room temperature and washed as above. Sections are incubated with alkaline phosphatase substrate (1 mg/ml Fast Violet; 0.2 mg/ml Napthol AS-MX phosphate in Tris-Saline pH 8.5) for 10-20 minutes until the desired positive staining is achieved at which point the reaction is stopped by washing twice with Tris-saline. Slides are counter-stained with Mayer's hematoxylin for 30 seconds and washed with tap water for 2-5 minutes. Sections are mounted with Mount coverslips and mounting media.

10. RNAi Assays in Cell Lines

RNAi Transfections

Expression of a marker can be knocked down by transfection with small interfering RNA (siRNA) to that marker. Synthetic siRNA oligonucleotides can be obtained from Dharmacon (Lafayette, Colo.) or Qiagen (Valencia, Calif.). For siRNA transfection, cells (e.g., disease cells) can be seeded into 96 well tissue culture plates at a density of 2,500 cells per well 24 hours before transfection. Culture medium is removed and 50 µl of reaction mix containing siRNA (final concentration 1 to 100 nM) and 0.4 µl of DharmaFECT4 (Dharmacon, Lafayette, Colo.) diluted in Opti-MEM is added to each well. An equal volume of complete medium follows and the cells are then incubated at 5% $CO_2$ at 37° C. for 1 to 4 days.

Alternatively, in the initial screening phase, RNAi can be performed using 100 nM (final) of Smartpools (Dharmacon, Lafayette, Colo.), pool of 4—for Silencing siRNA duplexes (Qiagen, Valencia, Calif.), or non-targeting negative control siRNA (Dharmacon or Qiagen). In the breakout phase, each individual duplex is used at 100 nM (final). In the titration phase, individual duplex is used at 0.1-100 nM (final). Transient transfections are carried out using either Lipofectamine 2000 from Invitrogen (Carlsbad, Calif.) or GeneSilencer from Gene Therapy Systems (San Diego, Calif.) (see below). One day after transfections, total RNA is isolated using the RNeasy 96 Kit (Qiagen) according to manufacturer's instructions and expression of mRNA is quantitated using TaqMan technology. Apoptosis and cell proliferation assays can be performed daily using Apop-one homogeneous caspase-3/7 kit and Alamar Blue or CellTiter 96 AQueous One Solution Cell Proliferation Assays (see below).

RNAi Transfections—Lipofectamine 2000 and GeneSilencer

Transient RNAi transfections can be carried out using Lipofectamine 2000 (Invitrogen, Carlsbad, Calif.) or GeneSilencer (Gene Therapy Systems, San Diego, Calif.), such as on sub-confluent disease cell lines, as described elsewhere (Elbashir et al., 2001, *Nature* 411: 494-498; Caplen et al., 2001, *Proc Natl Acad Sci USA* 98: 9742-9747; Sharp, 2001, *Genes and Development* 15: 485-490). Synthetic RNA to a gene of interest or non-targeting negative control siRNA are transfected using Lipofectamine 2000 or GeneSilencer according to manufacturer's instructions. Cells are plated in 96-well plates in antibiotic-free medium. The next day, the transfection reagent and siRNA are prepared for transfections as follows.

0.1-100 nM siRNA is resuspended in 20-25 µl serum-free media in each well (with Plus for Lipofectamine 2000) and incubated at room temperature for 15 minutes. 0.1-1 µl of Lipofectamine 2000 or 1-1.5 µl of GeneSilencer is also resuspended in serum-free medium to a final volume of 20-25 µl per well. After incubation, the diluted siRNA and either the Lipofectamine 2000 or the GeneSilencer are combined and incubated for 15 minutes (Lipofectamine 2000) or 5-20 minutes (GeneSilencer) at room temperature. Media is then removed from the cells and the combined siRNA-Lipofectamine 2000 reagent or siRNA-GeneSilencer reagent is added to a final volume of 50 µl per well. After further incubation at 37° C. for 4 hours, 50 µl serum-containing medium is added back to the cells. 1-4 days after transfection, expression of mRNA can be quantitated by RT-PCR using TaqMan technology, and protein expression levels can be measured by flow cytometry. Apoptosis and proliferation assays can be performed daily using Apop-one homogeneous caspase-3/7 kit and Alamar Blue or CellTiter 96 AQueous One Solution Cell Proliferation Assays (see below).

mRNA and Protein Knockdowns

Knockdown of marker mRNA levels can be monitored by Q-PCR one day after siRNA transfection by using a TaqMan® assay (Applied Biosystems, Foster City, Calif.). RT-PCR is accomplished in a one-step reaction by using M-MLV reverse transcriptase (Promega, Madison, Wis.) and AmpliTaq Gold® (ABI) and analyzed on the ABI Prism® 7900HT Sequence Detection System (ABI). Relative gene expression can be quantitated by the $\Delta\Delta Ct$ method (User Bulletin #2, ABI) with 18S rRNA serving as the endogenous control.

Protein knockdown can be monitored by FACS four days after transfection by using an antibody to the marker. The samples can be run on a LSR flow cytometer (BD Biosciences, San Jose, Calif.) and live cells monitored by using PI exclusion (50 µg/ml PI, 2.5 units/ml RNase A, 0.1% Triton X-100 in D-PBS). The data can be analyzed using CellQuest software.

Cell Proliferation—Alamar Blue

Cell growth can be assessed four days after transfection by adding a 1:10 dilution of Alamar blue reagent (Invitrogen, Carlsbad, Calif. or Biosource, Camarillo, Calif.) and incubated for 2 hours at 37° C. Analysis can be performed on a Spectrafluor Plus (Tecan, Durham, N.C.) set at excitation wavelength of 530 nm and emission wavelength of 595 nm.

Cell Proliferation—MTS

Alternatively, cell proliferation assays can be performed using a CellTiter 96 AQueous One Solution Cell Proliferation Assay kit (Promega, Madison, Wis.). 200 of CellTiter 96 AQueous One Solution is added to 100 µl of culture medium. The plates are then incubated for 1-4 hours at 37° C. in a humidified 5% $CO_2$ incubator. After incubation, the change in absorbance is read at 490 nm.

Apoptosis

Apoptosis assays can be performed using the Apop-one homogeneous caspase-3/7 kit (Promega, Madison, Wis.). Briefly, the caspase-3/7 substrate is thawed to room temperature and diluted 1:100 with buffer. The diluted substrate is then added 1:1 to cells, control, or blank. The plates are then placed on a plate shaker for 30 minutes to 18 hours at 300-500 rpm. The fluorescence of each well is then measured using an excitation wavelength of 485+/−20 nm and an emission wavelength of 530+/−25 nm.

11. Antibody Assays in Cell Lines

Cytotoxicity Assays

Cytotoxicity can be measured using a Resazurin (Sigma, Mo.) dye reduction assay (McMillian et al., 2002, *Cell Biol. Toxicol.* 18:157-173). Briefly, cells are plated at 1,000-5,500 cells/well in 96 well plates, allowed to attach to the plates for 18 hours before addition of fresh media with or without antibody. After 96-144 hours of exposure to antibody, resazurin is added to cells to a final concentration of 50 µM. Cells are incubated for 2-6 hours depending on dye conversion of cell lines, and dye reduction is measured on a Fusion HT fluorescent plate reader (Packard Instruments, Meridien, Conn.) with excitation and emission wavelengths of 530 nm and 590 nm, respectively. The $IC_{50}$ value is defined here as the drug concentration that results in 50% reduction in growth or viability as compared with untreated control cultures.

Assays for Antibody-Dependent Cellular Cytotoxicity

Antibody-dependent cellular cytotoxicity (ADCC) assays can be carried out as follows. Cultured disease cells (e.g., tumor cells) are labeled with 100 µCi $^{51}$Cr for 1 hour (Livingston et al., 1997, *Cancer Immunol. Immunother.* 43, 324-330). After being washed three times with culture medium, cells are resuspended at $10^5$/ml, and 100 µl/well are plated onto 96-well round-bottom plates. A range of antibody concentrations are applied to the wells, including an isotype control together with donor peripheral blood mononuclear cells that are plated at a 100:1 and 50:1 ratio. After an 18 hour incubation at 37° C., supernatant (30 µl/well) is harvested and transferred onto Lumaplate 96 (Packard), dried, and read in a Packard Top-Count NXT γ counter. Spontaneous release is determined by cpm of disease cells incubated with medium and maximum release by cpm of disease cells plus 1% Triton X-100 (Sigma). Specific lysis is defined as: % specific lysis= [(experimental release−spontaneous release)/(maximum release−spontaneous release)]×100. The percent ADCC is expressed as peak specific lysis postimmune subtracted by preimmune percent specific lysis. A doubling of the ADCC to >20% can typically be considered significant.

Assays for Complement Dependent Cytotoxicity

Chromium release assays to assess complement dependent cytotoxicity (CDC) can be carried out as follows (Dickler et al., 1999, *Clin. Cancer Res.* 5, 2773-2779). Cultured disease cells (e.g., tumor cells) are washed in FCS-free media two times, resuspended in 500 µl of media, and incubated with 100 µCi $^{51}$Cr per 10 million cells for 2 hours at 37° C. The cells are then shaken every 15 min for 2 hours, washed 3 times in media to achieve a concentration of approximately 20,000 cells/well, and then plated in round-bottom plates. The plates contain either 50 µl cells plus 50 µl monoclonal antibody, 50 µl cells plus serum (pre- and post-therapy), or 50 µl cells plus mouse serum as a control. The plates are incubated in a cold room on a shaker for 45 min. Human complement of a 1:5 dilution (resuspended in 1 ml of ice-cold water and diluted with 3% human serum albumin) is added to each well at a volume of 100 µl. Control wells include those for maximum release of isotype in 10% Triton X-100 (Sigma) and for spontaneous release in the absence of complement with medium alone. The plates are incubated for 2 hours at 37° C., centrifuged for 3 min, and then 100 µl of supernatant is removed for radioactivity counting. The percentage of specific lysis is calculated as follows: % cytotoxicity=[(experimental release−spontaneous release)/(maximum release−spontaneous release)]×100. A doubling of the CDC to >20% can typically be considered significant.

Cell Proliferation Assays

To measure cell proliferation, cells can be plated, grown and treated as for the cytotoxicity assay (above) in 96 well plates. After 96-144 hours of treatment, 0.5 µCi/well $^3$H-Thymidine (PerkinElmer, 6.7 Ci/mmol) is added to cells and incubated for 4-6 hours at 37° C., 5% $CO_2$ in an incubator. To lyse cells, plates are frozen overnight at −20° C. and then cell lysates are harvested using FilterMate (Packard Instrument, Meridien, Conn.) into 96 well filter plates. Radioactivity associated with cells is measured on a TopCount (Packard) scintillation counter.

Other cell assays (e.g., proliferation assays such as Alamar blue and MTS, and apoptosis assays) can be carried out using antibodies, as described above for RNAi.

Testing of Function-Blocking Antibodies

For testing of function-blocking antibodies, sub-confluent disease cell lines are serum-starved overnight. The next day, serum-containing media is added back to the cells in the presence of 5-50 ng/ml of function-blocking antibodies. After 2 or 5 days incubation at 37° C. 5% $CO_2$, antibody binding is examined by flow cytometry, and apoptosis and proliferation are measured.

Cell Invasion

Cell invasion assays can be performed using a 96-well cell invasion assay kit (Chemicon). After the cell invasion chamber plates are adjusted to room temperature, 100 µl serum-free media is added to the interior of the inserts. 1-2 hours later, cell suspensions of 1×10$^6$ cells/ml are prepared. Media is then carefully removed from the inserts and 100 µl of prepared cells are added into the insert +/−0 to 50 ng function blocking antibodies. The cells are pre-incubated for 15 minutes at 37° C. before 150 µl of media containing 10% FBS is added to the lower chamber. The cells are then incubated for 48 hours at 37° C. After incubation, the cells from the top side of the insert are discarded and the invasion chamber plates are then placed on a new 96-well feeder tray containing 150 µl of pre-warmed cell detachment solution in the wells. The plates are incubated for 30 minutes at 37° C. and are periodically shaken. Lysis buffer/dye solution (4 µl CyQuant Dye/300 µl 4× lysis buffer) is prepared and added to each well of dissociation buffer/cells on feeder tray. The plates are incubated for 15 minutes at room temperature before 150 µl is transferred to a new 96-well plate. Fluorescence of invading cells is then read at 480 nm excitation and 520 nm emission.

Receptor Internalization

For quantification of receptor internalization, ELISA assays can be performed essentially as described by Daunt et al. (Daunt et al., 1997, *Mol. Pharmacol.* 51, 711-720). Cell lines are plated at 6×10$^5$ cells per in a 24-well tissue culture dishes that have previously been coated with 0.1 mg/ml poly-L-lysine. The next day, the cells are washed once with PBS and incubated in DMEM at 37° C. for several minutes. Agonist to the cell surface marker of interest is then added to the wells at a pre-determined concentration in prewarmed DMEM. The cells are then incubated for various times at 37° C. and reactions are stopped by removing the media and fixing the cells in 3.7% formaldehyde/TBS for 5 min at room temperature. The cells are then washed three times with TBS and nonspecific binding blocked with TBS containing 1% BSA for 45 min at room temperature. The first antibody is added at a pre-determined dilution in TBS/BSA for 1 hr at room temperature. Three washes with TBS follow, and cells are briefly reblocked for 15 min at room temperature. Incubation with goat anti-mouse conjugated alkaline phosphatase (Bio-Rad) diluted 1:1000 in TBS/BSA is carried out for 1 hr at room temperature. The cells are washed three times with TBS and a colorimetric alkaline phosphatase substrate is added. When the adequate color change is reached, 100 µl samples are taken for colorimetric readings.

12. Treatment with Antibodies

Treatment of Disease Cells with Monoclonal Antibodies.

Disease cells (e.g., cancer cells), or cells such as NIH 3T3 cells that express a marker of interest, are seeded at a density of 4×10$^4$ cells per well in 96-well microtiter plates and allowed to adhere for 2 hours. The cells are then treated with different concentrations of monoclonal antibody (Mab) specific for the marker protein of interest, or irrelevant isotype matched (e.g., anti-rHuIFN-gamma) Mab, at 0.05, 0.5 or 5.0 µg/ml. After a 72 hour incubation, the cell monolayers are stained with crystal violet dye for determination of relative percent viability (RPV) compared to control (untreated) cells. Each treatment group can have replicates. Cell growth inhibition is monitored.

In Vivo Treatment with Monoclonal Antibodies.

NIH 3T3 cells transfected with either an expression plasmid that expresses the marker of interest or a neo-DHFR vector are injected into nu/nu (athymic) mice subcutaneously at a dose of $10^6$ cells in 0.1 ml of phosphate-buffered saline. On days 0, 1, 5, and every 4 days thereafter, 100 µg (0.1 ml in PBS) of a Mab specific for the marker protein of interest, or an irrelevant Mab, of the IgA2 subclass is injected intraperitoneally. Disease progression (e.g., tumor occurrence and size) can be monitored for a one month period of treatment, for example.

13. Identification of LCM

A mass spectrometry (MS)-based proteomics platform was used for the identification of secreted and shed proteins (secreted and shed proteins are collectively referred to herein as soluble proteins) and cell surface antigens that combines the discovery of candidate biomarkers from human lung tumor specimens resected from surgery and in a panel of lung cancer cell lines, followed by validation of expression levels in patient serum (such as by using ELISA). For example, proteomic analysis techniques such as MALDI-TOF/TOF LC/MS-based protein expression analysis was used to determine the expression levels of certain proteins in lung tumor tissues and/or lung cancer cell lines (tissues and cell lines may be collectively referred to herein as "samples") and in normal tissues and/or normal cell lines, such that proteins that are differentially expressed (e.g., over- or under-expressed) in lung cancer samples compared with normal samples were identified.

Certain candidate markers were identified by mass spectrometry-based methods that were differentially expressed on the cell surface of lung tumors, lung cancer cell lines, or secreted into the conditioned medium of cell lines. Certain of these candidate markers that were identified as differentially expressed by mass spectrometry, as well as certain other candidate markers, were assayed by ELISA and scored in panels of lung cancer patient sera and sera from individuals without lung cancer (individuals without lung cancer are referred to herein as "normal", "control", or "healthy" individuals). Individual markers were scored "positive" for a given cancer sample if the value exceeded a defined threshold (e.g., greater than or equal to two standard deviations above the mean value for a group of "normal" samples tested). From these candidate markers, lung cancer markers ("LCM") were identified that, particularly when used in combination, distinguished lung cancer samples from healthy control samples with various degrees of sensitivity and specificity.

Several methods and algorithms were applied to select optimum panels/combinations of LCM including sum of the logs of the ratios of the tumor concentration to the mean of the normal concentration, defining a concentration cutoff manually for each marker to optimize sensitivity and specificity, and use of Naïve Bayes to assign a probability that a sample is a tumor based on the expression level of each marker. Additionally, ROC curves may be constructed for each panel and their effectiveness may be evaluated in several ways, such as maximizing the AUC of the ROC curve as well as maximizing the sensitivity at a desired specificity or maximizing the specificity at a desired sensitivity.

To further validate the specificity of certain panels, co-morbidity studies were carried out to challenge certain panels with other lung disease samples besides lung cancer, particularly chronic obstructive pulmonary disease (COPD), asthma, bronchitis, and other benign lung diseases (FIG. 20). Prevalence of COPD/asthma is 10-25% in smokers. An initial panel of 30 bronchitis/asthma/benign lung disease samples was tested. Results indicated that these co-morbidities may reduce specificity only marginally if considered independent of false positives in 54 control samples (the specificity of the 9-member panel of Cyfra, SLPI, TIMP1, SCC, TFPI, CEACAM5, MMP2, OPN, and MDK in a 54 normal/53 lung tumor sample set was 98% on samples from smoking controls).

14. ELISA Immunoassays

Immunoassay kits, such as for performing ELISA assays, for various LCM disclosed herein are commercially available. For example, immunoassay kits can be obtained from a variety of commercial sources, as follows: SLPI, MMP2, MIF, and OPN immunoassay kits can be obtained from R&D Systems (Minneapolis, Minn.); CYFRA 21-1 and SCC immunoassay kits can be obtained from DRG-International (Mountainside, N.J.); DEFA1 immunoassay kits can be obtained from Cell Sciences (Canton, Mass.); TIMP1 immunoassay kits can be obtained from Siemens Healthcare Diagnostics (Cambridge, Mass.); CEA and GRP immunoassay kits can be obtained from IBL International (Toronto, Ontario); TFPI immunoassay kits can be obtained from American Diagnostica (Stamford, Conn.); and MDK immunoassay kits can be obtained from BioVendor (Candler, N.C.) or R&D Systems (Minneapolis, Minn.). Assays can be performed following manufacturers instructions. Plates can be read on a Spectra Max M2 Microplate Reader (Molecular Devices, Sunnyvale, Calif.) with the appropriate baseline correction for each assay.

HNP1-3 (defensin, DEFA1) is employed as a representative marker in the following exemplary ELISA protocol, which can be used for the analysis of LCM. An HNP1-3 ELISA test kit can be used that is a solid-phase enzyme-linked immunosorbent assay based on the sandwich principle. Samples and standards are incubated in microtiter wells coated with antibodies recognizing human HNP1-3. During this incubation, human HNP1-3 is captured by solid bound antibody. Unbound material present in the sample is removed by washing. Biotinylated second antibody (tracer) to human HNP1-3 is then added to the wells. If HNP1-3 is present in the sample, the tracer antibodies will bind to the captured HNP1-3. The excess tracer is removed by washing. A streptavidin-peroxidase conjugate is then applied to the wells, which reacts specifically with the biotinylated tracer antibody bound onto the detected HNP1-3. The excess streptavidin-peroxidase conjugate is removed by washing and substrate tetramethylbenzidine (TMB) is added to the wells. Color develops proportionally to the amount of human HNP1-3 present in the sample. The enzyme reaction is stopped by the addition of citric acid and the absorption at 450 nm is measured with a spectrophotometer. A standard curve is obtained by plotting the absorptions versus the corresponding concentrations of the known standards. The concentration of human HNP1-3 in test samples, which are run concurrently with the standards, can be determined from the standard curve.

15. Scoring of LCM Levels

This example describes an exemplary method of scoring LCM levels using split-point analysis.

The term "split-point analysis" refers to a method adapted from Mor et al., *PNAS*, (2005) 102, 7677-7682. In this exemplary method, measurements for each marker are taken on all samples. A cutoff value is determined for each marker. This cutoff value may be set to, for example, maximize the accuracy of correct classifications between the groups of interest (e.g., tumor and control sample groups) or may be set to maximize the sensitivity or specificity of one group. For each marker, a score is assigned to that sample whenever the value of that marker is found to be on the diseased side of the cutoff value (e.g., the side of the cutoff corresponding to lung tumor samples). After all the measurements have been taken on one sample, the scores are summed to produce a total score for the panel of markers. All markers can be weighted equally such that a panel of 9 markers may have a maximum score of 9 (each marker having a score of either 1 or 0) and a minimum score of 0, for example. Alternatively, markers can be weighted unequally, with a higher individual score for more significant measures.

Other more sophisticated statistical modeling methods can also be applied such as logistic regression (see, e.g., Planque et al., *Clin Cancer Res* (2008), 14, 1355-1362) and decision tree modeling (see, e.g., Patz et al., *J Clin Oncol* (2007), 25, 5578-5583).

An exemplary method of applying split-point analysis to an LCM panel is described for illustrative purposes.

A patients sample can be tested to determine the patient's likelihood of having lung cancer using a panel comprising the 9 biomarkers Cyfra, CEA, SLPI, OPN, MDK, TFPI, TIMP1, MMP2, and SCC and the split and score method. The predetermined total score (or threshold) for the panel can be set at 1 (or other value).

After obtaining a test sample from the patient, the amount of each of the 9 biomarkers (Cyfra, CEA, SLPI, OPN, MDK, TFPI, TIMP1, MMP2, SCC) in the patient's test sample is quantified. For the purpose of this example, the amount of each of the 9 biomarkers in the test sample is determined to be as follows (values are expressed in ng/ml): Cyfra=0.891, CEA=4.087, SLPI=62.94, OPN=21.514, MDK=0.174, TFPI=104.503, TIMP1=398.7, MMP2=194.41, and SCC=1.35. The amount of each of these biomarkers is then compared to the corresponding predetermined cutoff (or split point). For the purpose of this example, the predetermined cutoffs for each of the biomarkers are as follows: Cyfra=1.20, CEA=5.00, SLPI=52, OPN=32, MDK=0.15, TFPI=150, TIMP1=385, MMP2=210, and SCC=2.2. For each biomarker having an amount that is higher than its corresponding predetermined cutoff (split point), a score of 1 can be assigned. For each biomarker having an amount that is less than or equal to its corresponding predetermined cutoff, a score of 0 can be assigned. Thereupon, based on said comparison, each biomarker would be assigned a score as follows: Cyfra=0, CEA=0, SLPI=1, OPN=0, MDK=1, TFPI=0, TIMP1=1, MMP2=0, and SCC=O.

The score for each of the 9 biomarkers can then be combined mathematically (e.g., by adding each of the scores of the biomarkers together) to arrive at the total score for the patient. In this particular example, the total score for the patient is 3 (the total score is calculated as follows: 0+0+1+0+1+0+1+0+0=3). The total score for the patient is compared to the predetermined total score, which is 1 in this particular example. A total score greater than the predetermined total score of 1 would indicate a positive result for the patient (i.e., in this particular example, a total score of 2 or greater would indicate that the patient has lung cancer). A total score equal to or less than 1 would indicate a negative result for the patient. In this example, because the patient's total score is greater than 1, the patient would be considered to have a positive result (and thus may be referred for further testing for an indication or suspicion of lung cancer). In contrast, had the patient's total score been 1 or 0, the patient would have been considered to have a negative result (and thus would not be referred for any further testing).

All publications and patents mentioned in the above specification are herein incorporated by reference. Various modifications and variations of the described methods and compositions of the invention will be apparent to those skilled in the art without departing from the scope and spirit of the invention. Although the invention has been described in connection with specific exemplary embodiments, it should be understood that the invention as claimed should not be unduly limited to such specific embodiments. Indeed, various modifications of the above-described modes for carrying out the invention, which are obvious to those skilled in the field of molecular biology or related fields, are intended to be within the scope of the following claims.

Lengthy table referenced here

US08808997-20140819-T00001

Please refer to the end of the specification for access instructions.

Lengthy table referenced here

US08808997-20140819-T00002

Please refer to the end of the specification for access instructions.

Lengthy table referenced here

US08808997-20140819-T00003

Please refer to the end of the specification for access instructions.

Lengthy table referenced here

US08808997-20140819-T00004

Please refer to the end of the specification for access instructions.

Lengthy table referenced here

US08808997-20140819-T00005

Please refer to the end of the specification for access instructions.

Lengthy table referenced here

US08808997-20140819-T00006

Please refer to the end of the specification for access instructions.

Lengthy table referenced here

US08808997-20140819-T00007

Please refer to the end of the specification for access instructions.

Lengthy table referenced here

US08808997-20140819-T00008

Please refer to the end of the specification for access instructions.

Lengthy table referenced here

US08808997-20140819-T00009

Please refer to the end of the specification for access instructions.

Lengthy table referenced here

US08808997-20140819-T00010

Please refer to the end of the specification for access instructions.

Lengthy table referenced here

US08808997-20140819-T00011

Please refer to the end of the specification for access instructions.

Lengthy table referenced here

US08808997-20140819-T00012

Please refer to the end of the specification for access instructions.

LENGTHY TABLES

The patent contains a lengthy table section. A copy of the table is available in electronic form from the USPTO web site (http://seqdata.uspto.gov/?pageRequest=docDetail&DocID=US08808997B2). An electronic copy of the table will also be available from the USPTO upon request and payment of the fee set forth in 37 CFR 1.19(b)(3).

That which is claimed is:

1. A method for diagnosing a human as having lung cancer, the method comprising detecting the levels of tissue factor pathway inhibitor (TFPI) protein, carcinoembryonic antigen-related cell adhesion molecule 5 (CEACAM5) protein, Cyfra 21-1 (Cyfra) protein, squamous cell carcinoma antigen (SCC) protein, and midkine (MDK) protein in a body fluid sample from said human, and diagnosing said human as having lung cancer if the level of at least one of said proteins is elevated.

2. The method of claim 1, wherein the method comprises analyzing said levels by split-point analysis or logistic regression analysis.

3. The method of claim 2, wherein said split-point analysis or said logistic regression analysis is performed by computer software.

4. The method of claim 1, wherein the method comprises diagnosing said human as having lung cancer if said level is at or above a predetermined cutoff level.

5. The method of claim 4, wherein said predetermined cutoff level comprises a number of standard deviations above the normal mean level of said protein established for individuals who do not have lung cancer.

6. The method of claim 5, wherein said number of standard deviations is two standard deviations.

7. The method of claim 1, wherein the level of each of said proteins is added together to obtain a total value that indicates whether said human has lung cancer.

8. The method of claim 7, wherein the total value being at or above a predetermined cutoff value indicates that said human has lung cancer.

9. The method of claim 7, wherein the level of each of said proteins is analyzed by split-point analysis or logistic regression analysis to obtain said total value.

10. The method of claim 1, wherein the method comprises diagnosing said human as having lung cancer if the level of at least two of said proteins is elevated.

11. The method of claim 1, wherein the method comprises diagnosing said human as having lung cancer if the level of at least three of said proteins is elevated.

12. The method of claim 1, wherein the method comprises diagnosing said human as having lung cancer if the level of at least four of said proteins is elevated.

13. The method of claim 1, wherein the method comprises diagnosing said human as having lung cancer if the level of all five of said proteins is elevated.

14. The method of claim 1, wherein the level of said TFPI protein is elevated.

15. The method of claim 10, wherein the level of said TFPI protein is elevated.

16. The method of claim 11, wherein the level of said TFPI protein is elevated.

17. The method of claim 12, wherein the level of said TFPI protein is elevated.

18. The method of claim 1, wherein the level of said TFPI protein and at least one other of said proteins is elevated.

19. The method of claim 1, wherein the detecting comprises detecting the proteins by immunoassay.

20. The method of claim 19, wherein the immunoassay comprises ELISA.

21. The method of claim 1, wherein the detecting comprises contacting the sample with antibodies that selectively bind to each of the proteins and detecting the binding of the antibodies to the proteins.

22. The method of claim 1, wherein the detecting comprises contacting the sample with aptamers that selectively bind to each of the proteins and detecting the binding of the aptamers to the proteins.

23. The method of claim 1, wherein said proteins are detected by reagents which are configured in a multiplex format.

24. The method of claim 1, wherein the body fluid sample is blood, serum, plasma, or bronchial lavage.

25. The method of claim 1, further comprising obtaining said sample from said human prior to said detecting.

26. The method of claim 1, wherein said body fluid sample is serum or plasma, and wherein the method further comprises separating said serum or said plasma from a blood sample from said human.

27. The method of claim 1, wherein said human has been identified as having a lung nodule prior to said detecting.

28. The method of claim 27, wherein said lung nodule was observed by computed tomography (CT) screening.

29. The method of claim 27, further comprising classifying said lung nodule as either malignant or benign.

30. The method of claim 1, further comprising performing computed tomography (CT) screening of said human if said human is diagnosed as having lung cancer.

31. The method of claim 1, wherein the method is carried out following computed tomography (CT) screening of said human.

32. The method of claim 1, wherein the method is carried out following lung cancer treatment of said human, wherein said lung cancer treatment comprises administration of a therapeutic agent, surgical resection of at least a portion of a lung tumor, or radiation therapy.

33. The method of claim 1, further comprising administering a therapeutic agent to treat lung cancer to said human if said human is diagnosed as having lung cancer.

34. The method of claim 1, further comprising enrolling said human in a clinical trial of a therapeutic agent.

35. The method of claim 1, wherein said diagnosing is performed by computer software.

36. The method of claim 1, wherein the method comprises diagnosing said human as not having lung cancer if the level of no protein is elevated.

37. The method of claim 1, further comprising determining one or more supplemental biomedical parameters.

38. The method of claim 37, wherein said supplemental biomedical parameters include lung nodule size.

* * * * *

```
                           SEQUENCE LISTING

<160> NUMBER OF SEQ ID NOS: 65

<210> SEQ ID NO 1
<211> LENGTH: 132
<212> TYPE: PRT
<213> ORGANISM: Homo sapiens

<400> SEQUENCE: 1

Met Lys Ser Ser Gly Leu Phe Pro Phe Leu Val Leu Leu Ala Leu Gly
1               5                   10                  15

Thr Leu Ala Pro Trp Ala Val Glu Gly Ser Gly Lys Ser Phe Lys Ala
            20                  25                  30

Gly Val Cys Pro Pro Lys Lys Ser Ala Gln Cys Leu Arg Tyr Lys Lys
        35                  40                  45

Pro Glu Cys Gln Ser Asp Trp Gln Cys Pro Gly Lys Lys Arg Cys Cys
    50                  55                  60

Pro Asp Thr Cys Gly Ile Lys Cys Leu Asp Pro Val Asp Thr Pro Asn
65                  70                  75                  80

Pro Thr Arg Arg Lys Pro Gly Lys Cys Pro Val Thr Tyr Gly Gln Cys
                85                  90                  95

Leu Met Leu Asn Pro Pro Asn Phe Cys Glu Met Asp Gly Gln Cys Lys
            100                 105                 110

Arg Asp Leu Lys Cys Cys Met Gly Met Cys Gly Lys Ser Cys Val Ser
        115                 120                 125

Pro Val Lys Ala
```

130

<210> SEQ ID NO 2
<211> LENGTH: 115
<212> TYPE: PRT
<213> ORGANISM: Homo sapiens

<400> SEQUENCE: 2

Met Pro Met Phe Ile Val Asn Thr Asn Val Pro Arg Ala Ser Val Pro
1               5                   10                  15

Asp Gly Phe Leu Ser Glu Leu Thr Gln Gln Leu Ala Gln Ala Thr Gly
            20                  25                  30

Lys Pro Pro Gln Tyr Ile Ala Val His Val Val Pro Asp Gln Leu Met
        35                  40                  45

Ala Phe Gly Gly Ser Ser Glu Pro Cys Ala Leu Cys Ser Leu His Ser
    50                  55                  60

Ile Gly Lys Ile Gly Gly Ala Gln Asn Arg Ser Tyr Ser Lys Leu Leu
65                  70                  75                  80

Cys Gly Leu Leu Ala Glu Arg Leu Arg Ile Ser Pro Asp Arg Val Tyr
                85                  90                  95

Ile Asn Tyr Tyr Asp Met Asn Ala Ala Asn Val Gly Trp Asn Asn Ser
            100                 105                 110

Thr Phe Ala
        115

<210> SEQ ID NO 3
<211> LENGTH: 207
<212> TYPE: PRT
<213> ORGANISM: Homo sapiens

<400> SEQUENCE: 3

Met Ala Pro Phe Glu Pro Leu Ala Ser Gly Ile Leu Leu Leu Leu Trp
1               5                   10                  15

Leu Ile Ala Pro Ser Arg Ala Cys Thr Cys Val Pro Pro His Pro Gln
            20                  25                  30

Thr Ala Phe Cys Asn Ser Asp Leu Val Ile Arg Ala Lys Phe Val Gly
        35                  40                  45

Thr Pro Glu Val Asn Gln Thr Thr Leu Tyr Gln Arg Tyr Glu Ile Lys
    50                  55                  60

Met Thr Lys Met Tyr Lys Gly Phe Gln Ala Leu Gly Asp Ala Ala Asp
65                  70                  75                  80

Ile Arg Phe Val Tyr Thr Pro Ala Met Glu Ser Val Cys Gly Tyr Phe
                85                  90                  95

His Arg Ser His Asn Arg Ser Glu Glu Phe Leu Ile Ala Gly Lys Leu
            100                 105                 110

Gln Asp Gly Leu Leu His Ile Thr Thr Cys Ser Phe Val Ala Pro Trp
        115                 120                 125

Asn Ser Leu Ser Leu Ala Gln Arg Arg Gly Phe Thr Lys Thr Tyr Thr
    130                 135                 140

Val Gly Cys Glu Glu Cys Thr Val Phe Pro Cys Leu Ser Ile Pro Cys
145                 150                 155                 160

Lys Leu Gln Ser Gly Thr His Cys Leu Trp Thr Asp Gln Leu Leu Gln
                165                 170                 175

Gly Ser Glu Lys Gly Phe Gln Ser Arg His Leu Ala Cys Leu Pro Arg
            180                 185                 190

Glu Pro Gly Leu Cys Thr Trp Gln Ser Leu Arg Ser Gln Ile Ala
        195                 200                 205

-continued

```
<210> SEQ ID NO 4
<211> LENGTH: 304
<212> TYPE: PRT
<213> ORGANISM: Homo sapiens

<400> SEQUENCE: 4

Met Ile Tyr Thr Met Lys Lys Val His Ala Leu Trp Ala Ser Val Cys
  1               5                  10                  15

Leu Leu Leu Asn Leu Ala Pro Ala Pro Leu Asn Ala Asp Ser Glu Glu
             20                  25                  30

Asp Glu Glu His Thr Ile Ile Thr Asp Thr Glu Leu Pro Pro Leu Lys
         35                  40                  45

Leu Met His Ser Phe Cys Ala Phe Lys Ala Asp Asp Gly Pro Cys Lys
     50                  55                  60

Ala Ile Met Lys Arg Phe Phe Phe Asn Ile Phe Thr Arg Gln Cys Glu
 65                  70                  75                  80

Glu Phe Ile Tyr Gly Gly Cys Glu Gly Asn Gln Asn Arg Phe Glu Ser
                 85                  90                  95

Leu Glu Glu Cys Lys Lys Met Cys Thr Arg Asp Asn Ala Asn Arg Ile
            100                 105                 110

Ile Lys Thr Thr Leu Gln Gln Glu Lys Pro Asp Phe Cys Phe Leu Glu
        115                 120                 125

Glu Asp Pro Gly Ile Cys Arg Gly Tyr Ile Thr Arg Tyr Phe Tyr Asn
    130                 135                 140

Asn Gln Thr Lys Gln Cys Glu Arg Phe Lys Tyr Gly Gly Cys Leu Gly
145                 150                 155                 160

Asn Met Asn Asn Phe Glu Thr Leu Glu Glu Cys Lys Asn Ile Cys Glu
                165                 170                 175

Asp Gly Pro Asn Gly Phe Gln Val Asp Asn Tyr Gly Thr Gln Leu Asn
            180                 185                 190

Ala Val Asn Asn Ser Leu Thr Pro Gln Ser Thr Lys Val Pro Ser Leu
        195                 200                 205

Phe Glu Phe His Gly Pro Ser Trp Cys Leu Thr Pro Ala Asp Arg Gly
    210                 215                 220

Leu Cys Arg Ala Asn Glu Asn Arg Phe Tyr Tyr Asn Ser Val Ile Gly
225                 230                 235                 240

Lys Cys Arg Pro Phe Lys Tyr Ser Gly Cys Gly Gly Asn Glu Asn Asn
                245                 250                 255

Phe Thr Ser Lys Gln Glu Cys Leu Arg Ala Cys Lys Lys Gly Phe Ile
            260                 265                 270

Gln Arg Ile Ser Lys Gly Gly Leu Ile Lys Thr Lys Arg Lys Arg Lys
        275                 280                 285

Lys Gln Arg Val Lys Ile Ala Tyr Glu Glu Ile Phe Val Lys Asn Met
    290                 295                 300

<210> SEQ ID NO 5
<211> LENGTH: 434
<212> TYPE: PRT
<213> ORGANISM: Homo sapiens

<400> SEQUENCE: 5

Met Ser Ile Glu Lys Ile Trp Ala Arg Glu Ile Leu Asp Ser Arg Gly
  1               5                  10                  15

Asn Pro Thr Val Glu Val Asp Leu Tyr Thr Ala Lys Gly Leu Phe Arg
```

```
            20                  25                  30
Ala Ala Val Pro Ser Gly Ala Ser Thr Gly Ile Tyr Glu Ala Leu Glu
            35                  40                  45

Leu Arg Asp Gly Asp Lys Gln Arg Tyr Leu Gly Lys Gly Val Leu Lys
 50                  55                  60

Ala Val Asp His Ile Asn Ser Thr Ile Ala Pro Ala Leu Ile Ser Ser
 65                  70                  75                  80

Gly Leu Ser Val Val Glu Gln Glu Lys Leu Asp Asn Leu Met Leu Glu
                 85                  90                  95

Leu Asp Gly Thr Glu Asn Lys Ser Lys Phe Gly Ala Asn Ala Ile Leu
            100                 105                 110

Gly Val Ser Leu Ala Val Cys Lys Ala Gly Ala Ala Glu Arg Glu Leu
            115                 120                 125

Pro Leu Tyr Arg His Ile Ala Gln Leu Ala Gly Asn Ser Asp Leu Ile
            130                 135                 140

Leu Pro Val Pro Ala Phe Asn Val Ile Asn Gly Gly Ser His Ala Gly
145                 150                 155                 160

Asn Lys Leu Ala Met Gln Glu Phe Met Ile Leu Pro Val Gly Ala Glu
                165                 170                 175

Ser Phe Arg Asp Ala Met Arg Leu Gly Ala Glu Val Tyr His Thr Leu
            180                 185                 190

Lys Gly Val Ile Lys Asp Lys Tyr Gly Lys Asp Ala Thr Asn Val Gly
            195                 200                 205

Asp Glu Gly Gly Phe Ala Pro Asn Ile Leu Glu Asn Ser Glu Ala Leu
        210                 215                 220

Glu Leu Val Lys Glu Ala Ile Asp Lys Ala Gly Tyr Thr Glu Lys Ile
225                 230                 235                 240

Val Ile Gly Met Asp Val Ala Ala Ser Glu Phe Tyr Arg Asp Gly Lys
                245                 250                 255

Tyr Asp Leu Asp Phe Lys Ser Pro Thr Asp Pro Ser Arg Tyr Ile Thr
            260                 265                 270

Gly Asp Gln Leu Gly Ala Leu Tyr Gln Asp Phe Val Arg Asp Tyr Pro
            275                 280                 285

Val Val Ser Ile Glu Asp Pro Phe Asp Gln Asp Asp Trp Ala Ala Trp
        290                 295                 300

Ser Lys Phe Thr Ala Asn Val Gly Ile Gln Ile Val Gly Asp Asp Leu
305                 310                 315                 320

Thr Val Thr Asn Pro Lys Arg Ile Glu Arg Ala Val Glu Glu Lys Ala
                325                 330                 335

Cys Asn Cys Leu Leu Leu Lys Val Asn Gln Ile Gly Ser Val Thr Glu
            340                 345                 350

Ala Ile Gln Ala Cys Lys Leu Ala Gln Glu Asn Gly Trp Gly Val Met
            355                 360                 365

Val Ser His Arg Ser Gly Glu Thr Glu Asp Thr Phe Ile Ala Asp Leu
        370                 375                 380

Val Val Gly Leu Cys Thr Gly Gln Ile Lys Thr Gly Ala Pro Cys Arg
385                 390                 395                 400

Ser Glu Arg Leu Ala Lys Tyr Asn Gln Leu Met Arg Ile Glu Glu Glu
                405                 410                 415

Leu Gly Asp Glu Ala Arg Phe Ala Gly His Asn Phe Arg Asn Pro Ser
            420                 425                 430

Val Leu
```

<210> SEQ ID NO 6
<211> LENGTH: 702
<212> TYPE: PRT
<213> ORGANISM: Homo sapiens

<400> SEQUENCE: 6

```
Met Glu Ser Pro Ser Ala Pro Pro His Arg Trp Cys Ile Pro Trp Gln
 1               5                  10                  15

Arg Leu Leu Leu Thr Ala Ser Leu Leu Thr Phe Trp Asn Pro Pro Thr
            20                  25                  30

Thr Ala Lys Leu Thr Ile Glu Ser Thr Pro Phe Asn Val Ala Glu Gly
        35                  40                  45

Lys Glu Val Leu Leu Leu Val His Asn Leu Pro Gln His Leu Phe Gly
 50                  55                  60

Tyr Ser Trp Tyr Lys Gly Glu Arg Val Asp Gly Asn Arg Gln Ile Ile
 65                  70                  75                  80

Gly Tyr Val Ile Gly Thr Gln Gln Ala Thr Pro Gly Pro Ala Tyr Ser
                85                  90                  95

Gly Arg Glu Ile Ile Tyr Pro Asn Ala Ser Leu Leu Ile Gln Asn Ile
            100                 105                 110

Ile Gln Asn Asp Thr Gly Phe Tyr Thr Leu His Val Ile Lys Ser Asp
        115                 120                 125

Leu Val Asn Glu Glu Ala Thr Gly Gln Phe Arg Val Tyr Pro Glu Leu
130                 135                 140

Pro Lys Pro Ser Ile Ser Ser Asn Asn Ser Lys Pro Val Glu Asp Lys
145                 150                 155                 160

Asp Ala Val Ala Phe Thr Cys Glu Pro Glu Thr Gln Asp Ala Thr Tyr
                165                 170                 175

Leu Trp Trp Val Asn Asn Gln Ser Leu Pro Val Ser Pro Arg Leu Gln
            180                 185                 190

Leu Ser Asn Gly Asn Arg Thr Leu Thr Leu Phe Asn Val Thr Arg Asn
        195                 200                 205

Asp Thr Ala Ser Tyr Lys Cys Glu Thr Gln Asn Pro Val Ser Ala Arg
210                 215                 220

Arg Ser Asp Ser Val Ile Leu Asn Val Leu Tyr Gly Pro Asp Ala Pro
225                 230                 235                 240

Thr Ile Ser Pro Leu Asn Thr Ser Tyr Arg Ser Gly Glu Asn Leu Asn
                245                 250                 255

Leu Ser Cys His Ala Ala Ser Asn Pro Pro Ala Gln Tyr Ser Trp Phe
            260                 265                 270

Val Asn Gly Thr Phe Gln Gln Ser Thr Gln Glu Leu Phe Ile Pro Asn
        275                 280                 285

Ile Thr Val Asn Asn Ser Gly Ser Tyr Thr Cys Gln Ala His Asn Ser
290                 295                 300

Asp Thr Gly Leu Asn Arg Thr Thr Val Thr Thr Ile Thr Val Tyr Ala
305                 310                 315                 320

Glu Pro Pro Lys Pro Phe Ile Thr Ser Asn Asn Ser Asn Pro Val Glu
                325                 330                 335

Asp Glu Asp Ala Val Ala Leu Thr Cys Glu Pro Glu Ile Gln Asn Thr
            340                 345                 350

Thr Tyr Leu Trp Trp Val Asn Asn Gln Ser Leu Pro Val Ser Pro Arg
        355                 360                 365

Leu Gln Leu Ser Asn Asp Asn Arg Thr Leu Thr Leu Leu Ser Val Thr
370                 375                 380
```

```
Arg Asn Asp Val Gly Pro Tyr Glu Cys Gly Ile Gln Asn Lys Leu Ser
385                 390                 395                 400

Val Asp His Ser Asp Pro Val Ile Leu Asn Val Leu Tyr Gly Pro Asp
            405                 410                 415

Asp Pro Thr Ile Ser Pro Ser Tyr Thr Tyr Tyr Arg Pro Gly Val Asn
        420                 425                 430

Leu Ser Leu Ser Cys His Ala Ala Ser Asn Pro Pro Ala Gln Tyr Ser
    435                 440                 445

Trp Leu Ile Asp Gly Asn Ile Gln Gln His Thr Gln Glu Leu Phe Ile
    450                 455                 460

Ser Asn Ile Thr Glu Lys Asn Ser Gly Leu Tyr Thr Cys Gln Ala Asn
465                 470                 475                 480

Asn Ser Ala Ser Gly His Ser Arg Thr Thr Val Lys Thr Ile Thr Val
            485                 490                 495

Ser Ala Glu Leu Pro Lys Pro Ser Ile Ser Ser Asn Asn Ser Lys Pro
        500                 505                 510

Val Glu Asp Lys Asp Ala Val Ala Phe Thr Cys Glu Pro Glu Ala Gln
        515                 520                 525

Asn Thr Thr Tyr Leu Trp Trp Val Asn Gly Gln Ser Leu Pro Val Ser
        530                 535                 540

Pro Arg Leu Gln Leu Ser Asn Gly Asn Arg Thr Leu Thr Leu Phe Asn
545                 550                 555                 560

Val Thr Arg Asn Asp Ala Arg Ala Tyr Val Cys Gly Ile Gln Asn Ser
            565                 570                 575

Val Ser Ala Asn Arg Ser Asp Pro Val Thr Leu Asp Val Leu Tyr Gly
            580                 585                 590

Pro Asp Thr Pro Ile Ile Ser Pro Pro Asp Ser Ser Tyr Leu Ser Gly
        595                 600                 605

Ala Asn Leu Asn Leu Ser Cys His Ser Ala Ser Asn Pro Ser Pro Gln
        610                 615                 620

Tyr Ser Trp Arg Ile Asn Gly Ile Pro Gln Gln His Thr Gln Val Leu
625                 630                 635                 640

Phe Ile Ala Lys Ile Thr Pro Asn Asn Asn Gly Thr Tyr Ala Cys Phe
            645                 650                 655

Val Ser Asn Leu Ala Thr Gly Arg Asn Asn Ser Ile Val Lys Ser Ile
            660                 665                 670

Thr Val Ser Ala Ser Gly Thr Ser Pro Gly Leu Ser Ala Gly Ala Thr
            675                 680                 685

Val Gly Ile Met Ile Gly Val Leu Val Gly Val Ala Leu Ile
        690                 695                 700

<210> SEQ ID NO 7
<211> LENGTH: 660
<212> TYPE: PRT
<213> ORGANISM: Homo sapiens

<400> SEQUENCE: 7

Met Glu Ala Leu Met Ala Arg Gly Ala Leu Thr Gly Pro Leu Arg Ala
1               5                   10                  15

Leu Cys Leu Leu Gly Cys Leu Leu Ser His Ala Ala Ala Pro Ser
            20                  25                  30

Pro Ile Ile Lys Phe Pro Gly Asp Val Ala Pro Lys Thr Asp Lys Glu
        35                  40                  45

Leu Ala Val Gln Tyr Leu Asn Thr Phe Tyr Gly Cys Pro Lys Glu Ser
```

-continued

```
                50                  55                  60
Cys Asn Leu Phe Val Leu Lys Asp Thr Leu Lys Lys Met Gln Lys Phe
 65                  70                  75                  80

Phe Gly Leu Pro Gln Thr Gly Asp Leu Asp Gln Asn Thr Ile Glu Thr
                     85                  90                  95

Met Arg Lys Pro Arg Cys Gly Asn Pro Asp Val Ala Asn Tyr Asn Phe
                100                 105                 110

Phe Pro Arg Lys Pro Lys Trp Asp Lys Asn Gln Ile Thr Tyr Arg Ile
                115                 120                 125

Ile Gly Tyr Thr Pro Asp Leu Asp Pro Glu Thr Val Asp Asp Ala Phe
                130                 135                 140

Ala Arg Ala Phe Gln Val Trp Ser Asp Val Thr Pro Leu Arg Phe Ser
145                 150                 155                 160

Arg Ile His Asp Gly Glu Ala Asp Ile Met Ile Asn Phe Gly Arg Trp
                165                 170                 175

Glu His Gly Asp Gly Tyr Pro Phe Asp Gly Lys Asp Gly Leu Leu Ala
                180                 185                 190

His Ala Phe Ala Pro Gly Thr Gly Val Gly Gly Asp Ser His Phe Asp
                195                 200                 205

Asp Asp Glu Leu Trp Thr Leu Gly Glu Gly Gln Val Val Arg Val Lys
                210                 215                 220

Tyr Gly Asn Ala Asp Gly Glu Tyr Cys Lys Phe Pro Phe Leu Phe Asn
225                 230                 235                 240

Gly Lys Glu Tyr Asn Ser Cys Thr Asp Thr Gly Arg Ser Asp Gly Phe
                245                 250                 255

Leu Trp Cys Ser Thr Thr Tyr Asn Phe Glu Lys Asp Gly Lys Tyr Gly
                260                 265                 270

Phe Cys Pro His Glu Ala Leu Phe Thr Met Gly Gly Asn Ala Glu Gly
                275                 280                 285

Gln Pro Cys Lys Phe Pro Phe Arg Phe Gln Gly Thr Ser Tyr Asp Ser
                290                 295                 300

Cys Thr Thr Glu Gly Arg Thr Asp Gly Tyr Arg Trp Cys Gly Thr Thr
305                 310                 315                 320

Glu Asp Tyr Asp Arg Asp Lys Lys Tyr Gly Phe Cys Pro Glu Thr Ala
                325                 330                 335

Met Ser Thr Val Gly Gly Asn Ser Glu Gly Ala Pro Cys Val Phe Pro
                340                 345                 350

Phe Thr Phe Leu Gly Asn Lys Tyr Glu Ser Cys Thr Ser Ala Gly Arg
                355                 360                 365

Ser Asp Gly Lys Met Trp Cys Ala Thr Thr Ala Asn Tyr Asp Asp Asp
                370                 375                 380

Arg Lys Trp Gly Phe Cys Pro Asp Gln Gly Tyr Ser Leu Phe Leu Val
385                 390                 395                 400

Ala Ala His Glu Phe Gly His Ala Met Gly Leu Glu His Ser Gln Asp
                405                 410                 415

Pro Gly Ala Leu Met Ala Pro Ile Tyr Thr Tyr Thr Lys Asn Phe Arg
                420                 425                 430

Leu Ser Gln Asp Asp Ile Lys Gly Ile Gln Glu Leu Tyr Gly Ala Ser
                435                 440                 445

Pro Asp Ile Asp Leu Gly Thr Gly Pro Thr Pro Thr Leu Gly Pro Val
                450                 455                 460

Thr Pro Glu Ile Cys Lys Gln Asp Ile Val Phe Asp Gly Ile Ala Gln
465                 470                 475                 480
```

```
Ile Arg Gly Glu Ile Phe Phe Lys Asp Arg Phe Ile Trp Arg Thr
            485                 490                 495

Val Thr Pro Arg Asp Lys Pro Met Gly Pro Leu Leu Val Ala Thr Phe
        500                 505                 510

Trp Pro Glu Leu Pro Glu Lys Ile Asp Ala Val Tyr Glu Ala Pro Gln
        515                 520                 525

Glu Glu Lys Ala Val Phe Phe Ala Gly Asn Glu Tyr Trp Ile Tyr Ser
        530                 535                 540

Ala Ser Thr Leu Glu Arg Gly Tyr Pro Lys Pro Leu Thr Ser Leu Gly
545                 550                 555                 560

Leu Pro Pro Asp Val Gln Arg Val Asp Ala Ala Phe Asn Trp Ser Lys
                565                 570                 575

Asn Lys Lys Thr Tyr Ile Phe Ala Gly Asp Lys Phe Trp Arg Tyr Asn
            580                 585                 590

Glu Val Lys Lys Lys Met Asp Pro Gly Phe Pro Lys Leu Ile Ala Asp
            595                 600                 605

Ala Trp Asn Ala Ile Pro Asp Asn Leu Asp Ala Val Val Asp Leu Gln
        610                 615                 620

Gly Gly Gly His Ser Tyr Phe Phe Lys Gly Ala Tyr Tyr Leu Lys Leu
625                 630                 635                 640

Glu Asn Gln Ser Leu Lys Ser Val Lys Phe Gly Ser Ile Lys Ser Asp
                645                 650                 655

Trp Leu Gly Cys
            660

<210> SEQ ID NO 8
<211> LENGTH: 352
<212> TYPE: PRT
<213> ORGANISM: Homo sapiens

<400> SEQUENCE: 8

Met Arg Ser Leu Gly Ala Leu Leu Leu Leu Leu Ser Ala Cys Leu Ala
 1               5                  10                  15

Val Ser Ala Gly Pro Val Pro Thr Pro Pro Asp Asn Ile Gln Val Gln
            20                  25                  30

Glu Asn Phe Asn Ile Ser Arg Ile Tyr Gly Lys Trp Tyr Asn Leu Ala
        35                  40                  45

Ile Gly Ser Thr Cys Pro Trp Leu Lys Lys Ile Met Asp Arg Met Thr
    50                  55                  60

Val Ser Thr Leu Val Leu Gly Glu Gly Ala Thr Glu Ala Glu Ile Ser
65                  70                  75                  80

Met Thr Ser Thr Arg Trp Arg Lys Gly Val Cys Glu Glu Thr Ser Gly
                85                  90                  95

Ala Tyr Glu Lys Thr Asp Thr Asp Gly Lys Phe Leu Tyr His Lys Ser
            100                 105                 110

Lys Trp Asn Ile Thr Met Glu Ser Tyr Val Val His Thr Asn Tyr Asp
        115                 120                 125

Glu Tyr Ala Ile Phe Leu Thr Lys Lys Phe Ser Arg His His Gly Pro
    130                 135                 140

Thr Ile Thr Ala Lys Leu Tyr Gly Arg Ala Pro Gln Leu Arg Glu Thr
145                 150                 155                 160

Leu Leu Gln Asp Phe Arg Val Val Ala Gln Gly Val Gly Ile Pro Glu
                165                 170                 175

Asp Ser Ile Phe Thr Met Ala Asp Arg Gly Glu Cys Val Pro Gly Glu
```

-continued

```
                180                 185                 190
    Gln Glu Pro Glu Pro Ile Leu Ile Pro Arg Val Arg Arg Ala Val Leu
                    195                 200                 205

Pro Gln Glu Glu Glu Gly Ser Gly Gly Gly Gln Leu Val Thr Glu Val
        210                 215                 220

Thr Lys Lys Glu Asp Ser Cys Gln Leu Gly Tyr Ser Ala Gly Pro Cys
    225                 230                 235                 240

Met Gly Met Thr Ser Arg Tyr Phe Tyr Asn Gly Thr Ser Met Ala Cys
                    245                 250                 255

Glu Thr Phe Gln Tyr Gly Gly Cys Met Gly Asn Gly Asn Asn Phe Val
        260                 265                 270

Thr Glu Lys Glu Cys Leu Gln Thr Cys Arg Thr Val Ala Ala Cys Asn
    275                 280                 285

Leu Pro Ile Val Arg Gly Pro Cys Arg Ala Phe Ile Gln Leu Trp Ala
                    290                 295                 300

Phe Asp Ala Val Lys Gly Lys Cys Val Leu Phe Pro Tyr Gly Gly Cys
    305                 310                 315                 320

Gln Gly Asn Gly Asn Lys Phe Tyr Ser Glu Lys Glu Cys Arg Glu Tyr
                    325                 330                 335

Cys Gly Val Pro Gly Asp Gly Asp Glu Leu Leu Arg Phe Ser Asn
                    340                 345                 350
```

<210> SEQ ID NO 9
<211> LENGTH: 400
<212> TYPE: PRT
<213> ORGANISM: Homo sapiens

<400> SEQUENCE: 9

```
    Met Thr Ser Tyr Ser Tyr Arg Gln Ser Ser Ala Thr Ser Ser Phe Gly
    1               5                   10                  15

Gly Leu Gly Gly Gly Ser Val Arg Phe Gly Pro Gly Val Ala Phe Arg
                    20                  25                  30

Ala Pro Ser Ile His Gly Gly Ser Gly Arg Gly Val Ser Val Ser
                35                  40                  45

Ser Ala Arg Phe Val Ser Ser Ser Ser Gly Gly Tyr Gly Gly Gly
        50                  55                  60

Tyr Gly Gly Val Leu Thr Ala Ser Asp Gly Leu Leu Ala Gly Asn Glu
    65                  70                  75                  80

Lys Leu Thr Met Gln Asn Leu Asn Asp Arg Leu Ala Ser Tyr Leu Asp
                    85                  90                  95

Lys Val Arg Ala Leu Glu Ala Ala Asn Gly Glu Leu Glu Val Lys Ile
                    100                 105                 110

Arg Asp Trp Tyr Gln Lys Gln Gly Pro Gly Pro Ser Arg Asp Tyr Ser
                    115                 120                 125

His Tyr Tyr Thr Thr Ile Gln Asp Leu Arg Asp Lys Ile Leu Gly Ala
        130                 135                 140

Thr Ile Glu Asn Ser Arg Ile Val Leu Gln Ile Asp Asn Ala Arg Leu
    145                 150                 155                 160

Ala Ala Asp Asp Phe Arg Thr Lys Phe Glu Thr Glu Gln Ala Leu Arg
                    165                 170                 175

Met Ser Val Glu Ala Asp Ile Asn Gly Leu Arg Arg Val Leu Asp Glu
                    180                 185                 190

Leu Thr Leu Ala Arg Thr Asp Leu Glu Met Gln Ile Glu Gly Leu Lys
                    195                 200                 205
```

Glu Glu Leu Ala Tyr Leu Lys Lys Asn His Glu Glu Ile Ser Thr
210                 215                 220

Leu Arg Gly Gln Val Gly Gly Gln Val Ser Val Glu Val Asp Ser Ala
225                 230                 235                 240

Pro Gly Thr Asp Leu Ala Lys Ile Leu Ser Asp Met Arg Ser Gln Tyr
                245                 250                 255

Glu Val Met Ala Glu Gln Asn Arg Lys Asp Ala Glu Ala Trp Phe Thr
                260                 265                 270

Ser Arg Thr Glu Glu Leu Asn Arg Glu Val Ala Gly His Thr Glu Gln
                275                 280                 285

Leu Gln Met Ser Arg Ser Glu Val Thr Asp Leu Arg Arg Thr Leu Gln
290                 295                 300

Gly Leu Glu Ile Glu Leu Gln Ser Gln Leu Ser Met Lys Ala Ala Leu
305                 310                 315                 320

Glu Asp Thr Leu Ala Glu Thr Glu Ala Arg Phe Gly Ala Gln Leu Ala
                325                 330                 335

His Ile Gln Ala Leu Ile Ser Gly Ile Glu Ala Gln Leu Gly Asp Val
                340                 345                 350

Arg Ala Asp Ser Glu Arg Gln Asn Gln Glu Tyr Gln Arg Leu Met Asp
                355                 360                 365

Ile Lys Ser Arg Leu Glu Gln Glu Ile Ala Thr Tyr Arg Ser Leu Leu
                370                 375                 380

Glu Gly Gln Glu Asp His Tyr Asn Asn Leu Ser Ala Ser Lys Val Leu
385                 390                 395                 400

<210> SEQ ID NO 10
<211> LENGTH: 390
<212> TYPE: PRT
<213> ORGANISM: Homo sapiens

<400> SEQUENCE: 10

Met Asn Ser Leu Ser Glu Ala Asn Thr Lys Phe Met Phe Asp Leu Phe
1               5                   10                  15

Gln Gln Phe Arg Lys Ser Lys Glu Asn Asn Ile Phe Tyr Ser Pro Ile
                20                  25                  30

Ser Ile Thr Ser Ala Leu Gly Met Val Leu Leu Gly Ala Lys Asp Asn
                35                  40                  45

Thr Ala Gln Gln Ile Lys Lys Val Leu His Phe Asp Gln Val Thr Glu
50                  55                  60

Asn Thr Thr Gly Lys Ala Ala Thr Tyr His Val Asp Arg Ser Gly Asn
65                  70                  75                  80

Val His His Gln Phe Gln Lys Leu Leu Thr Glu Phe Asn Lys Ser Thr
                85                  90                  95

Asp Ala Tyr Glu Leu Lys Ile Ala Asn Lys Leu Phe Gly Glu Lys Thr
                100                 105                 110

Tyr Leu Phe Leu Gln Glu Tyr Leu Asp Ala Ile Lys Lys Phe Tyr Gln
                115                 120                 125

Thr Ser Val Glu Ser Val Asp Phe Ala Asn Ala Pro Glu Glu Ser Arg
130                 135                 140

Lys Lys Ile Asn Ser Trp Val Glu Ser Gln Thr Asn Gly Lys Ile Lys
145                 150                 155                 160

Asn Leu Ile Pro Glu Gly Asn Ile Gly Ser Asn Thr Thr Leu Val Leu
                165                 170                 175

Val Asn Ala Ile Tyr Phe Lys Gly Gln Trp Glu Lys Lys Phe Asn Lys
                180                 185                 190

Glu Asp Thr Lys Glu Lys Phe Trp Pro Asn Lys Asn Thr Tyr Lys
        195                 200                 205

Ser Ile Gln Met Met Arg Gln Tyr Thr Ser Phe His Phe Ala Ser Leu
    210                 215                 220

Glu Asp Val Gln Ala Lys Val Leu Glu Ile Pro Tyr Lys Gly Lys Asp
225                 230                 235                 240

Leu Ser Met Ile Val Leu Leu Pro Asn Glu Ile Asp Gly Leu Gln Lys
                245                 250                 255

Leu Glu Glu Lys Leu Thr Ala Glu Lys Leu Met Glu Trp Thr Ser Leu
            260                 265                 270

Gln Asn Met Arg Glu Thr Arg Val Asp Leu His Leu Pro Arg Phe Lys
        275                 280                 285

Val Glu Glu Ser Tyr Asp Leu Lys Asp Thr Leu Arg Thr Met Gly Met
    290                 295                 300

Val Asp Ile Phe Asn Gly Asp Ala Asp Leu Ser Gly Met Thr Gly Ser
305                 310                 315                 320

Arg Gly Leu Val Leu Ser Gly Val Leu His Lys Ala Phe Val Glu Val
                325                 330                 335

Thr Glu Glu Gly Ala Glu Ala Ala Ala Thr Ala Val Val Gly Phe
            340                 345                 350

Gly Ser Ser Pro Thr Ser Thr Asn Glu Glu Phe His Cys Asn His Pro
        355                 360                 365

Phe Leu Phe Phe Ile Arg Gln Asn Lys Thr Asn Ser Ile Leu Phe Tyr
    370                 375                 380

Gly Arg Phe Ser Ser Pro
385                 390

<210> SEQ ID NO 11
<211> LENGTH: 314
<212> TYPE: PRT
<213> ORGANISM: Homo sapiens

<400> SEQUENCE: 11

Met Arg Ile Ala Val Ile Cys Phe Cys Leu Leu Gly Ile Thr Cys Ala
1               5                   10                  15

Ile Pro Val Lys Gln Ala Asp Ser Gly Ser Ser Glu Glu Lys Gln Leu
            20                  25                  30

Tyr Asn Lys Tyr Pro Asp Ala Val Ala Thr Trp Leu Asn Pro Asp Pro
        35                  40                  45

Ser Gln Lys Gln Asn Leu Leu Ala Pro Gln Asn Ala Val Ser Ser Glu
    50                  55                  60

Glu Thr Asn Asp Phe Lys Gln Glu Thr Leu Pro Ser Lys Ser Asn Glu
65                  70                  75                  80

Ser His Asp His Met Asp Asp Met Asp Glu Asp Asp Asp His
                85                  90                  95

Val Asp Ser Gln Asp Ser Ile Asp Ser Asn Asp Ser Asp Val Asp
                100                 105                 110

Asp Thr Asp Asp Ser His Gln Ser Asp Glu Ser His His Ser Asp Glu
            115                 120                 125

Ser Asp Glu Leu Val Thr Asp Phe Pro Thr Asp Leu Pro Ala Thr Glu
        130                 135                 140

Val Phe Thr Pro Val Val Pro Thr Val Asp Thr Tyr Asp Gly Arg Gly
145                 150                 155                 160

Asp Ser Val Val Tyr Gly Leu Arg Ser Lys Ser Lys Lys Phe Arg Arg

```
                165                 170                 175
Pro Asp Ile Gln Tyr Pro Asp Ala Thr Asp Glu Asp Ile Thr Ser His
            180                 185                 190

Met Glu Ser Glu Glu Leu Asn Gly Ala Tyr Lys Ala Ile Pro Val Ala
        195                 200                 205

Gln Asp Leu Asn Ala Pro Ser Asp Trp Asp Ser Arg Gly Lys Asp Ser
    210                 215                 220

Tyr Glu Thr Ser Gln Leu Asp Asp Gln Ser Ala Glu Thr His Ser His
225                 230                 235                 240

Lys Gln Ser Arg Leu Tyr Lys Arg Lys Ala Asn Asp Glu Ser Asn Glu
                245                 250                 255

His Ser Asp Val Ile Asp Ser Gln Glu Leu Ser Lys Val Ser Arg Glu
            260                 265                 270

Phe His Ser His Glu Phe His Ser His Glu Asp Met Leu Val Val Asp
        275                 280                 285

Pro Lys Ser Lys Glu Glu Asp Lys His Leu Lys Phe Arg Ile Ser His
    290                 295                 300

Glu Leu Asp Ser Ala Ser Ser Glu Val Asn
305                 310
```

`<210> SEQ ID NO 12`
`<211> LENGTH: 94`
`<212> TYPE: PRT`
`<213> ORGANISM: Homo sapiens`

`<400> SEQUENCE: 12`

```
Met Arg Thr Leu Ala Ile Leu Ala Ala Ile Leu Leu Val Ala Leu Gln
1               5                   10                  15

Ala Gln Ala Glu Pro Leu Gln Ala Arg Ala Asp Glu Val Ala Ala Ala
            20                  25                  30

Pro Glu Gln Ile Ala Ala Asp Ile Pro Glu Val Val Val Ser Leu Ala
        35                  40                  45

Trp Asp Glu Ser Leu Ala Pro Lys His Pro Gly Ser Arg Lys Asn Met
    50                  55                  60

Ala Cys Tyr Cys Arg Ile Pro Ala Cys Ile Ala Gly Glu Arg Arg Tyr
65                  70                  75                  80

Gly Thr Cys Ile Tyr Gln Gly Arg Leu Trp Ala Phe Cys Cys
                85                  90
```

`<210> SEQ ID NO 13`
`<211> LENGTH: 459`
`<212> TYPE: PRT`
`<213> ORGANISM: Homo sapiens`

`<400> SEQUENCE: 13`

```
Met Ala Pro Leu Cys Pro Ser Pro Trp Leu Pro Leu Leu Ile Pro Ala
1               5                   10                  15

Pro Ala Pro Gly Leu Thr Val Gln Leu Leu Leu Ser Leu Leu Leu Leu
            20                  25                  30

Val Pro Val His Pro Gln Arg Leu Pro Arg Met Gln Glu Asp Ser Pro
        35                  40                  45

Leu Gly Gly Gly Ser Ser Gly Glu Asp Asp Pro Leu Gly Glu Glu Asp
    50                  55                  60

Leu Pro Ser Glu Glu Asp Ser Pro Arg Glu Glu Asp Pro Pro Gly Glu
65                  70                  75                  80

Glu Asp Leu Pro Gly Glu Glu Asp Leu Pro Gly Glu Glu Asp Leu Pro
```

```
                    85                  90                  95
Glu Val Lys Pro Lys Ser Glu Glu Gly Ser Leu Lys Leu Glu Asp
                100                 105                 110
Leu Pro Thr Val Glu Ala Pro Gly Asp Pro Gln Glu Pro Gln Asn Asn
            115                 120                 125
Ala His Arg Asp Lys Glu Gly Asp Asp Gln Ser His Trp Arg Tyr Gly
        130                 135                 140
Gly Asp Pro Pro Trp Pro Arg Val Ser Pro Ala Cys Ala Gly Arg Phe
145                 150                 155                 160
Gln Ser Pro Val Asp Ile Arg Pro Gln Leu Ala Ala Phe Cys Pro Ala
                165                 170                 175
Leu Arg Pro Leu Glu Leu Leu Gly Phe Gln Leu Pro Pro Leu Pro Glu
            180                 185                 190
Leu Arg Leu Arg Asn Asn Gly His Ser Val Gln Leu Thr Leu Pro Pro
        195                 200                 205
Gly Leu Glu Met Ala Leu Gly Pro Gly Arg Glu Tyr Arg Ala Leu Gln
210                 215                 220
Leu His Leu His Trp Gly Ala Ala Gly Arg Pro Gly Ser Glu His Thr
225                 230                 235                 240
Val Glu Gly His Arg Phe Pro Ala Glu Ile His Val Val His Leu Ser
                245                 250                 255
Thr Ala Phe Ala Arg Val Asp Glu Ala Leu Gly Arg Pro Gly Gly Leu
            260                 265                 270
Ala Val Leu Ala Ala Phe Leu Glu Glu Gly Pro Glu Glu Asn Ser Ala
        275                 280                 285
Tyr Glu Gln Leu Leu Ser Arg Leu Glu Glu Ile Ala Glu Glu Gly Ser
    290                 295                 300
Glu Thr Gln Val Pro Gly Leu Asp Ile Ser Ala Leu Leu Pro Ser Asp
305                 310                 315                 320
Phe Ser Arg Tyr Phe Gln Tyr Glu Gly Ser Leu Thr Thr Pro Pro Cys
                325                 330                 335
Ala Gln Gly Val Ile Trp Thr Val Phe Asn Gln Thr Val Met Leu Ser
            340                 345                 350
Ala Lys Gln Leu His Thr Leu Ser Asp Thr Leu Trp Gly Pro Gly Asp
        355                 360                 365
Ser Arg Leu Gln Leu Asn Phe Arg Ala Thr Gln Pro Leu Asn Gly Arg
    370                 375                 380
Val Ile Glu Ala Ser Phe Pro Ala Gly Val Asp Ser Ser Pro Arg Ala
385                 390                 395                 400
Ala Glu Pro Val Gln Leu Asn Ser Cys Leu Ala Ala Gly Asp Ile Leu
                405                 410                 415
Ala Leu Val Phe Gly Leu Leu Phe Ala Val Thr Ser Val Ala Phe Leu
            420                 425                 430
Val Gln Met Arg Arg Gln His Arg Arg Gly Thr Lys Gly Gly Val Ser
        435                 440                 445
Tyr Arg Pro Ala Glu Val Ala Glu Thr Gly Ala
    450                 455

<210> SEQ ID NO 14
<211> LENGTH: 148
<212> TYPE: PRT
<213> ORGANISM: Homo sapiens

<400> SEQUENCE: 14
```

```
Met Arg Gly Ser Glu Leu Pro Leu Val Leu Leu Ala Leu Val Leu Cys
 1               5                  10                  15

Leu Ala Pro Arg Gly Arg Ala Val Pro Leu Pro Ala Gly Gly Gly Thr
            20                  25                  30

Val Leu Thr Lys Met Tyr Pro Arg Gly Asn His Trp Ala Val Gly His
        35                  40                  45

Leu Met Gly Lys Lys Ser Thr Gly Glu Ser Ser Val Ser Glu Arg
 50                  55                  60

Gly Ser Leu Lys Gln Gln Leu Arg Glu Tyr Ile Arg Trp Glu Glu Ala
 65                  70                  75                  80

Ala Arg Asn Leu Leu Gly Leu Ile Glu Ala Lys Glu Asn Arg Asn His
                85                  90                  95

Gln Pro Pro Gln Pro Lys Ala Leu Gly Asn Gln Gln Pro Ser Trp Asp
                100                 105                 110

Ser Glu Asp Ser Ser Asn Phe Lys Asp Val Gly Ser Lys Gly Lys Val
            115                 120                 125

Gly Arg Leu Ser Ala Pro Gly Ser Gln Arg Glu Gly Arg Asn Pro Gln
 130                 135                 140

Leu Asn Gln Gln
145

<210> SEQ ID NO 15
<211> LENGTH: 430
<212> TYPE: PRT
<213> ORGANISM: Homo sapiens

<400> SEQUENCE: 15

Met Ser Phe Thr Thr Arg Ser Thr Phe Ser Thr Asn Tyr Arg Ser Leu
 1               5                  10                  15

Gly Ser Val Gln Ala Pro Ser Tyr Gly Ala Arg Pro Val Ser Ser Ala
            20                  25                  30

Ala Ser Val Tyr Ala Gly Ala Gly Gly Ser Gly Ser Arg Ile Ser Val
        35                  40                  45

Ser Arg Ser Thr Ser Phe Arg Gly Gly Met Gly Ser Gly Gly Leu Ala
 50                  55                  60

Thr Gly Ile Ala Gly Gly Leu Ala Gly Met Gly Gly Ile Gln Asn Glu
 65                  70                  75                  80

Lys Glu Thr Met Gln Ser Leu Asn Asp Arg Leu Ala Ser Tyr Leu Asp
                85                  90                  95

Arg Val Arg Ser Leu Glu Thr Glu Asn Arg Arg Leu Glu Ser Lys Ile
                100                 105                 110

Arg Glu His Leu Glu Lys Lys Gly Pro Gln Val Arg Asp Trp Ser His
            115                 120                 125

Tyr Phe Lys Ile Ile Glu Asp Leu Arg Ala Gln Ile Phe Ala Asn Thr
 130                 135                 140

Val Asp Asn Ala Arg Ile Val Leu Gln Ile Asp Asn Ala Arg Leu Ala
145                 150                 155                 160

Ala Asp Asp Phe Arg Val Lys Tyr Glu Thr Glu Leu Ala Met Arg Gln
                165                 170                 175

Ser Val Glu Asn Asp Ile His Gly Leu Arg Lys Val Ile Asp Asp Thr
            180                 185                 190

Asn Ile Thr Arg Leu Gln Leu Glu Thr Glu Ile Glu Ala Leu Lys Glu
            195                 200                 205

Glu Leu Leu Phe Met Lys Lys Asn His Glu Glu Glu Val Lys Gly Leu
 210                 215                 220
```

```
Gln Ala Gln Ile Ala Ser Ser Gly Leu Thr Val Glu Val Asp Ala Pro
225                 230                 235                 240

Lys Ser Gln Asp Leu Ala Lys Ile Met Ala Asp Ile Arg Ala Gln Tyr
            245                 250                 255

Asp Glu Leu Ala Arg Lys Asn Arg Glu Glu Leu Asp Lys Tyr Trp Ser
        260                 265                 270

Gln Gln Ile Glu Glu Ser Thr Thr Val Val Thr Thr Gln Ser Ala Glu
    275                 280                 285

Val Gly Ala Ala Glu Thr Thr Leu Thr Glu Leu Arg Arg Thr Val Gln
290                 295                 300

Ser Leu Glu Ile Asp Leu Asp Ser Met Arg Asn Leu Lys Ala Ser Leu
305                 310                 315                 320

Glu Asn Ser Leu Arg Glu Val Glu Ala Arg Tyr Ala Leu Gln Met Glu
                325                 330                 335

Gln Leu Asn Gly Ile Leu Leu His Leu Glu Ser Glu Leu Ala Gln Thr
            340                 345                 350

Arg Ala Glu Gly Gln Arg Gln Ala Gln Glu Tyr Glu Ala Leu Leu Asn
        355                 360                 365

Ile Lys Val Lys Leu Glu Ala Glu Ile Ala Thr Tyr Arg Arg Leu Leu
    370                 375                 380

Glu Asp Gly Glu Asp Phe Asn Leu Gly Asp Ala Leu Asp Ser Ser Asn
385                 390                 395                 400

Ser Met Gln Thr Ile Gln Lys Thr Thr Thr Arg Arg Ile Val Asp Gly
                405                 410                 415

Lys Val Val Ser Glu Thr Asn Asp Thr Lys Val Leu Arg His
            420                 425                 430

<210> SEQ ID NO 16
<211> LENGTH: 882
<212> TYPE: PRT
<213> ORGANISM: Homo sapiens

<400> SEQUENCE: 16

Met Gly Pro Trp Ser Arg Ser Leu Ser Ala Leu Leu Leu Leu Leu Gln
1               5                   10                  15

Val Ser Ser Trp Leu Cys Gln Glu Pro Glu Pro Cys His Pro Gly Phe
            20                  25                  30

Asp Ala Glu Ser Tyr Thr Phe Thr Val Pro Arg Arg His Leu Glu Arg
        35                  40                  45

Gly Arg Val Leu Gly Arg Val Asn Phe Glu Asp Cys Thr Gly Arg Gln
    50                  55                  60

Arg Thr Ala Tyr Phe Ser Leu Asp Thr Arg Phe Lys Val Gly Thr Asp
65                  70                  75                  80

Gly Val Ile Thr Val Lys Arg Pro Leu Arg Phe His Asn Pro Gln Ile
                85                  90                  95

His Phe Leu Val Tyr Ala Trp Asp Ser Thr Tyr Arg Lys Phe Ser Thr
            100                 105                 110

Lys Val Thr Leu Asn Thr Val Gly His His His Arg Pro Pro Pro His
        115                 120                 125

Gln Ala Ser Val Ser Gly Ile Gln Ala Glu Leu Leu Thr Phe Pro Asn
    130                 135                 140

Ser Ser Pro Gly Leu Arg Arg Gln Lys Arg Asp Trp Val Ile Pro Pro
145                 150                 155                 160

Ile Ser Cys Pro Glu Asn Glu Lys Gly Pro Phe Pro Lys Asn Leu Val
```

```
                  165                 170                 175
Gln Ile Lys Ser Asn Lys Asp Lys Glu Gly Lys Val Phe Tyr Ser Ile
            180                 185                 190

Thr Gly Gln Gly Ala Asp Thr Pro Pro Val Gly Val Phe Ile Ile Glu
            195                 200                 205

Arg Glu Thr Gly Trp Leu Lys Val Thr Glu Pro Leu Asp Arg Glu Arg
        210                 215                 220

Ile Ala Thr Tyr Thr Leu Phe Ser His Ala Val Ser Ser Asn Gly Asn
225                 230                 235                 240

Ala Val Glu Asp Pro Met Glu Ile Leu Ile Thr Val Thr Asp Gln Asn
                245                 250                 255

Asp Asn Lys Pro Glu Phe Thr Gln Glu Val Phe Lys Gly Ser Val Met
            260                 265                 270

Glu Gly Ala Leu Pro Gly Thr Ser Val Met Glu Val Thr Ala Thr Asp
            275                 280                 285

Ala Asp Asp Asp Val Asn Thr Tyr Asn Ala Ala Ile Ala Tyr Thr Ile
        290                 295                 300

Leu Ser Gln Asp Pro Glu Leu Pro Asp Lys Asn Met Phe Thr Ile Asn
305                 310                 315                 320

Arg Asn Thr Gly Val Ile Ser Val Val Thr Thr Gly Leu Asp Arg Glu
                325                 330                 335

Ser Phe Pro Thr Tyr Thr Leu Val Val Gln Ala Ala Asp Leu Gln Gly
            340                 345                 350

Glu Gly Leu Ser Thr Thr Ala Thr Ala Val Ile Thr Val Thr Asp Thr
            355                 360                 365

Asn Asp Asn Pro Pro Ile Phe Asn Pro Thr Thr Tyr Lys Gly Gln Val
        370                 375                 380

Pro Glu Asn Glu Ala Asn Val Val Ile Thr Thr Leu Lys Val Thr Asp
385                 390                 395                 400

Ala Asp Ala Pro Asn Thr Pro Ala Trp Glu Ala Val Tyr Thr Ile Leu
                405                 410                 415

Asn Asp Asp Gly Gly Gln Phe Val Val Thr Thr Asn Pro Val Asn Asn
            420                 425                 430

Asp Gly Ile Leu Lys Thr Ala Lys Gly Leu Asp Phe Glu Ala Lys Gln
            435                 440                 445

Gln Tyr Ile Leu His Val Ala Val Thr Asn Val Val Pro Phe Glu Val
        450                 455                 460

Ser Leu Thr Thr Ser Thr Ala Thr Val Thr Val Asp Val Leu Asp Val
465                 470                 475                 480

Asn Glu Ala Pro Ile Phe Val Pro Pro Glu Lys Arg Val Glu Val Ser
                485                 490                 495

Glu Asp Phe Gly Val Gly Gln Glu Ile Thr Ser Tyr Thr Ala Gln Glu
            500                 505                 510

Pro Asp Thr Phe Met Glu Gln Lys Ile Thr Tyr Arg Ile Trp Arg Asp
            515                 520                 525

Thr Ala Asn Trp Leu Glu Ile Asn Pro Asp Thr Gly Ala Ile Ser Thr
        530                 535                 540

Arg Ala Glu Leu Asp Arg Glu Asp Phe Glu His Val Lys Asn Ser Thr
545                 550                 555                 560

Tyr Thr Ala Leu Ile Ile Ala Thr Asp Asn Gly Ser Pro Val Ala Thr
                565                 570                 575

Gly Thr Gly Thr Leu Leu Leu Ile Leu Ser Asp Val Asn Asp Asn Ala
            580                 585                 590
```

```
Pro Ile Pro Glu Pro Arg Thr Ile Phe Phe Cys Glu Arg Asn Pro Lys
            595                 600                 605

Pro Gln Val Ile Asn Ile Ile Asp Ala Asp Leu Pro Pro Asn Thr Ser
        610                 615                 620

Pro Phe Thr Ala Glu Leu Thr His Gly Ala Ser Ala Asn Trp Thr Ile
625                 630                 635                 640

Gln Tyr Asn Asp Pro Thr Gln Glu Ser Ile Ile Leu Lys Pro Lys Met
                645                 650                 655

Ala Leu Glu Val Gly Asp Tyr Lys Ile Asn Leu Lys Leu Met Asp Asn
            660                 665                 670

Gln Asn Lys Asp Gln Val Thr Thr Leu Glu Val Ser Val Cys Asp Cys
        675                 680                 685

Glu Gly Ala Ala Gly Val Cys Arg Lys Ala Gln Pro Val Glu Ala Gly
690                 695                 700

Leu Gln Ile Pro Ala Ile Leu Gly Ile Leu Gly Gly Ile Leu Ala Leu
705                 710                 715                 720

Leu Ile Leu Ile Leu Leu Leu Leu Phe Leu Arg Arg Arg Ala Val
                725                 730                 735

Val Lys Glu Pro Leu Leu Pro Pro Glu Asp Asp Thr Arg Asp Asn Val
            740                 745                 750

Tyr Tyr Tyr Asp Glu Glu Gly Gly Gly Glu Glu Asp Gln Asp Phe Asp
        755                 760                 765

Leu Ser Gln Leu His Arg Gly Leu Asp Ala Arg Pro Glu Val Thr Arg
770                 775                 780

Asn Asp Val Ala Pro Thr Leu Met Ser Val Pro Arg Tyr Leu Pro Arg
785                 790                 795                 800

Pro Ala Asn Pro Asp Glu Ile Gly Asn Phe Ile Asp Glu Asn Leu Lys
                805                 810                 815

Ala Ala Asp Thr Asp Pro Thr Ala Pro Pro Tyr Asp Ser Leu Leu Val
            820                 825                 830

Phe Asp Tyr Glu Gly Ser Gly Ser Glu Ala Ala Ser Leu Ser Ser Leu
        835                 840                 845

Asn Ser Ser Glu Ser Asp Lys Asp Gln Asp Tyr Asp Tyr Leu Asn Glu
850                 855                 860

Trp Gly Asn Arg Phe Lys Lys Leu Ala Asp Met Tyr Gly Gly Gly Glu
865                 870                 875                 880

Asp Asp

<210> SEQ ID NO 17
<211> LENGTH: 220
<212> TYPE: PRT
<213> ORGANISM: Homo sapiens

<400> SEQUENCE: 17

Met Gly Ala Ala Ala Arg Thr Leu Arg Leu Ala Leu Gly Leu Leu Leu
1               5                   10                  15

Leu Ala Thr Leu Leu Arg Pro Ala Asp Ala Cys Ser Cys Ser Pro Val
            20                  25                  30

His Pro Gln Gln Ala Phe Cys Asn Ala Asp Val Val Ile Arg Ala Lys
        35                  40                  45

Ala Val Ser Glu Lys Glu Val Asp Ser Gly Asn Asp Ile Tyr Gly Asn
    50                  55                  60

Pro Ile Lys Arg Ile Gln Tyr Glu Ile Lys Gln Ile Lys Met Phe Lys
65                  70                  75                  80
```

Gly Pro Glu Lys Asp Ile Glu Phe Ile Tyr Thr Ala Pro Ser Ser Ala
            85                  90                  95

Val Cys Gly Val Ser Leu Asp Val Gly Lys Lys Glu Tyr Leu Ile
            100                 105                 110

Ala Gly Lys Ala Glu Gly Asp Gly Lys Met His Ile Thr Leu Cys Asp
            115                 120                 125

Phe Ile Val Pro Trp Asp Thr Leu Ser Thr Gln Lys Lys Ser Leu
        130                 135                 140

Asn His Arg Tyr Gln Met Gly Cys Glu Cys Lys Ile Thr Arg Cys Pro
145                 150                 155                 160

Met Ile Pro Cys Tyr Ile Ser Ser Pro Asp Glu Cys Leu Trp Met Asp
                165                 170                 175

Trp Val Thr Glu Lys Asn Ile Asn Gly His Gln Ala Lys Phe Phe Ala
                180                 185                 190

Cys Ile Lys Arg Ser Asp Gly Ser Cys Ala Trp Tyr Arg Gly Ala Ala
                195                 200                 205

Pro Pro Lys Gln Glu Phe Leu Asp Ile Glu Asp Pro
            210                 215                 220

<210> SEQ ID NO 18
<211> LENGTH: 742
<212> TYPE: PRT
<213> ORGANISM: Homo sapiens

<400> SEQUENCE: 18

Met Asp Lys Phe Trp Trp His Ala Ala Trp Gly Leu Cys Leu Val Pro
1               5                   10                  15

Leu Ser Leu Ala Gln Ile Asp Leu Asn Ile Thr Cys Arg Phe Ala Gly
            20                  25                  30

Val Phe His Val Glu Lys Asn Gly Arg Tyr Ser Ile Ser Arg Thr Glu
        35                  40                  45

Ala Ala Asp Leu Cys Lys Ala Phe Asn Ser Thr Leu Pro Thr Met Ala
    50                  55                  60

Gln Met Glu Lys Ala Leu Ser Ile Gly Phe Glu Thr Cys Arg Tyr Gly
65                  70                  75                  80

Phe Ile Glu Gly His Val Val Ile Pro Arg Ile His Pro Asn Ser Ile
                85                  90                  95

Cys Ala Ala Asn Asn Thr Gly Val Tyr Ile Leu Thr Ser Asn Thr Ser
                100                 105                 110

Gln Tyr Asp Thr Tyr Cys Phe Asn Ala Ser Ala Pro Pro Glu Glu Asp
            115                 120                 125

Cys Thr Ser Val Thr Asp Leu Pro Asn Ala Phe Asp Gly Pro Ile Thr
        130                 135                 140

Ile Thr Ile Val Asn Arg Asp Gly Thr Arg Tyr Val Gln Lys Gly Glu
145                 150                 155                 160

Tyr Arg Thr Asn Pro Glu Asp Ile Tyr Pro Ser Asn Pro Thr Asp Asp
                165                 170                 175

Asp Val Ser Ser Gly Ser Ser Ser Glu Arg Ser Ser Thr Ser Gly Gly
                180                 185                 190

Tyr Ile Phe Tyr Thr Phe Ser Thr Val His Pro Ile Pro Asp Glu Asp
                195                 200                 205

Ser Pro Trp Ile Thr Asp Ser Thr Asp Arg Ile Pro Ala Thr Thr Leu
            210                 215                 220

Met Ser Thr Ser Ala Thr Ala Thr Glu Thr Ala Thr Lys Arg Gln Glu

```
        225                 230                 235                 240

Thr Trp Asp Trp Phe Ser Trp Leu Phe Leu Pro Ser Glu Ser Lys Asn
                245                 250                 255

His Leu His Thr Thr Thr Gln Met Ala Gly Thr Ser Ser Asn Thr Ile
                260                 265                 270

Ser Ala Gly Trp Glu Pro Asn Glu Asn Glu Asp Glu Arg Asp Arg
            275                 280                 285

His Leu Ser Phe Ser Gly Ser Gly Ile Asp Asp Glu Asp Phe Ile
        290                 295                 300

Ser Ser Thr Ile Ser Thr Thr Pro Arg Ala Phe Asp His Thr Lys Gln
305                 310                 315                 320

Asn Gln Asp Trp Thr Gln Trp Asn Pro Ser His Ser Asn Pro Glu Val
                325                 330                 335

Leu Leu Gln Thr Thr Thr Arg Met Thr Asp Val Asp Arg Asn Gly Thr
                340                 345                 350

Thr Ala Tyr Glu Gly Asn Trp Asn Pro Glu Ala His Pro Pro Leu Ile
                355                 360                 365

His His Glu His His Glu Glu Glu Thr Pro His Ser Thr Ser Thr
                370                 375                 380

Ile Gln Ala Thr Pro Ser Ser Thr Thr Glu Glu Thr Ala Thr Gln Lys
385                 390                 395                 400

Glu Gln Trp Phe Gly Asn Arg Trp His Glu Gly Tyr Arg Gln Thr Pro
                405                 410                 415

Arg Glu Asp Ser His Ser Thr Thr Gly Thr Ala Ala Ala Ser Ala His
                420                 425                 430

Thr Ser His Pro Met Gln Gly Arg Thr Thr Pro Ser Pro Glu Asp Ser
                435                 440                 445

Ser Trp Thr Asp Phe Phe Asn Pro Ile Ser His Pro Met Gly Arg Gly
                450                 455                 460

His Gln Ala Gly Arg Arg Met Asp Met Asp Ser Ser His Ser Thr Thr
465                 470                 475                 480

Leu Gln Pro Thr Ala Asn Pro Asn Thr Gly Leu Val Glu Asp Leu Asp
                485                 490                 495

Arg Thr Gly Pro Leu Ser Met Thr Thr Gln Gln Ser Asn Ser Gln Ser
                500                 505                 510

Phe Ser Thr Ser His Glu Gly Leu Glu Glu Asp Lys Asp His Pro Thr
                515                 520                 525

Thr Ser Thr Leu Thr Ser Ser Asn Arg Asn Asp Val Thr Gly Gly Arg
                530                 535                 540

Arg Asp Pro Asn His Ser Glu Gly Ser Thr Thr Leu Leu Glu Gly Tyr
545                 550                 555                 560

Thr Ser His Tyr Pro His Thr Lys Glu Ser Arg Thr Phe Ile Pro Val
                565                 570                 575

Thr Ser Ala Lys Thr Gly Ser Phe Gly Val Thr Ala Val Thr Val Gly
                580                 585                 590

Asp Ser Asn Ser Asn Val Asn Arg Ser Leu Ser Gly Asp Gln Asp Thr
                595                 600                 605

Phe His Pro Ser Gly Gly Ser Thr Thr His Gly Ser Glu Ser Asp
        610                 615                 620

Gly His Ser His Gly Ser Gln Glu Gly Gly Ala Asn Thr Thr Ser Gly
625                 630                 635                 640

Pro Ile Arg Thr Pro Gln Ile Pro Glu Trp Leu Ile Ile Leu Ala Ser
                645                 650                 655
```

```
Leu Leu Ala Leu Ala Leu Ile Leu Ala Val Cys Ile Ala Val Asn Ser
            660                 665                 670

Arg Arg Arg Cys Gly Gln Lys Lys Leu Val Ile Asn Ser Gly Asn
        675                 680                 685

Gly Ala Val Glu Asp Arg Lys Pro Ser Gly Leu Asn Gly Glu Ala Ser
    690                 695                 700

Lys Ser Gln Glu Met Val His Leu Val Asn Lys Glu Ser Ser Glu Thr
705                 710                 715                 720

Pro Asp Gln Phe Met Thr Ala Asp Glu Thr Arg Asn Leu Gln Asn Val
                725                 730                 735

Asp Met Lys Ile Gly Val
            740

<210> SEQ ID NO 19
<211> LENGTH: 585
<212> TYPE: PRT
<213> ORGANISM: Homo sapiens

<400> SEQUENCE: 19

Met Thr Pro Pro Arg Leu Phe Trp Val Trp Leu Leu Val Ala Gly Thr
1               5                   10                  15

Gln Gly Val Asn Asp Gly Asp Met Arg Leu Ala Asp Gly Gly Ala Thr
                20                  25                  30

Asn Gln Gly Arg Val Glu Ile Phe Tyr Arg Gly Gln Trp Gly Thr Val
            35                  40                  45

Cys Asp Asn Leu Trp Asp Leu Thr Asp Ala Ser Val Val Cys Arg Ala
50                  55                  60

Leu Gly Phe Glu Asn Ala Thr Gln Ala Leu Gly Arg Ala Ala Phe Gly
65                  70                  75                  80

Gln Gly Ser Gly Pro Ile Met Leu Asp Glu Val Gln Cys Thr Gly Thr
                85                  90                  95

Glu Ala Ser Leu Ala Asp Cys Lys Ser Leu Gly Trp Leu Lys Ser Asn
            100                 105                 110

Cys Arg His Glu Arg Asp Ala Gly Val Val Cys Thr Asn Glu Thr Arg
        115                 120                 125

Ser Thr His Thr Leu Asp Leu Ser Arg Glu Leu Ser Glu Ala Leu Gly
    130                 135                 140

Gln Ile Phe Asp Ser Gln Arg Gly Cys Asp Leu Ser Ile Ser Val Asn
145                 150                 155                 160

Val Gln Gly Glu Asp Ala Leu Gly Phe Cys Gly His Thr Val Ile Leu
                165                 170                 175

Thr Ala Asn Leu Glu Ala Gln Ala Leu Trp Lys Glu Pro Gly Ser Asn
            180                 185                 190

Val Thr Met Ser Val Asp Ala Glu Cys Val Pro Met Val Arg Asp Leu
        195                 200                 205

Leu Arg Tyr Phe Tyr Ser Arg Arg Ile Asp Ile Thr Leu Ser Ser Val
    210                 215                 220

Lys Cys Phe His Lys Leu Ala Ser Ala Tyr Gly Ala Arg Gln Leu Gln
225                 230                 235                 240

Gly Tyr Cys Ala Ser Leu Phe Ala Ile Leu Leu Pro Gln Asp Pro Ser
                245                 250                 255

Phe Gln Met Pro Leu Asp Leu Tyr Ala Tyr Ala Val Ala Thr Gly Asp
            260                 265                 270

Ala Leu Leu Glu Lys Leu Cys Leu Gln Phe Leu Ala Trp Asn Phe Glu
```

```
                275                 280                 285
Ala Leu Thr Gln Ala Glu Ala Trp Pro Ser Val Pro Thr Asp Leu Leu
        290                 295                 300

Gln Leu Leu Pro Arg Ser Asp Leu Ala Val Pro Ser Glu Leu Ala
305                 310                 315                 320

Leu Leu Lys Ala Val Asp Thr Trp Ser Trp Gly Glu Arg Ala Ser His
                325                 330                 335

Glu Glu Val Glu Gly Leu Val Glu Lys Ile Arg Phe Pro Met Met Leu
            340                 345                 350

Pro Glu Glu Leu Phe Glu Leu Gln Phe Asn Leu Ser Leu Tyr Trp Ser
                355                 360                 365

His Glu Ala Leu Phe Gln Lys Lys Thr Leu Gln Ala Leu Glu Phe His
        370                 375                 380

Thr Val Pro Phe Gln Leu Leu Ala Arg Tyr Lys Gly Leu Asn Leu Thr
385                 390                 395                 400

Glu Asp Thr Tyr Lys Pro Arg Ile Tyr Thr Ser Pro Thr Trp Ser Ala
                405                 410                 415

Phe Val Thr Asp Ser Ser Trp Ser Ala Arg Lys Ser Gln Leu Val Tyr
            420                 425                 430

Gln Ser Arg Arg Gly Pro Leu Val Lys Tyr Ser Ser Asp Tyr Phe Gln
        435                 440                 445

Ala Pro Ser Asp Tyr Arg Tyr Tyr Pro Tyr Gln Ser Phe Gln Thr Pro
    450                 455                 460

Gln His Pro Ser Phe Leu Phe Gln Asp Lys Arg Val Ser Trp Ser Leu
465                 470                 475                 480

Val Tyr Leu Pro Thr Ile Gln Ser Cys Trp Asn Tyr Gly Phe Ser Cys
                485                 490                 495

Ser Ser Asp Glu Leu Pro Val Leu Gly Leu Thr Lys Ser Gly Gly Ser
            500                 505                 510

Asp Arg Thr Ile Ala Tyr Glu Asn Lys Ala Leu Met Leu Cys Glu Gly
        515                 520                 525

Leu Phe Val Ala Asp Val Thr Asp Phe Glu Gly Trp Lys Ala Ala Ile
    530                 535                 540

Pro Ser Ala Leu Asp Thr Asn Ser Ser Lys Ser Thr Ser Ser Phe Pro
545                 550                 555                 560

Cys Pro Ala Gly His Phe Asn Gly Phe Arg Thr Val Ile Arg Pro Phe
                565                 570                 575

Tyr Leu Thr Asn Ser Ser Gly Val Asp
            580                 585

<210> SEQ ID NO 20
<211> LENGTH: 1255
<212> TYPE: PRT
<213> ORGANISM: Homo sapiens

<400> SEQUENCE: 20

Met Glu Leu Ala Ala Leu Cys Arg Trp Gly Leu Leu Ala Leu Leu
1               5                   10                  15

Pro Pro Gly Ala Ala Ser Thr Gln Val Cys Thr Gly Thr Asp Met Lys
                20                  25                  30

Leu Arg Leu Pro Ala Ser Pro Glu Thr His Leu Asp Met Leu Arg His
            35                  40                  45

Leu Tyr Gln Gly Cys Gln Val Val Gln Gly Asn Leu Glu Leu Thr Tyr
        50                  55                  60
```

```
Leu Pro Thr Asn Ala Ser Leu Ser Phe Leu Gln Asp Ile Gln Glu Val
 65                  70                  75                  80

Gln Gly Tyr Val Leu Ile Ala His Asn Gln Val Arg Gln Val Pro Leu
                 85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
            115                 120                 125

Val Thr Gly Ala Ser Pro Gly Gly Leu Arg Glu Leu Gln Leu Arg Ser
130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
            195                 200                 205

Ser Glu Asp Cys Gln Ser Leu Thr Arg Thr Val Cys Ala Gly Gly Cys
210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
            275                 280                 285

Tyr Thr Phe Gly Ala Ser Cys Val Thr Ala Cys Pro Tyr Asn Tyr Leu
            290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
            355                 360                 365

Lys Ile Phe Gly Ser Leu Ala Phe Leu Pro Glu Ser Phe Asp Gly Asp
370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
            435                 440                 445

Gly Ile Ser Trp Leu Gly Leu Arg Ser Leu Arg Glu Leu Gly Ser Gly
            450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
```

```
                485                 490                 495
Ala Asn Arg Pro Glu Asp Glu Cys Val Gly Glu Gly Leu Ala Cys His
                500                 505                 510

Gln Leu Cys Ala Arg Gly His Cys Trp Gly Pro Gly Pro Thr Gln Cys
                515                 520                 525

Val Asn Cys Ser Gln Phe Leu Arg Gly Gln Glu Cys Val Glu Glu Cys
                530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                    565                 570                 575

Phe Gly Pro Glu Ala Asp Gln Cys Val Ala Cys Ala His Tyr Lys Asp
                580                 585                 590

Pro Pro Phe Cys Val Ala Arg Cys Pro Ser Gly Val Lys Pro Asp Leu
                595                 600                 605

Ser Tyr Met Pro Ile Trp Lys Phe Pro Asp Glu Glu Gly Ala Cys Gln
                610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
                    645                 650                 655

Ala Val Val Gly Ile Leu Leu Val Val Val Leu Gly Val Val Phe Gly
                    660                 665                 670

Ile Leu Ile Lys Arg Arg Gln Gln Lys Ile Arg Lys Tyr Thr Met Arg
                    675                 680                 685

Arg Leu Leu Gln Glu Thr Glu Leu Val Glu Pro Leu Thr Pro Ser Gly
                690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
                    725                 730                 735

Gly Ile Trp Ile Pro Asp Gly Glu Asn Val Lys Ile Pro Val Ala Ile
                    740                 745                 750

Lys Val Leu Arg Glu Asn Thr Ser Pro Lys Ala Asn Lys Glu Ile Leu
                755                 760                 765

Asp Glu Ala Tyr Val Met Ala Gly Val Gly Ser Pro Tyr Val Ser Arg
                770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
                    805                 810                 815

Leu Gly Ser Gln Asp Leu Leu Asn Trp Cys Met Gln Ile Ala Lys Gly
                    820                 825                 830

Met Ser Tyr Leu Glu Asp Val Arg Leu Val His Arg Asp Leu Ala Ala
                    835                 840                 845

Arg Asn Val Leu Val Lys Ser Pro Asn His Val Lys Ile Thr Asp Phe
                850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
                    885                 890                 895

Arg Arg Phe Thr His Gln Ser Asp Val Trp Ser Tyr Gly Val Thr Val
                    900                 905                 910
```

```
Trp Glu Leu Met Thr Phe Gly Ala Lys Pro Tyr Asp Gly Ile Pro Ala
            915                 920                 925

Arg Glu Ile Pro Asp Leu Leu Glu Lys Gly Glu Arg Leu Pro Gln Pro
            930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
            965                 970                 975

Ser Arg Met Ala Arg Asp Pro Gln Arg Phe Val Val Ile Gln Asn Glu
            980                 985                 990

Asp Leu Gly Pro Ala Ser Pro Leu Asp Ser Thr Phe Tyr Arg Ser Leu
            995                1000                1005

Leu Glu Asp Asp Asp Met Gly Asp Leu Val Asp Ala Glu Glu Tyr Leu
           1010                1015                1020

Val Pro Gln Gln Gly Phe Phe Cys Pro Asp Pro Ala Pro Gly Ala Gly
1025                1030                1035                1040

Gly Met Val His His Arg His Arg Ser Ser Ser Thr Arg Ser Gly Gly
                   1045                1050                1055

Gly Asp Leu Thr Leu Gly Leu Glu Pro Ser Glu Glu Glu Ala Pro Arg
           1060                1065                1070

Ser Pro Leu Ala Pro Ser Glu Gly Ala Gly Ser Asp Val Phe Asp Gly
           1075                1080                1085

Asp Leu Gly Met Gly Ala Ala Lys Gly Leu Gln Ser Leu Pro Thr His
           1090                1095                1100

Asp Pro Ser Pro Leu Gln Arg Tyr Ser Glu Asp Pro Thr Val Pro Leu
1105                1110                1115                1120

Pro Ser Glu Thr Asp Gly Tyr Val Ala Pro Leu Thr Cys Ser Pro Gln
                   1125                1130                1135

Pro Glu Tyr Val Asn Gln Pro Asp Val Arg Pro Gln Pro Pro Ser Pro
           1140                1145                1150

Arg Glu Gly Pro Leu Pro Ala Ala Arg Pro Ala Gly Ala Thr Leu Glu
           1155                1160                1165

Arg Pro Lys Thr Leu Ser Pro Gly Lys Asn Gly Val Val Lys Asp Val
           1170                1175                1180

Phe Ala Phe Gly Gly Ala Val Glu Asn Pro Glu Tyr Leu Thr Pro Gln
1185                1190                1195                1200

Gly Gly Ala Ala Pro Gln Pro His Pro Pro Pro Ala Phe Ser Pro Ala
                   1205                1210                1215

Phe Asp Asn Leu Tyr Tyr Trp Asp Gln Asp Pro Pro Glu Arg Gly Ala
           1220                1225                1230

Pro Pro Ser Thr Phe Lys Gly Thr Pro Thr Ala Glu Asn Pro Glu Tyr
           1235                1240                1245

Leu Gly Leu Asp Val Pro Val
           1250                1255

<210> SEQ ID NO 21
<211> LENGTH: 431
<212> TYPE: PRT
<213> ORGANISM: Homo sapiens

<400> SEQUENCE: 21

Met Arg Ala Leu Leu Ala Arg Leu Leu Leu Cys Val Leu Val Val Ser
1               5                   10                  15

Asp Ser Lys Gly Ser Asn Glu Leu His Gln Val Pro Ser Asn Cys Asp
```

```
            20                  25                  30
Cys Leu Asn Gly Gly Thr Cys Val Ser Asn Lys Tyr Phe Ser Asn Ile
        35                  40                  45
His Trp Cys Asn Cys Pro Lys Lys Phe Gly Gly Gln His Cys Glu Ile
 50                  55                  60
Asp Lys Ser Lys Thr Cys Tyr Glu Gly Asn Gly His Phe Tyr Arg Gly
 65                  70                  75                  80
Lys Ala Ser Thr Asp Thr Met Gly Arg Pro Cys Leu Pro Trp Asn Ser
                 85                  90                  95
Ala Thr Val Leu Gln Gln Thr Tyr His Ala His Arg Ser Asp Ala Leu
            100                 105                 110
Gln Leu Gly Leu Gly Lys His Asn Tyr Cys Arg Asn Pro Asp Asn Arg
        115                 120                 125
Arg Arg Pro Trp Cys Tyr Val Gln Val Gly Leu Lys Pro Leu Val Gln
130                 135                 140
Glu Cys Met Val His Asp Cys Ala Asp Gly Lys Lys Pro Ser Ser Pro
145                 150                 155                 160
Pro Glu Glu Leu Lys Phe Gln Cys Gly Gln Lys Thr Leu Arg Pro Arg
                165                 170                 175
Phe Lys Ile Ile Gly Gly Glu Phe Thr Thr Ile Glu Asn Gln Pro Trp
            180                 185                 190
Phe Ala Ala Ile Tyr Arg Arg His Arg Gly Gly Ser Val Thr Tyr Val
        195                 200                 205
Cys Gly Gly Ser Leu Met Ser Pro Cys Trp Val Ile Ser Ala Thr His
    210                 215                 220
Cys Phe Ile Asp Tyr Pro Lys Lys Glu Asp Tyr Ile Val Tyr Leu Gly
225                 230                 235                 240
Arg Ser Arg Leu Asn Ser Asn Thr Gln Gly Glu Met Lys Phe Glu Val
                245                 250                 255
Glu Asn Leu Ile Leu His Lys Asp Tyr Ser Ala Asp Thr Leu Ala His
            260                 265                 270
His Asn Asp Ile Ala Leu Leu Lys Ile Arg Ser Lys Glu Gly Arg Cys
        275                 280                 285
Ala Gln Pro Ser Arg Thr Ile Gln Thr Ile Cys Leu Pro Ser Met Tyr
290                 295                 300
Asn Asp Pro Gln Phe Gly Thr Ser Cys Glu Ile Thr Gly Phe Gly Lys
305                 310                 315                 320
Glu Asn Ser Thr Asp Tyr Leu Tyr Pro Glu Gln Leu Lys Met Thr Val
                325                 330                 335
Val Lys Leu Ile Ser His Arg Glu Cys Gln Gln Pro His Tyr Tyr Gly
            340                 345                 350
Ser Glu Val Thr Thr Lys Met Leu Cys Ala Ala Asp Pro Gln Trp Lys
        355                 360                 365
Thr Asp Ser Cys Gln Gly Asp Ser Gly Gly Pro Leu Val Cys Ser Leu
370                 375                 380
Gln Gly Arg Met Thr Leu Thr Gly Ile Val Ser Trp Gly Arg Gly Cys
385                 390                 395                 400
Ala Leu Lys Asp Lys Pro Gly Val Tyr Thr Arg Val Ser His Phe Leu
                405                 410                 415
Pro Trp Ile Arg Ser His Thr Lys Glu Glu Asn Gly Leu Ala Leu
            420                 425                 430

<210> SEQ ID NO 22
```

```
<211> LENGTH: 266
<212> TYPE: PRT
<213> ORGANISM: Homo sapiens

<400> SEQUENCE: 22

Met Met Ala Leu Gly Ala Ala Gly Ala Thr Arg Val Phe Val Ala Met
 1               5                  10                  15

Val Ala Ala Ala Leu Gly Gly His Pro Leu Leu Gly Val Ser Ala Thr
             20                  25                  30

Leu Asn Ser Val Leu Asn Ser Asn Ala Ile Lys Asn Leu Pro Pro Pro
         35                  40                  45

Leu Gly Gly Ala Ala Gly His Pro Gly Ser Ala Val Ser Ala Ala Pro
 50                  55                  60

Gly Ile Leu Tyr Pro Gly Gly Asn Lys Tyr Gln Thr Ile Asp Asn Tyr
 65                  70                  75                  80

Gln Pro Tyr Pro Cys Ala Glu Asp Glu Glu Cys Gly Thr Asp Glu Tyr
                 85                  90                  95

Cys Ala Ser Pro Thr Arg Gly Gly Asp Ala Gly Val Gln Ile Cys Leu
            100                 105                 110

Ala Cys Arg Lys Arg Arg Lys Arg Cys Met Arg His Ala Met Cys Cys
        115                 120                 125

Pro Gly Asn Tyr Cys Lys Asn Gly Ile Cys Val Ser Ser Asp Gln Asn
    130                 135                 140

His Phe Arg Gly Glu Ile Glu Glu Thr Ile Thr Glu Ser Phe Gly Asn
145                 150                 155                 160

Asp His Ser Thr Leu Asp Gly Tyr Ser Arg Arg Thr Thr Leu Ser Ser
                165                 170                 175

Lys Met Tyr His Thr Lys Gly Gln Glu Gly Ser Val Cys Leu Arg Ser
            180                 185                 190

Ser Asp Cys Ala Ser Gly Leu Cys Cys Ala Arg His Phe Trp Ser Lys
        195                 200                 205

Ile Cys Lys Pro Val Leu Lys Glu Gly Gln Val Cys Thr Lys His Arg
    210                 215                 220

Arg Lys Gly Ser His Gly Leu Glu Ile Phe Gln Arg Cys Tyr Cys Gly
225                 230                 235                 240

Glu Gly Leu Ser Cys Arg Ile Gln Lys Asp His His Gln Ala Ser Asn
                245                 250                 255

Ser Ser Arg Leu His Thr Cys Gln Arg His
            260                 265

<210> SEQ ID NO 23
<211> LENGTH: 457
<212> TYPE: PRT
<213> ORGANISM: Homo sapiens

<400> SEQUENCE: 23

Met Arg Ser Ala Ala Val Leu Ala Leu Leu Leu Cys Ala Gly Gln Val
 1               5                  10                  15

Thr Ala Leu Pro Val Asn Ser Pro Met Asn Lys Gly Asp Thr Glu Val
             20                  25                  30

Met Lys Cys Ile Val Glu Val Ile Ser Asp Thr Leu Ser Lys Pro Ser
         35                  40                  45

Pro Met Pro Val Ser Gln Glu Cys Phe Glu Thr Leu Arg Gly Asp Glu
 50                  55                  60

Arg Ile Leu Ser Ile Leu Arg His Gln Asn Leu Leu Lys Glu Leu Gln
 65                  70                  75                  80
```

```
Asp Leu Ala Leu Gln Gly Ala Lys Glu Arg Ala His Gln Gln Lys Lys
                 85                  90                  95

His Ser Gly Phe Glu Asp Glu Leu Ser Glu Val Leu Glu Asn Gln Ser
            100                 105                 110

Ser Gln Ala Glu Leu Lys Glu Ala Val Glu Glu Pro Ser Ser Lys Asp
        115                 120                 125

Val Met Glu Lys Arg Glu Asp Ser Lys Glu Ala Glu Lys Ser Gly Glu
    130                 135                 140

Ala Thr Asp Gly Ala Arg Pro Gln Ala Leu Pro Glu Pro Met Gln Glu
145                 150                 155                 160

Ser Lys Ala Glu Gly Asn Asn Gln Ala Pro Gly Glu Glu Glu Glu
            165                 170                 175

Glu Glu Glu Ala Thr Asn Thr His Pro Pro Ala Ser Leu Pro Ser Gln
            180                 185                 190

Lys Tyr Pro Gly Pro Gln Ala Glu Gly Asp Ser Glu Gly Leu Ser Gln
            195                 200                 205

Gly Leu Val Asp Arg Glu Lys Gly Leu Ser Ala Glu Pro Gly Trp Gln
    210                 215                 220

Ala Lys Arg Glu Glu Glu Glu Glu Glu Glu Glu Ala Glu Ala Gly
225                 230                 235                 240

Glu Glu Ala Val Pro Glu Glu Glu Gly Pro Thr Val Val Leu Asn Pro
                245                 250                 255

His Pro Ser Leu Gly Tyr Lys Glu Ile Arg Lys Gly Glu Ser Arg Ser
            260                 265                 270

Glu Ala Leu Ala Val Asp Gly Ala Gly Lys Pro Gly Ala Glu Glu Ala
        275                 280                 285

Gln Asp Pro Glu Gly Lys Gly Glu Gln Glu His Ser Gln Gln Lys Glu
    290                 295                 300

Glu Glu Glu Glu Met Ala Val Val Pro Gln Gly Leu Phe Arg Gly Gly
305                 310                 315                 320

Lys Ser Gly Glu Leu Glu Gln Glu Glu Glu Arg Leu Ser Lys Glu Trp
            325                 330                 335

Glu Asp Ser Lys Arg Trp Ser Lys Met Asp Gln Leu Ala Lys Glu Leu
            340                 345                 350

Thr Ala Glu Lys Arg Leu Glu Gly Gln Glu Glu Glu Glu Asp Asn Arg
        355                 360                 365

Asp Ser Ser Met Lys Leu Ser Phe Arg Ala Arg Ala Tyr Gly Phe Arg
    370                 375                 380

Gly Pro Gly Pro Gln Leu Arg Arg Gly Trp Arg Pro Ser Arg Glu Glu
385                 390                 395                 400

Asp Ser Leu Glu Ala Gly Leu Pro Leu Gln Val Arg Gly Tyr Pro Glu
                405                 410                 415

Glu Lys Lys Glu Glu Glu Gly Ser Ala Asn Arg Arg Pro Glu Asp Gln
            420                 425                 430

Glu Leu Glu Ser Leu Ser Ala Ile Glu Ala Glu Leu Glu Lys Val Ala
        435                 440                 445

His Gln Leu Gln Ala Leu Arg Arg Gly
    450                 455

<210> SEQ ID NO 24
<211> LENGTH: 232
<212> TYPE: PRT
<213> ORGANISM: Homo sapiens
```

```
<400> SEQUENCE: 24

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
            35                  40                  45

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
                100                 105                 110

Gln Gly Gln His Ile Gly Glu Met Ser Phe Leu Gln His Asn Lys Cys
            115                 120                 125

Glu Cys Arg Pro Lys Lys Asp Arg Ala Arg Gln Glu Lys Lys Ser Val
            130                 135                 140

Arg Gly Lys Gly Lys Gly Gln Lys Arg Lys Arg Lys Lys Ser Arg Tyr
145                 150                 155                 160

Lys Ser Trp Ser Val Tyr Val Gly Ala Arg Cys Cys Leu Met Pro Trp
                165                 170                 175

Ser Leu Pro Gly Pro His Pro Cys Gly Pro Cys Ser Glu Arg Arg Lys
            180                 185                 190

His Leu Phe Val Gln Asp Pro Gln Thr Cys Lys Cys Ser Cys Lys Asn
        195                 200                 205

Thr Asp Ser Arg Cys Lys Ala Arg Gln Leu Glu Leu Asn Glu Arg Thr
    210                 215                 220

Cys Arg Cys Asp Lys Pro Arg Arg
225                 230

<210> SEQ ID NO 25
<211> LENGTH: 273
<212> TYPE: PRT
<213> ORGANISM: Homo sapiens

<400> SEQUENCE: 25

Met Lys Lys Thr Gln Thr Trp Ile Leu Thr Cys Ile Tyr Leu Gln Leu
1               5                   10                  15

Leu Leu Phe Asn Pro Leu Val Lys Thr Glu Gly Ile Cys Arg Asn Arg
                20                  25                  30

Val Thr Asn Asn Val Lys Asp Val Thr Lys Leu Val Ala Asn Leu Pro
            35                  40                  45

Lys Asp Tyr Met Ile Thr Leu Lys Tyr Val Pro Gly Met Asp Val Leu
    50                  55                  60

Pro Ser His Cys Trp Ile Ser Glu Met Val Val Gln Leu Ser Asp Ser
65                  70                  75                  80

Leu Thr Asp Leu Leu Asp Lys Phe Ser Asn Ile Ser Glu Gly Leu Ser
                85                  90                  95

Asn Tyr Ser Ile Ile Asp Lys Leu Val Asn Ile Val Asp Asp Leu Val
            100                 105                 110

Glu Cys Val Lys Glu Asn Ser Ser Lys Asp Leu Lys Lys Ser Phe Lys
            115                 120                 125
```

```
Ser Pro Glu Pro Arg Leu Phe Thr Pro Glu Glu Phe Arg Ile Phe
    130                 135                 140

Asn Arg Ser Ile Asp Ala Phe Lys Asp Phe Val Val Ala Ser Glu Thr
145                 150                 155                 160

Ser Asp Cys Val Val Ser Ser Thr Leu Ser Pro Glu Lys Asp Ser Arg
                165                 170                 175

Val Ser Val Thr Lys Pro Phe Met Leu Pro Pro Val Ala Ala Ser Ser
            180                 185                 190

Leu Arg Asn Asp Ser Ser Ser Asn Arg Lys Ala Lys Asn Pro Pro
        195                 200                 205

Gly Asp Ser Ser Leu His Trp Ala Ala Met Ala Leu Pro Ala Leu Phe
    210                 215                 220

Ser Leu Ile Ile Gly Phe Ala Phe Gly Ala Leu Tyr Trp Lys Lys Arg
225                 230                 235                 240

Gln Pro Ser Leu Thr Arg Ala Val Glu Asn Ile Gln Ile Asn Glu Glu
                245                 250                 255

Asp Asn Glu Ile Ser Met Leu Gln Glu Lys Glu Arg Glu Phe Gln Glu
                260                 265                 270

Val

<210> SEQ ID NO 26
<211> LENGTH: 491
<212> TYPE: PRT
<213> ORGANISM: Homo sapiens

<400> SEQUENCE: 26

Met Asn Pro Ala Ala Glu Ala Glu Phe Asn Ile Leu Leu Ala Thr Asp
1               5                   10                  15

Ser Tyr Lys Val Thr His Tyr Lys Gln Tyr Pro Pro Asn Thr Ser Lys
            20                  25                  30

Val Tyr Ser Tyr Phe Glu Cys Arg Glu Lys Lys Thr Glu Asn Ser Lys
        35                  40                  45

Leu Arg Lys Val Lys Tyr Glu Glu Thr Val Phe Tyr Gly Leu Gln Tyr
    50                  55                  60

Ile Leu Asn Lys Tyr Leu Lys Gly Lys Val Val Thr Lys Glu Lys Ile
65                  70                  75                  80

Gln Glu Ala Lys Asp Val Tyr Lys Glu His Phe Gln Asp Asp Val Phe
                85                  90                  95

Asn Glu Lys Gly Trp Asn Tyr Ile Leu Glu Lys Tyr Asp Gly His Leu
            100                 105                 110

Pro Ile Glu Ile Lys Ala Val Pro Glu Gly Phe Val Ile Pro Arg Gly
        115                 120                 125

Asn Val Leu Phe Thr Val Glu Asn Thr Asp Pro Glu Cys Tyr Trp Leu
    130                 135                 140

Thr Asn Trp Ile Glu Thr Ile Leu Val Gln Ser Trp Tyr Pro Ile Thr
145                 150                 155                 160

Val Ala Thr Asn Ser Arg Glu Gln Lys Lys Ile Leu Ala Lys Tyr Leu
                165                 170                 175

Leu Glu Thr Ser Gly Asn Leu Asp Gly Leu Glu Tyr Lys Leu His Asp
            180                 185                 190

Phe Gly Tyr Arg Gly Val Ser Ser Gln Glu Thr Ala Gly Ile Gly Ala
        195                 200                 205

Ser Ala His Leu Val Asn Phe Lys Gly Thr Asp Thr Val Ala Gly Leu
    210                 215                 220
```

-continued

```
Ala Leu Ile Lys Lys Tyr Tyr Gly Thr Lys Asp Pro Val Pro Gly Tyr
225                 230                 235                 240

Ser Val Pro Ala Ala Glu His Ser Thr Ile Thr Ala Trp Gly Lys Asp
                245                 250                 255

His Glu Lys Asp Ala Phe Glu His Ile Val Thr Gln Phe Ser Ser Val
                260                 265                 270

Pro Val Ser Val Val Ser Asp Ser Tyr Asp Ile Tyr Asn Ala Cys Glu
                275                 280                 285

Lys Ile Trp Gly Glu Asp Leu Arg His Leu Ile Val Ser Arg Ser Thr
            290                 295                 300

Gln Ala Pro Leu Ile Ile Arg Pro Asp Ser Gly Asn Pro Leu Asp Thr
305                 310                 315                 320

Val Leu Lys Val Leu Glu Ile Leu Gly Lys Lys Phe Pro Val Thr Glu
                325                 330                 335

Asn Ser Lys Gly Tyr Lys Leu Leu Pro Pro Tyr Leu Arg Val Ile Gln
                340                 345                 350

Gly Asp Gly Val Asp Ile Asn Thr Leu Gln Glu Ile Val Glu Gly Met
                355                 360                 365

Lys Gln Lys Met Trp Ser Ile Glu Asn Ile Ala Phe Gly Ser Gly Gly
            370                 375                 380

Gly Leu Leu Gln Lys Leu Thr Arg Asp Leu Leu Asn Cys Ser Phe Lys
385                 390                 395                 400

Cys Ser Tyr Val Val Thr Asn Gly Leu Gly Ile Asn Val Phe Lys Asp
                405                 410                 415

Pro Val Ala Asp Pro Asn Lys Arg Ser Lys Lys Gly Arg Leu Ser Leu
                420                 425                 430

His Arg Thr Pro Ala Gly Asn Phe Val Thr Leu Glu Glu Gly Lys Gly
                435                 440                 445

Asp Leu Glu Glu Tyr Gly Gln Asp Leu Leu His Thr Val Phe Lys Asn
                450                 455                 460

Gly Lys Val Thr Lys Ser Tyr Ser Phe Asp Glu Ile Arg Lys Asn Ala
465                 470                 475                 480

Gln Leu Asn Ile Glu Leu Glu Ala Ala His His
                485                 490

<210> SEQ ID NO 27
<211> LENGTH: 831
<212> TYPE: PRT
<213> ORGANISM: Homo sapiens

<400> SEQUENCE: 27

Met Glu Arg Pro Trp Gly Ala Ala Asp Gly Leu Ser Arg Trp Pro His
1               5                   10                  15

Gly Leu Gly Leu Leu Leu Leu Gln Leu Leu Pro Pro Ser Thr Leu
                20                  25                  30

Ser Gln Asp Arg Leu Asp Ala Pro Pro Pro Ala Ala Pro Leu Pro
                35                  40                  45

Arg Trp Ser Gly Pro Ile Gly Val Ser Trp Gly Leu Arg Ala Ala Ala
            50                  55                  60

Ala Gly Gly Ala Phe Pro Arg Gly Gly Trp Arg Arg Ser Ala Pro
65                  70                  75                  80

Gly Glu Asp Glu Glu Cys Gly Arg Val Arg Asp Phe Val Ala Lys Leu
                85                  90                  95

Ala Asn Asn Thr His Gln His Val Phe Asp Asp Leu Arg Gly Ser Val
                100                 105                 110
```

-continued

Ser Leu Ser Trp Val Gly Asp Ser Thr Gly Val Ile Leu Val Leu Thr
            115                 120                 125

Thr Phe His Val Pro Leu Val Ile Met Thr Phe Gly Gln Ser Lys Leu
    130                 135                 140

Tyr Arg Ser Glu Asp Tyr Gly Lys Asn Phe Lys Asp Ile Thr Asp Leu
145                 150                 155                 160

Ile Asn Asn Thr Phe Ile Arg Thr Glu Phe Gly Met Ala Ile Gly Pro
                165                 170                 175

Glu Asn Ser Gly Lys Val Val Leu Thr Ala Glu Val Ser Gly Gly Ser
                180                 185                 190

Arg Gly Gly Arg Ile Phe Arg Ser Ser Asp Phe Ala Lys Asn Phe Val
            195                 200                 205

Gln Thr Asp Leu Pro Phe His Pro Leu Thr Gln Met Met Tyr Ser Pro
    210                 215                 220

Gln Asn Ser Asp Tyr Leu Leu Ala Leu Ser Thr Glu Asn Gly Leu Trp
225                 230                 235                 240

Val Ser Lys Asn Phe Gly Gly Lys Trp Glu Glu Ile His Lys Ala Val
                245                 250                 255

Cys Leu Ala Lys Trp Gly Ser Asp Asn Thr Ile Phe Thr Thr Tyr
            260                 265                 270

Ala Asn Gly Ser Cys Lys Ala Asp Leu Gly Ala Leu Glu Leu Trp Arg
            275                 280                 285

Thr Ser Asp Leu Gly Lys Ser Phe Lys Thr Ile Gly Val Lys Ile Tyr
    290                 295                 300

Ser Phe Gly Leu Gly Arg Phe Leu Phe Ala Ser Val Met Ala Asp
305                 310                 315                 320

Lys Asp Thr Thr Arg Arg Ile His Val Ser Thr Asp Gln Gly Asp Thr
                325                 330                 335

Trp Ser Met Ala Gln Leu Pro Ser Val Gly Gln Glu Gln Phe Tyr Ser
            340                 345                 350

Ile Leu Ala Ala Asn Asp Asp Met Val Phe Met His Val Asp Glu Pro
    355                 360                 365

Gly Asp Thr Gly Phe Gly Thr Ile Phe Thr Ser Asp Asp Arg Gly Ile
    370                 375                 380

Val Tyr Ser Lys Ser Leu Asp Arg His Leu Tyr Thr Thr Thr Gly Gly
385                 390                 395                 400

Glu Thr Asp Phe Thr Asn Val Thr Ser Leu Arg Gly Val Tyr Ile Thr
                405                 410                 415

Ser Val Leu Ser Glu Asp Asn Ser Ile Gln Thr Met Ile Thr Phe Asp
            420                 425                 430

Gln Gly Gly Arg Trp Thr His Leu Arg Lys Pro Glu Asn Ser Glu Cys
            435                 440                 445

Asp Ala Thr Ala Lys Asn Lys Asn Glu Cys Ser Leu His Ile His Ala
    450                 455                 460

Ser Tyr Ser Ile Ser Gln Lys Leu Asn Val Pro Met Ala Pro Leu Ser
465                 470                 475                 480

Glu Pro Asn Ala Val Gly Ile Val Ile Ala His Gly Ser Val Gly Asp
                485                 490                 495

Ala Ile Ser Val Met Val Pro Asp Val Tyr Ile Ser Asp Asp Gly Gly
            500                 505                 510

Tyr Ser Trp Thr Lys Met Leu Glu Gly Pro His Tyr Tyr Thr Ile Leu
            515                 520                 525

```
Asp Ser Gly Gly Ile Ile Val Ala Ile Glu His Ser Ser Arg Pro Ile
    530                 535                 540

Asn Val Ile Lys Phe Ser Thr Asp Glu Gly Gln Cys Trp Gln Thr Tyr
545                 550                 555                 560

Thr Phe Thr Arg Asp Pro Ile Tyr Phe Thr Gly Leu Ala Ser Glu Pro
                565                 570                 575

Gly Ala Arg Ser Met Asn Ile Ser Ile Trp Gly Phe Thr Glu Ser Phe
            580                 585                 590

Leu Thr Ser Gln Trp Val Ser Tyr Thr Ile Asp Phe Lys Asp Ile Leu
        595                 600                 605

Glu Arg Asn Cys Glu Lys Asp Tyr Thr Ile Trp Leu Ala His Ser
    610                 615                 620

Thr Asp Pro Glu Asp Tyr Glu Asp Gly Cys Ile Leu Gly Tyr Lys Glu
625                 630                 635                 640

Gln Phe Leu Arg Leu Arg Lys Ser Ser Val Cys Gln Asn Gly Arg Asp
                645                 650                 655

Tyr Val Val Thr Lys Gln Pro Ser Ile Cys Leu Cys Ser Leu Glu Asp
            660                 665                 670

Phe Leu Cys Asp Phe Gly Tyr Tyr Arg Pro Glu Asn Asp Ser Lys Cys
        675                 680                 685

Val Glu Gln Pro Glu Leu Lys Gly His Asp Leu Glu Phe Cys Leu Tyr
    690                 695                 700

Gly Arg Glu Glu His Leu Thr Thr Asn Gly Tyr Arg Lys Ile Pro Gly
705                 710                 715                 720

Asp Lys Cys Gln Gly Gly Val Asn Pro Val Arg Glu Val Lys Asp Leu
                725                 730                 735

Lys Lys Lys Cys Thr Ser Asn Phe Leu Ser Pro Glu Lys Gln Asn Ser
            740                 745                 750

Lys Ser Asn Ser Val Pro Ile Ile Leu Ala Ile Val Gly Leu Met Leu
        755                 760                 765

Val Thr Val Val Ala Gly Val Leu Ile Val Lys Lys Tyr Val Cys Gly
    770                 775                 780

Gly Arg Phe Leu Val His Arg Tyr Ser Val Leu Gln Gln His Ala Glu
785                 790                 795                 800

Ala Asn Gly Val Asp Gly Val Asp Ala Leu Asp Thr Ala Ser His Thr
                805                 810                 815

Asn Lys Ser Gly Tyr His Asp Asp Ser Asp Glu Asp Leu Leu Glu
            820                 825                 830

<210> SEQ ID NO 28
<211> LENGTH: 143
<212> TYPE: PRT
<213> ORGANISM: Homo sapiens

<400> SEQUENCE: 28

Met Gln His Arg Gly Phe Leu Leu Thr Leu Leu Ala Leu Leu Ala
 1                5                10                  15

Leu Thr Ser Ala Val Ala Lys Lys Asp Lys Val Lys Lys Gly Gly
                 20                25                  30

Pro Gly Ser Glu Cys Ala Glu Trp Ala Trp Gly Pro Cys Thr Pro Ser
             35                  40                  45

Ser Lys Asp Cys Gly Val Gly Phe Arg Glu Gly Thr Cys Gly Ala Gln
         50                  55                  60

Thr Gln Arg Ile Arg Cys Arg Val Pro Cys Asn Trp Lys Lys Glu Phe
65                  70                  75                  80
```

```
Gly Ala Asp Cys Lys Tyr Lys Phe Glu Asn Trp Gly Ala Cys Asp Gly
                85                  90                  95

Gly Thr Gly Thr Lys Val Arg Gln Gly Thr Leu Lys Lys Ala Arg Tyr
               100                 105                 110

Asn Ala Gln Cys Gln Glu Thr Ile Arg Val Thr Lys Pro Cys Thr Pro
           115                 120                 125

Lys Thr Lys Ala Lys Ala Lys Ala Lys Gly Lys Gly Lys Asp
       130                 135                 140

<210> SEQ ID NO 29
<211> LENGTH: 291
<212> TYPE: PRT
<213> ORGANISM: Homo sapiens

<400> SEQUENCE: 29

Met Gln Arg Ala Arg Pro Thr Leu Trp Ala Ala Leu Thr Leu Leu
 1               5                  10                  15

Val Leu Leu Arg Gly Pro Val Ala Arg Ala Gly Ala Ser Ser Ala
                20                  25                  30

Gly Leu Gly Pro Val Val Arg Cys Glu Pro Cys Asp Ala Arg Ala Leu
                35                  40                  45

Ala Gln Cys Ala Pro Pro Pro Ala Val Cys Ala Glu Leu Val Arg Glu
     50                  55                  60

Pro Gly Cys Gly Cys Cys Leu Thr Cys Ala Leu Ser Glu Gly Gln Pro
 65                  70                  75                  80

Cys Gly Ile Tyr Thr Glu Arg Cys Gly Ser Gly Leu Arg Cys Gln Pro
                 85                  90                  95

Ser Pro Asp Glu Ala Arg Pro Leu Gln Ala Leu Leu Asp Gly Arg Gly
                100                 105                 110

Leu Cys Val Asn Ala Ser Ala Val Ser Arg Leu Arg Ala Tyr Leu Leu
            115                 120                 125

Pro Ala Pro Pro Ala Pro Gly Asn Ala Ser Glu Ser Glu Glu Asp Arg
        130                 135                 140

Ser Ala Gly Ser Val Glu Ser Pro Ser Val Ser Ser Thr His Arg Val
145                 150                 155                 160

Ser Asp Pro Lys Phe His Pro Leu His Ser Lys Ile Ile Ile Lys
                165                 170                 175

Lys Gly His Ala Lys Asp Ser Gln Arg Tyr Lys Val Asp Tyr Glu Ser
            180                 185                 190

Gln Ser Thr Asp Thr Gln Asn Phe Ser Ser Glu Ser Lys Arg Glu Thr
        195                 200                 205

Glu Tyr Gly Pro Cys Arg Arg Glu Met Glu Asp Thr Leu Asn His Leu
    210                 215                 220

Lys Phe Leu Asn Val Leu Ser Pro Arg Gly Val His Ile Pro Asn Cys
225                 230                 235                 240

Asp Lys Lys Gly Phe Tyr Lys Lys Lys Gln Cys Arg Pro Ser Lys Gly
                245                 250                 255

Arg Lys Arg Gly Phe Cys Trp Cys Val Asp Lys Tyr Gly Gln Pro Leu
            260                 265                 270

Pro Gly Tyr Thr Thr Lys Gly Lys Glu Asp Val His Cys Tyr Ser Met
        275                 280                 285

Gln Ser Lys
    290
```

```
<210> SEQ ID NO 30
<211> LENGTH: 258
<212> TYPE: PRT
<213> ORGANISM: Homo sapiens

<400> SEQUENCE: 30

Met Leu Pro Leu Cys Leu Val Ala Ala Leu Leu Ala Ala Gly Pro
1               5                   10                  15

Gly Pro Ser Leu Gly Asp Glu Ala Ile His Cys Pro Pro Cys Ser Glu
            20                  25                  30

Glu Lys Leu Ala Arg Cys Arg Pro Val Gly Cys Glu Glu Leu Val
        35                  40                  45

Arg Glu Pro Gly Cys Gly Cys Cys Ala Thr Cys Ala Leu Gly Leu Gly
50                  55                  60

Met Pro Cys Gly Val Tyr Thr Pro Arg Cys Gly Ser Gly Leu Arg Cys
65                  70                  75                  80

Tyr Pro Pro Arg Gly Val Glu Lys Pro Leu His Thr Leu Met His Gly
                85                  90                  95

Gln Gly Val Cys Met Glu Leu Ala Glu Ile Glu Ala Ile Gln Glu Ser
            100                 105                 110

Leu Gln Pro Ser Asp Lys Asp Glu Gly Asp His Pro Asn Asn Ser Phe
        115                 120                 125

Ser Pro Cys Ser Ala His Asp Arg Arg Cys Leu Gln Lys His Phe Ala
130                 135                 140

Lys Ile Arg Asp Arg Ser Thr Ser Gly Gly Lys Met Lys Val Asn Gly
145                 150                 155                 160

Ala Pro Arg Glu Asp Ala Arg Pro Val Pro Gln Gly Ser Cys Gln Ser
                165                 170                 175

Glu Leu His Arg Ala Leu Glu Arg Leu Ala Ala Ser Gln Ser Arg Thr
            180                 185                 190

His Glu Asp Leu Tyr Ile Ile Pro Ile Pro Asn Cys Asp Arg Asn Gly
        195                 200                 205

Asn Phe His Pro Lys Gln Cys His Pro Ala Leu Asp Gly Gln Arg Gly
210                 215                 220

Lys Cys Trp Cys Val Asp Arg Lys Thr Gly Val Lys Leu Pro Gly Gly
225                 230                 235                 240

Leu Glu Pro Lys Gly Glu Leu Asp Cys His Gln Leu Ala Asp Ser Phe
                245                 250                 255

Arg Glu

<210> SEQ ID NO 31
<211> LENGTH: 463
<212> TYPE: PRT
<213> ORGANISM: Homo sapiens

<400> SEQUENCE: 31

Met Gly Ala Gly Pro Ser Leu Leu Leu Ala Ala Leu Leu Leu Leu
1               5                   10                  15

Ser Gly Asp Gly Ala Val Arg Cys Asp Thr Pro Ala Asn Cys Thr Tyr
            20                  25                  30

Leu Asp Leu Leu Gly Thr Trp Val Phe Gln Val Gly Ser Ser Gly Ser
        35                  40                  45

Gln Arg Asp Val Asn Cys Ser Val Met Gly Pro Gln Glu Lys Lys Val
    50                  55                  60

Val Val Tyr Leu Gln Lys Leu Asp Thr Ala Tyr Asp Asp Leu Gly Asn
65                  70                  75                  80
```

Ser Gly His Phe Thr Ile Ile Tyr Asn Gln Gly Phe Glu Ile Val Leu
             85                  90                  95

Asn Asp Tyr Lys Trp Phe Ala Phe Lys Tyr Lys Glu Glu Gly Ser
            100                 105                 110

Lys Val Thr Thr Tyr Cys Asn Glu Thr Met Thr Gly Trp Val His Asp
            115                 120                 125

Val Leu Gly Arg Asn Trp Ala Cys Phe Thr Gly Lys Lys Val Gly Thr
130                 135                 140

Ala Ser Glu Asn Val Tyr Val Asn Thr Ala His Leu Lys Asn Ser Gln
145                 150                 155                 160

Glu Lys Tyr Ser Asn Arg Leu Tyr Lys Tyr Asp His Asn Phe Val Lys
                165                 170                 175

Ala Ile Asn Ala Ile Gln Lys Ser Trp Thr Ala Thr Thr Tyr Met Glu
            180                 185                 190

Tyr Glu Thr Leu Thr Leu Gly Asp Met Ile Arg Arg Ser Gly Gly His
            195                 200                 205

Ser Arg Lys Ile Pro Arg Pro Lys Pro Ala Pro Leu Thr Ala Glu Ile
210                 215                 220

Gln Gln Lys Ile Leu His Leu Pro Thr Ser Trp Asp Trp Arg Asn Val
225                 230                 235                 240

His Gly Ile Asn Phe Val Ser Pro Val Arg Asn Gln Ala Ser Cys Gly
                245                 250                 255

Ser Cys Tyr Ser Phe Ala Ser Met Gly Met Leu Glu Ala Arg Ile Arg
                260                 265                 270

Ile Leu Thr Asn Asn Ser Gln Thr Pro Ile Leu Ser Pro Gln Glu Val
            275                 280                 285

Val Ser Cys Ser Gln Tyr Ala Gln Gly Cys Glu Gly Gly Phe Pro Tyr
290                 295                 300

Leu Ile Ala Gly Lys Tyr Ala Gln Asp Phe Gly Leu Val Glu Glu Ala
305                 310                 315                 320

Cys Phe Pro Tyr Thr Gly Thr Asp Ser Pro Cys Lys Met Lys Glu Asp
                325                 330                 335

Cys Phe Arg Tyr Tyr Ser Ser Glu Tyr His Tyr Val Gly Gly Phe Tyr
                340                 345                 350

Gly Gly Cys Asn Glu Ala Leu Met Lys Leu Glu Leu Val His His Gly
            355                 360                 365

Pro Met Ala Val Ala Phe Glu Val Tyr Asp Asp Phe Leu His Tyr Lys
370                 375                 380

Lys Gly Ile Tyr His His Thr Gly Leu Arg Asp Pro Phe Asn Pro Phe
385                 390                 395                 400

Glu Leu Thr Asn His Ala Val Leu Leu Val Gly Tyr Gly Thr Asp Ser
                405                 410                 415

Ala Ser Gly Met Asp Tyr Trp Ile Val Lys Asn Ser Trp Gly Thr Gly
                420                 425                 430

Trp Gly Glu Asn Gly Tyr Phe Arg Ile Arg Arg Gly Thr Asp Glu Cys
            435                 440                 445

Ala Ile Glu Ser Ile Ala Val Ala Ala Thr Pro Ile Pro Lys Leu
450                 455                 460

<210> SEQ ID NO 32
<211> LENGTH: 547
<212> TYPE: PRT
<213> ORGANISM: Homo sapiens

<400> SEQUENCE: 32

```
Met Ala Thr Met Val Pro Ser Val Leu Trp Pro Arg Ala Cys Trp Thr
1               5                   10                  15
Leu Leu Val Cys Cys Leu Leu Thr Pro Gly Val Gln Gly Gln Glu Phe
            20                  25                  30
Leu Leu Arg Val Glu Pro Gln Asn Pro Val Leu Ser Ala Gly Gly Ser
        35                  40                  45
Leu Phe Val Asn Cys Ser Thr Asp Cys Pro Ser Ser Glu Lys Ile Ala
    50                  55                  60
Leu Glu Thr Ser Leu Ser Lys Glu Leu Val Ala Ser Gly Met Gly Trp
65                  70                  75                  80
Ala Ala Phe Asn Leu Ser Asn Val Thr Gly Asn Ser Arg Ile Leu Cys
            85                  90                  95
Ser Val Tyr Cys Asn Gly Ser Gln Ile Thr Gly Ser Ser Asn Ile Thr
            100                 105                 110
Val Tyr Gly Leu Pro Glu Arg Val Glu Leu Ala Pro Leu Pro Pro Trp
            115                 120                 125
Gln Pro Val Gly Gln Asn Phe Thr Leu Arg Cys Gln Val Glu Gly Gly
        130                 135                 140
Ser Pro Arg Thr Ser Leu Thr Val Val Leu Leu Arg Trp Glu Glu Glu
145                 150                 155                 160
Leu Ser Arg Gln Pro Ala Val Glu Glu Pro Ala Glu Val Thr Ala Thr
            165                 170                 175
Val Leu Ala Ser Arg Asp Asp His Gly Ala Pro Phe Ser Cys Arg Thr
            180                 185                 190
Glu Leu Asp Met Gln Pro Gln Gly Leu Gly Leu Phe Val Asn Thr Ser
            195                 200                 205
Ala Pro Arg Gln Leu Arg Thr Phe Val Leu Pro Val Thr Pro Pro Arg
        210                 215                 220
Leu Val Ala Pro Arg Phe Leu Glu Val Glu Thr Ser Trp Pro Val Asp
225                 230                 235                 240
Cys Thr Leu Asp Gly Leu Phe Pro Ala Ser Glu Ala Gln Val Tyr Leu
            245                 250                 255
Ala Leu Gly Asp Gln Met Leu Asn Ala Thr Val Met Asn His Gly Asp
            260                 265                 270
Thr Leu Thr Ala Thr Ala Thr Ala Thr Ala Arg Ala Asp Gln Glu Gly
            275                 280                 285
Ala Arg Glu Ile Val Cys Asn Val Thr Leu Gly Gly Glu Arg Arg Glu
        290                 295                 300
Ala Arg Glu Asn Leu Thr Val Phe Ser Phe Leu Gly Pro Ile Val Asn
305                 310                 315                 320
Leu Ser Glu Pro Thr Ala His Glu Gly Ser Thr Val Thr Val Ser Cys
            325                 330                 335
Met Ala Gly Ala Arg Val Gln Val Thr Leu Asp Gly Val Pro Ala Ala
            340                 345                 350
Ala Pro Gly Gln Pro Ala Gln Leu Gln Leu Asn Ala Thr Glu Ser Asp
        355                 360                 365
Asp Gly Arg Ser Phe Phe Cys Ser Ala Thr Leu Glu Val Asp Gly Glu
    370                 375                 380
Phe Leu His Arg Asn Ser Ser Val Gln Leu Arg Val Leu Tyr Gly Pro
385                 390                 395                 400
Lys Ile Asp Arg Ala Thr Cys Pro Gln His Leu Lys Trp Lys Asp Lys
            405                 410                 415
```

```
Thr Arg His Val Leu Gln Cys Gln Ala Arg Gly Asn Pro Tyr Pro Glu
            420                 425                 430

Leu Arg Cys Leu Lys Glu Gly Ser Arg Glu Val Pro Val Gly Ile
        435                 440                 445

Pro Phe Phe Val Asn Val Thr His Asn Gly Thr Tyr Gln Cys Gln Ala
            450                 455                 460

Ser Ser Ser Arg Gly Lys Tyr Thr Leu Val Val Met Asp Ile Glu
465                 470                 475                 480

Ala Gly Ser Ser His Phe Val Pro Val Phe Ala Val Leu Leu Thr
                485                 490                 495

Leu Gly Val Val Thr Ile Val Leu Ala Leu Met Tyr Val Phe Arg Glu
            500                 505                 510

His Gln Arg Ser Gly Ser Tyr His Val Arg Glu Glu Ser Thr Tyr Leu
            515                 520                 525

Pro Leu Thr Ser Met Gln Pro Thr Glu Ala Met Gly Glu Glu Pro Ser
            530                 535                 540

Arg Ala Glu
545

<210> SEQ ID NO 33
<211> LENGTH: 349
<212> TYPE: PRT
<213> ORGANISM: Homo sapiens

<400> SEQUENCE: 33

Met Thr Ala Ala Ser Met Gly Pro Val Arg Val Ala Phe Val Val Leu
 1               5                  10                  15

Leu Ala Leu Cys Ser Arg Pro Ala Val Gly Gln Asn Cys Ser Gly Pro
            20                  25                  30

Cys Arg Cys Pro Asp Glu Pro Ala Pro Arg Cys Pro Ala Gly Val Ser
        35                  40                  45

Leu Val Leu Asp Gly Cys Gly Cys Cys Arg Val Cys Ala Lys Gln Leu
    50                  55                  60

Gly Glu Leu Cys Thr Glu Arg Asp Pro Cys Asp Pro His Lys Gly Leu
65                  70                  75                  80

Phe Cys His Phe Gly Ser Pro Ala Asn Arg Lys Ile Gly Val Cys Thr
                85                  90                  95

Ala Lys Asp Gly Ala Pro Cys Ile Phe Gly Gly Thr Val Tyr Arg Ser
            100                 105                 110

Gly Glu Ser Phe Gln Ser Ser Cys Lys Tyr Gln Cys Thr Cys Leu Asp
        115                 120                 125

Gly Ala Val Gly Cys Met Pro Leu Cys Ser Met Asp Val Arg Leu Pro
    130                 135                 140

Ser Pro Asp Cys Pro Phe Pro Arg Arg Val Lys Leu Pro Gly Lys Cys
145                 150                 155                 160

Cys Glu Glu Trp Val Cys Asp Glu Pro Lys Asp Gln Thr Val Val Gly
                165                 170                 175

Pro Ala Leu Ala Ala Tyr Arg Leu Glu Asp Thr Phe Gly Pro Asp Pro
            180                 185                 190

Thr Met Ile Arg Ala Asn Cys Leu Val Gln Thr Thr Glu Trp Ser Ala
        195                 200                 205

Cys Ser Lys Thr Cys Gly Met Gly Ile Ser Thr Arg Val Thr Asn Asp
    210                 215                 220

Asn Ala Ser Cys Arg Leu Glu Lys Gln Ser Arg Leu Cys Met Val Arg
```

```
                225                 230                 235                 240
        Pro Cys Glu Ala Asp Leu Glu Glu Asn Ile Lys Lys Gly Lys Lys Cys
                        245                 250                 255
        Ile Arg Thr Pro Lys Ile Ser Lys Pro Ile Lys Phe Glu Leu Ser Gly
                        260                 265                 270
        Cys Thr Ser Met Lys Thr Tyr Arg Ala Lys Phe Cys Gly Val Cys Thr
                        275                 280                 285
        Asp Gly Arg Cys Cys Thr Pro His Arg Thr Thr Thr Leu Pro Val Glu
                        290                 295                 300
        Phe Lys Cys Pro Asp Gly Glu Val Met Lys Lys Asn Met Met Phe Ile
        305                 310                 315                 320
        Lys Thr Cys Ala Cys His Tyr Asn Cys Pro Gly Asp Asn Asp Ile Phe
                        325                 330                 335
        Glu Ser Leu Tyr Tyr Arg Lys Met Tyr Gly Asp Met Ala
                        340                 345

<210> SEQ ID NO 34
<211> LENGTH: 198
<212> TYPE: PRT
<213> ORGANISM: Homo sapiens

<400> SEQUENCE: 34

Met Pro Leu Gly Leu Leu Trp Leu Gly Leu Ala Leu Leu Gly Ala Leu
        1               5                   10                  15
        His Ala Gln Ala Gln Asp Ser Thr Ser Asp Leu Ile Pro Ala Pro Pro
                        20                  25                  30
        Leu Ser Lys Val Pro Leu Gln Gln Asn Phe Gln Asp Asn Gln Phe Gln
                        35                  40                  45
        Gly Lys Trp Tyr Val Val Gly Leu Ala Gly Asn Ala Ile Leu Arg Glu
                50                  55                  60
        Asp Lys Asp Pro Gln Lys Met Tyr Ala Thr Ile Tyr Glu Leu Lys Glu
        65                  70                  75                  80
        Asp Lys Ser Tyr Asn Val Thr Ser Val Leu Phe Arg Lys Lys Lys Cys
                        85                  90                  95
        Asp Tyr Trp Ile Arg Thr Phe Val Pro Gly Cys Gln Pro Gly Glu Phe
                        100                 105                 110
        Thr Leu Gly Asn Ile Lys Ser Tyr Pro Gly Leu Thr Ser Tyr Leu Val
                        115                 120                 125
        Arg Val Val Ser Thr Asn Tyr Asn Gln His Ala Met Val Phe Phe Lys
                130                 135                 140
        Lys Val Ser Gln Asn Arg Glu Tyr Phe Lys Ile Thr Leu Tyr Gly Arg
        145                 150                 155                 160
        Thr Lys Glu Leu Thr Ser Glu Leu Lys Glu Asn Phe Ile Arg Phe Ser
                        165                 170                 175
        Lys Ser Leu Gly Leu Pro Glu Asn His Ile Val Phe Pro Val Pro Ile
                        180                 185                 190
        Asp Gln Cys Ile Asp Gly
                        195

<210> SEQ ID NO 35
<211> LENGTH: 1210
<212> TYPE: PRT
<213> ORGANISM: Homo sapiens

<400> SEQUENCE: 35

Met Arg Pro Ser Gly Thr Ala Gly Ala Ala Leu Leu Ala Leu Leu Ala
```

-continued

```
  1               5              10              15
Ala Leu Cys Pro Ala Ser Arg Ala Leu Glu Glu Lys Lys Val Cys Gln
             20              25              30

Gly Thr Ser Asn Lys Leu Thr Gln Leu Gly Thr Phe Glu Asp His Phe
             35              40              45

Leu Ser Leu Gln Arg Met Phe Asn Asn Cys Glu Val Val Leu Gly Asn
 50              55              60

Leu Glu Ile Thr Tyr Val Gln Arg Asn Tyr Asp Leu Ser Phe Leu Lys
 65              70              75              80

Thr Ile Gln Glu Val Ala Gly Tyr Val Leu Ile Ala Leu Asn Thr Val
                 85              90              95

Glu Arg Ile Pro Leu Glu Asn Leu Gln Ile Ile Arg Gly Asn Met Tyr
            100             105             110

Tyr Glu Asn Ser Tyr Ala Leu Ala Val Leu Ser Asn Tyr Asp Ala Asn
            115             120             125

Lys Thr Gly Leu Lys Glu Leu Pro Met Arg Asn Leu Gln Glu Ile Leu
        130             135             140

His Gly Ala Val Arg Phe Ser Asn Asn Pro Ala Leu Cys Asn Val Glu
145             150             155             160

Ser Ile Gln Trp Arg Asp Ile Val Ser Ser Asp Phe Leu Ser Asn Met
                165             170             175

Ser Met Asp Phe Gln Asn His Leu Gly Ser Cys Gln Lys Cys Asp Pro
            180             185             190

Ser Cys Pro Asn Gly Ser Cys Trp Gly Ala Gly Glu Glu Asn Cys Gln
        195             200             205

Lys Leu Thr Lys Ile Ile Cys Ala Gln Gln Cys Ser Gly Arg Cys Arg
    210             215             220

Gly Lys Ser Pro Ser Asp Cys Cys His Asn Gln Cys Ala Ala Gly Cys
225             230             235             240

Thr Gly Pro Arg Glu Ser Asp Cys Leu Val Cys Arg Lys Phe Arg Asp
                245             250             255

Glu Ala Thr Cys Lys Asp Thr Cys Pro Pro Leu Met Leu Tyr Asn Pro
            260             265             270

Thr Thr Tyr Gln Met Asp Val Asn Pro Glu Gly Lys Tyr Ser Phe Gly
        275             280             285

Ala Thr Cys Val Lys Lys Cys Pro Arg Asn Tyr Val Val Thr Asp His
    290             295             300

Gly Ser Cys Val Arg Ala Cys Gly Ala Asp Ser Tyr Glu Met Glu Glu
305             310             315             320

Asp Gly Val Arg Lys Cys Lys Lys Cys Glu Gly Pro Cys Arg Lys Val
                325             330             335

Cys Asn Gly Ile Gly Ile Gly Glu Phe Lys Asp Ser Leu Ser Ile Asn
            340             345             350

Ala Thr Asn Ile Lys His Phe Lys Asn Cys Thr Ser Ile Ser Gly Asp
        355             360             365

Leu His Ile Leu Pro Val Ala Phe Arg Gly Asp Ser Phe Thr His Thr
    370             375             380

Pro Pro Leu Asp Pro Gln Glu Leu Asp Ile Leu Lys Thr Val Lys Glu
385             390             395             400

Ile Thr Gly Phe Leu Leu Ile Gln Ala Trp Pro Glu Asn Arg Thr Asp
                405             410             415

Leu His Ala Phe Glu Asn Leu Glu Ile Ile Arg Gly Arg Thr Lys Gln
            420             425             430
```

```
His Gly Gln Phe Ser Leu Ala Val Val Ser Leu Asn Ile Thr Ser Leu
            435                 440                 445

Gly Leu Arg Ser Leu Lys Glu Ile Ser Asp Gly Asp Val Ile Ile Ser
        450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
            515                 520                 525

Val Ser Arg Gly Arg Glu Cys Val Asp Lys Cys Asn Leu Leu Glu Gly
        530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
            595                 600                 605

Lys Tyr Ala Asp Ala Gly His Val Cys His Leu Cys His Pro Asn Cys
        610                 615                 620

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
                645                 650                 655

Leu Leu Val Val Ala Leu Gly Ile Gly Leu Phe Met Arg Arg Arg His
            660                 665                 670

Ile Val Arg Lys Arg Thr Leu Arg Arg Leu Leu Gln Glu Arg Glu Leu
        675                 680                 685

Val Glu Pro Leu Thr Pro Ser Gly Glu Ala Pro Asn Gln Ala Leu Leu
    690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
                725                 730                 735

Lys Val Lys Ile Pro Val Ala Ile Lys Glu Leu Arg Glu Ala Thr Ser
            740                 745                 750

Pro Lys Ala Asn Lys Glu Ile Leu Asp Glu Ala Tyr Val Met Ala Ser
        755                 760                 765

Val Asp Asn Pro His Val Cys Arg Leu Leu Gly Ile Cys Leu Thr Ser
    770                 775                 780

Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
                805                 810                 815

Trp Cys Val Gln Ile Ala Lys Gly Met Asn Tyr Leu Glu Asp Arg Arg
            820                 825                 830

Leu Val His Arg Asp Leu Ala Ala Arg Asn Val Leu Val Lys Thr Pro
        835                 840                 845
```

```
Gln His Val Lys Ile Thr Asp Phe Gly Leu Ala Lys Leu Leu Gly Ala
            850                 855                 860

Glu Glu Lys Glu Tyr His Ala Glu Gly Lys Val Pro Ile Lys Trp
865                 870                 875                 880

Met Ala Leu Glu Ser Ile Leu His Arg Ile Tyr Thr His Gln Ser Asp
                885                 890                 895

Val Trp Ser Tyr Gly Val Thr Val Trp Glu Leu Met Thr Phe Gly Ser
            900                 905                 910

Lys Pro Tyr Asp Gly Ile Pro Ala Ser Glu Ile Ser Ser Ile Leu Glu
            915                 920                 925

Lys Gly Glu Arg Leu Pro Gln Pro Pro Ile Cys Thr Ile Asp Val Tyr
            930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
                965                 970                 975

Arg Tyr Leu Val Ile Gln Gly Asp Glu Arg Met His Leu Pro Ser Pro
            980                 985                 990

Thr Asp Ser Asn Phe Tyr Arg Ala Leu Met Asp Glu Glu Asp Met Asp
            995                 1000                1005

Asp Val Val Asp Ala Asp Glu Tyr Leu Ile Pro Gln Gln Gly Phe Phe
1010                1015                1020

Ser Ser Pro Ser Thr Ser Arg Thr Pro Leu Leu Ser Ser Leu Ser Ala
1025                1030                1035                1040

Thr Ser Asn Asn Ser Thr Val Ala Cys Ile Asp Arg Asn Gly Leu Gln
                1045                1050                1055

Ser Cys Pro Ile Lys Glu Asp Ser Phe Leu Gln Arg Tyr Ser Ser Asp
            1060                1065                1070

Pro Thr Gly Ala Leu Thr Glu Asp Ser Ile Asp Asp Thr Phe Leu Pro
            1075                1080                1085

Val Pro Glu Tyr Ile Asn Gln Ser Val Pro Lys Arg Pro Ala Gly Ser
            1090                1095                1100

Val Gln Asn Pro Val Tyr His Asn Gln Pro Leu Asn Pro Ala Pro Ser
1105                1110                1115                1120

Arg Asp Pro His Tyr Gln Asp Pro His Ser Thr Ala Val Gly Asn Pro
                1125                1130                1135

Glu Tyr Leu Asn Thr Val Gln Pro Thr Cys Val Asn Ser Thr Phe Asp
            1140                1145                1150

Ser Pro Ala His Trp Ala Gln Lys Gly Ser His Gln Ile Ser Leu Asp
            1155                1160                1165

Asn Pro Asp Tyr Gln Gln Asp Phe Phe Pro Lys Glu Ala Lys Pro Asn
            1170                1175                1180

Gly Ile Phe Lys Gly Ser Thr Ala Glu Asn Ala Glu Tyr Leu Arg Val
1185                1190                1195                1200

Ala Pro Gln Ser Ser Glu Phe Ile Gly Ala
            1205                1210

<210> SEQ ID NO 36
<211> LENGTH: 368
<212> TYPE: PRT
<213> ORGANISM: Homo sapiens

<400> SEQUENCE: 36

Met Trp Pro Leu Trp Arg Leu Val Ser Leu Leu Ala Leu Ser Gln Ala
1               5                   10                  15
```

```
Leu Pro Phe Glu Gln Arg Gly Phe Trp Asp Phe Thr Leu Asp Asp Gly
             20                  25                  30

Pro Phe Met Met Asn Asp Glu Glu Ala Ser Gly Ala Asp Thr Ser Gly
         35                  40                  45

Val Leu Asp Pro Asp Ser Val Thr Pro Thr Tyr Ser Ala Met Cys Pro
 50                  55                  60

Phe Gly Cys His Cys His Leu Arg Val Val Gln Cys Ser Asp Leu Gly
 65                  70                  75                  80

Leu Lys Ser Val Pro Lys Glu Ile Ser Pro Asp Thr Thr Leu Leu Asp
                 85                  90                  95

Leu Gln Asn Asn Asp Ile Ser Glu Leu Arg Lys Asp Asp Phe Lys Gly
             100                 105                 110

Leu Gln His Leu Tyr Ala Leu Val Leu Val Asn Asn Lys Ile Ser Lys
         115                 120                 125

Ile His Glu Lys Ala Phe Ser Pro Leu Arg Lys Leu Gln Lys Leu Tyr
130                 135                 140

Ile Ser Lys Asn His Leu Val Glu Ile Pro Pro Asn Leu Pro Ser Ser
145                 150                 155                 160

Leu Val Glu Leu Arg Ile His Asp Asn Arg Ile Arg Lys Val Pro Lys
                165                 170                 175

Gly Val Phe Ser Gly Leu Arg Asn Met Asn Cys Ile Glu Met Gly Gly
             180                 185                 190

Asn Pro Leu Glu Asn Ser Gly Phe Glu Pro Gly Ala Phe Asp Gly Leu
         195                 200                 205

Lys Leu Asn Tyr Leu Arg Ile Ser Glu Ala Lys Leu Thr Gly Ile Pro
210                 215                 220

Lys Asp Leu Pro Glu Thr Leu Asn Glu Leu His Leu Asp His Asn Lys
225                 230                 235                 240

Ile Gln Ala Ile Glu Leu Glu Asp Leu Leu Arg Tyr Ser Lys Leu Tyr
                245                 250                 255

Arg Leu Gly Leu Gly His Asn Gln Ile Arg Met Ile Glu Asn Gly Ser
             260                 265                 270

Leu Ser Phe Leu Pro Thr Leu Arg Glu Leu His Leu Asp Asn Asn Lys
         275                 280                 285

Leu Ala Arg Val Pro Ser Gly Leu Pro Asp Leu Lys Leu Leu Gln Val
290                 295                 300

Val Tyr Leu His Ser Asn Asn Ile Thr Lys Val Gly Val Asn Asp Phe
305                 310                 315                 320

Cys Pro Met Gly Phe Gly Val Lys Arg Ala Tyr Tyr Asn Gly Ile Ser
                325                 330                 335

Leu Phe Asn Asn Pro Val Pro Tyr Trp Glu Val Gln Pro Ala Thr Phe
             340                 345                 350

Arg Cys Val Thr Asp Arg Leu Ala Ile Gln Phe Gly Asn Tyr Lys Lys
         355                 360                 365

<210> SEQ ID NO 37
<211> LENGTH: 211
<212> TYPE: PRT
<213> ORGANISM: Homo sapiens

<400> SEQUENCE: 37

Met Thr Pro Trp Leu Gly Leu Ile Val Leu Leu Gly Ser Trp Ser Leu
 1               5                  10                  15

Gly Asp Trp Gly Ala Glu Ala Cys Thr Cys Ser Pro Ser His Pro Gln
```

```
                    20                  25                  30
Asp Ala Phe Cys Asn Ser Asp Ile Val Ile Arg Ala Lys Val Val Gly
                35                  40                  45
Lys Lys Leu Val Lys Glu Gly Pro Phe Gly Thr Leu Val Tyr Thr Ile
 50                  55                  60
Lys Gln Met Lys Met Tyr Arg Gly Phe Thr Lys Met Pro His Val Gln
 65                  70                  75                  80
Tyr Ile His Thr Glu Ala Ser Glu Ser Leu Cys Gly Leu Lys Leu Glu
                 85                  90                  95
Val Asn Lys Tyr Gln Tyr Leu Leu Thr Gly Arg Val Tyr Asp Gly Lys
                100                 105                 110
Met Tyr Thr Gly Leu Cys Asn Phe Val Glu Arg Trp Asp Gln Leu Thr
                115                 120                 125
Leu Ser Gln Arg Lys Gly Leu Asn Tyr Arg Tyr His Leu Gly Cys Asn
                130                 135                 140
Cys Lys Ile Lys Ser Cys Tyr Tyr Leu Pro Cys Phe Val Thr Ser Lys
145                 150                 155                 160
Asn Glu Cys Leu Trp Thr Asp Met Leu Ser Asn Phe Gly Tyr Pro Gly
                165                 170                 175
Tyr Gln Ser Lys His Tyr Ala Cys Ile Arg Gln Lys Gly Gly Tyr Cys
                180                 185                 190
Ser Trp Tyr Arg Gly Trp Ala Pro Pro Asp Lys Ser Ile Ile Asn Ala
                195                 200                 205
Thr Asp Pro
    210

<210> SEQ ID NO 38
<211> LENGTH: 728
<212> TYPE: PRT
<213> ORGANISM: Homo sapiens

<400> SEQUENCE: 38

Met Trp Val Thr Lys Leu Leu Pro Ala Leu Leu Leu Gln His Val Leu
  1               5                  10                  15
Leu His Leu Leu Leu Leu Pro Ile Ala Ile Pro Tyr Ala Glu Gly Gln
                 20                  25                  30
Arg Lys Arg Arg Asn Thr Ile His Glu Phe Lys Lys Ser Ala Lys Thr
                 35                  40                  45
Thr Leu Ile Lys Ile Asp Pro Ala Leu Lys Ile Lys Thr Lys Lys Val
 50                  55                  60
Asn Thr Ala Asp Gln Cys Ala Asn Arg Cys Thr Arg Asn Lys Gly Leu
 65                  70                  75                  80
Pro Phe Thr Cys Lys Ala Phe Val Phe Asp Lys Ala Arg Lys Gln Cys
                 85                  90                  95
Leu Trp Phe Pro Phe Asn Ser Met Ser Ser Gly Val Lys Lys Glu Phe
                100                 105                 110
Gly His Glu Phe Asp Leu Tyr Glu Asn Lys Asp Tyr Ile Arg Asn Cys
                115                 120                 125
Ile Ile Gly Lys Gly Arg Ser Tyr Lys Gly Thr Val Ser Ile Thr Lys
                130                 135                 140
Ser Gly Ile Lys Cys Gln Pro Trp Ser Ser Met Ile Pro His Glu His
145                 150                 155                 160
Ser Phe Leu Pro Ser Ser Tyr Arg Gly Lys Asp Leu Gln Glu Asn Tyr
                165                 170                 175
```

```
Cys Arg Asn Pro Arg Gly Glu Glu Gly Pro Trp Cys Phe Thr Ser
            180                 185                 190

Asn Pro Glu Val Arg Tyr Glu Val Cys Asp Ile Pro Gln Cys Ser Glu
        195                 200                 205

Val Glu Cys Met Thr Cys Asn Gly Glu Ser Tyr Arg Gly Leu Met Asp
    210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
                245                 250                 255

Asp Asn Tyr Cys Arg Asn Pro Asp Gly Gln Pro Arg Pro Trp Cys Tyr
            260                 265                 270

Thr Leu Asp Pro His Thr Arg Trp Glu Tyr Cys Ala Ile Lys Thr Cys
        275                 280                 285

Ala Asp Asn Thr Met Asn Asp Thr Asp Val Pro Leu Glu Thr Thr Glu
290                 295                 300

Cys Ile Gln Gly Gln Gly Glu Gly Tyr Arg Gly Thr Val Asn Thr Ile
305                 310                 315                 320

Trp Asn Gly Ile Pro Cys Gln Arg Trp Asp Ser Gln Tyr Pro His Glu
                325                 330                 335

His Asp Met Thr Pro Glu Asn Phe Lys Cys Lys Asp Leu Arg Glu Asn
            340                 345                 350

Tyr Cys Arg Asn Pro Asp Gly Ser Glu Ser Pro Trp Cys Phe Thr Thr
        355                 360                 365

Asp Pro Asn Ile Arg Val Gly Tyr Cys Ser Gln Ile Pro Asn Cys Asp
370                 375                 380

Met Ser His Gly Gln Asp Cys Tyr Arg Gly Asn Gly Lys Asn Tyr Met
385                 390                 395                 400

Gly Asn Leu Ser Gln Thr Arg Ser Gly Leu Thr Cys Ser Met Trp Asp
                405                 410                 415

Lys Asn Met Glu Asp Leu His Arg His Ile Phe Trp Glu Pro Asp Ala
            420                 425                 430

Ser Lys Leu Asn Glu Asn Tyr Cys Arg Asn Pro Asp Asp Asp Ala His
        435                 440                 445

Gly Pro Trp Cys Tyr Thr Gly Asn Pro Leu Ile Pro Trp Asp Tyr Cys
450                 455                 460

Pro Ile Ser Arg Cys Glu Gly Asp Thr Thr Pro Thr Ile Val Asn Leu
465                 470                 475                 480

Asp His Pro Val Ile Ser Cys Ala Lys Thr Lys Gln Leu Arg Val Val
                485                 490                 495

Asn Gly Ile Pro Thr Arg Thr Asn Ile Gly Trp Met Val Ser Leu Arg
            500                 505                 510

Tyr Arg Asn Lys His Ile Cys Gly Gly Ser Leu Ile Lys Glu Ser Trp
        515                 520                 525

Val Leu Thr Ala Arg Gln Cys Phe Pro Ser Arg Asp Leu Lys Asp Tyr
530                 535                 540

Glu Ala Trp Leu Gly Ile His Asp Val His Gly Arg Gly Asp Glu Lys
545                 550                 555                 560

Cys Lys Gln Val Leu Asn Val Ser Gln Leu Val Tyr Gly Pro Glu Gly
                565                 570                 575

Ser Asp Leu Val Leu Met Lys Leu Ala Arg Pro Ala Val Leu Asp Asp
            580                 585                 590

Phe Val Ser Thr Ile Asp Leu Pro Asn Tyr Gly Cys Thr Ile Pro Glu
```

```
               595                 600                 605
Lys Thr Ser Cys Ser Val Tyr Gly Trp Gly Tyr Thr Gly Leu Ile Asn
610                 615                 620

Tyr Asp Gly Leu Leu Arg Val Ala His Leu Tyr Ile Met Gly Asn Glu
625                 630                 635                 640

Lys Cys Ser Gln His His Arg Gly Lys Val Thr Leu Asn Glu Ser Glu
                645                 650                 655

Ile Cys Ala Gly Ala Glu Lys Ile Gly Ser Gly Pro Cys Glu Gly Asp
                660                 665                 670

Tyr Gly Gly Pro Leu Val Cys Glu Gln His Lys Met Arg Met Val Leu
                675                 680                 685

Gly Val Ile Val Pro Gly Arg Gly Cys Ala Ile Pro Asn Arg Pro Gly
                690                 695                 700

Ile Phe Val Arg Val Ala Tyr Tyr Ala Lys Trp Ile His Lys Ile Ile
705                 710                 715                 720

Leu Thr Tyr Lys Val Pro Gln Ser
                725

<210> SEQ ID NO 39
<211> LENGTH: 393
<212> TYPE: PRT
<213> ORGANISM: Homo sapiens

<400> SEQUENCE: 39

Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
                20                  25                  30

Ser Pro Leu Pro Ser Gln Ala Met Asp Asp Leu Met Leu Ser Pro Asp
                35                  40                  45

Asp Ile Glu Gln Trp Phe Thr Glu Asp Pro Gly Pro Asp Glu Ala Pro
            50                  55                  60

Arg Met Pro Glu Ala Ala Pro Pro Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
                100                 105                 110

Phe Leu His Ser Gly Thr Ala Lys Ser Val Thr Cys Thr Tyr Ser Pro
                115                 120                 125

Ala Leu Asn Lys Met Phe Cys Gln Leu Ala Lys Thr Cys Pro Val Gln
130                 135                 140

Leu Trp Val Asp Ser Thr Pro Pro Gly Thr Arg Val Arg Ala Met
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
                180                 185                 190

His Leu Ile Arg Val Glu Gly Asn Leu Arg Val Glu Tyr Leu Asp Asp
                195                 200                 205

Arg Asn Thr Phe Arg His Ser Val Val Val Pro Tyr Glu Pro Pro Glu
                210                 215                 220

Val Gly Ser Asp Cys Thr Thr Ile His Tyr Asn Tyr Met Cys Asn Ser
225                 230                 235                 240
```

```
Ser Cys Met Gly Gly Met Asn Arg Arg Pro Ile Leu Thr Ile Ile Thr
            245                 250                 255

Leu Glu Asp Ser Ser Gly Asn Leu Leu Gly Arg Asn Ser Phe Glu Val
        260                 265                 270

Arg Val Cys Ala Cys Pro Gly Arg Asp Arg Arg Thr Glu Glu Glu Asn
    275                 280                 285

Leu Arg Lys Lys Gly Glu Pro His His Glu Leu Pro Pro Gly Ser Thr
290                 295                 300

Lys Arg Ala Leu Pro Asn Asn Thr Ser Ser Ser Pro Gln Pro Lys Lys
305                 310                 315                 320

Lys Pro Leu Asp Gly Glu Tyr Phe Thr Leu Gln Ile Arg Gly Arg Glu
                325                 330                 335

Arg Phe Glu Met Phe Arg Glu Leu Asn Glu Ala Leu Glu Leu Lys Asp
                340                 345                 350

Ala Gln Ala Gly Lys Glu Pro Gly Gly Ser Arg Ala His Ser Ser His
            355                 360                 365

Leu Lys Ser Lys Lys Gly Gln Ser Thr Ser Arg His Lys Lys Leu Met
        370                 375                 380

Phe Lys Thr Glu Gly Pro Asp Ser Asp
385                 390

<210> SEQ ID NO 40
<211> LENGTH: 638
<212> TYPE: PRT
<213> ORGANISM: Homo sapiens

<400> SEQUENCE: 40

Met Ile Leu Phe Lys Gln Ala Thr Tyr Phe Ile Ser Leu Phe Ala Thr
1               5                   10                  15

Val Ser Cys Gly Cys Leu Thr Gln Leu Tyr Glu Asn Ala Phe Phe Arg
            20                  25                  30

Gly Gly Asp Val Ala Ser Met Tyr Thr Pro Asn Ala Gln Tyr Cys Gln
        35                  40                  45

Met Arg Cys Thr Phe His Pro Arg Cys Leu Leu Phe Ser Phe Leu Pro
    50                  55                  60

Ala Ser Ser Ile Asn Asp Met Glu Lys Arg Phe Gly Cys Phe Leu Lys
65                  70                  75                  80

Asp Ser Val Thr Gly Thr Leu Pro Lys Val His Arg Thr Gly Ala Val
                85                  90                  95

Ser Gly His Ser Leu Lys Gln Cys Gly His Gln Ile Ser Ala Cys His
            100                 105                 110

Arg Asp Ile Tyr Lys Gly Val Asp Met Arg Gly Val Asn Phe Asn Val
        115                 120                 125

Ser Lys Val Ser Ser Val Glu Glu Cys Gln Lys Arg Cys Thr Asn Asn
    130                 135                 140

Ile Arg Cys Gln Phe Phe Ser Tyr Ala Thr Gln Thr Phe His Lys Ala
145                 150                 155                 160

Glu Tyr Arg Asn Asn Cys Leu Leu Lys Tyr Ser Pro Gly Gly Thr Pro
                165                 170                 175

Thr Ala Ile Lys Val Leu Ser Asn Val Glu Ser Gly Phe Ser Leu Lys
            180                 185                 190

Pro Cys Ala Leu Ser Glu Ile Gly Cys His Met Asn Ile Phe Gln His
        195                 200                 205

Leu Ala Phe Ser Asp Val Asp Val Ala Arg Val Leu Thr Pro Asp Ala
    210                 215                 220
```

```
Phe Val Cys Arg Thr Ile Cys Thr Tyr His Pro Asn Cys Leu Phe Phe
225                 230                 235                 240

Thr Phe Tyr Thr Asn Val Trp Lys Ile Glu Ser Gln Arg Asn Val Cys
            245                 250                 255

Leu Leu Lys Thr Ser Glu Ser Gly Thr Pro Ser Ser Ser Thr Pro Gln
            260                 265                 270

Glu Asn Thr Ile Ser Gly Tyr Ser Leu Leu Thr Cys Lys Arg Thr Leu
        275                 280                 285

Pro Glu Pro Cys His Ser Lys Ile Tyr Pro Gly Val Asp Phe Gly Gly
        290                 295                 300

Glu Glu Leu Asn Val Thr Phe Val Lys Gly Val Asn Val Cys Gln Glu
305                 310                 315                 320

Thr Cys Thr Lys Met Ile Arg Cys Gln Phe Phe Thr Tyr Ser Leu Leu
                325                 330                 335

Pro Glu Asp Cys Lys Glu Lys Cys Lys Cys Phe Leu Arg Leu Ser
                340                 345                 350

Met Asp Gly Ser Pro Thr Arg Ile Ala Tyr Gly Thr Gln Gly Ser Ser
            355                 360                 365

Gly Tyr Ser Leu Arg Leu Cys Asn Thr Gly Asp Asn Ser Val Cys Thr
370                 375                 380

Thr Lys Thr Ser Thr Arg Ile Val Gly Gly Thr Asn Ser Ser Trp Gly
385                 390                 395                 400

Glu Trp Pro Trp Gln Val Ser Leu Gln Val Lys Leu Thr Ala Gln Arg
                405                 410                 415

His Leu Cys Gly Gly Ser Leu Ile Gly His Gln Trp Val Leu Thr Ala
            420                 425                 430

Ala His Cys Phe Asp Gly Leu Pro Leu Gln Asp Val Trp Arg Ile Tyr
        435                 440                 445

Ser Gly Ile Leu Asn Leu Ser Asp Ile Thr Lys Asp Thr Pro Phe Ser
450                 455                 460

Gln Ile Lys Glu Ile Ile Ile His Gln Asn Tyr Lys Val Ser Glu Gly
465                 470                 475                 480

Asn His Asp Ile Ala Leu Ile Lys Leu Gln Ala Pro Leu Asn Tyr Thr
            485                 490                 495

Glu Phe Gln Lys Pro Ile Cys Leu Pro Ser Lys Gly Asp Thr Ser Thr
            500                 505                 510

Ile Tyr Thr Asn Cys Trp Val Thr Gly Trp Gly Phe Ser Lys Glu Lys
        515                 520                 525

Gly Glu Ile Gln Asn Ile Leu Gln Lys Val Asn Ile Pro Leu Val Thr
530                 535                 540

Asn Glu Glu Cys Gln Lys Arg Tyr Gln Asp Tyr Lys Ile Thr Gln Arg
545                 550                 555                 560

Met Val Cys Ala Gly Tyr Lys Glu Gly Gly Lys Asp Ala Cys Lys Gly
                565                 570                 575

Asp Ser Gly Gly Pro Leu Val Cys Lys His Asn Gly Met Trp Arg Leu
            580                 585                 590

Val Gly Ile Thr Ser Trp Gly Glu Gly Cys Ala Arg Arg Glu Gln Pro
        595                 600                 605

Gly Val Tyr Thr Lys Val Ala Glu Tyr Met Asp Trp Ile Leu Glu Lys
        610                 615                 620

Thr Gln Ser Ser Asp Gly Lys Ala Gln Met Gln Ser Pro Ala
625                 630                 635
```

```
<210> SEQ ID NO 41
<211> LENGTH: 166
<212> TYPE: PRT
<213> ORGANISM: Homo sapiens

<400> SEQUENCE: 41

Met Ala Ser Gly Val Ala Val Ser Asp Gly Val Ile Lys Val Phe Asn
  1               5                  10                  15

Asp Met Lys Val Arg Lys Ser Ser Thr Pro Glu Glu Val Lys Lys Arg
             20                  25                  30

Lys Lys Ala Val Leu Phe Cys Leu Ser Glu Asp Lys Lys Asn Ile Ile
         35                  40                  45

Leu Glu Glu Gly Lys Glu Ile Leu Val Gly Asp Val Gly Gln Thr Val
     50                  55                  60

Asp Asp Pro Tyr Ala Thr Phe Val Lys Met Leu Pro Asp Lys Asp Cys
 65                  70                  75                  80

Arg Tyr Ala Leu Tyr Asp Ala Thr Tyr Glu Thr Lys Glu Ser Lys Lys
                 85                  90                  95

Glu Asp Leu Val Phe Ile Phe Trp Ala Pro Glu Ser Ala Pro Leu Lys
            100                 105                 110

Ser Lys Met Ile Tyr Ala Ser Ser Lys Asp Ala Ile Lys Lys Lys Leu
        115                 120                 125

Thr Gly Ile Lys His Glu Leu Gln Ala Asn Cys Tyr Glu Glu Val Lys
    130                 135                 140

Asp Arg Cys Thr Leu Ala Glu Lys Leu Gly Gly Ser Ala Val Ile Ser
145                 150                 155                 160

Leu Glu Gly Lys Pro Leu
                165

<210> SEQ ID NO 42
<211> LENGTH: 437
<212> TYPE: PRT
<213> ORGANISM: Homo sapiens

<400> SEQUENCE: 42

Met Ala Ala Gly Thr Leu Tyr Thr Tyr Pro Glu Asn Trp Arg Ala Phe
  1               5                  10                  15

Lys Ala Leu Ile Ala Ala Gln Tyr Ser Gly Ala Gln Val Arg Val Leu
             20                  25                  30

Ser Ala Pro Pro His Phe His Phe Gly Gln Thr Asn Arg Thr Pro Glu
         35                  40                  45

Phe Leu Arg Lys Phe Pro Ala Gly Lys Val Pro Ala Phe Glu Gly Asp
     50                  55                  60

Asp Gly Phe Cys Val Phe Glu Ser Asn Ala Ile Ala Tyr Tyr Val Ser
 65                  70                  75                  80

Asn Glu Glu Leu Arg Gly Ser Thr Pro Glu Ala Ala Gln Val Val
                 85                  90                  95

Gln Trp Val Ser Phe Ala Asp Ser Asp Ile Val Pro Ala Ser Thr
            100                 105                 110

Trp Val Phe Pro Thr Leu Gly Ile Met His His Asn Lys Gln Ala Thr
        115                 120                 125

Glu Asn Ala Lys Glu Glu Val Arg Arg Ile Leu Gly Leu Leu Asp Ala
    130                 135                 140

Tyr Leu Lys Thr Arg Thr Phe Leu Val Gly Glu Arg Val Thr Leu Ala
145                 150                 155                 160
```

```
Asp Ile Thr Val Val Cys Thr Leu Leu Trp Leu Tyr Lys Gln Val Leu
                165                 170                 175

Glu Pro Ser Phe Arg Gln Ala Phe Pro Asn Thr Asn Arg Trp Phe Leu
            180                 185                 190

Thr Cys Ile Asn Gln Pro Gln Phe Arg Ala Val Leu Gly Glu Val Lys
        195                 200                 205

Leu Cys Glu Lys Met Ala Gln Phe Asp Ala Lys Lys Phe Ala Glu Thr
    210                 215                 220

Gln Pro Lys Lys Asp Thr Pro Arg Lys Glu Lys Gly Ser Arg Glu Glu
225                 230                 235                 240

Lys Gln Lys Pro Gln Ala Glu Arg Lys Glu Lys Lys Ala Ala Ala
                245                 250                 255

Pro Ala Pro Glu Glu Met Asp Glu Cys Glu Gln Ala Leu Ala Ala
                260                 265                 270

Glu Pro Lys Ala Lys Asp Pro Phe Ala His Leu Pro Lys Ser Thr Phe
    275                 280                 285

Val Leu Asp Glu Phe Lys Arg Lys Tyr Ser Asn Glu Asp Thr Leu Ser
    290                 295                 300

Val Ala Leu Pro Tyr Phe Trp Glu His Phe Asp Lys Asp Gly Trp Ser
305                 310                 315                 320

Leu Trp Tyr Ser Glu Tyr Arg Phe Pro Glu Glu Leu Thr Gln Thr Phe
                325                 330                 335

Met Ser Cys Asn Leu Ile Thr Gly Met Phe Gln Arg Leu Asp Lys Leu
                340                 345                 350

Arg Lys Asn Ala Phe Ala Ser Val Ile Leu Phe Gly Thr Asn Asn Ser
            355                 360                 365

Ser Ser Ile Ser Gly Val Trp Val Phe Arg Gly Gln Glu Leu Ala Phe
        370                 375                 380

Pro Leu Ser Pro Asp Trp Gln Val Asp Tyr Glu Ser Tyr Thr Trp Arg
385                 390                 395                 400

Lys Leu Asp Pro Gly Ser Glu Glu Thr Gln Thr Leu Val Arg Glu Tyr
                405                 410                 415

Phe Ser Trp Glu Gly Ala Phe Gln His Val Gly Lys Ala Phe Asn Gln
                420                 425                 430

Gly Lys Ile Phe Lys
            435

<210> SEQ ID NO 43
<211> LENGTH: 854
<212> TYPE: PRT
<213> ORGANISM: Homo sapiens

<400> SEQUENCE: 43

Met Pro Pro Cys Ser Gly Gly Asp Gly Ser Thr Pro Pro Gly Pro Ser
  1               5                  10                  15

Leu Arg Asp Arg Asp Cys Pro Ala Gln Ser Ala Glu Tyr Pro Arg Asp
                20                  25                  30

Arg Leu Asp Pro Arg Pro Gly Ser Pro Ser Glu Ala Ser Ser Pro Pro
            35                  40                  45

Phe Leu Arg Ser Arg Ala Pro Val Asn Trp Tyr Gln Glu Lys Ala Gln
        50                  55                  60

Val Phe Leu Trp His Leu Met Val Ser Gly Ser Thr Thr Leu Leu Cys
65                  70                  75                  80

Leu Trp Lys Gln Pro Phe His Val Ser Ala Phe Pro Val Thr Ala Ser
                85                  90                  95
```

```
Leu Ala Phe Arg Gln Ser Gln Gly Ala Gly Gln His Leu Tyr Lys Asp
                100                 105                 110

Leu Gln Pro Phe Ile Leu Arg Leu Leu Met Pro Glu Glu Thr Gln
            115                 120                 125

Thr Gln Asp Gln Pro Met Glu Glu Glu Val Glu Thr Phe Ala Phe
    130                 135                 140

Gln Ala Glu Ile Ala Gln Leu Met Ser Leu Ile Ile Asn Thr Phe Tyr
145                 150                 155                 160

Ser Asn Lys Glu Ile Phe Leu Arg Glu Leu Ile Ser Asn Ser Ser Asp
                165                 170                 175

Ala Leu Asp Lys Ile Arg Tyr Glu Ser Leu Thr Asp Pro Ser Lys Leu
            180                 185                 190

Asp Ser Gly Lys Glu Leu His Ile Asn Leu Ile Pro Asn Lys Gln Asp
            195                 200                 205

Arg Thr Leu Thr Ile Val Asp Thr Gly Ile Gly Met Thr Lys Ala Asp
    210                 215                 220

Leu Ile Asn Asn Leu Gly Thr Ile Ala Lys Ser Gly Thr Lys Ala Phe
225                 230                 235                 240

Met Glu Ala Leu Gln Ala Gly Ala Asp Ile Ser Met Ile Gly Gln Phe
                245                 250                 255

Gly Val Gly Phe Tyr Ser Ala Tyr Leu Val Ala Glu Lys Val Thr Val
            260                 265                 270

Ile Thr Lys His Asn Asp Asp Glu Gln Tyr Ala Trp Glu Ser Ser Ala
            275                 280                 285

Gly Gly Ser Phe Thr Val Arg Thr Asp Thr Gly Glu Pro Met Gly Arg
    290                 295                 300

Gly Thr Lys Val Ile Leu His Leu Lys Glu Asp Gln Thr Glu Tyr Leu
305                 310                 315                 320

Glu Glu Arg Arg Ile Lys Glu Ile Val Lys Lys His Ser Gln Phe Ile
                325                 330                 335

Gly Tyr Pro Ile Thr Leu Phe Val Glu Lys Glu Arg Asp Lys Glu Val
            340                 345                 350

Ser Asp Asp Glu Ala Glu Glu Lys Glu Asp Lys Glu Glu Glu Lys Glu
    355                 360                 365

Lys Glu Glu Lys Glu Ser Glu Asp Lys Pro Glu Ile Glu Asp Val Gly
370                 375                 380

Ser Asp Glu Glu Glu Glu Lys Lys Asp Gly Asp Lys Lys Lys Lys Lys
385                 390                 395                 400

Lys Ile Lys Glu Lys Tyr Ile Asp Gln Glu Glu Leu Asn Lys Thr Lys
                405                 410                 415

Pro Ile Trp Thr Arg Asn Pro Asp Asp Ile Thr Asn Glu Glu Tyr Gly
            420                 425                 430

Glu Phe Tyr Lys Ser Leu Thr Asn Asp Trp Glu Asp His Leu Ala Val
            435                 440                 445

Lys His Phe Ser Val Glu Gly Gln Leu Glu Phe Arg Ala Leu Leu Phe
    450                 455                 460

Val Pro Arg Arg Ala Pro Phe Asp Leu Phe Glu Asn Arg Lys Lys Lys
465                 470                 475                 480

Asn Asn Ile Lys Leu Tyr Val Arg Arg Val Phe Ile Met Asp Asn Cys
                485                 490                 495

Glu Glu Leu Ile Pro Glu Tyr Leu Asn Phe Ile Arg Gly Val Val Asp
            500                 505                 510
```

```
Ser Glu Asp Leu Pro Leu Asn Ile Ser Arg Glu Met Leu Gln Gln Ser
            515                 520                 525

Lys Ile Leu Lys Val Ile Arg Lys Asn Leu Val Lys Lys Cys Leu Glu
        530                 535                 540

Leu Phe Thr Glu Leu Ala Glu Asp Lys Glu Asn Tyr Lys Lys Phe Tyr
545                 550                 555                 560

Glu Gln Phe Ser Lys Asn Ile Lys Leu Gly Ile His Glu Asp Ser Gln
                565                 570                 575

Asn Arg Lys Lys Leu Ser Glu Leu Leu Arg Tyr Tyr Thr Ser Ala Ser
            580                 585                 590

Gly Asp Glu Met Val Ser Leu Lys Asp Tyr Cys Thr Arg Met Lys Glu
        595                 600                 605

Asn Gln Lys His Ile Tyr Tyr Ile Thr Gly Glu Thr Lys Asp Gln Val
    610                 615                 620

Ala Asn Ser Ala Phe Val Glu Arg Leu Arg Lys His Gly Leu Glu Val
625                 630                 635                 640

Ile Tyr Met Ile Glu Pro Ile Asp Glu Tyr Cys Val Gln Gln Leu Lys
                645                 650                 655

Glu Phe Glu Gly Lys Thr Leu Val Ser Val Thr Lys Glu Gly Leu Glu
            660                 665                 670

Leu Pro Glu Asp Glu Glu Lys Lys Lys Gln Glu Glu Lys Lys Thr
        675                 680                 685

Lys Phe Glu Asn Leu Cys Lys Ile Met Lys Asp Ile Leu Glu Lys Lys
    690                 695                 700

Val Glu Lys Val Val Val Ser Asn Arg Leu Val Thr Ser Pro Cys Cys
705                 710                 715                 720

Ile Val Thr Ser Thr Tyr Gly Trp Thr Ala Asn Met Glu Arg Ile Met
                725                 730                 735

Lys Ala Gln Ala Leu Arg Asp Asn Ser Thr Met Gly Tyr Met Ala Ala
            740                 745                 750

Lys Lys His Leu Glu Ile Asn Pro Asp His Ser Ile Ile Glu Thr Leu
        755                 760                 765

Arg Gln Lys Ala Glu Ala Asp Lys Asn Asp Lys Ser Val Lys Asp Leu
    770                 775                 780

Val Ile Leu Leu Tyr Glu Thr Ala Leu Leu Ser Ser Gly Phe Ser Leu
785                 790                 795                 800

Glu Asp Pro Gln Thr His Ala Asn Arg Ile Tyr Arg Met Ile Lys Leu
                805                 810                 815

Gly Leu Gly Ile Asp Glu Asp Pro Thr Ala Asp Asp Thr Ser Ala
            820                 825                 830

Ala Val Thr Glu Glu Met Pro Pro Leu Glu Gly Asp Asp Asp Thr Ser
        835                 840                 845

Arg Met Glu Glu Val Asp
    850

<210> SEQ ID NO 44
<211> LENGTH: 1192
<212> TYPE: PRT
<213> ORGANISM: Homo sapiens

<400> SEQUENCE: 44

Met Glu Asp Leu Asp Gln Ser Pro Leu Val Ser Ser Ser Asp Ser Pro
1               5                   10                  15

Pro Arg Pro Gln Pro Ala Phe Lys Tyr Gln Phe Val Arg Glu Pro Glu
            20                  25                  30
```

-continued

```
Asp Glu Glu Glu Glu Glu Glu Glu Glu Asp Glu Asp Glu
        35                  40                  45

Leu Glu Glu Leu Glu Val Leu Glu Arg Lys Pro Ala Ala Gly Leu Ser
 50                  55                  60

Ala Ala Pro Val Pro Thr Ala Pro Ala Gly Ala Pro Leu Met Asp
 65                  70                  75                  80

Phe Gly Asn Asp Phe Val Pro Pro Ala Pro Arg Gly Pro Leu Pro Ala
                 85                  90                  95

Ala Pro Pro Val Ala Pro Glu Arg Gln Pro Ser Trp Asp Pro Ser Pro
                100                 105                 110

Val Ser Ser Thr Val Pro Ala Pro Ser Pro Leu Ser Ala Ala Ala Val
                115                 120                 125

Ser Pro Ser Lys Leu Pro Glu Asp Asp Glu Pro Pro Ala Arg Pro Pro
            130                 135                 140

Pro Pro Pro Pro Ala Ser Val Ser Pro Gln Ala Glu Pro Val Trp Thr
145                 150                 155                 160

Pro Pro Ala Pro Ala Pro Ala Ala Pro Pro Ser Thr Pro Ala Ala Pro
                165                 170                 175

Lys Arg Arg Gly Ser Ser Gly Ser Val Asp Glu Thr Leu Phe Ala Leu
                180                 185                 190

Pro Ala Ala Ser Glu Pro Val Ile Arg Ser Ser Ala Glu Asn Met Asp
            195                 200                 205

Leu Lys Glu Gln Pro Gly Asn Thr Ile Ser Ala Gly Gln Glu Asp Phe
210                 215                 220

Pro Ser Val Leu Leu Glu Thr Ala Ala Ser Leu Pro Ser Leu Ser Pro
225                 230                 235                 240

Leu Ser Ala Ala Ser Phe Lys Glu His Glu Tyr Leu Gly Asn Leu Ser
                245                 250                 255

Thr Val Leu Pro Thr Glu Gly Thr Leu Gln Glu Asn Val Ser Glu Ala
                260                 265                 270

Ser Lys Glu Val Ser Glu Lys Ala Lys Thr Leu Leu Ile Asp Arg Asp
            275                 280                 285

Leu Thr Glu Phe Ser Glu Leu Glu Tyr Ser Glu Met Gly Ser Ser Phe
            290                 295                 300

Ser Val Ser Pro Lys Ala Glu Ser Ala Val Ile Val Ala Asn Pro Arg
305                 310                 315                 320

Glu Glu Ile Ile Val Lys Asn Lys Asp Glu Glu Lys Leu Val Ser
                325                 330                 335

Asn Asn Ile Leu His Asn Gln Gln Glu Leu Pro Thr Ala Leu Thr Lys
                340                 345                 350

Leu Val Lys Glu Asp Glu Val Val Ser Ser Lys Ala Lys Asp Ser
            355                 360                 365

Phe Asn Glu Lys Arg Val Ala Val Glu Ala Pro Met Arg Glu Glu Tyr
370                 375                 380

Ala Asp Phe Lys Pro Phe Glu Arg Val Trp Glu Val Lys Asp Ser Lys
385                 390                 395                 400

Glu Asp Ser Asp Met Leu Ala Ala Gly Gly Lys Ile Glu Ser Asn Leu
                405                 410                 415

Glu Ser Lys Val Asp Lys Lys Cys Phe Ala Asp Ser Leu Glu Gln Thr
                420                 425                 430

Asn His Glu Lys Asp Ser Glu Ser Ser Asn Asp Asp Thr Ser Phe Pro
                435                 440                 445
```

-continued

```
Ser Thr Pro Glu Gly Ile Lys Asp Arg Ser Gly Ala Tyr Ile Thr Cys
    450                 455                 460
Ala Pro Phe Asn Pro Ala Ala Thr Glu Ser Ile Ala Thr Asn Ile Phe
465                 470                 475                 480
Pro Leu Leu Gly Asp Pro Thr Ser Glu Asn Lys Thr Asp Glu Lys Lys
                485                 490                 495
Ile Glu Glu Lys Lys Ala Gln Ile Val Thr Glu Lys Asn Thr Ser Thr
            500                 505                 510
Lys Thr Ser Asn Pro Phe Leu Val Ala Ala Gln Asp Ser Glu Thr Asp
        515                 520                 525
Tyr Val Thr Thr Asp Asn Leu Thr Lys Val Thr Glu Glu Val Val Ala
530                 535                 540
Asn Met Pro Glu Gly Leu Thr Pro Asp Leu Val Gln Glu Ala Cys Glu
545                 550                 555                 560
Ser Glu Leu Asn Glu Val Thr Gly Thr Lys Ile Ala Tyr Glu Thr Lys
                565                 570                 575
Met Asp Leu Val Gln Thr Ser Glu Val Met Gln Glu Ser Leu Tyr Pro
            580                 585                 590
Ala Ala Gln Leu Cys Pro Ser Phe Glu Glu Ser Glu Ala Thr Pro Ser
        595                 600                 605
Pro Val Leu Pro Asp Ile Val Met Glu Ala Pro Leu Asn Ser Ala Val
610                 615                 620
Pro Ser Ala Gly Ala Ser Val Ile Gln Pro Ser Ser Ser Pro Leu Glu
625                 630                 635                 640
Ala Ser Ser Val Asn Tyr Glu Ser Ile Lys His Glu Pro Glu Asn Pro
                645                 650                 655
Pro Pro Tyr Glu Glu Ala Met Ser Val Ser Leu Lys Lys Val Ser Gly
            660                 665                 670
Ile Lys Glu Glu Ile Lys Glu Pro Glu Asn Ile Asn Ala Ala Leu Gln
        675                 680                 685
Glu Thr Glu Ala Pro Tyr Ile Ser Ile Ala Cys Asp Leu Ile Lys Glu
690                 695                 700
Thr Lys Leu Ser Ala Glu Pro Ala Pro Asp Phe Ser Asp Tyr Ser Glu
705                 710                 715                 720
Met Ala Lys Val Glu Gln Pro Val Pro Asp His Ser Glu Leu Val Glu
                725                 730                 735
Asp Ser Ser Pro Asp Ser Glu Pro Val Asp Leu Phe Ser Asp Asp Ser
            740                 745                 750
Ile Pro Asp Val Pro Gln Lys Gln Asp Glu Thr Val Met Leu Val Lys
        755                 760                 765
Glu Ser Leu Thr Glu Thr Ser Phe Glu Ser Met Ile Glu Tyr Glu Asn
770                 775                 780
Lys Glu Lys Leu Ser Ala Leu Pro Pro Glu Gly Gly Lys Pro Tyr Leu
785                 790                 795                 800
Glu Ser Phe Lys Leu Ser Leu Asp Asn Thr Lys Asp Thr Leu Leu Pro
                805                 810                 815
Asp Glu Val Ser Thr Leu Ser Lys Lys Glu Lys Ile Pro Leu Gln Met
            820                 825                 830
Glu Glu Leu Ser Thr Ala Val Tyr Ser Asn Asp Asp Leu Phe Ile Ser
        835                 840                 845
Lys Glu Ala Gln Ile Arg Glu Thr Glu Thr Phe Ser Asp Ser Ser Pro
850                 855                 860
Ile Glu Ile Ile Asp Glu Phe Pro Thr Leu Ile Ser Ser Lys Thr Asp
```

```
                865                 870                 875                 880
        Ser Phe Ser Lys Leu Ala Arg Glu Tyr Thr Asp Leu Glu Val Ser His
                            885                 890                 895

Lys Ser Glu Ile Ala Asn Ala Pro Asp Gly Ala Gly Ser Leu Pro Cys
                        900                 905                 910

Thr Glu Leu Pro His Asp Leu Ser Leu Lys Asn Ile Gln Pro Lys Val
                        915                 920                 925

Glu Glu Lys Ile Ser Phe Ser Asp Phe Ser Lys Asn Gly Ser Ala
                    930                 935                 940

Thr Ser Lys Val Leu Leu Leu Pro Pro Asp Val Ser Ala Leu Ala Thr
        945                 950                 955                 960

Gln Ala Glu Ile Glu Ser Ile Val Lys Pro Lys Val Leu Val Lys Glu
                            965                 970                 975

Ala Glu Lys Lys Leu Pro Ser Asp Thr Glu Lys Glu Asp Arg Ser Pro
                        980                 985                 990

Ser Ala Ile Phe Ser Ala Glu Leu Ser Lys Thr Ser Val Val Asp Leu
                        995                 1000                1005

Leu Tyr Trp Arg Asp Ile Lys Lys Thr Gly Val Val Phe Gly Ala Ser
                    1010                1015                1020

Leu Phe Leu Leu Leu Ser Leu Thr Val Phe Ser Ile Val Ser Val Thr
        1025                1030                1035                1040

Ala Tyr Ile Ala Leu Ala Leu Leu Ser Val Thr Ile Ser Phe Arg Ile
                        1045                1050                1055

Tyr Lys Gly Val Ile Gln Ala Ile Gln Lys Ser Asp Glu Gly His Pro
                        1060                1065                1070

Phe Arg Ala Tyr Leu Glu Ser Glu Val Ala Ile Ser Glu Glu Leu Val
                        1075                1080                1085

Gln Lys Tyr Ser Asn Ser Ala Leu Gly His Val Asn Cys Thr Ile Lys
                    1090                1095                1100

Glu Leu Arg Arg Leu Phe Leu Val Asp Asp Leu Val Asp Ser Leu Lys
        1105                1110                1115                1120

Phe Ala Val Leu Met Trp Val Phe Thr Tyr Val Gly Ala Leu Phe Asn
                            1125                1130                1135

Gly Leu Thr Leu Leu Ile Leu Ala Leu Ile Ser Leu Phe Ser Val Pro
                        1140                1145                1150

Val Ile Tyr Glu Arg His Gln Ala Gln Ile Asp His Tyr Leu Gly Leu
                        1155                1160                1165

Ala Asn Lys Asn Val Lys Asp Ala Met Ala Lys Ile Gln Ala Lys Ile
                    1170                1175                1180

Pro Gly Leu Lys Arg Lys Ala Glu
        1185                1190

<210> SEQ ID NO 45
<211> LENGTH: 364
<212> TYPE: PRT
<213> ORGANISM: Homo sapiens

<400> SEQUENCE: 45

Met Pro Tyr Gln Tyr Pro Ala Leu Thr Pro Glu Gln Lys Lys Glu Leu
  1               5                  10                  15

Ser Asp Ile Ala His Arg Ile Val Ala Pro Gly Lys Gly Ile Leu Ala
                20                  25                  30

Ala Asp Glu Ser Thr Gly Ser Ile Ala Lys Arg Leu Gln Ser Ile Gly
            35                  40                  45
```

Thr Glu Asn Thr Glu Glu Asn Arg Arg Phe Tyr Arg Gln Leu Leu Leu
    50                  55                  60

Thr Ala Asp Asp Arg Val Asn Pro Cys Ile Gly Gly Val Ile Leu Phe
65                  70                  75                  80

His Glu Thr Leu Tyr Gln Lys Ala Asp Asp Gly Arg Pro Phe Pro Gln
                    85                  90                  95

Val Ile Lys Ser Lys Gly Gly Val Val Gly Ile Lys Val Asp Lys Gly
                100                 105                 110

Val Val Pro Leu Ala Gly Thr Asn Gly Glu Thr Thr Thr Gln Gly Leu
                115                 120                 125

Asp Gly Leu Ser Glu Arg Cys Ala Gln Tyr Lys Lys Asp Gly Ala Asp
    130                 135                 140

Phe Ala Lys Trp Arg Cys Val Leu Lys Ile Gly Glu His Thr Pro Ser
145                 150                 155                 160

Ala Leu Ala Ile Met Glu Asn Ala Asn Val Leu Ala Arg Tyr Ala Ser
                165                 170                 175

Ile Cys Gln Gln Asn Gly Ile Val Pro Ile Val Glu Pro Glu Ile Leu
                180                 185                 190

Pro Asp Gly Asp His Asp Leu Lys Arg Cys Gln Tyr Val Thr Glu Lys
    195                 200                 205

Val Leu Ala Ala Val Tyr Lys Ala Leu Ser Asp His His Ile Tyr Leu
210                 215                 220

Glu Gly Thr Leu Leu Lys Pro Asn Met Val Thr Pro Gly His Ala Cys
225                 230                 235                 240

Thr Gln Lys Phe Ser His Glu Glu Ile Ala Met Ala Thr Val Thr Ala
                245                 250                 255

Leu Arg Arg Thr Val Pro Pro Ala Val Thr Gly Ile Thr Phe Leu Ser
                260                 265                 270

Gly Gly Gln Ser Glu Glu Ala Ser Ile Asn Leu Asn Ala Ile Asn
    275                 280                 285

Lys Cys Pro Leu Leu Lys Pro Trp Ala Leu Thr Phe Ser Tyr Gly Arg
290                 295                 300

Ala Leu Gln Ala Ser Ala Leu Lys Ala Trp Gly Gly Lys Lys Glu Asn
305                 310                 315                 320

Leu Lys Ala Ala Gln Glu Glu Tyr Val Lys Arg Ala Leu Ala Asn Ser
                325                 330                 335

Leu Ala Cys Gln Gly Lys Tyr Thr Pro Ser Gly Gln Ala Gly Ala Ala
                340                 345                 350

Ala Ser Glu Ser Leu Phe Val Ser Asn His Ala Tyr
                355                 360

<210> SEQ ID NO 46
<211> LENGTH: 1203
<212> TYPE: PRT
<213> ORGANISM: Homo sapiens

<400> SEQUENCE: 46

Met Ala Ala Cys Gly Arg Val Arg Arg Met Phe Arg Leu Ser Ala Ala
1               5                   10                  15

Leu His Leu Leu Leu Leu Phe Ala Ala Gly Ala Glu Lys Leu Pro Gly
                20                  25                  30

Gln Gly Val His Ser Gln Gly Gln Gly Pro Gly Ala Asn Phe Val Ser
            35                  40                  45

Phe Val Gly Gln Ala Gly Gly Gly Gly Pro Ala Gly Gln Gln Leu Pro
    50                  55                  60

-continued

```
Gln Leu Pro Gln Ser Ser Gln Leu Gln Gln Gln Gln Gln Gln Gln Gln
65                  70                  75                  80

Gln Gln Gln Gln Pro Gln Pro Pro Gln Pro Pro Phe Pro Ala Gly Gly
            85                  90                  95

Pro Pro Ala Arg Arg Gly Gly Ala Gly Gly Gly Trp Lys Leu
            100                 105                 110

Ala Glu Glu Glu Ser Cys Arg Glu Asp Val Thr Arg Val Cys Pro Lys
            115                 120                 125

His Thr Trp Ser Asn Asn Leu Ala Val Leu Glu Cys Leu Gln Asp Val
            130                 135                 140

Arg Glu Pro Glu Asn Glu Ile Ser Ser Asp Cys Asn His Leu Leu Trp
145                 150                 155                 160

Asn Tyr Lys Leu Asn Leu Thr Thr Asp Pro Lys Phe Glu Ser Val Ala
                165                 170                 175

Arg Glu Val Cys Lys Ser Thr Ile Thr Glu Ile Lys Glu Cys Ala Asp
                180                 185                 190

Glu Pro Val Gly Lys Gly Tyr Met Val Ser Cys Leu Val Asp His Arg
            195                 200                 205

Gly Asn Ile Thr Glu Tyr Gln Cys His Gln Tyr Ile Thr Lys Met Thr
210                 215                 220

Ala Ile Ile Phe Ser Asp Tyr Arg Leu Ile Cys Gly Phe Met Asp Asp
225                 230                 235                 240

Cys Lys Asn Asp Ile Asn Ile Leu Lys Cys Gly Ser Ile Arg Leu Gly
                245                 250                 255

Glu Lys Asp Ala His Ser Gln Gly Glu Val Val Ser Cys Leu Glu Lys
            260                 265                 270

Gly Leu Val Lys Glu Ala Glu Arg Glu Pro Lys Ile Gln Val Ser
            275                 280                 285

Glu Leu Cys Lys Lys Ala Ile Leu Arg Val Ala Glu Leu Ser Ser Asp
            290                 295                 300

Asp Phe His Leu Asp Arg His Leu Tyr Phe Ala Cys Arg Asp Asp Arg
305                 310                 315                 320

Glu Arg Phe Cys Glu Asn Thr Gln Ala Gly Glu Gly Arg Val Tyr Lys
                325                 330                 335

Cys Leu Phe Asn His Lys Phe Glu Glu Ser Met Ser Glu Lys Cys Arg
                340                 345                 350

Glu Ala Leu Thr Thr Arg Gln Lys Leu Ile Ala Gln Asp Tyr Lys Val
            355                 360                 365

Ser Tyr Ser Leu Ala Lys Ser Cys Lys Ser Asp Leu Lys Lys Tyr Arg
            370                 375                 380

Cys Asn Val Glu Asn Leu Pro Arg Ser Arg Glu Ala Arg Leu Ser Tyr
385                 390                 395                 400

Leu Leu Met Cys Leu Glu Ser Ala Val His Arg Gly Arg Gln Val Ser
                405                 410                 415

Ser Glu Cys Gln Gly Glu Met Leu Asp Tyr Arg Arg Met Leu Met Glu
            420                 425                 430

Asp Phe Ser Leu Ser Pro Glu Ile Ile Leu Ser Cys Arg Gly Glu Ile
            435                 440                 445

Glu His His Cys Ser Gly Leu His Arg Lys Gly Arg Thr Leu His Cys
            450                 455                 460

Leu Met Lys Val Val Arg Gly Lys Gly Asn Leu Gly Met Asn Cys
465                 470                 475                 480
```

```
Gln Gln Ala Leu Gln Thr Leu Ile Gln Glu Thr Asp Pro Gly Ala Asp
            485                 490                 495

Tyr Arg Ile Asp Arg Ala Leu Asn Glu Ala Cys Glu Ser Val Ile Gln
        500                 505                 510

Thr Ala Cys Lys His Ile Arg Ser Gly Asp Pro Met Ile Leu Ser Cys
        515                 520                 525

Leu Met Glu His Leu Tyr Thr Glu Lys Met Val Glu Asp Cys Glu His
        530                 535                 540

Arg Leu Leu Glu Leu Gln Tyr Phe Ile Ser Arg Asp Trp Lys Leu Asp
545                 550                 555                 560

Pro Val Leu Tyr Arg Lys Cys Gln Gly Asp Ala Ser Arg Leu Cys His
                565                 570                 575

Thr His Gly Trp Asn Glu Thr Ser Glu Phe Met Pro Gln Gly Ala Val
            580                 585                 590

Phe Ser Cys Leu Tyr Arg His Ala Tyr Arg Thr Glu Glu Gln Gly Arg
        595                 600                 605

Arg Leu Ser Arg Glu Cys Arg Ala Glu Val Gln Arg Ile Leu His Gln
        610                 615                 620

Arg Ala Met Asp Val Lys Leu Asp Pro Ala Leu Gln Asp Lys Cys Leu
625                 630                 635                 640

Ile Asp Leu Gly Lys Trp Cys Ser Glu Lys Thr Glu Thr Gly Gln Glu
                645                 650                 655

Leu Glu Cys Leu Gln Asp His Leu Asp Asp Leu Val Val Glu Cys Arg
            660                 665                 670

Asp Ile Val Gly Asn Leu Thr Glu Leu Glu Ser Glu Asp Ile Gln Ile
        675                 680                 685

Glu Ala Leu Leu Met Arg Ala Cys Glu Pro Ile Ile Gln Asn Phe Cys
        690                 695                 700

His Asp Val Ala Asp Asn Gln Ile Asp Ser Gly Asp Leu Met Glu Cys
705                 710                 715                 720

Leu Ile Gln Asn Lys His Gln Lys Asp Met Asn Glu Lys Cys Ala Ile
                725                 730                 735

Gly Val Thr His Phe Gln Leu Val Gln Met Lys Asp Phe Arg Phe Ser
            740                 745                 750

Tyr Lys Phe Lys Met Ala Cys Lys Glu Asp Val Leu Lys Leu Cys Pro
        755                 760                 765

Asn Ile Lys Lys Lys Val Asp Val Val Ile Cys Leu Ser Thr Thr Val
        770                 775                 780

Arg Asn Asp Thr Leu Gln Glu Ala Lys Glu His Arg Val Ser Leu Lys
785                 790                 795                 800

Cys Arg Arg Gln Leu Arg Val Glu Glu Leu Glu Met Thr Glu Asp Ile
                805                 810                 815

Arg Leu Glu Pro Asp Leu Tyr Glu Ala Cys Lys Ser Asp Ile Lys Asn
            820                 825                 830

Phe Cys Ser Ala Val Gln Tyr Gly Asn Ala Gln Ile Ile Glu Cys Leu
        835                 840                 845

Lys Glu Asn Lys Lys Gln Leu Ser Thr Arg Cys His Gln Lys Val Phe
        850                 855                 860

Lys Leu Gln Glu Thr Glu Met Met Asp Pro Glu Leu Asp Tyr Thr Leu
865                 870                 875                 880

Met Arg Val Cys Lys Gln Met Ile Lys Arg Phe Cys Pro Glu Ala Asp
                885                 890                 895

Ser Lys Thr Met Leu Gln Cys Leu Lys Gln Asn Lys Asn Ser Glu Leu
```

```
                900             905             910
Met Asp Pro Lys Cys Lys Gln Met Ile Thr Lys Arg Gln Ile Thr Gln
            915                 920                 925

Asn Thr Asp Tyr Arg Leu Asn Pro Met Leu Arg Lys Ala Cys Lys Ala
            930                 935                 940

Asp Ile Pro Lys Phe Cys His Gly Ile Leu Thr Lys Ala Lys Asp Asp
945                 950                 955                 960

Ser Glu Leu Glu Gly Gln Val Ile Ser Cys Leu Lys Leu Arg Tyr Ala
                965                 970                 975

Asp Gln Arg Leu Ser Ser Asp Cys Glu Asp Gln Ile Arg Ile Ile Ile
            980                 985                 990

Gln Glu Ser Ala Leu Asp Tyr Arg Leu Asp Pro Gln Leu Gln Leu His
            995                 1000                1005

Cys Ser Asp Glu Ile Ser Ser Leu Cys Ala Glu Ala Ala Ala Gln
            1010                1015                1020

Glu Gln Thr Gly Gln Val Glu Glu Cys Leu Lys Val Asn Leu Leu Lys
1025                1030                1035                1040

Ile Lys Thr Glu Leu Cys Lys Lys Glu Val Leu Asn Met Leu Lys Glu
            1045                1050                1055

Ser Lys Ala Asp Ile Phe Val Asp Pro Val Leu His Thr Ala Cys Ala
            1060                1065                1070

Leu Asp Ile Lys His His Cys Ala Ala Ile Thr Pro Gly Arg Gly Arg
            1075                1080                1085

Gln Met Ser Cys Leu Met Glu Ala Leu Glu Asp Lys Arg Val Arg Leu
            1090                1095                1100

Gln Pro Glu Cys Lys Lys Arg Leu Asn Asp Arg Ile Glu Met Trp Ser
1105                1110                1115                1120

Tyr Ala Ala Lys Val Ala Pro Ala Asp Gly Phe Ser Asp Leu Ala Met
            1125                1130                1135

Gln Val Met Thr Ser Pro Ser Lys Asn Tyr Ile Leu Ser Val Ile Ser
            1140                1145                1150

Gly Ser Ile Cys Ile Leu Phe Leu Ile Gly Leu Met Cys Gly Arg Ile
            1155                1160                1165

Thr Lys Arg Val Thr Arg Glu Leu Lys Asp Arg Leu Gln Tyr Arg Ser
            1170                1175                1180

Glu Thr Met Ala Tyr Lys Gly Leu Val Trp Ser Gln Asp Val Thr Gly
1185                1190                1195                1200

Ser Pro Ala

<210> SEQ ID NO 47
<211> LENGTH: 1070
<212> TYPE: PRT
<213> ORGANISM: Homo sapiens

<400> SEQUENCE: 47

Met Gly Ala Ala Arg Gly Ser Pro Ala Arg Pro Arg Arg Leu Pro Leu
 1               5                  10                  15

Leu Ser Val Leu Leu Leu Pro Leu Leu Gly Gly Thr Gln Thr Ala Ile
            20                  25                  30

Val Phe Ile Lys Gln Pro Ser Ser Gln Asp Ala Leu Gln Gly Arg Arg
            35                  40                  45

Ala Leu Leu Arg Cys Glu Val Glu Ala Pro Gly Pro Val His Val Tyr
        50                  55                  60

Trp Leu Leu Asp Gly Ala Pro Val Gln Asp Thr Glu Arg Arg Phe Ala
```

```
                65                  70                  75                  80
        Gln Gly Ser Ser Leu Ser Phe Ala Ala Val Asp Arg Leu Gln Asp Ser
                        85                  90                  95
        Gly Thr Phe Gln Cys Val Ala Arg Asp Asp Val Thr Gly Glu Glu Ala
                        100                 105                 110
        Arg Ser Ala Asn Ala Ser Phe Asn Ile Lys Trp Ile Glu Ala Gly Pro
                        115                 120                 125
        Val Val Leu Lys His Pro Ala Ser Glu Ala Glu Ile Gln Pro Gln Thr
                        130                 135                 140
        Gln Val Thr Leu Arg Cys His Ile Asp Gly His Pro Arg Pro Thr Tyr
        145                 150                 155                 160
        Gln Trp Phe Arg Asp Gly Thr Pro Leu Ser Asp Gly Gln Ser Asn His
                        165                 170                 175
        Thr Val Ser Ser Lys Glu Arg Asn Leu Thr Leu Arg Pro Ala Gly Pro
                        180                 185                 190
        Glu His Ser Gly Leu Tyr Ser Cys Cys Ala His Ser Ala Phe Gly Gln
                        195                 200                 205
        Ala Cys Ser Ser Gln Asn Phe Thr Leu Ser Ile Ala Asp Glu Ser Phe
        210                 215                 220
        Ala Arg Val Val Leu Ala Pro Gln Asp Val Val Ala Arg Tyr Glu
        225                 230                 235                 240
        Glu Ala Met Phe His Cys Gln Phe Ser Ala Gln Pro Pro Ser Leu
                        245                 250                 255
        Gln Trp Leu Phe Glu Asp Glu Thr Pro Ile Thr Asn Arg Ser Arg Pro
                        260                 265                 270
        Pro His Leu Arg Arg Ala Thr Val Phe Ala Asn Gly Ser Leu Leu Leu
                        275                 280                 285
        Thr Gln Val Arg Pro Arg Asn Ala Gly Ile Tyr Arg Cys Ile Gly Gln
                        290                 295                 300
        Gly Gln Arg Gly Pro Pro Ile Ile Leu Glu Ala Thr Leu His Leu Ala
        305                 310                 315                 320
        Glu Ile Glu Asp Met Pro Leu Phe Glu Pro Arg Val Phe Thr Ala Gly
                        325                 330                 335
        Ser Glu Glu Arg Val Thr Cys Leu Pro Pro Lys Gly Leu Pro Glu Pro
                        340                 345                 350
        Ser Val Trp Trp Glu His Ala Gly Val Arg Leu Pro Thr His Gly Arg
                        355                 360                 365
        Val Tyr Gln Lys Gly His Glu Leu Val Leu Ala Asn Ile Ala Glu Ser
                        370                 375                 380
        Asp Ala Gly Val Tyr Thr Cys His Ala Ala Asn Leu Ala Gly Gln Arg
        385                 390                 395                 400
        Arg Gln Asp Val Asn Ile Thr Val Ala Thr Val Pro Ser Trp Leu Lys
                        405                 410                 415
        Lys Pro Gln Asp Ser Gln Leu Glu Glu Gly Lys Pro Gly Tyr Leu Asp
                        420                 425                 430
        Cys Leu Thr Gln Ala Thr Pro Lys Pro Thr Val Val Trp Tyr Arg Asn
                        435                 440                 445
        Gln Met Leu Ile Ser Glu Asp Ser Arg Phe Glu Val Phe Lys Asn Gly
                        450                 455                 460
        Thr Leu Arg Ile Asn Ser Val Glu Val Tyr Asp Gly Thr Trp Tyr Arg
        465                 470                 475                 480
        Cys Met Ser Ser Thr Pro Ala Gly Ser Ile Glu Ala Gln Ala Arg Val
                        485                 490                 495
```

```
Gln Val Leu Glu Lys Leu Lys Phe Thr Pro Pro Gln Pro Gln Gln
            500                 505                 510

Cys Met Glu Phe Asp Lys Glu Ala Thr Val Pro Cys Ser Ala Thr Gly
            515                 520                 525

Arg Glu Lys Pro Thr Ile Lys Trp Glu Arg Ala Asp Gly Ser Ser Leu
            530                 535                 540

Pro Glu Trp Val Thr Asp Asn Ala Gly Thr Leu His Phe Ala Arg Val
545                 550                 555                 560

Thr Arg Asp Asp Ala Gly Asn Tyr Thr Cys Ile Ala Ser Asn Gly Pro
                565                 570                 575

Gln Gly Gln Ile Arg Ala His Val Gln Leu Thr Val Ala Val Phe Ile
                580                 585                 590

Thr Phe Lys Val Glu Pro Glu Arg Thr Thr Val Tyr Gln Gly His Thr
            595                 600                 605

Ala Leu Leu Gln Cys Glu Ala Gln Gly Asp Pro Lys Pro Leu Ile Gln
            610                 615                 620

Trp Lys Gly Lys Asp Arg Ile Leu Asp Pro Thr Lys Leu Gly Pro Arg
625                 630                 635                 640

Met His Ile Phe Gln Asn Gly Ser Leu Val Ile His Asp Val Ala Pro
                645                 650                 655

Glu Asp Ser Gly Arg Tyr Thr Cys Ile Ala Gly Asn Ser Cys Asn Ile
                660                 665                 670

Lys His Thr Glu Ala Pro Leu Tyr Val Val Asp Lys Pro Val Pro Glu
            675                 680                 685

Glu Ser Glu Gly Pro Gly Ser Pro Pro Pro Tyr Lys Met Ile Gln Thr
            690                 695                 700

Ile Gly Leu Ser Val Gly Ala Ala Val Ala Tyr Ile Ile Ala Val Leu
705                 710                 715                 720

Gly Leu Met Phe Tyr Cys Lys Lys Arg Cys Lys Ala Lys Arg Leu Gln
                725                 730                 735

Lys Gln Pro Glu Gly Glu Glu Pro Glu Met Glu Cys Leu Asn Gly Gly
            740                 745                 750

Pro Leu Gln Asn Gly Gln Pro Ser Ala Glu Ile Gln Glu Glu Val Ala
            755                 760                 765

Leu Thr Ser Leu Gly Ser Gly Pro Ala Ala Thr Asn Lys Arg His Ser
770                 775                 780

Thr Ser Asp Lys Met His Phe Pro Arg Ser Ser Leu Gln Pro Ile Thr
785                 790                 795                 800

Thr Leu Gly Lys Ser Glu Phe Gly Glu Val Phe Leu Ala Lys Ala Gln
                805                 810                 815

Gly Leu Glu Glu Gly Val Ala Glu Thr Leu Val Leu Val Lys Ser Leu
            820                 825                 830

Gln Ser Lys Asp Glu Gln Gln Gln Leu Asp Phe Arg Arg Glu Leu Glu
            835                 840                 845

Met Phe Gly Lys Leu Asn His Ala Asn Val Val Arg Leu Leu Gly Leu
            850                 855                 860

Cys Arg Glu Ala Glu Pro His Tyr Met Val Leu Glu Tyr Val Asp Leu
865                 870                 875                 880

Gly Asp Leu Lys Gln Phe Leu Arg Ile Ser Lys Ser Lys Asp Glu Lys
                885                 890                 895

Leu Lys Ser Gln Pro Leu Ser Thr Lys Gln Lys Val Ala Leu Cys Thr
            900                 905                 910
```

-continued

```
Gln Val Ala Leu Gly Met Glu His Leu Ser Asn Asn Arg Phe Val His
            915                 920                 925
Lys Asp Leu Ala Ala Arg Asn Cys Leu Val Ser Ala Gln Arg Gln Val
930                 935                 940
Lys Val Ser Ala Leu Gly Leu Ser Lys Asp Val Tyr Asn Ser Glu Tyr
945                 950                 955                 960
Tyr His Phe Arg Gln Ala Trp Val Pro Leu Arg Trp Met Ser Pro Glu
                965                 970                 975
Ala Ile Leu Glu Gly Asp Phe Ser Thr Lys Ser Asp Val Trp Ala Phe
            980                 985                 990
Gly Val Leu Met Trp Glu Val Phe Thr His Gly Glu Met Pro His Gly
        995                 1000                1005
Gly Gln Ala Asp Asp Glu Val Leu Ala Asp Leu Gln Ala Gly Lys Ala
    1010                1015                1020
Arg Leu Pro Gln Pro Glu Gly Cys Pro Ser Lys Leu Tyr Arg Leu Met
1025                1030                1035                1040
Gln Arg Cys Trp Ala Leu Ser Pro Lys Asp Arg Pro Ser Phe Ser Glu
                1045                1050                1055
Ile Ala Ser Ala Leu Gly Asp Ser Thr Val Asp Ser Lys Pro
            1060                1065                1070

<210> SEQ ID NO 48
<211> LENGTH: 493
<212> TYPE: PRT
<213> ORGANISM: Homo sapiens

<400> SEQUENCE: 48

Met Leu Lys Ala Leu Phe Leu Thr Met Leu Thr Leu Ala Leu Val Lys
1               5                   10                  15
Ser Gln Asp Thr Glu Glu Thr Ile Thr Tyr Thr Gln Cys Thr Asp Gly
            20                  25                  30
Tyr Glu Trp Asp Pro Val Arg Gln Gln Cys Lys Asp Ile Asp Glu Cys
        35                  40                  45
Asp Ile Val Pro Asp Ala Cys Lys Gly Gly Met Lys Cys Val Asn His
    50                  55                  60
Tyr Gly Gly Tyr Leu Cys Leu Pro Lys Thr Ala Gln Ile Ile Val Asn
65                  70                  75                  80
Asn Glu Gln Pro Gln Gln Glu Thr Gln Pro Ala Glu Gly Thr Ser Gly
                85                  90                  95
Ala Thr Thr Gly Val Val Ala Ala Ser Ser Met Ala Thr Ser Gly Val
            100                 105                 110
Leu Pro Gly Gly Gly Phe Val Ala Ser Ala Ala Val Ala Gly Pro
        115                 120                 125
Glu Met Gln Thr Gly Arg Asn Asn Phe Val Ile Arg Arg Asn Pro Ala
    130                 135                 140
Asp Pro Gln Arg Ile Pro Ser Asn Pro Ser His Arg Ile Gln Cys Ala
145                 150                 155                 160
Ala Gly Tyr Glu Gln Ser Glu His Asn Val Cys Gln Asp Ile Asp Glu
                165                 170                 175
Cys Thr Ala Gly Thr His Asn Cys Arg Ala Asp Gln Val Cys Ile Asn
            180                 185                 190
Leu Arg Gly Ser Phe Ala Cys Gln Cys Pro Pro Gly Tyr Gln Lys Arg
        195                 200                 205
Gly Glu Gln Cys Val Asp Ile Asp Glu Cys Thr Ile Pro Pro Tyr Cys
    210                 215                 220
```

His Gln Arg Cys Val Asn Thr Pro Gly Ser Phe Tyr Cys Gln Cys Ser
225                 230                 235                 240

Pro Gly Phe Gln Leu Ala Ala Asn Asn Tyr Thr Cys Val Asp Ile Asn
            245                 250                 255

Glu Cys Asp Ala Ser Asn Gln Cys Ala Gln Cys Tyr Asn Ile Leu
        260                 265                 270

Gly Ser Phe Ile Cys Gln Cys Asn Gln Gly Tyr Glu Leu Ser Ser Asp
        275                 280                 285

Arg Leu Asn Cys Glu Asp Ile Asp Glu Cys Arg Thr Ser Ser Tyr Leu
        290                 295                 300

Cys Gln Tyr Gln Cys Val Asn Glu Pro Gly Lys Phe Ser Cys Met Cys
305                 310                 315                 320

Pro Gln Gly Tyr Gln Val Val Arg Ser Arg Thr Cys Gln Asp Ile Asn
                325                 330                 335

Glu Cys Glu Thr Thr Asn Glu Cys Arg Glu Asp Glu Met Cys Trp Asn
            340                 345                 350

Tyr His Gly Gly Phe Arg Cys Tyr Pro Arg Asn Pro Cys Gln Asp Pro
            355                 360                 365

Tyr Ile Leu Thr Pro Glu Asn Arg Cys Val Cys Pro Val Ser Asn Ala
        370                 375                 380

Met Cys Arg Glu Leu Pro Gln Ser Ile Val Tyr Lys Tyr Met Ser Ile
385                 390                 395                 400

Arg Ser Asp Arg Ser Val Pro Ser Asp Ile Phe Gln Ile Gln Ala Thr
                405                 410                 415

Thr Ile Tyr Ala Asn Thr Ile Asn Thr Phe Arg Ile Lys Ser Gly Asn
            420                 425                 430

Glu Asn Gly Glu Phe Tyr Leu Arg Gln Thr Ser Pro Val Ser Ala Met
            435                 440                 445

Leu Val Leu Val Lys Ser Leu Ser Gly Pro Arg Glu His Ile Val Asp
450                 455                 460

Leu Glu Met Leu Thr Val Ser Ser Ile Gly Thr Phe Arg Thr Ser Ser
465                 470                 475                 480

Val Leu Arg Leu Thr Ile Ile Val Gly Pro Phe Ser Phe
                485                 490

<210> SEQ ID NO 49
<211> LENGTH: 661
<212> TYPE: PRT
<213> ORGANISM: Homo sapiens

<400> SEQUENCE: 49

Met Glu Leu Gln Pro Pro Glu Ala Ser Ile Ala Val Val Ser Ile Pro
1               5                   10                  15

Arg Gln Leu Pro Gly Ser His Ser Glu Ala Gly Val Gln Gly Leu Ser
            20                  25                  30

Ala Gly Asp Asp Ser Glu Leu Gly Ser His Cys Val Ala Gln Thr Gly
        35                  40                  45

Leu Glu Leu Leu Ala Ser Gly Asp Pro Leu Pro Ser Ala Ser Gln Asn
    50                  55                  60

Ala Glu Met Ile Glu Thr Gly Ser Asp Cys Val Thr Gln Ala Gly Leu
65                  70                  75                  80

Gln Leu Leu Ala Ser Ser Asp Pro Pro Ala Leu Ala Ser Lys Asn Ala
                85                  90                  95

Glu Val Thr Glu Thr Gly Phe His His Val Ser Gln Ala Asp Ile Glu

```
            100             105             110
Phe Leu Thr Ser Ile Asp Pro Thr Ala Ser Ala Ser Gly Ser Ala Gly
        115             120             125
Ile Thr Gly Thr Met Ser Gln Asp Thr Glu Val Asp Met Lys Glu Val
        130             135             140
Glu Leu Asn Glu Leu Glu Pro Glu Lys Gln Pro Met Asn Ala Ala Ser
145             150             155             160
Gly Ala Ala Met Ser Leu Ala Gly Ala Glu Lys Asn Gly Leu Val Lys
                165             170             175
Ile Lys Val Ala Glu Asp Glu Ala Glu Ala Ala Ala Ala Ala Lys Phe
            180             185             190
Thr Gly Leu Ser Lys Glu Glu Leu Leu Lys Val Ala Gly Ser Pro Gly
        195             200             205
Trp Val Arg Thr Arg Trp Ala Leu Leu Leu Phe Trp Leu Gly Trp
        210             215             220
Leu Gly Met Leu Ala Gly Ala Val Val Ile Ile Val Arg Ala Pro Arg
225             230             235             240
Cys Arg Glu Leu Pro Ala Gln Lys Trp Trp His Thr Gly Ala Leu Tyr
                245             250             255
Arg Ile Gly Asp Leu Gln Ala Phe Gln Gly His Gly Ala Gly Asn Leu
            260             265             270
Ala Gly Leu Lys Gly Arg Leu Asp Tyr Leu Ser Ser Leu Lys Val Lys
        275             280             285
Gly Leu Val Leu Gly Pro Ile His Lys Asn Gln Lys Asp Asp Val Ala
        290             295             300
Gln Thr Asp Leu Leu Gln Ile Asp Pro Asn Phe Gly Ser Lys Glu Asp
305             310             315             320
Phe Asp Ser Leu Leu Gln Ser Ala Lys Lys Lys Ser Ile Arg Val Ile
                325             330             335
Leu Asp Leu Thr Pro Asn Tyr Arg Gly Glu Asn Ser Trp Phe Ser Thr
            340             345             350
Gln Val Asp Thr Val Ala Thr Lys Val Lys Asp Ala Leu Glu Phe Trp
        355             360             365
Leu Gln Ala Gly Val Asp Gly Phe Gln Val Arg Asp Ile Glu Asn Leu
        370             375             380
Lys Asp Ala Ser Ser Phe Leu Ala Glu Trp Gln Asn Ile Thr Lys Gly
385             390             395             400
Phe Ser Glu Asp Arg Leu Leu Ile Ala Gly Thr Asn Ser Ser Asp Leu
                405             410             415
Gln Gln Ile Leu Ser Leu Leu Glu Ser Asn Lys Asp Leu Leu Leu Thr
            420             425             430
Ser Ser Tyr Leu Ser Asp Ser Gly Ser Thr Gly Glu His Thr Lys Ser
        435             440             445
Leu Val Thr Gln Tyr Leu Asn Ala Thr Gly Asn Arg Trp Cys Ser Trp
        450             455             460
Ser Leu Ser Gln Ala Arg Leu Leu Thr Ser Phe Leu Pro Ala Gln Leu
465             470             475             480
Leu Arg Leu Tyr Gln Leu Met Leu Phe Thr Leu Pro Gly Thr Pro Val
                485             490             495
Phe Ser Tyr Gly Asp Glu Ile Gly Leu Asp Ala Ala Ala Leu Pro Gly
            500             505             510
Gln Pro Met Glu Ala Pro Val Met Leu Trp Asp Glu Ser Ser Phe Pro
        515             520             525
```

```
Asp Ile Pro Gly Ala Val Ser Ala Asn Met Thr Val Lys Gly Gln Ser
        530                 535                 540

Glu Asp Pro Gly Ser Leu Leu Ser Leu Phe Arg Arg Leu Ser Asp Gln
545                 550                 555                 560

Arg Ser Lys Glu Arg Ser Leu Leu His Gly Asp Phe His Ala Phe Ser
                565                 570                 575

Ala Gly Pro Gly Leu Phe Ser Tyr Ile Arg His Trp Asp Gln Asn Glu
                580                 585                 590

Arg Phe Leu Val Val Leu Asn Phe Gly Asp Val Gly Leu Ser Ala Gly
                595                 600                 605

Leu Gln Ala Ser Asp Leu Pro Ala Ser Ala Ser Leu Pro Ala Lys Ala
        610                 615                 620

Asp Leu Leu Leu Ser Thr Gln Pro Gly Arg Glu Glu Gly Ser Pro Leu
625                 630                 635                 640

Glu Leu Glu Arg Leu Lys Leu Glu Pro His Glu Gly Leu Leu Leu Arg
                645                 650                 655

Phe Pro Tyr Ala Ala
                660

<210> SEQ ID NO 50
<211> LENGTH: 677
<212> TYPE: PRT
<213> ORGANISM: Homo sapiens

<400> SEQUENCE: 50

Met Gln Pro Thr Leu Leu Leu Ser Leu Leu Gly Ala Val Gly Leu Ala
1               5                   10                  15

Ala Val Asn Ser Met Pro Val Asp Asn Arg Asn His Asn Glu Gly Met
                20                  25                  30

Val Thr Arg Cys Ile Ile Glu Val Leu Ser Asn Ala Leu Ser Lys Ser
            35                  40                  45

Ser Ala Pro Pro Ile Thr Pro Glu Cys Arg Gln Val Leu Lys Thr Ser
    50                  55                  60

Arg Lys Asp Val Lys Asp Lys Glu Thr Thr Glu Asn Glu Asn Thr Lys
65                  70                  75                  80

Phe Glu Val Arg Leu Leu Arg Asp Pro Ala Asp Ala Ser Glu Ala His
                85                  90                  95

Glu Ser Ser Ser Arg Gly Glu Ala Gly Ala Pro Gly Glu Glu Asp Ile
                100                 105                 110

Gln Gly Pro Thr Lys Ala Asp Thr Glu Lys Trp Ala Glu Gly Gly Gly
            115                 120                 125

His Ser Arg Glu Arg Ala Asp Glu Pro Gln Trp Ser Leu Tyr Pro Ser
    130                 135                 140

Asp Ser Gln Val Ser Glu Glu Val Lys Thr Arg His Ser Glu Lys Ser
145                 150                 155                 160

Gln Arg Glu Asp Glu Glu Glu Glu Gly Asn Tyr Gln Lys Gly
                165                 170                 175

Glu Arg Gly Glu Asp Ser Ser Glu Glu Lys His Leu Glu Glu Pro Gly
                180                 185                 190

Glu Thr Gln Asn Ala Phe Leu Asn Glu Arg Lys Gln Ala Ser Ala Ile
            195                 200                 205

Lys Lys Glu Glu Leu Val Ala Arg Ser Glu Thr His Ala Ala Gly His
    210                 215                 220

Ser Gln Glu Lys Thr His Ser Arg Glu Lys Ser Ser Gln Glu Ser Gly
```

```
              225                 230                 235                 240
         Glu Glu Ala Gly Ser Gln Glu Asn His Pro Gln Glu Ser Lys Gly Gln
                         245                 250                 255
         Pro Arg Ser Gln Glu Ser Glu Glu Gly Glu Glu Asp Ala Thr Ser
                         260                 265                 270
         Glu Val Asp Lys Arg Arg Thr Arg Pro Arg His His Gly Arg Ser
                 275                 280                 285
         Arg Pro Asp Arg Ser Ser Gln Gly Gly Ser Leu Pro Ser Glu Glu Lys
             290                 295                 300
         Gly His Pro Gln Glu Glu Ser Glu Glu Ser Asn Val Ser Met Ala Ser
         305                 310                 315                 320
         Leu Gly Glu Lys Arg Asp His His Ser Thr His Tyr Arg Ala Ser Glu
                         325                 330                 335
         Glu Glu Pro Glu Tyr Gly Glu Glu Ile Lys Gly Tyr Pro Gly Val Gln
                     340                 345                 350
         Ala Pro Glu Asp Leu Glu Trp Glu Arg Tyr Arg Gly Arg Gly Ser Glu
                     355                 360                 365
         Glu Tyr Arg Ala Pro Arg Pro Gln Ser Glu Glu Ser Trp Asp Glu Glu
                 370                 375                 380
         Asp Lys Arg Asn Tyr Pro Ser Leu Glu Leu Asp Lys Met Ala His Gly
         385                 390                 395                 400
         Tyr Gly Glu Glu Ser Glu Glu Arg Gly Leu Glu Pro Gly Lys Gly
                         405                 410                 415
         Arg His His Arg Gly Arg Gly Glu Pro Arg Ala Tyr Phe Met Ser
                         420                 425                 430
         Asp Thr Arg Glu Glu Lys Arg Phe Leu Gly Glu Gly His His Arg Val
                 435                 440                 445
         Gln Glu Asn Gln Met Asp Lys Ala Arg Arg His Pro Gln Gly Ala Trp
             450                 455                 460
         Lys Glu Leu Asp Arg Asn Tyr Leu Asn Tyr Gly Glu Glu Gly Ala Pro
         465                 470                 475                 480
         Gly Lys Trp Gln Gln Gln Gly Asp Leu Gln Asp Thr Lys Glu Asn Arg
                         485                 490                 495
         Glu Glu Ala Arg Phe Gln Asp Lys Gln Tyr Ser Ser His His Thr Ala
                     500                 505                 510
         Glu Lys Arg Lys Arg Leu Gly Glu Leu Phe Asn Pro Tyr Tyr Asp Pro
                     515                 520                 525
         Leu Gln Trp Lys Ser Ser His Phe Glu Arg Arg Asp Asn Met Asn Asp
                 530                 535                 540
         Asn Phe Leu Glu Gly Glu Glu Asn Glu Leu Thr Leu Asn Glu Lys
         545                 550                 555                 560
         Asn Phe Phe Pro Glu Tyr Asn Tyr Asp Trp Trp Glu Lys Lys Pro Phe
                         565                 570                 575
         Ser Glu Asp Val Asn Trp Gly Tyr Glu Lys Arg Asn Leu Ala Arg Val
                     580                 585                 590
         Pro Lys Leu Asp Leu Lys Arg Gln Tyr Asp Arg Val Ala Gln Leu Asp
                     595                 600                 605
         Gln Leu Leu His Tyr Arg Lys Lys Ser Ala Glu Phe Pro Asp Phe Tyr
                 610                 615                 620
         Asp Ser Glu Glu Pro Val Ser Thr His Gln Glu Ala Glu Asn Glu Lys
         625                 630                 635                 640
         Asp Arg Ala Asp Gln Thr Val Leu Thr Glu Asp Glu Lys Lys Glu Leu
                         645                 650                 655
```

Glu Asn Leu Ala Ala Met Asp Leu Glu Leu Gln Lys Ile Ala Glu Lys
            660                 665                 670

Phe Ser Gln Arg Gly
        675

<210> SEQ ID NO 51
<211> LENGTH: 526
<212> TYPE: PRT
<213> ORGANISM: Homo sapiens

<400> SEQUENCE: 51

Met Gly His Leu Ser Ala Pro Leu His Arg Val Arg Val Pro Trp Gln
  1               5                  10                  15

Gly Leu Leu Leu Thr Ala Ser Leu Leu Thr Phe Trp Asn Pro Pro Thr
             20                  25                  30

Thr Ala Gln Leu Thr Thr Glu Ser Met Pro Phe Asn Val Ala Glu Gly
         35                  40                  45

Lys Glu Val Leu Leu Val His Asn Leu Pro Gln Gln Leu Phe Gly
 50                  55                  60

Tyr Ser Trp Tyr Lys Gly Glu Arg Val Asp Gly Asn Arg Gln Ile Val
 65                  70                  75                  80

Gly Tyr Ala Ile Gly Thr Gln Gln Ala Thr Pro Gly Pro Ala Asn Ser
                 85                  90                  95

Gly Arg Glu Thr Ile Tyr Pro Asn Ala Ser Leu Leu Ile Gln Asn Val
            100                 105                 110

Thr Gln Asn Asp Thr Gly Phe Tyr Thr Leu Gln Val Ile Lys Ser Asp
        115                 120                 125

Leu Val Asn Glu Glu Ala Thr Gly Gln Phe His Val Tyr Pro Glu Leu
    130                 135                 140

Pro Lys Pro Ser Ile Ser Ser Asn Asn Ser Asn Pro Val Glu Asp Lys
145                 150                 155                 160

Asp Ala Val Ala Phe Thr Cys Glu Pro Glu Thr Gln Asp Thr Thr Tyr
                165                 170                 175

Leu Trp Trp Ile Asn Asn Gln Ser Leu Pro Val Ser Pro Arg Leu Gln
            180                 185                 190

Leu Ser Asn Gly Asn Arg Thr Leu Thr Leu Leu Ser Val Thr Arg Asn
        195                 200                 205

Asp Thr Gly Pro Tyr Glu Cys Glu Ile Gln Asn Pro Val Ser Ala Asn
    210                 215                 220

Arg Ser Asp Pro Val Thr Leu Asn Val Thr Tyr Gly Pro Asp Thr Pro
225                 230                 235                 240

Thr Ile Ser Pro Ser Asp Thr Tyr Tyr Arg Pro Gly Ala Asn Leu Ser
                245                 250                 255

Leu Ser Cys Tyr Ala Ala Ser Asn Pro Pro Ala Gln Tyr Ser Trp Leu
            260                 265                 270

Ile Asn Gly Thr Phe Gln Gln Ser Thr Gln Glu Leu Phe Ile Pro Asn
        275                 280                 285

Ile Thr Val Asn Asn Ser Gly Ser Tyr Thr Cys His Ala Asn Asn Ser
    290                 295                 300

Val Thr Gly Cys Asn Arg Thr Thr Val Lys Thr Ile Ile Val Thr Glu
305                 310                 315                 320

Leu Ser Pro Val Val Ala Lys Pro Gln Ile Lys Ala Ser Lys Thr Thr
                325                 330                 335

Val Thr Gly Asp Lys Asp Ser Val Asn Leu Thr Cys Ser Thr Asn Asp

```
            340                 345                 350
Thr Gly Ile Ser Ile Arg Trp Phe Phe Lys Asn Gln Ser Leu Pro Ser
            355                 360                 365
Ser Glu Arg Met Lys Leu Ser Gln Gly Asn Thr Thr Leu Ser Ile Asn
        370                 375                 380
Pro Val Lys Arg Glu Asp Ala Gly Thr Tyr Trp Cys Glu Val Phe Asn
385                 390                 395                 400
Pro Ile Ser Lys Asn Gln Ser Asp Pro Ile Met Leu Asn Val Asn Tyr
                405                 410                 415
Asn Ala Leu Pro Gln Glu Asn Gly Leu Ser Pro Gly Ala Ile Ala Gly
                420                 425                 430
Ile Val Ile Gly Val Val Ala Leu Val Ala Leu Ile Ala Val Ala Leu
            435                 440                 445
Ala Cys Phe Leu His Phe Gly Lys Thr Gly Arg Ala Ser Asp Gln Arg
            450                 455                 460
Asp Leu Thr Glu His Lys Pro Ser Val Ser Asn His Thr Gln Asp His
465                 470                 475                 480
Ser Asn Asp Pro Pro Asn Lys Met Asn Glu Val Thr Tyr Ser Thr Leu
                485                 490                 495
Asn Phe Glu Ala Gln Gln Pro Thr Gln Pro Thr Ser Ala Ser Pro Ser
                500                 505                 510
Leu Thr Ala Thr Glu Ile Ile Tyr Ser Glu Val Lys Lys Gln
            515                 520                 525

<210> SEQ ID NO 52
<211> LENGTH: 583
<212> TYPE: PRT
<213> ORGANISM: Homo sapiens

<400> SEQUENCE: 52

Met Glu Ser Lys Gly Ala Ser Ser Cys Arg Leu Leu Phe Cys Leu Leu
1               5                   10                  15
Ile Ser Ala Thr Val Phe Arg Pro Gly Leu Gly Trp Tyr Thr Val Asn
                20                  25                  30
Ser Ala Tyr Gly Asp Thr Ile Ile Ile Pro Cys Arg Leu Asp Val Pro
            35                  40                  45
Gln Asn Leu Met Phe Gly Lys Trp Lys Tyr Glu Lys Pro Asp Gly Ser
        50                  55                  60
Pro Val Phe Ile Ala Phe Arg Ser Ser Thr Lys Lys Ser Val Gln Tyr
65                  70                  75                  80
Asp Asp Val Pro Glu Tyr Lys Asp Arg Leu Asn Leu Ser Glu Asn Tyr
                85                  90                  95
Thr Leu Ser Ile Ser Asn Ala Arg Ile Ser Asp Glu Lys Arg Phe Val
                100                 105                 110
Cys Met Leu Val Thr Glu Asp Asn Val Phe Glu Ala Pro Thr Ile Val
            115                 120                 125
Lys Val Phe Lys Gln Pro Ser Lys Pro Glu Ile Val Ser Lys Ala Leu
        130                 135                 140
Phe Leu Glu Thr Glu Gln Leu Lys Lys Leu Gly Asp Cys Ile Ser Glu
145                 150                 155                 160
Asp Ser Tyr Pro Asp Gly Asn Ile Thr Trp Tyr Arg Asn Gly Lys Val
                165                 170                 175
Leu His Pro Leu Glu Gly Ala Val Val Ile Ile Phe Lys Lys Glu Met
                180                 185                 190
```

Asp Pro Val Thr Gln Leu Tyr Thr Met Thr Ser Thr Leu Glu Tyr Lys
            195                 200                 205

Thr Thr Lys Ala Asp Ile Gln Met Pro Phe Thr Cys Ser Val Thr Tyr
    210                 215                 220

Tyr Gly Pro Ser Gly Gln Lys Thr Ile His Ser Glu Gln Ala Val Phe
225                 230                 235                 240

Asp Ile Tyr Tyr Pro Thr Glu Gln Val Thr Ile Gln Val Leu Pro Pro
            245                 250                 255

Lys Asn Ala Ile Lys Glu Gly Asp Asn Ile Thr Leu Lys Cys Leu Gly
        260                 265                 270

Asn Gly Asn Pro Pro Glu Glu Phe Leu Phe Tyr Leu Pro Gly Gln
    275                 280                 285

Pro Glu Gly Ile Arg Ser Ser Asn Thr Tyr Thr Leu Thr Asp Val Arg
    290                 295                 300

Arg Asn Ala Thr Gly Asp Tyr Lys Cys Ser Leu Ile Asp Lys Lys Ser
305                 310                 315                 320

Met Ile Ala Ser Thr Ala Ile Thr Val His Tyr Leu Asp Leu Ser Leu
            325                 330                 335

Asn Pro Ser Gly Glu Val Thr Arg Gln Ile Gly Asp Ala Leu Pro Val
        340                 345                 350

Ser Cys Thr Ile Ser Ala Ser Arg Asn Ala Thr Val Val Trp Met Lys
    355                 360                 365

Asp Asn Ile Arg Leu Arg Ser Ser Pro Ser Phe Ser Ser Leu His Tyr
    370                 375                 380

Gln Asp Ala Gly Asn Tyr Val Cys Glu Thr Ala Leu Gln Glu Val Glu
385                 390                 395                 400

Gly Leu Lys Lys Arg Glu Ser Leu Thr Leu Ile Val Glu Gly Lys Pro
            405                 410                 415

Gln Ile Lys Met Thr Lys Lys Thr Asp Pro Ser Gly Leu Ser Lys Thr
        420                 425                 430

Ile Ile Cys His Val Glu Gly Phe Pro Lys Pro Ala Ile Gln Trp Thr
    435                 440                 445

Ile Thr Gly Ser Gly Ser Val Ile Asn Gln Thr Glu Glu Ser Pro Tyr
    450                 455                 460

Ile Asn Gly Arg Tyr Tyr Ser Lys Ile Ile Ser Pro Glu Glu Asn
465                 470                 475                 480

Val Thr Leu Thr Cys Thr Ala Glu Asn Gln Leu Glu Arg Thr Val Asn
            485                 490                 495

Ser Leu Asn Val Ser Ala Ile Ser Ile Pro Glu His Asp Glu Ala Asp
        500                 505                 510

Glu Ile Ser Asp Glu Asn Arg Glu Lys Val Asn Asp Gln Ala Lys Leu
    515                 520                 525

Ile Val Gly Ile Val Gly Leu Leu Leu Ala Ala Leu Val Ala Gly
    530                 535                 540

Val Val Tyr Trp Leu Tyr Met Lys Lys Ser Lys Thr Ala Ser Lys His
545                 550                 555                 560

Val Asn Lys Asp Leu Gly Asn Met Glu Glu Asn Lys Lys Leu Glu Glu
            565                 570                 575

Asn Asn His Lys Thr Glu Ala
            580

<210> SEQ ID NO 53
<211> LENGTH: 205
<212> TYPE: PRT

<213> ORGANISM: Homo sapiens

<400> SEQUENCE: 53

```
Met Thr Glu Arg Arg Val Pro Phe Ser Leu Leu Arg Gly Pro Ser Trp
  1               5                  10                  15
Asp Pro Phe Arg Asp Trp Tyr Pro His Ser Arg Leu Phe Asp Gln Ala
             20                  25                  30
Phe Gly Leu Pro Arg Leu Pro Glu Glu Trp Ser Gln Trp Leu Gly Gly
         35                  40                  45
Ser Ser Trp Pro Gly Tyr Val Arg Pro Leu Pro Pro Ala Ala Ile Glu
 50                  55                  60
Ser Pro Ala Val Ala Ala Pro Ala Tyr Ser Arg Ala Leu Ser Arg Gln
 65                  70                  75                  80
Leu Ser Ser Gly Val Ser Glu Ile Arg His Thr Ala Asp Arg Trp Arg
                 85                  90                  95
Val Ser Leu Asp Val Asn His Phe Ala Pro Asp Glu Leu Thr Val Lys
            100                 105                 110
Thr Lys Asp Gly Val Val Glu Ile Thr Gly Lys His Glu Glu Arg Gln
        115                 120                 125
Asp Glu His Gly Tyr Ile Ser Arg Cys Phe Thr Arg Lys Tyr Thr Leu
130                 135                 140
Pro Pro Gly Val Asp Pro Thr Gln Val Ser Ser Ser Leu Ser Pro Glu
145                 150                 155                 160
Gly Thr Leu Thr Val Glu Ala Pro Met Pro Lys Leu Ala Thr Gln Ser
                165                 170                 175
Asn Glu Ile Thr Ile Pro Val Thr Phe Glu Ser Arg Ala Gln Leu Gly
            180                 185                 190
Gly Pro Glu Ala Ala Lys Ser Asp Glu Thr Ala Ala Lys
        195                 200                 205
```

<210> SEQ ID NO 54
<211> LENGTH: 135
<212> TYPE: PRT
<213> ORGANISM: Homo sapiens

<400> SEQUENCE: 54

```
Met Ala Cys Gly Leu Val Ala Ser Asn Leu Asn Leu Lys Pro Gly Glu
  1               5                  10                  15
Cys Leu Arg Val Arg Gly Glu Val Ala Pro Asp Ala Lys Ser Phe Val
             20                  25                  30
Leu Asn Leu Gly Lys Asp Ser Asn Asn Leu Cys Leu His Phe Asn Pro
         35                  40                  45
Arg Phe Asn Ala His Gly Asp Ala Asn Thr Ile Val Cys Asn Ser Lys
 50                  55                  60
Asp Gly Gly Ala Trp Gly Thr Glu Gln Arg Glu Ala Val Phe Pro Phe
 65                  70                  75                  80
Gln Pro Gly Ser Val Ala Glu Val Cys Ile Thr Phe Asp Gln Ala Asn
                 85                  90                  95
Leu Thr Val Lys Leu Pro Asp Gly Tyr Glu Phe Lys Phe Pro Asn Arg
            100                 105                 110
Leu Asn Leu Glu Ala Ile Asn Tyr Met Ala Ala Asp Gly Asp Phe Lys
        115                 120                 125
Ile Lys Cys Val Ala Phe Asp
130                 135
```

<210> SEQ ID NO 55
<211> LENGTH: 534
<212> TYPE: PRT
<213> ORGANISM: Homo sapiens

<400> SEQUENCE: 55

Met Leu Arg Arg Gly Ser Pro Gly Met Gly Val His Val Gly Ala
1               5                   10                  15

Ala Leu Gly Ala Leu Trp Phe Cys Leu Thr Gly Ala Leu Glu Val Gln
            20                  25                  30

Val Pro Glu Asp Pro Val Val Ala Leu Val Gly Thr Asp Ala Thr Leu
            35                  40                  45

Cys Cys Ser Phe Ser Pro Glu Pro Gly Phe Ser Leu Ala Gln Leu Asn
    50                  55                  60

Leu Ile Trp Gln Leu Thr Asp Thr Lys Gln Leu Val His Ser Phe Ala
65                  70                  75                  80

Glu Gly Gln Asp Gln Gly Ser Ala Tyr Ala Asn Arg Thr Ala Leu Phe
                85                  90                  95

Pro Asp Leu Leu Ala Gln Gly Asn Ala Ser Leu Arg Leu Gln Arg Val
            100                 105                 110

Arg Val Ala Asp Glu Gly Ser Phe Thr Cys Phe Val Ser Ile Arg Asp
            115                 120                 125

Phe Gly Ser Ala Ala Val Ser Leu Gln Val Ala Pro Tyr Ser Lys
130                 135                 140

Pro Ser Met Thr Leu Glu Pro Asn Lys Asp Leu Arg Pro Gly Asp Thr
145                 150                 155                 160

Val Thr Ile Thr Cys Ser Ser Tyr Gln Gly Tyr Pro Glu Ala Glu Val
                165                 170                 175

Phe Trp Gln Asp Gly Gln Gly Val Pro Leu Thr Gly Asn Val Thr Thr
            180                 185                 190

Ser Gln Met Ala Asn Glu Gln Gly Leu Phe Asp Val His Ser Ile Leu
            195                 200                 205

Arg Val Val Leu Gly Ala Asn Gly Thr Tyr Ser Cys Leu Val Arg Asn
210                 215                 220

Pro Val Leu Gln Gln Asp Ala His Ser Ser Val Thr Ile Thr Pro Gln
225                 230                 235                 240

Arg Ser Pro Thr Gly Ala Val Glu Val Gln Val Pro Glu Asp Pro Val
                245                 250                 255

Val Ala Leu Val Gly Thr Asp Ala Thr Leu Arg Cys Ser Phe Ser Pro
            260                 265                 270

Glu Pro Gly Phe Ser Leu Ala Gln Leu Asn Leu Ile Trp Gln Leu Thr
            275                 280                 285

Asp Thr Lys Gln Leu Val His Ser Phe Thr Glu Gly Arg Asp Gln Gly
290                 295                 300

Ser Ala Tyr Ala Asn Arg Thr Ala Leu Phe Pro Asp Leu Leu Ala Gln
305                 310                 315                 320

Gly Asn Ala Ser Leu Arg Leu Gln Arg Val Arg Val Ala Asp Glu Gly
                325                 330                 335

Ser Phe Thr Cys Phe Val Ser Ile Arg Asp Phe Gly Ser Ala Ala Val
            340                 345                 350

Ser Leu Gln Val Ala Ala Pro Tyr Ser Lys Pro Ser Met Thr Leu Glu
            355                 360                 365

Pro Asn Lys Asp Leu Arg Pro Gly Asp Thr Val Thr Ile Thr Cys Ser
370                 375                 380

-continued

```
Ser Tyr Arg Gly Tyr Pro Glu Ala Glu Val Phe Trp Gln Asp Gly Gln
385                 390                 395                 400

Gly Val Pro Leu Thr Gly Asn Val Thr Thr Ser Gln Met Ala Asn Glu
            405                 410                 415

Gln Gly Leu Phe Asp Val His Ser Val Leu Arg Val Val Leu Gly Ala
        420                 425                 430

Asn Gly Thr Tyr Ser Cys Leu Val Arg Asn Pro Val Leu Gln Gln Asp
    435                 440                 445

Ala His Gly Ser Val Thr Ile Thr Gly Gln Pro Met Thr Phe Pro Pro
450                 455                 460

Glu Ala Leu Trp Val Thr Val Gly Leu Ser Val Cys Leu Ile Ala Leu
465                 470                 475                 480

Leu Val Ala Leu Ala Phe Val Cys Trp Arg Lys Ile Lys Gln Ser Cys
                485                 490                 495

Glu Glu Glu Asn Ala Gly Ala Glu Asp Gln Asp Gly Glu Gly Glu Gly
            500                 505                 510

Ser Lys Thr Ala Leu Gln Pro Leu Lys His Ser Asp Ser Lys Glu Asp
        515                 520                 525

Asp Gly Gln Glu Ile Ala
    530
```

<210> SEQ ID NO 56
<211> LENGTH: 10064
<212> TYPE: PRT
<213> ORGANISM: Homo sapiens
<220> FEATURE:
<221> NAME/KEY: VARIANT
<222> LOCATION: (1)...(10064)
<223> OTHER INFORMATION: Xaa = Any Amino Acid

<400> SEQUENCE: 56

```
Met Leu Lys Pro Ser Gly Leu Pro Gly Ser Ser Pro Thr Arg Ser
1               5                   10                  15

Leu Met Thr Gly Ser Arg Ser Thr Lys Ala Thr Pro Glu Met Asp Ser
                20                  25                  30

Gly Leu Thr Gly Ala Thr Leu Ser Pro Lys Thr Ser Thr Gly Ala Ile
            35                  40                  45

Val Val Thr Glu His Thr Leu Pro Phe Thr Ser Pro Asp Lys Thr Leu
        50                  55                  60

Ala Ser Pro Thr Ser Ser Val Val Gly Arg Thr Thr Gln Ser Leu Gly
65                  70                  75                  80

Val Met Ser Ser Ala Leu Pro Glu Ser Thr Ser Arg Gly Met Thr His
                85                  90                  95

Ser Glu Gln Arg Thr Ser Pro Ser Leu Ser Pro Gln Val Asn Gly Thr
            100                 105                 110

Pro Ser Arg Asn Tyr Pro Ala Thr Ser Met Val Ser Gly Leu Ser Ser
        115                 120                 125

Pro Arg Thr Arg Thr Ser Ser Thr Glu Gly Asn Phe Thr Lys Glu Ala
    130                 135                 140

Ser Thr Tyr Thr Leu Thr Val Glu Thr Ser Gly Pro Val Thr Glu
145                 150                 155                 160

Lys Tyr Thr Val Pro Thr Glu Thr Ser Thr Glu Gly Asp Ser Thr
                165                 170                 175

Glu Thr Pro Trp Asp Thr Arg Tyr Ile Pro Val Lys Ile Thr Ser Pro
            180                 185                 190

Met Lys Thr Phe Ala Asp Ser Thr Ala Ser Lys Glu Asn Ala Pro Val
```

```
            195                 200                 205
Ser Met Thr Pro Ala Glu Thr Thr Val Thr Asp Ser His Thr Pro Gly
210                 215                 220

Arg Thr Asn Pro Ser Phe Gly Thr Leu Tyr Ser Ser Phe Leu Asp Leu
225                 230                 235                 240

Ser Pro Lys Gly Thr Pro Asn Ser Arg Gly Thr Ser Leu Glu Leu
            245                 250                 255

Ile Leu Ser Thr Thr Gly Tyr Pro Phe Ser Ser Pro Glu Pro Gly Ser
            260                 265                 270

Ala Gly His Ser Arg Ile Ser Thr Ser Ala Pro Leu Ser Ser Ser Ala
            275                 280                 285

Ser Val Leu Asp Asn Lys Ile Ser Glu Thr Ser Ile Phe Ser Gly Gln
290                 295                 300

Ser Leu Thr Ser Pro Leu Ser Pro Gly Val Pro Glu Ala Arg Ala Ser
305                 310                 315                 320

Thr Met Pro Asn Ser Ala Ile Pro Phe Ser Met Thr Leu Ser Asn Ala
                325                 330                 335

Glu Thr Ser Ala Glu Arg Val Arg Ser Thr Ile Ser Ser Leu Gly Thr
            340                 345                 350

Pro Ser Ile Ser Thr Lys Gln Thr Ala Glu Thr Ile Leu Thr Phe His
            355                 360                 365

Ala Phe Ala Glu Thr Met Asp Ile Pro Ser Thr His Ile Ala Lys Thr
370                 375                 380

Leu Ala Ser Glu Trp Leu Gly Ser Pro Gly Thr Leu Gly Gly Thr Ser
385                 390                 395                 400

Thr Ser Ala Leu Thr Thr Thr Ser Pro Ser Thr Thr Leu Val Ser Glu
                405                 410                 415

Glu Thr Asn Thr His His Ser Ser Gly Lys Glu Thr Glu Gly Thr
            420                 425                 430

Leu Asn Thr Ser Met Thr Pro Leu Glu Thr Ser Ala Pro Gly Glu Glu
            435                 440                 445

Ser Glu Met Thr Ala Thr Leu Val Pro Thr Leu Gly Phe Thr Thr Leu
450                 455                 460

Asp Ser Lys Ile Arg Ser Pro Ser Gln Val Ser Ser Ser His Pro Thr
465                 470                 475                 480

Arg Glu Leu Arg Thr Thr Gly Ser Thr Ser Gly Arg Gln Ser Ser Ser
                485                 490                 495

Thr Ala Ala His Gly Ser Ser Asp Ile Leu Arg Ala Thr Thr Ser Ser
            500                 505                 510

Thr Ser Lys Ala Ser Ser Trp Thr Ser Glu Ser Thr Ala Gln Gln Phe
            515                 520                 525

Ser Glu Pro Gln His Thr Gln Trp Val Glu Thr Ser Pro Ser Met Lys
            530                 535                 540

Thr Glu Arg Pro Pro Ala Ser Thr Ser Val Ala Ala Pro Ile Thr Thr
545                 550                 555                 560

Ser Val Pro Ser Val Val Ser Gly Phe Thr Thr Leu Lys Thr Ser Ser
                565                 570                 575

Thr Lys Gly Ile Trp Leu Glu Glu Thr Ser Ala Asp Thr Leu Ile Gly
            580                 585                 590

Glu Ser Thr Ala Gly Pro Thr Thr His Gln Phe Ala Val Pro Thr Gly
            595                 600                 605

Ile Ser Met Thr Gly Gly Ser Ser Thr Arg Gly Ser Gln Gly Thr Thr
            610                 615                 620
```

```
His Leu Leu Thr Arg Ala Thr Ala Ser Ser Glu Thr Ser Ala Asp Leu
625                 630                 635                 640

Thr Leu Ala Thr Asn Gly Val Pro Val Ser Val Ser Pro Ala Val Ser
            645                 650                 655

Lys Thr Ala Ala Gly Ser Ser Pro Pro Gly Gly Thr Lys Pro Ser Tyr
        660                 665                 670

Thr Met Val Ser Ser Val Ile Pro Glu Thr Ser Ser Leu Gln Ser Ser
            675                 680                 685

Ala Phe Arg Glu Gly Thr Ser Leu Gly Leu Thr Pro Leu Asn Thr Arg
        690                 695                 700

His Pro Phe Ser Ser Pro Glu Pro Asp Ser Ala Gly His Thr Lys Ile
705                 710                 715                 720

Ser Thr Ser Ile Pro Leu Leu Ser Ser Ala Ser Val Leu Glu Asp Lys
                725                 730                 735

Val Ser Ala Thr Ser Thr Phe Ser His His Lys Ala Thr Ser Ser Ile
            740                 745                 750

Thr Thr Gly Thr Pro Glu Ile Ser Thr Lys Thr Lys Pro Ser Ser Ala
            755                 760                 765

Val Leu Ser Ser Met Thr Leu Ser Asn Ala Ala Thr Ser Pro Glu Arg
770                 775                 780

Val Arg Asn Ala Thr Ser Pro Leu Thr His Pro Ser Pro Ser Gly Glu
785                 790                 795                 800

Glu Thr Ala Gly Ser Val Leu Thr Leu Ser Thr Ser Ala Glu Thr Thr
                805                 810                 815

Asp Ser Pro Asn Ile His Pro Thr Gly Thr Leu Thr Ser Glu Ser Ser
            820                 825                 830

Glu Ser Pro Ser Thr Leu Ser Leu Pro Ser Val Ser Gly Val Lys Thr
            835                 840                 845

Thr Phe Ser Ser Ser Thr Pro Ser Thr His Leu Phe Thr Ser Gly Glu
    850                 855                 860

Glu Thr Glu Glu Thr Ser Asn Pro Ser Val Ser Gln Pro Glu Thr Ser
865                 870                 875                 880

Val Ser Arg Val Arg Thr Thr Leu Ala Ser Thr Ser Val Pro Thr Pro
                885                 890                 895

Val Phe Pro Thr Met Asp Thr Trp Pro Thr Arg Ser Ala Gln Phe Ser
            900                 905                 910

Ser Ser His Leu Val Ser Glu Leu Arg Ala Thr Ser Ser Thr Ser Val
        915                 920                 925

Thr Asn Ser Thr Gly Ser Ala Leu Pro Lys Ile Ser His Leu Thr Gly
    930                 935                 940

Thr Ala Thr Met Ser Gln Thr Asn Arg Asp Thr Phe Asn Asp Ser Ala
945                 950                 955                 960

Ala Pro Gln Ser Thr Thr Trp Pro Glu Thr Ser Pro Arg Phe Lys Thr
            965                 970                 975

Gly Leu Pro Ser Ala Thr Thr Thr Val Ser Thr Ser Ala Thr Ser Leu
            980                 985                 990

Ser Ala Thr Val Met Val Ser Lys Phe Thr Ser Pro Ala Thr Ser Ser
        995                 1000                1005

Met Glu Ala Thr Ser Ile Arg Glu Pro Ser Thr Thr Ile Leu Thr Thr
        1010                1015                1020

Glu Thr Thr Asn Gly Pro Gly Ser Met Ala Val Ala Ser Thr Asn Ile
1025                1030                1035                1040
```

```
Pro Ile Gly Lys Gly Tyr Ile Thr Glu Gly Arg Leu Asp Thr Ser His
            1045                1050                1055

Leu Pro Ile Gly Thr Thr Ala Ser Ser Glu Ser Met Asp Phe Thr
        1060                1065                1070

Met Ala Lys Glu Ser Val Ser Met Ser Val Ser Pro Ser Gln Ser Met
        1075                1080                1085

Asp Ala Ala Gly Ser Ser Thr Pro Gly Arg Thr Ser Gln Phe Val Asp
        1090                1095                1100

Thr Phe Ser Asp Asp Val Tyr His Leu Thr Ser Arg Glu Ile Thr Ile
1105                1110                1115                1120

Pro Arg Asp Gly Thr Ser Ser Ala Leu Thr Pro Gln Met Thr Ala Thr
                1125                1130                1135

His Pro Pro Ser Pro Asp Pro Gly Ser Ala Arg Ser Thr Trp Leu Gly
                1140                1145                1150

Ile Leu Ser Ser Ser Pro Ser Ser Pro Thr Pro Lys Val Thr Met Ser
                1155                1160                1165

Ser Thr Phe Ser Thr Gln Arg Val Thr Thr Ser Met Ile Met Asp Thr
            1170                1175                1180

Val Glu Thr Ser Arg Trp Asn Met Pro Asn Leu Pro Ser Thr Thr Ser
1185                1190                1195                1200

Leu Thr Pro Ser Asn Ile Pro Thr Ser Gly Ala Ile Gly Lys Ser Thr
                1205                1210                1215

Leu Val Pro Leu Asp Thr Pro Ser Pro Ala Thr Ser Leu Glu Ala Ser
                1220                1225                1230

Glu Gly Gly Leu Pro Thr Leu Ser Thr Tyr Pro Glu Ser Thr Asn Thr
            1235                1240                1245

Pro Ser Ile His Leu Gly Ala His Ala Ser Ser Glu Ser Pro Ser Thr
            1250                1255                1260

Ile Lys Leu Thr Met Ala Ser Val Val Lys Pro Gly Ser Tyr Thr Pro
1265                1270                1275                1280

Leu Thr Phe Pro Ser Ile Glu Thr His Ile His Val Ser Thr Ala Arg
                1285                1290                1295

Met Ala Tyr Ser Ser Gly Ser Ser Pro Glu Met Thr Ala Pro Gly Glu
            1300                1305                1310

Thr Asn Thr Gly Ser Thr Trp Asp Pro Thr Thr Tyr Ile Thr Thr Thr
            1315                1320                1325

Asp Pro Lys Asp Thr Ser Ser Ala Gln Val Ser Thr Pro His Ser Val
            1330                1335                1340

Arg Thr Leu Arg Thr Thr Glu Asn His Pro Lys Thr Glu Ser Ala Thr
1345                1350                1355                1360

Pro Ala Ala Tyr Ser Gly Ser Pro Lys Ile Ser Ser Ser Pro Asn Leu
                1365                1370                1375

Thr Ser Pro Ala Thr Lys Ala Trp Thr Ile Thr Asp Thr Thr Glu His
            1380                1385                1390

Ser Thr Gln Leu His Tyr Thr Lys Leu Ala Glu Lys Ser Ser Gly Phe
            1395                1400                1405

Glu Thr Gln Ser Ala Pro Gly Pro Val Ser Val Val Ile Pro Thr Ser
        1410                1415                1420

Pro Thr Ile Gly Ser Ser Thr Leu Glu Leu Thr Ser Asp Val Pro Gly
1425                1430                1435                1440

Glu Pro Leu Val Leu Ala Pro Ser Glu Gln Thr Thr Ile Thr Leu Pro
                1445                1450                1455

Met Ala Thr Trp Leu Ser Thr Ser Leu Thr Glu Glu Met Ala Ser Thr
```

-continued

```
              1460              1465              1470

Asp Leu Asp Ile Ser Ser Pro Ser Ser Pro Met Ser Thr Phe Ala Ile
            1475              1480              1485

Phe Pro Pro Met Ser Thr Pro Ser His Glu Leu Ser Lys Ser Glu Ala
            1490              1495              1500

Asp Thr Ser Ala Ile Arg Asn Thr Asp Ser Thr Thr Leu Asp Gln His
1505              1510              1515              1520

Leu Gly Ile Arg Ser Leu Gly Arg Thr Gly Asp Leu Thr Thr Val Pro
            1525              1530              1535

Ile Thr Pro Leu Thr Thr Thr Trp Thr Ser Val Ile Glu His Ser Thr
            1540              1545              1550

Gln Ala Gln Asp Thr Leu Ser Ala Thr Met Ser Pro Thr His Val Thr
            1555              1560              1565

Gln Ser Leu Lys Asp Gln Thr Ser Ile Pro Ala Ser Ala Ser Pro Ser
            1570              1575              1580

His Leu Thr Glu Val Tyr Pro Glu Leu Gly Thr Gln Gly Arg Ser Ser
1585              1590              1595              1600

Ser Glu Ala Thr Thr Phe Trp Lys Pro Ser Thr Asp Thr Leu Ser Arg
            1605              1610              1615

Glu Ile Glu Thr Gly Pro Thr Asn Ile Gln Ser Thr Pro Pro Met Asp
            1620              1625              1630

Asn Thr Thr Thr Gly Ser Ser Ser Gly Val Thr Leu Gly Ile Ala
            1635              1640              1645

His Leu Pro Ile Gly Thr Ser Ser Pro Ala Glu Thr Ser Thr Asn Met
1650              1655              1660

Ala Leu Glu Arg Arg Ser Ser Thr Ala Thr Val Ser Met Ala Gly Thr
1665              1670              1675              1680

Met Gly Leu Leu Val Thr Ser Ala Pro Gly Arg Ser Ile Ser Gln Ser
            1685              1690              1695

Leu Gly Arg Val Ser Ser Val Leu Ser Glu Ser Thr Thr Glu Gly Val
            1700              1705              1710

Thr Asp Ser Ser Lys Gly Ser Ser Pro Arg Leu Asn Thr Gln Gly Asn
            1715              1720              1725

Thr Ala Leu Ser Ser Ser Leu Glu Pro Ser Tyr Ala Glu Gly Ser Gln
            1730              1735              1740

Met Ser Thr Ser Ile Pro Leu Thr Ser Ser Pro Thr Thr Pro Asp Val
1745              1750              1755              1760

Glu Phe Ile Gly Gly Ser Thr Phe Trp Thr Lys Glu Val Thr Thr Val
            1765              1770              1775

Met Thr Ser Asp Ile Ser Lys Ser Ser Ala Arg Thr Glu Ser Ser Ser
            1780              1785              1790

Ala Thr Leu Met Ser Thr Ala Leu Gly Ser Thr Glu Asn Thr Gly Lys
            1795              1800              1805

Glu Lys Leu Arg Thr Ala Ser Met Asp Leu Pro Ser Pro Thr Pro Ser
            1810              1815              1820

Met Glu Val Thr Pro Trp Ile Ser Leu Thr Leu Ser Asn Ala Pro Asn
1825              1830              1835              1840

Thr Thr Asp Ser Leu Asp Leu Ser His Gly Val His Thr Ser Ser Ala
            1845              1850              1855

Gly Thr Leu Ala Thr Asp Arg Ser Leu Asn Thr Gly Val Thr Arg Ala
            1860              1865              1870

Ser Arg Leu Glu Asn Gly Ser Asp Thr Ser Ser Lys Ser Leu Ser Met
            1875              1880              1885
```

```
Gly Asn Ser Thr His Thr Ser Met Thr Asp Thr Glu Lys Ser Glu Val
            1890                1895                1900

Ser Ser Ser Ile His Pro Arg Pro Glu Thr Ser Ala Pro Gly Ala Glu
1905                1910                1915                1920

Thr Thr Leu Thr Ser Thr Pro Gly Asn Arg Ala Ile Ser Leu Thr Leu
                1925                1930                1935

Pro Phe Ser Ser Ile Pro Val Glu Glu Val Ile Ser Thr Gly Ile Thr
            1940                1945                1950

Ser Gly Pro Asp Ile Asn Ser Ala Pro Met Thr His Ser Pro Ile Thr
            1955                1960                1965

Pro Pro Thr Ile Val Trp Thr Ser Thr Gly Thr Ile Glu Gln Ser Thr
1970                1975                1980

Gln Pro Leu His Ala Val Ser Ser Glu Lys Val Ser Val Gln Thr Gln
1985                1990                1995                2000

Ser Thr Pro Tyr Val Asn Ser Val Ala Val Ser Ala Ser Pro Thr His
                2005                2010                2015

Glu Asn Ser Val Ser Ser Gly Ser Ser Thr Ser Ser Pro Tyr Ser Ser
                2020                2025                2030

Ala Ser Leu Glu Ser Leu Asp Ser Thr Ile Ser Arg Arg Asn Ala Ile
            2035                2040                2045

Thr Ser Trp Leu Trp Asp Leu Thr Thr Ser Leu Pro Thr Thr Thr Trp
            2050                2055                2060

Pro Ser Thr Ser Leu Ser Glu Ala Leu Ser Ser Gly His Ser Gly Val
2065                2070                2075                2080

Ser Asn Pro Ser Ser Thr Thr Thr Glu Phe Pro Leu Phe Ser Ala Ala
                2085                2090                2095

Ser Thr Ser Ala Ala Lys Gln Arg Asn Pro Glu Thr Glu Thr His Gly
            2100                2105                2110

Pro Gln Asn Thr Ala Ala Ser Thr Leu Asn Thr Asp Ala Ser Ser Val
            2115                2120                2125

Thr Gly Leu Ser Glu Thr Pro Val Gly Ala Ser Ile Ser Ser Glu Val
            2130                2135                2140

Pro Leu Pro Met Ala Ile Thr Ser Arg Ser Asp Val Ser Gly Leu Thr
2145                2150                2155                2160

Ser Glu Ser Thr Ala Asn Pro Ser Leu Gly Thr Ala Ser Ser Ala Gly
                2165                2170                2175

Thr Lys Leu Thr Arg Thr Ile Ser Leu Pro Thr Ser Glu Ser Leu Val
            2180                2185                2190

Ser Phe Arg Met Asn Lys Asp Pro Trp Thr Val Ser Ile Pro Leu Gly
            2195                2200                2205

Ser His Pro Thr Thr Asn Thr Glu Thr Ser Ile Pro Val Asn Ser Ala
            2210                2215                2220

Gly Pro Pro Gly Leu Ser Thr Val Ala Ser Asp Val Ile Asp Thr Pro
2225                2230                2235                2240

Ser Asp Gly Ala Glu Ser Ile Pro Thr Val Ser Phe Ser Pro Ser Pro
            2245                2250                2255

Asp Thr Glu Val Thr Thr Ile Ser His Phe Pro Glu Lys Thr Thr His
            2260                2265                2270

Ser Phe Arg Thr Ile Ser Ser Leu Thr His Glu Leu Thr Ser Arg Val
            2275                2280                2285

Thr Pro Ile Pro Gly Asp Trp Met Ser Ser Ala Met Ser Thr Lys Pro
            2290                2295                2300
```

```
Thr Gly Ala Ser Pro Ser Ile Thr Leu Gly Glu Arg Arg Thr Ile Thr
2305                2310                2315                2320

Ser Ala Ala Pro Thr Thr Ser Pro Ile Val Leu Thr Ala Ser Phe Thr
            2325                2330                2335

Glu Thr Ser Thr Val Ser Leu Asp Asn Glu Thr Thr Val Lys Thr Ser
        2340                2345                2350

Asp Ile Leu Asp Ala Arg Lys Thr Asn Glu Leu Pro Ser Asp Ser Ser
    2355                2360                2365

Ser Ser Ser Asp Leu Ile Asn Thr Ser Ile Ala Ser Ser Thr Met Asp
2370                2375                2380

Val Thr Lys Thr Ala Ser Ile Ser Pro Thr Ser Ile Ser Gly Met Thr
2385                2390                2395                2400

Ala Ser Ser Ser Pro Ser Leu Phe Ser Ser Asp Arg Pro Gln Val Pro
                2405                2410                2415

Thr Ser Thr Thr Glu Thr Asn Thr Ala Thr Ser Pro Ser Val Ser Ser
            2420                2425                2430

Asn Thr Tyr Ser Leu Asp Gly Gly Ser Asn Val Gly Gly Thr Pro Ser
        2435                2440                2445

Thr Leu Pro Pro Phe Thr Ile Thr His Pro Val Glu Thr Ser Ser Ala
2450                2455                2460

Leu Leu Ala Trp Ser Arg Pro Val Arg Thr Phe Ser Thr Met Val Ser
2465                2470                2475                2480

Thr Asp Thr Ala Ser Gly Glu Asn Pro Thr Ser Ser Asn Ser Val Val
                2485                2490                2495

Thr Ser Val Pro Ala Pro Gly Thr Trp Ala Ser Val Gly Ser Thr Thr
            2500                2505                2510

Asp Leu Pro Ala Met Gly Phe Leu Lys Thr Ser Pro Ala Gly Glu Ala
        2515                2520                2525

His Ser Leu Leu Ala Ser Thr Ile Glu Pro Ala Thr Ala Phe Thr Pro
2530                2535                2540

His Leu Ser Ala Ala Val Val Thr Gly Ser Ser Ala Thr Ser Glu Ala
2545                2550                2555                2560

Ser Leu Leu Thr Thr Ser Glu Ser Lys Ala Ile His Ser Ser Pro Gln
                2565                2570                2575

Thr Pro Thr Thr Pro Thr Ser Gly Ala Asn Trp Glu Thr Ser Ala Thr
            2580                2585                2590

Pro Glu Ser Leu Leu Val Val Thr Glu Thr Ser Asp Thr Thr Leu Thr
        2595                2600                2605

Ser Lys Ile Leu Val Thr Asp Thr Ile Leu Phe Ser Thr Val Ser Thr
    2610                2615                2620

Pro Pro Ser Lys Phe Pro Ser Thr Gly Thr Leu Ser Gly Ala Ser Phe
2625                2630                2635                2640

Pro Thr Leu Leu Pro Asp Thr Pro Ala Ile Pro Leu Thr Ala Thr Glu
                2645                2650                2655

Pro Thr Ser Ser Leu Ala Thr Ser Phe Asp Ser Thr Pro Leu Val Thr
            2660                2665                2670

Ile Ala Ser Asp Ser Leu Gly Thr Val Pro Glu Thr Thr Leu Thr Met
        2675                2680                2685

Ser Glu Thr Ser Asn Gly Asp Ala Leu Val Leu Lys Thr Val Ser Asn
    2690                2695                2700

Pro Asp Arg Ser Ile Pro Gly Ile Thr Ile Gln Gly Val Thr Glu Ser
2705                2710                2715                2720

Pro Leu His Pro Ser Ser Thr Ser Pro Ser Lys Ile Val Ala Pro Arg
```

```
                2725                2730                2735
Asn Thr Thr Tyr Glu Gly Ser Ile Thr Val Ala Leu Ser Thr Leu Pro
            2740                2745                2750

Ala Gly Thr Thr Gly Ser Leu Val Phe Ser Gln Ser Ser Glu Asn Ser
        2755                2760                2765

Glu Thr Thr Ala Leu Val Asp Ser Ser Ala Gly Leu Glu Arg Ala Ser
    2770                2775                2780

Val Met Pro Leu Thr Thr Gly Ser Gln Gly Met Ala Ser Ser Gly Gly
2785                2790                2795                2800

Ile Arg Ser Gly Ser Thr His Ser Thr Gly Thr Lys Thr Phe Ser Ser
                2805                2810                2815

Leu Pro Leu Thr Met Asn Pro Gly Glu Val Thr Ala Met Ser Glu Ile
            2820                2825                2830

Thr Thr Asn Arg Leu Thr Ala Thr Gln Ser Thr Ala Pro Lys Gly Ile
        2835                2840                2845

Pro Val Lys Pro Thr Ser Ala Glu Ser Gly Leu Leu Thr Pro Val Ser
    2850                2855                2860

Ala Ser Ser Ser Pro Ser Lys Ala Phe Ala Ser Leu Thr Thr Ala Pro
2865                2870                2875                2880

Pro Ser Thr Trp Gly Ile Pro Gln Ser Thr Leu Thr Phe Glu Phe Ser
                2885                2890                2895

Glu Val Pro Ser Leu Asp Thr Lys Ser Ala Ser Leu Pro Thr Pro Gly
            2900                2905                2910

Gln Ser Leu Asn Thr Ile Pro Asp Ser Asp Ala Ser Thr Ala Ser Ser
        2915                2920                2925

Ser Leu Ser Lys Ser Pro Glu Lys Asn Pro Arg Ala Arg Met Met Thr
    2930                2935                2940

Ser Thr Lys Ala Ile Ser Ala Ser Ser Phe Gln Ser Thr Gly Phe Thr
2945                2950                2955                2960

Glu Thr Pro Glu Gly Ser Ala Ser Pro Ser Met Ala Gly His Glu Pro
                2965                2970                2975

Arg Val Pro Thr Ser Gly Thr Gly Asp Pro Arg Tyr Ala Ser Glu Ser
            2980                2985                2990

Met Ser Tyr Pro Asp Pro Ser Lys Ala Ser Ser Ala Met Thr Ser Thr
        2995                3000                3005

Ser Leu Ala Ser Lys Leu Thr Thr Leu Phe Ser Thr Gly Gln Ala Ala
    3010                3015                3020

Arg Ser Gly Ser Ser Ser Ser Pro Ile Ser Leu Ser Thr Glu Lys Glu
3025                3030                3035                3040

Thr Ser Phe Leu Ser Pro Thr Ala Ser Thr Ser Arg Lys Thr Ser Leu
                3045                3050                3055

Phe Leu Gly Pro Ser Met Ala Arg Gln Pro Asn Ile Leu Val His Leu
            3060                3065                3070

Gln Thr Ser Ala Leu Thr Leu Ser Pro Thr Ser Thr Leu Asn Met Ser
        3075                3080                3085

Gln Glu Glu Pro Pro Glu Leu Thr Ser Ser Gln Thr Ile Ala Glu Glu
    3090                3095                3100

Glu Gly Thr Thr Ala Glu Thr Gln Thr Leu Thr Phe Thr Pro Ser Glu
3105                3110                3115                3120

Thr Pro Thr Ser Leu Leu Pro Val Ser Ser Pro Thr Glu Pro Thr Ala
                3125                3130                3135

Arg Arg Lys Ser Ser Pro Glu Thr Trp Ala Ser Ser Ile Ser Val Pro
            3140                3145                3150
```

```
Ala Lys Thr Ser Leu Val Glu Thr Thr Asp Gly Thr Leu Val Thr Thr
        3155                3160                3165

Ile Lys Met Ser Ser Gln Ala Ala Gln Gly Asn Ser Thr Trp Pro Ala
    3170                3175                3180

Pro Ala Glu Glu Thr Gly Thr Ser Pro Ala Gly Thr Ser Pro Gly Ser
3185                3190                3195                3200

Pro Glu Val Ser Thr Thr Leu Lys Ile Met Ser Ser Lys Glu Pro Ser
                3205                3210                3215

Ile Ser Pro Glu Ile Arg Ser Thr Val Arg Asn Ser Pro Trp Lys Thr
            3220                3225                3230

Pro Glu Thr Thr Val Pro Met Glu Thr Thr Val Glu Pro Val Thr Leu
        3235                3240                3245

Gln Ser Thr Ala Leu Gly Ser Gly Ser Thr Ser Ile Ser His Leu Pro
    3250                3255                3260

Thr Gly Thr Thr Ser Pro Thr Lys Ser Pro Thr Glu Asn Met Leu Ala
3265                3270                3275                3280

Thr Glu Arg Val Ser Leu Ser Pro Ser Pro Glu Ala Trp Thr Asn
                3285                3290                3295

Leu Tyr Ser Gly Thr Pro Gly Gly Thr Arg Gln Ser Leu Ala Thr Met
            3300                3305                3310

Ser Ser Val Ser Leu Glu Ser Pro Thr Ala Arg Ser Ile Thr Gly Thr
        3315                3320                3325

Gly Gln Gln Ser Ser Pro Glu Leu Val Ser Lys Thr Thr Gly Met Glu
    3330                3335                3340

Phe Ser Met Trp His Gly Ser Thr Gly Gly Thr Thr Gly Asp Thr His
3345                3350                3355                3360

Val Ser Leu Ser Thr Ser Ser Asn Ile Leu Glu Asp Pro Val Thr Ser
                3365                3370                3375

Pro Asn Ser Val Ser Ser Leu Thr Asp Lys Ser Lys His Lys Thr Glu
            3380                3385                3390

Thr Trp Val Ser Thr Thr Ala Ile Pro Ser Thr Val Leu Asn Asn Lys
        3395                3400                3405

Ile Met Ala Ala Glu Gln Gln Thr Ser Arg Ser Val Asp Glu Ala Tyr
    3410                3415                3420

Ser Ser Thr Ser Ser Trp Ser Asp Gln Thr Ser Gly Ser Asp Ile Thr
3425                3430                3435                3440

Leu Gly Ala Ser Pro Asp Val Thr Asn Thr Leu Tyr Ile Thr Ser Thr
                3445                3450                3455

Ala Gln Thr Thr Ser Leu Val Ser Leu Pro Ser Gly Asp Gln Gly Ile
            3460                3465                3470

Thr Ser Leu Thr Asn Pro Ser Gly Gly Lys Thr Ser Ser Ala Ser Ser
        3475                3480                3485

Val Thr Ser Pro Ser Ile Gly Leu Glu Thr Leu Arg Ala Asn Val Ser
    3490                3495                3500

Ala Val Lys Ser Asp Ile Ala Pro Thr Ala Gly His Leu Ser Gln Thr
3505                3510                3515                3520

Ser Ser Pro Ala Glu Val Ser Ile Leu Asp Val Thr Thr Ala Pro Thr
                3525                3530                3535

Pro Gly Ile Ser Thr Thr Ile Thr Thr Met Gly Thr Asn Ser Ile Ser
            3540                3545                3550

Thr Thr Thr Pro Asn Pro Glu Val Gly Met Ser Thr Met Asp Ser Thr
        3555                3560                3565
```

```
Pro Ala Thr Glu Arg Arg Thr Thr Ser Thr Glu His Pro Ser Thr Trp
    3570                3575                3580

Ser Ser Thr Ala Ala Ser Asp Ser Trp Thr Val Thr Asp Met Thr Ser
3585                3590                3595                3600

Asn Leu Lys Val Ala Arg Ser Pro Gly Thr Ile Ser Thr Met His Thr
            3605                3610                3615

Thr Ser Phe Leu Ala Ser Ser Thr Glu Leu Asp Ser Met Ser Thr Pro
        3620                3625                3630

His Gly Arg Ile Thr Val Ile Gly Thr Ser Leu Val Thr Pro Ser Ser
    3635                3640                3645

Asp Ala Ser Ala Val Lys Thr Glu Thr Ser Thr Ser Glu Arg Thr Leu
3650                3655                3660

Ser Pro Ser Asp Thr Thr Ala Ser Thr Pro Ile Ser Thr Phe Ser Arg
3665                3670                3675                3680

Val Gln Arg Met Ser Ile Ser Val Pro Asp Ile Leu Ser Thr Ser Trp
            3685                3690                3695

Thr Pro Ser Ser Thr Glu Ala Glu Asp Val Pro Val Ser Met Val Ser
        3700                3705                3710

Thr Asp His Ala Ser Thr Lys Thr Asp Pro Asn Thr Pro Leu Ser Thr
    3715                3720                3725

Phe Leu Phe Asp Ser Leu Ser Thr Leu Asp Trp Asp Thr Gly Arg Ser
    3730                3735                3740

Leu Ser Ser Ala Thr Ala Thr Thr Ser Ala Pro Gln Gly Ala Thr Thr
3745                3750                3755                3760

Pro Gln Glu Leu Thr Leu Glu Thr Met Ile Ser Pro Ala Thr Ser Gln
        3765                3770                3775

Leu Pro Phe Ser Ile Gly His Ile Thr Ser Ala Val Thr Pro Ala Ala
            3780                3785                3790

Met Ala Arg Ser Ser Gly Val Thr Phe Ser Arg Pro Asp Pro Thr Ser
        3795                3800                3805

Lys Lys Ala Glu Gln Thr Ser Thr Gln Leu Pro Thr Thr Thr Ser Ala
    3810                3815                3820

His Pro Gly Gln Val Pro Arg Ser Ala Ala Thr Thr Leu Asp Val Ile
3825                3830                3835                3840

Pro His Thr Ala Lys Thr Pro Asp Ala Thr Phe Gln Arg Gln Gly Gln
            3845                3850                3855

Thr Ala Leu Thr Thr Glu Ala Arg Ala Thr Ser Asp Ser Trp Asn Glu
        3860                3865                3870

Lys Glu Lys Ser Thr Pro Ser Ala Pro Trp Ile Thr Glu Met Met Asn
    3875                3880                3885

Ser Val Ser Glu Asp Thr Ile Lys Glu Val Thr Ser Ser Ser Ser Val
        3890                3895                3900

Leu Lys Asp Pro Glu Tyr Ala Gly His Lys Leu Gly Ile Trp Asp Asp
3905                3910                3915                3920

Phe Ile Pro Lys Phe Gly Lys Ala Ala His Met Arg Glu Leu Pro Leu
            3925                3930                3935

Leu Ser Pro Pro Gln Asp Lys Glu Ala Ile His Pro Ser Thr Asn Thr
        3940                3945                3950

Val Glu Thr Thr Gly Trp Val Thr Ser Ser Glu His Ala Ser His Ser
    3955                3960                3965

Thr Ile Pro Ala His Ser Ala Ser Ser Lys Leu Thr Ser Pro Val Val
    3970                3975                3980

Thr Thr Ser Thr Arg Glu Gln Ala Ile Val Ser Met Ser Thr Thr Thr
```

```
                3985              3990              3995              4000
Trp Pro Glu Ser Thr Arg Ala Arg Thr Glu Pro Asn Ser Phe Leu Thr
                    4005              4010              4015
Ile Glu Leu Arg Asp Val Ser Pro Tyr Met Asp Thr Ser Ser Thr Thr
                    4020              4025              4030
Gln Thr Ser Ile Ile Ser Ser Pro Gly Ser Thr Ala Ile Thr Lys Gly
                    4035              4040              4045
Pro Arg Thr Glu Ile Thr Ser Ser Lys Arg Ile Ser Ser Ser Phe Leu
        4050              4055              4060
Ala Gln Ser Met Arg Ser Ser Asp Ser Pro Ser Glu Ala Ile Thr Arg
4065              4070              4075              4080
Leu Ser Asn Phe Pro Ala Met Thr Glu Ser Gly Gly Met Ile Leu Ala
                    4085              4090              4095
Met Gln Thr Ser Pro Pro Gly Ala Thr Ser Leu Ser Ala Pro Thr Leu
                    4100              4105              4110
Asp Thr Ser Ala Thr Ala Ser Trp Thr Gly Thr Pro Leu Ala Thr Thr
                    4115              4120              4125
Gln Arg Phe Thr Tyr Ser Glu Lys Thr Thr Leu Phe Ser Lys Gly Pro
                    4130              4135              4140
Glu Asp Thr Ser Gln Pro Ser Pro Ser Val Glu Glu Thr Ser Ser
4145              4150              4155              4160
Ser Ser Ser Leu Val Pro Ile His Ala Thr Thr Ser Pro Ser Asn Ile
                    4165              4170              4175
Leu Leu Thr Ser Gln Gly His Ser Pro Ser Ser Thr Pro Pro Val Thr
                    4180              4185              4190
Ser Val Phe Leu Ser Glu Thr Ser Gly Leu Gly Lys Thr Thr Asp Met
                    4195              4200              4205
Ser Arg Ile Ser Leu Glu Pro Gly Thr Ser Leu Pro Asn Leu Ser
        4210              4215              4220
Ser Thr Ala Gly Glu Ala Leu Ser Thr Tyr Glu Ala Ser Arg Asp Thr
4225              4230              4235              4240
Lys Ala Ile His His Ser Ala Asp Thr Ala Val Thr Asn Met Glu Ala
                    4245              4250              4255
Thr Ser Ser Glu Tyr Ser Pro Ile Pro Gly His Thr Lys Pro Ser Lys
                    4260              4265              4270
Ala Thr Ser Pro Leu Val Thr Ser His Ile Met Gly Asp Ile Thr Ser
                    4275              4280              4285
Ser Thr Ser Val Phe Gly Ser Ser Glu Thr Thr Glu Ile Glu Thr Val
                    4290              4295              4300
Ser Ser Val Asn Gln Gly Leu Gln Glu Arg Ser Thr Ser Gln Val Ala
4305              4310              4315              4320
Ser Ser Ala Thr Glu Thr Ser Thr Val Ile Thr His Val Ser Ser Gly
                    4325              4330              4335
Asp Ala Thr Thr His Val Thr Lys Thr Gln Ala Thr Phe Ser Ser Gly
                    4340              4345              4350
Thr Ser Ile Ser Ser Pro His Gln Phe Ile Thr Ser Thr Asn Thr Phe
                    4355              4360              4365
Thr Asp Val Ser Thr Asn Pro Ser Thr Ser Leu Ile Met Thr Glu Ser
                    4370              4375              4380
Ser Gly Val Thr Ile Thr Thr Gln Thr Gly Pro Thr Gly Ala Ala Thr
4385              4390              4395              4400
Gln Gly Pro Tyr Leu Leu Asp Thr Ser Thr Met Pro Tyr Leu Thr Glu
                    4405              4410              4415
```

```
Thr Pro Leu Ala Val Thr Pro Asp Phe Met Gln Ser Glu Lys Thr Thr
            4420                4425                4430

Leu Ile Ser Lys Gly Pro Lys Asp Val Thr Trp Ser Pro Pro Ser
            4435                4440                4445

Val Ala Glu Thr Ser Tyr Pro Ser Ser Leu Thr Pro Phe Leu Val Thr
            4450                4455                4460

Thr Ile Pro Pro Ala Thr Ser Thr Leu Gln Gly Gln His Thr Ser Ser
4465                4470                4475                4480

Pro Val Ser Ala Thr Ser Val Leu Thr Ser Gly Leu Val Lys Thr Thr
                4485                4490                4495

Asp Met Leu Asn Thr Ser Met Glu Pro Val Thr Asn Ser Pro Gln Asn
            4500                4505                4510

Leu Asn Asn Pro Ser Asn Glu Ile Leu Ala Thr Leu Ala Ala Thr Thr
            4515                4520                4525

Asp Ile Glu Thr Ile His Pro Ser Ile Asn Lys Ala Val Thr Asn Met
4530                4535                4540

Gly Thr Ala Ser Ser Ala His Val Leu His Ser Thr Leu Pro Val Ser
4545                4550                4555                4560

Ser Glu Pro Ser Thr Ala Thr Ser Pro Met Val Pro Ala Ser Ser Met
            4565                4570                4575

Gly Asp Ala Leu Ala Ser Ile Ser Ile Pro Gly Ser Glu Thr Thr Asp
            4580                4585                4590

Ile Glu Gly Glu Pro Thr Ser Ser Leu Thr Ala Gly Arg Lys Glu Asn
            4595                4600                4605

Ser Thr Leu Gln Glu Met Asn Ser Thr Glu Ser Asn Ile Ile Leu
            4610                4615                4620

Ser Asn Val Ser Val Gly Ala Ile Thr Glu Ala Thr Lys Met Glu Val
4625                4630                4635                4640

Pro Ser Phe Asp Ala Thr Phe Ile Pro Thr Pro Ala Gln Ser Thr Lys
            4645                4650                4655

Phe Pro Asp Ile Phe Ser Val Ala Ser Ser Arg Leu Ser Asn Ser Pro
            4660                4665                4670

Pro Met Thr Ile Ser Thr His Met Thr Thr Thr Gln Thr Gly Ser Ser
            4675                4680                4685

Gly Ala Thr Ser Lys Ile Pro Leu Ala Leu Asp Thr Ser Thr Leu Glu
            4690                4695                4700

Thr Ser Ala Gly Thr Pro Ser Val Val Thr Glu Gly Phe Ala His Ser
4705                4710                4715                4720

Lys Ile Thr Thr Ala Met Asn Asn Asp Val Lys Asp Val Ser Gln Thr
            4725                4730                4735

Asn Pro Pro Phe Gln Asp Glu Ser Ser Pro Ser Ser Gln Ala Pro
            4740                4745                4750

Val Leu Val Thr Thr Leu Pro Ser Ser Val Ala Phe Thr Pro Gln Trp
            4755                4760                4765

His Ser Thr Ser Ser Pro Val Ser Met Ser Ser Val Leu Thr Ser Ser
            4770                4775                4780

Leu Val Lys Thr Ala Gly Lys Val Asp Thr Ser Leu Glu Thr Val Thr
4785                4790                4795                4800

Ser Ser Pro Gln Ser Met Ser Asn Thr Leu Asp Asp Ile Ser Val Thr
            4805                4810                4815

Ser Ala Ala Thr Thr Asp Ile Glu Thr Thr His Pro Ser Ile Asn Thr
            4820                4825                4830
```

-continued

```
Val Val Thr Asn Val Gly Thr Thr Gly Ser Ala Phe Glu Ser His Ser
            4835                4840                4845

Thr Val Ser Ala Tyr Pro Glu Pro Ser Lys Val Thr Ser Pro Asn Val
4850                4855                4860

Thr Thr Ser Thr Met Glu Asp Thr Thr Ile Ser Arg Ser Ile Pro Lys
4865                4870                4875                4880

Ser Ser Lys Thr Thr Arg Thr Glu Thr Glu Thr Ser Ser Leu Thr
            4885                4890                4895

Pro Lys Leu Arg Glu Thr Ser Ile Ser Gln Ile Thr Ser Ser Thr
            4900                4905                4910

Glu Thr Ser Thr Val Pro Tyr Lys Glu Leu Thr Gly Ala Thr Thr Glu
            4915                4920                4925

Val Ser Arg Thr Asp Val Thr Ser Ser Ser Thr Ser Phe Pro Gly
            4930                4935                4940

Pro Asp Gln Ser Thr Val Ser Leu Asp Ile Ser Thr Glu Thr Asn Thr
4945                4950                4955                4960

Arg Leu Ser Thr Ser Pro Ile Met Thr Glu Ser Ala Glu Ile Thr Ile
            4965                4970                4975

Thr Thr Gln Thr Gly Pro His Gly Ala Thr Ser Gln Asp Thr Phe Thr
            4980                4985                4990

Met Asp Pro Ser Asn Thr Thr Pro Gln Ala Gly Ile His Ser Ala Met
            4995                5000                5005

Thr His Gly Phe Ser Gln Leu Asp Val Thr Thr Leu Met Ser Arg Ile
            5010                5015                5020

Pro Gln Asp Val Ser Trp Thr Ser Pro Pro Ser Val Asp Lys Thr Ser
5025                5030                5035                5040

Ser Pro Ser Ser Phe Leu Ser Ser Pro Ala Met Thr Thr Pro Ser Leu
            5045                5050                5055

Ile Ser Ser Thr Leu Pro Glu Asp Lys Leu Ser Ser Pro Met Thr Ser
            5060                5065                5070

Leu Leu Thr Ser Gly Leu Val Lys Ile Thr Asp Ile Leu Arg Thr Arg
            5075                5080                5085

Leu Glu Pro Val Thr Ser Ser Leu Pro Asn Phe Ser Ser Thr Ser Asp
            5090                5095                5100

Lys Ile Leu Ala Thr Ser Lys Asp Ser Lys Asp Thr Lys Glu Ile Phe
5105                5110                5115                5120

Pro Ser Ile Asn Thr Glu Glu Thr Asn Val Lys Ala Asn Asn Ser Gly
            5125                5130                5135

His Glu Ser His Ser Pro Ala Leu Ala Asp Ser Glu Thr Pro Lys Ala
            5140                5145                5150

Thr Thr Gln Met Val Ile Thr Thr Val Gly Asp Pro Ala Pro Ser
            5155                5160                5165

Thr Ser Met Pro Val His Gly Ser Ser Glu Thr Thr Asn Ile Lys Arg
            5170                5175                5180

Glu Pro Thr Tyr Phe Leu Thr Pro Arg Leu Arg Glu Thr Ser Thr Ser
5185                5190                5195                5200

Gln Glu Ser Ser Phe Pro Thr Asp Thr Ser Phe Leu Leu Ser Lys Val
            5205                5210                5215

Pro Thr Gly Thr Ile Thr Glu Val Ser Ser Thr Gly Val Asn Ser Ser
            5220                5225                5230

Ser Lys Ile Ser Thr Pro Asp His Asp Lys Ser Thr Val Pro Pro Asp
            5235                5240                5245

Thr Phe Thr Gly Glu Ile Pro Arg Val Phe Thr Ser Ser Ile Lys Thr
```

```
                5250                5255                5260
Lys Ser Ala Glu Met Thr Ile Thr Thr Gln Ala Ser Pro Pro Glu Ser
5265                5270                5275                5280

Ala Ser His Ser Thr Leu Pro Leu Asp Thr Ser Thr Thr Leu Ser Gln
                5285                5290                5295

Gly Gly Thr His Ser Thr Val Thr Gln Gly Phe Pro Tyr Ser Glu Val
            5300                5305                5310

Thr Thr Leu Met Gly Met Gly Pro Gly Asn Val Ser Trp Met Thr Thr
            5315                5320                5325

Pro Pro Val Glu Glu Thr Ser Ser Val Ser Ser Leu Met Ser Ser Pro
        5330                5335                5340

Ala Met Thr Ser Pro Ser Pro Val Ser Ser Thr Ser Pro Gln Ser Ile
5345                5350                5355                5360

Pro Ser Ser Pro Leu Pro Val Thr Ala Leu Pro Thr Ser Val Leu Val
            5365                5370                5375

Thr Thr Thr Asp Val Leu Gly Thr Thr Ser Pro Glu Ser Val Thr Ser
            5380                5385                5390

Ser Pro Pro Asn Leu Ser Ser Ile Thr His Glu Arg Pro Ala Thr Tyr
            5395                5400                5405

Lys Asp Thr Ala His Thr Glu Ala Ala Met His His Ser Thr Asn Thr
        5410                5415                5420

Ala Val Thr Asn Val Gly Thr Ser Gly Ser Gly His Lys Ser Gln Ser
5425                5430                5435                5440

Ser Val Leu Ala Asp Ser Glu Thr Ser Lys Ala Thr Pro Leu Met Ser
            5445                5450                5455

Thr Thr Ser Thr Leu Gly Asp Thr Ser Val Ser Thr Ser Thr Pro Asn
            5460                5465                5470

Ile Ser Gln Thr Asn Gln Ile Gln Thr Glu Pro Thr Ala Ser Leu Ser
            5475                5480                5485

Pro Arg Leu Arg Glu Ser Ser Thr Ser Glu Lys Thr Ser Ser Thr Thr
            5490                5495                5500

Glu Thr Asn Thr Ala Phe Ser Tyr Val Pro Thr Gly Ala Ile Thr Gln
5505                5510                5515                5520

Ala Ser Arg Thr Glu Ile Ser Ser Ser Arg Thr Ser Ile Ser Asp Leu
            5525                5530                5535

Asp Arg Pro Thr Ile Ala Pro Asp Ile Ser Thr Gly Met Ile Thr Arg
            5540                5545                5550

Leu Phe Thr Ser Pro Ile Met Thr Lys Ser Ala Glu Met Thr Val Thr
            5555                5560                5565

Thr Gln Thr Thr Thr Pro Gly Ala Thr Ser Gln Gly Ile Leu Pro Trp
            5570                5575                5580

Asp Thr Ser Thr Thr Leu Phe Gln Gly Gly Thr His Ser Thr Val Ser
5585                5590                5595                5600

Gln Gly Phe Pro His Ser Glu Ile Thr Thr Leu Arg Ser Arg Thr Pro
            5605                5610                5615

Gly Asp Val Ser Trp Met Thr Thr Pro Pro Val Glu Glu Thr Ser Ser
            5620                5625                5630

Gly Phe Ser Leu Met Ser Pro Ser Met Thr Ser Pro Ser Pro Val Ser
            5635                5640                5645

Ser Thr Ser Pro Glu Ser Ile Pro Ser Ser Pro Leu Pro Val Thr Ala
            5650                5655                5660

Leu Leu Thr Ser Val Leu Val Thr Thr Thr Asn Val Leu Gly Thr Thr
5665                5670                5675                5680
```

-continued

Ser Pro Glu Thr Val Thr Ser Ser Pro Asn Leu Ser Pro Thr
            5685                5690                5695

Gln Glu Arg Leu Thr Thr Tyr Lys Asp Thr Ala His Thr Glu Ala Met
            5700                5705                5710

His Ala Ser Met His Thr Asn Thr Ala Val Ala Asn Val Gly Thr Ser
            5715                5720                5725

Ile Ser Gly His Glu Ser Gln Ser Ser Val Pro Ala Asp Ser His Thr
            5730                5735                5740

Ser Lys Ala Thr Ser Pro Met Gly Ile Thr Phe Ala Met Gly Asp Thr
5745                5750                5755                5760

Ser Val Ser Thr Ser Thr Pro Ala Phe Phe Glu Thr Arg Ile Gln Thr
            5765                5770                5775

Glu Ser Thr Ser Ser Leu Ile Pro Gly Leu Arg Asp Thr Arg Thr Ser
            5780                5785                5790

Glu Glu Ile Asn Thr Val Thr Glu Thr Ser Thr Val Leu Ser Glu Val
            5795                5800                5805

Pro Thr Thr Thr Thr Thr Glu Val Ser Arg Thr Glu Val Ile Thr Ser
            5810                5815                5820

Ser Arg Thr Thr Ile Ser Gly Pro Asp His Ser Lys Met Ser Pro Tyr
5825                5830                5835                5840

Ile Ser Thr Glu Thr Ile Thr Arg Leu Ser Thr Phe Pro Phe Val Thr
            5845                5850                5855

Gly Ser Thr Glu Met Ala Ile Thr Asn Gln Thr Gly Pro Ile Gly Thr
            5860                5865                5870

Ile Ser Gln Ala Thr Leu Thr Leu Asp Thr Ser Ser Thr Ala Ser Trp
            5875                5880                5885

Glu Gly Thr His Ser Pro Val Thr Gln Arg Phe Pro His Ser Glu Glu
            5890                5895                5900

Thr Thr Thr Met Ser Arg Ser Thr Lys Gly Val Ser Trp Gln Ser Pro
5905                5910                5915                5920

Pro Ser Val Glu Glu Thr Ser Ser Pro Ser Ser Pro Val Pro Leu Pro
            5925                5930                5935

Ala Ile Thr Ser His Ser Ser Leu Tyr Ser Ala Val Ser Gly Ser Ser
            5940                5945                5950

Pro Thr Ser Ala Leu Pro Val Thr Ser Leu Leu Thr Ser Gly Arg Arg
            5955                5960                5965

Lys Thr Ile Asp Met Leu Asp Thr His Ser Glu Leu Val Thr Ser Ser
5970                5975                5980

Leu Pro Ser Ala Ser Ser Phe Ser Gly Glu Ile Leu Thr Ser Glu Ala
5985                5990                5995                6000

Ser Thr Asn Thr Glu Thr Ile His Phe Ser Glu Asn Thr Ala Glu Thr
            6005                6010                6015

Asn Met Gly Thr Thr Asn Ser Met His Lys Leu His Ser Ser Val Ser
            6020                6025                6030

Ile His Ser Gln Pro Ser Gly His Thr Pro Lys Val Thr Gly Ser
            6035                6040                6045

Met Met Glu Asp Ala Ile Val Ser Thr Ser Thr Pro Gly Ser Pro Glu
            6050                6055                6060

Thr Lys Asn Val Asp Arg Asp Ser Thr Ser Pro Leu Thr Pro Glu Leu
6065                6070                6075                6080

Lys Glu Asp Ser Thr Ala Leu Val Met Asn Ser Thr Thr Glu Ser Asn
            6085                6090                6095

```
Thr Val Phe Ser Ser Val Ser Leu Asp Ala Ala Thr Glu Val Ser Arg
              6100                6105                6110

Ala Glu Val Thr Tyr Tyr Asp Pro Thr Phe Met Pro Ala Ser Ala Gln
        6115                6120                6125

Ser Thr Lys Ser Pro Asp Ile Ser Pro Glu Ala Ser Ser Ser His Ser
        6130                6135                6140

Asn Ser Pro Pro Leu Thr Ile Ser Thr His Lys Thr Ile Ala Thr Gln
6145                6150                6155                6160

Thr Gly Pro Ser Gly Val Thr Ser Leu Gly Gln Leu Thr Leu Asp Thr
                6165                6170                6175

Ser Thr Ile Ala Thr Ser Ala Gly Thr Pro Ser Ala Arg Thr Gln Asp
            6180                6185                6190

Phe Val Asp Ser Glu Thr Thr Ser Val Met Asn Asn Asp Leu Asn Asp
        6195                6200                6205

Val Leu Lys Thr Ser Pro Phe Ser Ala Glu Glu Ala Asn Ser Leu Ser
        6210                6215                6220

Ser Gln Ala Pro Leu Leu Val Thr Thr Ser Pro Ser Pro Val Thr Ser
6225                6230                6235                6240

Thr Leu Gln Glu His Ser Thr Ser Ser Leu Val Ser Val Thr Ser Val
                6245                6250                6255

Pro Thr Pro Thr Leu Ala Lys Ile Thr Asp Met Asp Thr Asn Leu Glu
            6260                6265                6270

Pro Val Thr Arg Ser Pro Gln Asn Leu Arg Asn Thr Leu Ala Thr Ser
        6275                6280                6285

Glu Ala Thr Thr Asp Thr His Thr Met His Pro Ser Ile Asn Thr Ala
        6290                6295                6300

Met Ala Asn Val Gly Thr Thr Ser Ser Pro Asn Glu Phe Tyr Phe Thr
6305                6310                6315                6320

Val Ser Pro Asp Ser Asp Pro Tyr Lys Ala Thr Ser Ala Val Val Ile
                6325                6330                6335

Thr Ser Thr Ser Gly Asp Ser Ile Val Ser Thr Ser Met Pro Arg Ser
            6340                6345                6350

Ser Ala Met Lys Lys Ile Glu Ser Glu Thr Thr Phe Ser Leu Ile Phe
        6355                6360                6365

Arg Leu Arg Glu Thr Ser Thr Ser Gln Lys Ile Gly Ser Ser Ser Asp
        6370                6375                6380

Thr Ser Thr Val Phe Asp Lys Ala Phe Thr Ala Ala Thr Thr Glu Val
6385                6390                6395                6400

Ser Arg Thr Glu Leu Thr Ser Ser Arg Thr Ser Ile Gln Gly Thr
                6405                6410                6415

Glu Lys Pro Thr Met Ser Pro Asp Thr Ser Thr Arg Ser Val Thr Met
            6420                6425                6430

Leu Ser Thr Phe Ala Gly Leu Thr Lys Ser Glu Glu Arg Thr Ile Ala
        6435                6440                6445

Thr Gln Thr Gly Pro His Arg Ala Thr Ser Gln Gly Thr Leu Thr Trp
        6450                6455                6460

Asp Thr Ser Ile Thr Thr Ser Gln Ala Gly Thr His Ser Ala Met Thr
6465                6470                6475                6480

His Gly Phe Ser Gln Leu Asp Leu Ser Thr Leu Thr Ser Arg Val Pro
                6485                6490                6495

Glu Tyr Ile Ser Gly Thr Ser Pro Pro Ser Val Glu Lys Thr Ser Ser
            6500                6505                6510

Ser Ser Ser Leu Leu Ser Leu Pro Ala Ile Thr Ser Pro Ser Pro Val
```

```
                    6515                6520                6525
Pro Thr Thr Leu Pro Glu Ser Arg Pro Ser Ser Pro Val His Leu Thr
                6530                6535            6540

Ser Leu Pro Thr Ser Gly Leu Val Lys Thr Thr Asp Met Leu Ala Ser
6545            6550                6555                6560

Val Ala Ser Leu Pro Pro Asn Leu Gly Ser Thr Ser His Lys Ile Pro
            6565                6570                6575

Thr Thr Ser Glu Asp Ile Lys Asp Thr Glu Lys Met Tyr Pro Ser Thr
        6580                6585                6590

Asn Ile Ala Val Thr Asn Val Gly Thr Thr Ser Glu Lys Glu Ser
            6595                6600                6605

Tyr Ser Ser Val Pro Ala Tyr Ser Glu Pro Pro Lys Val Thr Ser Pro
            6610                6615                6620

Met Val Thr Ser Phe Asn Ile Arg Asp Thr Ile Val Ser Thr Ser Met
6625                6630                6635                6640

Pro Gly Ser Ser Glu Ile Thr Arg Ile Glu Met Glu Ser Thr Phe Ser
                6645                6650                6655

Val Ala His Gly Leu Lys Gly Thr Ser Thr Ser Gln Asp Pro Ile Val
            6660                6665                6670

Ser Thr Glu Lys Ser Ala Val Leu His Lys Leu Thr Thr Gly Ala Thr
        6675                6680                6685

Glu Thr Ser Arg Thr Glu Val Ala Ser Ser Arg Arg Thr Ser Ile Pro
        6690                6695            6700

Gly Pro Asp His Ser Thr Glu Ser Pro Asp Ile Ser Thr Glu Val Ile
6705                6710                6715                6720

Pro Ser Leu Pro Ile Ser Leu Gly Ile Thr Glu Ser Ser Asn Met Thr
                6725                6730                6735

Ile Ile Thr Arg Thr Gly Pro Pro Leu Gly Ser Thr Ser Gln Gly Thr
            6740                6745                6750

Phe Thr Leu Asp Thr Pro Thr Thr Ser Ser Arg Ala Gly Thr His Ser
        6755                6760                6765

Met Ala Thr Gln Glu Phe Pro His Ser Glu Met Thr Thr Val Met Asn
        6770                6775                6780

Lys Asp Pro Glu Ile Leu Ser Trp Thr Ile Pro Pro Ser Ile Glu Lys
6785                6790                6795                6800

Thr Ser Phe Ser Ser Ser Leu Met Pro Ser Pro Ala Met Thr Ser Pro
                6805                6810                6815

Pro Val Ser Ser Thr Leu Pro Lys Thr Ile His Thr Thr Pro Ser Pro
                6820                6825                6830

Met Thr Ser Leu Leu Thr Pro Ser Leu Val Met Thr Thr Asp Thr Leu
            6835                6840                6845

Gly Thr Ser Pro Glu Pro Thr Thr Ser Ser Pro Pro Asn Leu Ser Ser
            6850                6855                6860

Thr Ser His Val Ile Leu Thr Thr Asp Glu Asp Thr Thr Ala Ile Glu
6865                6870                6875                6880

Ala Met His Pro Ser Thr Ser Thr Ala Ala Thr Asn Val Glu Thr Thr
                6885                6890                6895

Cys Ser Gly His Gly Ser Gln Ser Ser Val Leu Thr Asp Ser Glu Lys
            6900                6905                6910

Thr Lys Ala Thr Ala Pro Met Asp Thr Thr Ser Thr Met Gly His Thr
        6915                6920                6925

Thr Val Ser Thr Ser Met Ser Val Ser Ser Glu Thr Thr Lys Ile Lys
        6930                6935                6940
```

```
Arg Glu Ser Thr Tyr Ser Leu Thr Pro Gly Leu Arg Glu Thr Ser Ile
6945                6950                6955                6960

Ser Gln Asn Ala Ser Phe Ser Thr Asp Thr Ser Ile Val Leu Ser Glu
            6965                6970                6975

Val Pro Thr Gly Thr Thr Ala Glu Val Ser Arg Thr Glu Val Thr Ser
        6980                6985                6990

Ser Gly Arg Thr Ser Ile Pro Gly Pro Ser Gln Ser Thr Val Leu Pro
            6995                7000                7005

Glu Ile Ser Thr Arg Thr Met Thr Arg Leu Phe Ala Ser Pro Thr Met
7010                7015                7020

Thr Glu Ser Ala Glu Met Thr Ile Pro Thr Gln Thr Gly Pro Ser Gly
7025                7030                7035                7040

Ser Thr Ser Gln Asp Thr Leu Thr Leu Asp Thr Ser Thr Thr Lys Ser
            7045                7050                7055

Gln Ala Lys Thr His Ser Thr Leu Thr Gln Arg Phe Pro His Ser Glu
            7060                7065                7070

Met Thr Thr Leu Met Ser Arg Gly Pro Gly Asp Met Ser Trp Gln Ser
        7075                7080                7085

Ser Pro Ser Leu Glu Asn Pro Ser Ser Leu Pro Ser Leu Leu Ser Leu
            7090                7095                7100

Pro Ala Thr Thr Ser Pro Pro Ile Ser Ser Thr Leu Pro Val Thr
7105                7110                7115                7120

Ile Ser Ser Ser Pro Leu Pro Val Thr Ser Leu Leu Thr Ser Ser Pro
                7125                7130                7135

Val Thr Thr Thr Asp Met Leu His Thr Ser Pro Glu Leu Val Thr Ser
            7140                7145                7150

Ser Pro Pro Lys Leu Ser His Thr Ser Asp Glu Arg Leu Thr Thr Gly
            7155                7160                7165

Lys Asp Thr Thr Asn Thr Glu Ala Val His Pro Ser Thr Asn Thr Ala
            7170                7175                7180

Ala Ser Asn Val Glu Ile Pro Ser Phe Gly His Glu Ser Pro Ser Ser
7185                7190                7195                7200

Ala Leu Ala Asp Ser Glu Thr Ser Lys Ala Thr Ser Pro Met Phe Ile
            7205                7210                7215

Thr Ser Thr Gln Glu Asp Thr Val Ala Ile Ser Thr Pro His Phe
            7220                7225                7230

Leu Glu Thr Ser Arg Ile Gln Lys Glu Ser Ile Ser Ser Leu Ser Pro
            7235                7240                7245

Lys Leu Arg Glu Thr Gly Ser Ser Val Glu Thr Ser Ser Ala Ile Glu
            7250                7255                7260

Thr Ser Ala Val Leu Ser Glu Val Ser Ile Gly Ala Thr Thr Glu Ile
7265                7270                7275                7280

Ser Arg Thr Glu Val Thr Ser Ser Ser Arg Thr Ser Ile Ser Gly Ser
                7285                7290                7295

Ala Glu Ser Thr Met Leu Pro Glu Ile Ser Thr Thr Arg Lys Ile Ile
            7300                7305                7310

Lys Phe Pro Thr Ser Pro Ile Leu Ala Glu Ser Ser Glu Met Thr Ile
            7315                7320                7325

Lys Thr Gln Thr Ser Pro Pro Gly Ser Thr Ser Glu Ser Thr Phe Thr
            7330                7335                7340

Leu Asp Thr Ser Thr Thr Pro Ser Leu Val Ile Thr His Ser Thr Met
7345                7350                7355                7360
```

```
Thr Gln Arg Leu Pro His Ser Glu Ile Thr Thr Leu Val Ser Arg Gly
            7365                7370                7375

Ala Gly Asp Val Pro Arg Pro Ser Ser Leu Pro Val Glu Glu Thr Ser
            7380                7385                7390

Pro Pro Ser Ser Gln Leu Ser Leu Ser Ala Met Ile Ser Pro Ser Pro
            7395                7400                7405

Val Ser Ser Thr Leu Pro Ala Ser Ser His Ser Ser Ala Ser Val
            7410                7415                7420

Thr Ser Pro Leu Thr Pro Gly Gln Val Lys Thr Thr Glu Val Leu Asp
7425                7430                7435                7440

Ala Ser Ala Glu Pro Glu Thr Ser Ser Pro Ser Leu Ser Ser Thr
            7445                7450                7455

Ser Val Glu Ile Leu Ala Thr Ser Glu Val Thr Thr Asp Thr Glu Lys
            7460                7465                7470

Ile His Pro Phe Pro Asn Thr Ala Val Thr Lys Val Gly Thr Ser Ser
            7475                7480                7485

Ser Gly His Glu Ser Pro Ser Ser Val Leu Pro Asp Ser Glu Thr Thr
            7490                7495                7500

Lys Ala Thr Ser Ala Met Gly Thr Ile Ser Ile Met Gly Asp Thr Ser
7505                7510                7515                7520

Val Ser Thr Leu Thr Pro Ala Leu Ser Asn Thr Arg Lys Ile Gln Ser
            7525                7530                7535

Glu Pro Ala Ser Ser Leu Thr Thr Arg Leu Arg Glu Thr Ser Thr Ser
            7540                7545                7550

Glu Glu Thr Ser Leu Ala Thr Glu Ala Asn Thr Val Leu Ser Lys Val
            7555                7560                7565

Ser Thr Gly Ala Thr Thr Glu Val Ser Arg Thr Glu Ala Ile Ser Phe
            7570                7575                7580

Ser Arg Thr Ser Met Ser Gly Pro Glu Gln Ser Thr Met Ser Gln Asp
7585                7590                7595                7600

Ile Ser Ile Gly Thr Ile Pro Arg Ile Ser Ala Ser Ser Val Leu Thr
            7605                7610                7615

Glu Ser Ala Lys Met Thr Ile Thr Thr Gln Thr Gly Pro Ser Glu Ser
            7620                7625                7630

Thr Leu Glu Ser Thr Leu Asn Leu Asn Thr Ala Thr Thr Pro Ser Trp
            7635                7640                7645

Val Glu Thr His Ser Ile Val Ile Gln Gly Phe Pro His Pro Glu Met
            7650                7655                7660

Thr Thr Ser Met Gly Arg Gly Pro Gly Gly Val Ser Trp Pro Ser Pro
7665                7670                7675                7680

Pro Phe Val Lys Glu Thr Ser Pro Pro Ser Ser Pro Leu Ser Leu Pro
            7685                7690                7695

Ala Val Thr Ser Pro His Pro Val Ser Thr Thr Phe Leu Ala His Ile
            7700                7705                7710

Pro Pro Ser Pro Leu Pro Val Thr Ser Leu Leu Thr Ser Gly Pro Ala
            7715                7720                7725

Thr Thr Thr Asp Ile Leu Gly Thr Ser Thr Glu Pro Gly Thr Ser Ser
            7730                7735                7740

Ser Ser Ser Leu Ser Thr Ser Ser His Glu Arg Leu Thr Thr Tyr Lys
7745                7750                7755                7760

Asp Thr Ala His Thr Glu Ala Val His Pro Ser Thr Asn Thr Gly Gly
            7765                7770                7775

Thr Asn Val Ala Thr Thr Ser Ser Gly Tyr Lys Ser Gln Ser Ser Val
```

-continued

```
                 7780           7785           7790

Leu Ala Asp Ser Ser Pro Met Cys Thr Thr Ser Thr Met Gly Asp Thr
        7795            7800            7805

Ser Val Leu Thr Ser Thr Pro Ala Phe Leu Glu Thr Arg Arg Ile Gln
        7810            7815            7820

Thr Glu Leu Ala Ser Ser Leu Thr Pro Gly Leu Arg Glu Ser Ser Gly
7825            7830            7835            7840

Ser Glu Gly Thr Ser Ser Gly Thr Lys Met Ser Thr Val Leu Ser Lys
            7845            7850            7855

Val Pro Thr Gly Ala Thr Thr Glu Ile Ser Lys Glu Asp Val Thr Ser
            7860            7865            7870

Ile Pro Gly Pro Ala Gln Ser Thr Ile Ser Pro Asp Ile Ser Thr Arg
            7875            7880            7885

Thr Val Ser Trp Phe Ser Thr Ser Pro Val Met Thr Glu Ser Ala Glu
            7890            7895            7900

Ile Thr Met Asn Thr His Thr Ser Pro Leu Gly Ala Thr Thr Gln Gly
7905            7910            7915            7920

Thr Ser Thr Leu Ala Thr Ser Ser Thr Thr Ser Leu Thr Met Thr His
                7925            7930            7935

Ser Thr Ile Ser Gln Gly Phe Ser His Ser Gln Met Ser Thr Leu Met
                7940            7945            7950

Arg Arg Gly Pro Glu Asp Val Ser Trp Met Ser Pro Pro Leu Leu Glu
            7955            7960            7965

Lys Thr Arg Pro Ser Phe Ser Leu Met Ser Ser Pro Ala Thr Thr Ser
            7970            7975            7980

Pro Ser Pro Val Ser Ser Thr Leu Pro Glu Ser Ile Ser Ser Ser Pro
7985            7990            7995            8000

Leu Pro Val Thr Ser Leu Leu Thr Ser Gly Leu Ala Lys Thr Thr Asp
                8005            8010            8015

Met Leu His Lys Ser Ser Glu Pro Val Thr Asn Ser Pro Ala Asn Leu
            8020            8025            8030

Ser Ser Thr Ser Val Glu Ile Leu Ala Thr Ser Glu Val Thr Thr Asp
            8035            8040            8045

Thr Glu Lys Thr His Pro Ser Ser Asn Arg Thr Val Thr Asp Val Gly
            8050            8055            8060

Thr Ser Ser Ser Gly His Glu Ser Thr Ser Phe Val Leu Ala Asp Ser
8065            8070            8075            8080

Gln Thr Ser Lys Val Thr Ser Pro Met Val Ile Thr Ser Thr Met Glu
            8085            8090            8095

Asp Thr Ser Val Ser Thr Ser Thr Pro Gly Phe Phe Glu Thr Ser Arg
            8100            8105            8110

Ile Gln Thr Glu Pro Thr Ser Ser Leu Thr Leu Gly Leu Arg Lys Thr
            8115            8120            8125

Ser Ser Ser Glu Gly Thr Ser Leu Ala Thr Glu Met Ser Thr Val Leu
            8130            8135            8140

Ser Gly Val Pro Thr Gly Ala Thr Ala Glu Val Ser Arg Thr Glu Val
8145            8150            8155            8160

Thr Ser Ser Ser Arg Thr Ser Ile Ser Gly Phe Ala Gln Leu Thr Val
                8165            8170            8175

Ser Pro Glu Thr Ser Thr Glu Thr Ile Thr Arg Leu Pro Thr Ser Ser
                8180            8185            8190

Ile Met Thr Glu Ser Ala Glu Met Met Ile Lys Thr Gln Thr Asp Pro
            8195            8200            8205
```

```
Pro Gly Ser Thr Pro Glu Ser Thr His Thr Val Asp Ile Ser Thr Thr
    8210                8215                8220

Pro Asn Trp Val Glu Thr His Ser Thr Val Thr Gln Arg Phe Ser His
8225                8230                8235                8240

Ser Glu Met Thr Thr Leu Val Ser Arg Ser Pro Gly Asp Met Leu Trp
            8245                8250                8255

Pro Ser Gln Ser Ser Val Glu Glu Thr Ser Ser Ala Ser Ser Leu Leu
        8260                8265                8270

Ser Leu Pro Ala Thr Thr Ser Pro Ser Pro Val Ser Ser Thr Leu Val
            8275                8280                8285

Glu Asp Phe Pro Ser Ala Ser Leu Pro Val Thr Ser Leu Leu Thr Pro
        8290                8295                8300

Gly Leu Val Ile Thr Thr Asp Arg Met Gly Ile Ser Arg Glu Pro Gly
8305                8310                8315                8320

Thr Ser Ser Thr Ser Asn Leu Ser Ser Thr Ser His Glu Arg Leu Thr
            8325                8330                8335

Thr Leu Glu Asp Thr Val Asp Thr Glu Asp Met Gln Pro Ser Thr His
            8340                8345                8350

Thr Ala Val Thr Asn Val Arg Thr Ser Ile Ser Gly His Glu Ser Gln
        8355                8360                8365

Ser Ser Val Leu Ser Asp Ser Glu Thr Pro Lys Ala Thr Ser Pro Met
8370                8375                8380

Gly Thr Thr Tyr Thr Met Gly Glu Thr Ser Val Ser Ile Ser Thr Ser
8385                8390                8395                8400

Asp Phe Phe Glu Thr Ser Arg Ile Gln Ile Glu Pro Thr Ser Ser Leu
            8405                8410                8415

Thr Ser Gly Leu Arg Glu Thr Ser Ser Ser Glu Arg Ile Ser Ser Ala
        8420                8425                8430

Thr Glu Gly Ser Thr Val Leu Ser Glu Val Pro Ser Gly Ala Thr Thr
            8435                8440                8445

Glu Val Ser Arg Thr Glu Val Ile Ser Ser Arg Gly Thr Ser Met Ser
        8450                8455                8460

Gly Pro Asp Gln Phe Thr Ile Ser Pro Asp Ile Ser Thr Glu Ala Ile
8465                8470                8475                8480

Thr Arg Leu Ser Thr Ser Pro Ile Met Thr Glu Ser Ala Glu Ser Ala
            8485                8490                8495

Ile Thr Ile Glu Thr Gly Ser Pro Gly Ala Thr Ser Glu Gly Thr Leu
        8500                8505                8510

Thr Leu Asp Thr Ser Thr Thr Phe Trp Ser Gly Thr His Ser Thr
            8515                8520                8525

Ala Ser Pro Gly Phe Ser His Ser Glu Met Thr Thr Leu Met Ser Arg
    8530                8535                8540

Thr Pro Gly Asp Val Pro Trp Pro Ser Leu Pro Ser Val Glu Glu Ala
8545                8550                8555                8560

Ser Ser Val Ser Ser Ser Leu Ser Ser Pro Ala Met Thr Ser Thr Ser
            8565                8570                8575

Phe Phe Ser Ala Leu Pro Glu Ser Ile Ser Ser Pro His Pro Val
        8580                8585                8590

Thr Ala Leu Leu Thr Leu Gly Pro Val Lys Thr Thr Asp Met Leu Arg
        8595                8600                8605

Thr Ser Ser Glu Pro Glu Thr Ser Ser Pro Pro Asn Leu Ser Ser Thr
    8610                8615                8620
```

-continued

```
Ser Ala Glu Ile Leu Ala Thr Ser Glu Val Thr Lys Asp Arg Glu Lys
8625                8630                8635                8640

Ile His Pro Ser Ser Asn Thr Pro Val Val Asn Val Gly Thr Val Ile
                8645                8650                8655

Tyr Lys His Leu Ser Pro Ser Ser Val Leu Ala Asp Leu Val Thr Thr
                8660                8665                8670

Lys Pro Thr Ser Pro Met Ala Thr Thr Ser Thr Leu Gly Asn Thr Ser
                8675                8680                8685

Val Ser Thr Ser Thr Pro Ala Phe Pro Glu Thr Met Met Thr Gln Pro
    8690                8695                8700

Thr Ser Ser Leu Thr Ser Gly Leu Arg Glu Ile Ser Thr Ser Gln Glu
8705                8710                8715                8720

Thr Ser Ser Ala Thr Glu Arg Ser Ala Ser Leu Ser Gly Met Pro Thr
                8725                8730                8735

Gly Ala Thr Thr Lys Val Ser Arg Thr Glu Ala Leu Ser Leu Gly Arg
                8740                8745                8750

Thr Ser Thr Pro Gly Pro Ala Gln Ser Thr Ile Ser Pro Glu Ile Ser
                8755                8760                8765

Thr Glu Thr Ile Thr Arg Ile Ser Thr Pro Leu Thr Thr Thr Gly Ser
    8770                8775                8780

Ala Glu Met Thr Ile Thr Pro Lys Thr Gly His Ser Gly Ala Ser Ser
8785                8790                8795                8800

Gln Gly Thr Phe Thr Leu Asp Thr Ser Ser Arg Ala Ser Trp Pro Gly
                8805                8810                8815

Thr His Ser Ala Ala Thr His Arg Ser Pro His Ser Gly Met Thr Thr
                8820                8825                8830

Pro Met Ser Arg Gly Pro Glu Asp Val Ser Trp Pro Ser Arg Pro Ser
                8835                8840                8845

Val Glu Lys Thr Ser Pro Ser Ser Leu Val Ser Leu Ser Ala Val
    8850                8855                8860

Thr Ser Pro Ser Pro Leu Tyr Ser Thr Pro Ser Glu Ser Ser His Ser
8865                8870                8875                8880

Ser Pro Leu Arg Val Thr Ser Leu Phe Thr Pro Val Met Met Lys Thr
                8885                8890                8895

Thr Asp Met Leu Asp Thr Ser Leu Glu Pro Val Thr Thr Ser Pro Pro
                8900                8905                8910

Ser Met Asn Ile Thr Ser Asp Glu Ser Leu Ala Thr Ser Lys Ala Thr
                8915                8920                8925

Met Glu Thr Glu Ala Ile Gln Leu Ser Glu Asn Thr Ala Val Thr Gln
                8930                8935                8940

Met Gly Thr Ile Ser Ala Arg Gln Glu Phe Tyr Ser Ser Tyr Pro Gly
8945                8950                8955                8960

Leu Pro Glu Pro Ser Lys Val Thr Ser Pro Val Val Thr Ser Ser Thr
                8965                8970                8975

Ile Lys Asp Ile Val Ser Thr Thr Ile Pro Ala Ser Ser Glu Ile Thr
                8980                8985                8990

Arg Ile Glu Met Glu Ser Thr Ser Thr Leu Thr Pro Thr Pro Arg Glu
                8995                9000                9005

Thr Ser Thr Ser Gln Glu Ile His Ser Ala Thr Lys Pro Ser Thr Val
    9010                9015                9020

Pro Tyr Lys Ala Leu Thr Ser Ala Thr Ile Glu Asp Ser Met Thr Gln
9025                9030                9035                9040

Val Met Ser Ser Ser Arg Gly Pro Ser Pro Asp Gln Ser Thr Met Ser
```

```
                     9045           9050           9055

Gln Asp Ile Ser Ser Glu Val Ile Thr Arg Leu Ser Thr Ser Pro Ile
            9060            9065            9070

Lys Ala Glu Ser Thr Glu Met Thr Ile Thr Thr Gln Thr Gly Ser Pro
        9075            9080            9085

Gly Ala Thr Ser Arg Gly Thr Leu Thr Leu Asp Thr Ser Thr Thr Phe
        9090            9095            9100

Met Ser Gly Thr His Ser Thr Ala Ser Gln Gly Phe Ser His Ser Gln
9105            9110            9115            9120

Met Thr Ala Leu Met Ser Arg Thr Pro Gly Asp Val Pro Trp Leu Ser
            9125            9130            9135

His Pro Ser Val Glu Glu Ala Ser Ser Ala Ser Phe Ser Leu Ser Ser
            9140            9145            9150

Pro Val Met Thr Ser Ser Pro Val Ser Ser Thr Leu Pro Asp Ser
            9155            9160            9165

Ile His Ser Ser Ser Leu Pro Val Thr Ser Leu Leu Thr Ser Gly Leu
            9170            9175            9180

Val Lys Thr Thr Glu Leu Leu Gly Thr Ser Ser Glu Pro Glu Thr Ser
9185            9190            9195            9200

Ser Pro Pro Asn Leu Ser Ser Thr Ser Ala Glu Ile Leu Ala Thr Thr
            9205            9210            9215

Glu Val Thr Thr Asp Thr Glu Lys Leu Glu Met Thr Asn Val Val Thr
            9220            9225            9230

Ser Gly Tyr Thr His Glu Ser Pro Ser Ser Val Leu Ala Asp Ser Val
            9235            9240            9245

Thr Thr Lys Ala Thr Ser Ser Met Gly Ile Thr Tyr Pro Thr Gly Asp
            9250            9255            9260

Thr Asn Val Leu Thr Ser Thr Pro Ala Phe Ser Asp Thr Ser Arg Ile
9265            9270            9275            9280

Gln Thr Lys Ser Lys Leu Ser Leu Thr Pro Gly Leu Met Glu Thr Ser
            9285            9290            9295

Ile Ser Glu Glu Thr Ser Ser Ala Thr Glu Lys Ser Thr Val Leu Ser
            9300            9305            9310

Ser Val Pro Thr Gly Ala Thr Thr Glu Val Ser Arg Thr Glu Ala Ile
            9315            9320            9325

Ser Ser Ser Arg Thr Ser Ile Pro Gly Pro Ala Gln Ser Thr Met Ser
            9330            9335            9340

Ser Asp Thr Ser Met Glu Thr Ile Thr Arg Ile Ser Thr Pro Leu Thr
9345            9350            9355            9360

Arg Lys Glu Ser Thr Asp Met Ala Ile Thr Pro Lys Thr Gly Pro Ser
            9365            9370            9375

Gly Ala Thr Ser Gln Gly Thr Phe Thr Leu Asp Ser Ser Ser Thr Ala
            9380            9385            9390

Ser Trp Pro Gly Thr His Ser Ala Thr Thr Gln Arg Phe Pro Gln Ser
            9395            9400            9405

Val Val Thr Thr Pro Met Ser Arg Gly Pro Glu Asp Val Ser Trp Pro
            9410            9415            9420

Ser Pro Leu Ser Val Glu Lys Asn Ser Pro Ser Ser Leu Val Ser
9425            9430            9435            9440

Ser Ser Ser Val Thr Ser Pro Ser Pro Leu Tyr Ser Thr Pro Ser Gly
            9445            9450            9455

Ser Ser His Ser Ser Pro Val Pro Val Thr Ser Leu Phe Thr Ser Ile
            9460            9465            9470
```

```
Met Met Lys Ala Thr Asp Met Leu Asp Ala Ser Leu Glu Pro Glu Thr
            9475                9480                9485

Thr Ser Ala Pro Asn Met Asn Ile Thr Ser Asp Glu Ser Leu Ala Thr
9490                9495                9500

Ser Lys Ala Thr Thr Glu Thr Glu Ala Ile His Val Phe Glu Asn Thr
9505                9510                9515                9520

Ala Ala Ser His Val Glu Thr Thr Ser Ala Thr Glu Glu Leu Tyr Ser
            9525                9530                9535

Ser Ser Pro Gly Phe Ser Glu Pro Thr Lys Val Ile Ser Pro Val Val
            9540                9545                9550

Thr Ser Ser Ser Ile Arg Asp Asn Met Val Ser Thr Thr Met Pro Gly
            9555                9560                9565

Ser Ser Gly Ile Thr Arg Ile Glu Ile Glu Ser Met Ser Ser Leu Thr
            9570                9575                9580

Pro Gly Leu Arg Glu Thr Arg Thr Ser Gln Asp Ile Thr Ser Ser Thr
9585                9590                9595                9600

Glu Thr Ser Thr Val Leu Tyr Lys Met Ser Ser Gly Ala Thr Pro Glu
            9605                9610                9615

Val Ser Arg Thr Glu Val Met Pro Ser Ser Arg Thr Ser Ile Pro Gly
            9620                9625                9630

Pro Ala Gln Ser Thr Met Ser Leu Asp Ile Ser Asp Glu Val Val Thr
            9635                9640                9645

Arg Leu Ser Thr Ser Pro Ile Met Thr Glu Ser Ala Glu Ile Thr Ile
            9650                9655                9660

Thr Thr Gln Thr Gly Tyr Ser Leu Ala Thr Ser Gln Val Thr Leu Pro
9665                9670                9675                9680

Leu Gly Thr Ser Met Thr Phe Leu Ser Gly Thr His Ser Thr Met Ser
            9685                9690                9695

Gln Gly Leu Ser His Ser Glu Met Thr Asn Leu Met Ser Arg Gly Pro
            9700                9705                9710

Glu Ser Leu Ser Trp Thr Ser Pro Arg Phe Val Glu Thr Thr Arg Ser
            9715                9720                9725

Ser Ser Ser Leu Thr Ser Leu Pro Leu Thr Thr Ser Leu Ser Pro Val
            9730                9735                9740

Ser Ser Thr Leu Leu Asp Ser Ser Pro Ser Ser Pro Leu Pro Val Thr
9745                9750                9755                9760

Ser Leu Ile Leu Pro Gly Leu Val Lys Thr Thr Glu Val Leu Asp Thr
            9765                9770                9775

Ser Ser Glu Pro Lys Thr Ser Ser Ser Pro Asn Leu Ser Ser Thr Ser
            9780                9785                9790

Val Glu Ile Pro Ala Thr Ser Glu Ile Met Thr Asp Thr Glu Lys Ile
            9795                9800                9805

His Pro Ser Ser Asn Thr Ala Val Ala Lys Val Arg Thr Ser Ser Ser
            9810                9815                9820

Val His Glu Ser His Ser Ser Val Leu Ala Asp Ser Glu Thr Thr Ile
9825                9830                9835                9840

Thr Ile Pro Ser Met Gly Ile Thr Ser Ala Val Asp Asp Thr Thr Val
            9845                9850                9855

Phe Thr Ser Asn Pro Ala Phe Ser Glu Thr Arg Arg Ile Pro Thr Glu
            9860                9865                9870

Pro Thr Phe Ser Leu Thr Pro Gly Phe Arg Glu Thr Ser Thr Ser Glu
            9875                9880                9885
```

```
Glu Thr Thr Ser Ile Thr Glu Thr Ser Ala Val Leu Tyr Gly Val Pro
            9890                9895                9900

Thr Ser Ala Thr Thr Glu Val Ser Met Thr Glu Ile Met Ser Ser Asn
9905                9910                9915                9920

Arg Thr His Ile Pro Asp Ser Asp Gln Ser Thr Met Ser Pro Asp Ile
                9925                9930                9935

Ile Thr Glu Val Ile Thr Arg Leu Ser Ser Ser Met Met Ser Glu
            9940                9945                9950

Ser Thr Gln Met Thr Ile Thr Thr Gln Lys Ser Ser Pro Gly Ala Thr
                9955                9960                9965

Ala Gln Ser Thr Leu Thr Leu Ala Thr Thr Ala Pro Leu Ala Arg
    9970                9975                9980

Thr His Ser Thr Val Pro Pro Arg Phe Leu His Ser Glu Met Thr Thr
9985                9990                9995                10000

Leu Met Ser Arg Ser Pro Glu Asn Pro Ser Trp Lys Ser Ser Pro Phe
                10005               10010               10015

Val Glu Lys Thr Ser Ser Ser Ser Leu Leu Ser Leu Pro Val Thr
            10020               10025               10030

Thr Ser Pro Ser Val Ser Ser Thr Leu Pro Gln Ser Ile Pro Ser Ser
        10035               10040               10045

Ser Phe Ser Val Thr Ser Leu Leu Thr Pro Gly Met Val Lys Thr Thr
    10050               10055               10060

<210> SEQ ID NO 57
<211> LENGTH: 858
<212> TYPE: PRT
<213> ORGANISM: Homo sapiens

<400> SEQUENCE: 57

Met Leu Gln Thr Lys Asp Leu Ile Trp Thr Leu Phe Phe Leu Gly Thr
1               5                   10                  15

Ala Val Ser Leu Gln Val Asp Ile Val Pro Ser Gln Gly Glu Ile Ser
            20                  25                  30

Val Gly Glu Ser Lys Phe Phe Leu Cys Gln Val Ala Gly Asp Ala Lys
        35                  40                  45

Asp Lys Asp Ile Ser Trp Phe Ser Pro Asn Gly Glu Lys Leu Thr Pro
50                  55                  60

Asn Gln Gln Arg Ile Ser Val Val Trp Asn Asp Asp Ser Ser Ser Thr
65                  70                  75                  80

Leu Thr Ile Tyr Asn Ala Asn Ile Asp Asp Ala Gly Ile Tyr Lys Cys
                85                  90                  95

Val Val Thr Gly Glu Asp Gly Ser Glu Ser Glu Ala Thr Val Asn Val
            100                 105                 110

Lys Ile Phe Gln Lys Leu Met Phe Lys Asn Ala Pro Thr Pro Gln Glu
        115                 120                 125

Phe Arg Glu Gly Glu Asp Ala Val Ile Val Cys Asp Val Val Ser Ser
130                 135                 140

Leu Pro Pro Thr Ile Ile Trp Lys His Lys Gly Arg Asp Val Ile Leu
145                 150                 155                 160

Lys Lys Asp Val Arg Phe Ile Val Leu Ser Asn Asn Tyr Leu Gln Ile
                165                 170                 175

Arg Gly Ile Lys Lys Thr Asp Glu Gly Thr Tyr Arg Cys Glu Gly Arg
            180                 185                 190

Ile Leu Ala Arg Gly Glu Ile Asn Phe Lys Asp Ile Gln Val Ile Val
        195                 200                 205
```

```
Asn Val Pro Pro Thr Ile Gln Ala Arg Gln Asn Ile Val Asn Ala Thr
    210                 215                 220
Ala Asn Leu Gly Gln Ser Val Thr Leu Val Cys Asp Ala Glu Gly Phe
225                 230                 235                 240
Pro Glu Pro Thr Met Ser Trp Thr Lys Asp Gly Glu Gln Ile Glu Gln
                245                 250                 255
Glu Glu Asp Asp Glu Lys Tyr Ile Phe Ser Asp Ser Ser Gln Leu
            260                 265                 270
Thr Ile Lys Lys Val Asp Lys Asn Asp Glu Ala Glu Tyr Ile Cys Ile
        275                 280                 285
Ala Glu Asn Lys Ala Gly Glu Gln Asp Ala Thr Ile His Leu Lys Val
    290                 295                 300
Phe Ala Lys Pro Lys Ile Thr Tyr Val Glu Asn Gln Thr Ala Met Glu
305                 310                 315                 320
Leu Glu Glu Gln Val Thr Leu Thr Cys Glu Ala Ser Gly Asp Pro Ile
                325                 330                 335
Pro Ser Ile Thr Trp Arg Thr Ser Thr Arg Asn Ile Ser Ser Glu Glu
            340                 345                 350
Lys Ala Ser Trp Thr Arg Pro Glu Lys Gln Glu Thr Leu Asp Gly His
        355                 360                 365
Met Val Val Arg Ser His Ala Arg Val Ser Ser Leu Thr Leu Lys Ser
    370                 375                 380
Ile Gln Tyr Thr Asp Ala Gly Glu Tyr Ile Cys Thr Ala Ser Asn Thr
385                 390                 395                 400
Ile Gly Gln Asp Ser Gln Ser Met Tyr Leu Glu Val Gln Tyr Ala Pro
                405                 410                 415
Lys Leu Gln Gly Pro Val Ala Val Tyr Thr Trp Glu Gly Asn Gln Val
            420                 425                 430
Asn Ile Thr Cys Glu Val Phe Ala Tyr Pro Ser Ala Thr Ile Ser Trp
        435                 440                 445
Phe Arg Asp Gly Gln Leu Leu Pro Ser Ser Asn Tyr Ser Asn Ile Lys
    450                 455                 460
Ile Tyr Asn Thr Pro Ser Ala Ser Tyr Leu Glu Val Thr Pro Asp Ser
465                 470                 475                 480
Glu Asn Asp Phe Gly Asn Tyr Asn Cys Thr Ala Val Asn Arg Ile Gly
                485                 490                 495
Gln Glu Ser Leu Glu Phe Ile Leu Val Gln Ala Asp Thr Pro Ser Ser
            500                 505                 510
Pro Ser Ile Asp Gln Val Glu Pro Tyr Ser Ser Thr Ala Gln Val Gln
        515                 520                 525
Phe Asp Glu Pro Glu Ala Thr Gly Gly Val Pro Ile Leu Lys Tyr Lys
    530                 535                 540
Ala Glu Trp Arg Ala Val Gly Glu Glu Val Trp His Ser Lys Trp Tyr
545                 550                 555                 560
Asp Ala Lys Glu Ala Ser Met Glu Gly Ile Val Thr Ile Val Gly Leu
                565                 570                 575
Lys Pro Glu Thr Thr Tyr Ala Val Arg Leu Ala Ala Leu Asn Gly Lys
            580                 585                 590
Gly Leu Gly Glu Ile Ser Ala Ala Ser Glu Phe Lys Thr Gln Pro Val
        595                 600                 605
Gln Gly Glu Pro Ser Ala Pro Lys Leu Glu Gly Gln Met Gly Glu Asp
    610                 615                 620
```

```
Gly Asn Ser Ile Lys Val Asn Leu Ile Lys Gln Asp Asp Gly Gly Ser
625                 630                 635                 640

Pro Ile Arg His Tyr Leu Val Arg Tyr Arg Ala Leu Ser Ser Glu Trp
            645                 650                 655

Lys Pro Glu Ile Arg Leu Pro Ser Gly Ser Asp His Val Met Leu Lys
            660                 665                 670

Ser Leu Asp Trp Asn Ala Glu Tyr Glu Val Tyr Val Ala Glu Asn
            675                 680                 685

Gln Gln Gly Lys Ser Lys Ala His Phe Val Arg Thr Ser Ala
        690                 695                 700

Gln Pro Thr Ala Ile Pro Ala Asn Gly Ser Pro Thr Ser Gly Leu Ser
705                 710                 715                 720

Thr Gly Ala Ile Val Gly Ile Leu Ile Val Ile Phe Val Leu Leu Leu
            725                 730                 735

Val Val Val Asp Ile Thr Cys Tyr Phe Leu Asn Lys Cys Gly Leu Phe
            740                 745                 750

Met Cys Ile Ala Val Asn Leu Cys Gly Lys Ala Gly Pro Gly Ala Lys
            755                 760                 765

Gly Lys Asp Met Glu Glu Gly Lys Ala Ala Phe Ser Lys Asp Glu Ser
770                 775                 780

Lys Glu Pro Ile Val Glu Val Arg Thr Glu Glu Glu Arg Thr Pro Asn
785                 790                 795                 800

His Asp Gly Gly Lys His Thr Glu Pro Asn Glu Thr Thr Pro Leu Thr
            805                 810                 815

Glu Pro Glu Lys Gly Pro Val Ala Lys Pro Glu Cys Gln Glu Thr
        820                 825                 830

Glu Thr Lys Pro Ala Pro Ala Glu Val Lys Thr Val Pro Asn Asp Ala
835                 840                 845

Thr Gln Thr Lys Glu Asn Glu Ser Lys Ala
850                 855

<210> SEQ ID NO 58
<211> LENGTH: 224
<212> TYPE: PRT
<213> ORGANISM: Homo sapiens

<400> SEQUENCE: 58

Met Glu Lys Leu Leu Cys Phe Leu Val Leu Thr Ser Leu Ser His Ala
1               5                   10                  15

Phe Gly Gln Thr Asp Met Ser Arg Lys Ala Phe Val Phe Pro Lys Glu
            20                  25                  30

Ser Asp Thr Ser Tyr Val Ser Leu Lys Ala Pro Leu Thr Lys Pro Leu
            35                  40                  45

Lys Ala Phe Thr Val Cys Leu His Phe Tyr Thr Glu Leu Ser Ser Thr
        50                  55                  60

Arg Gly Tyr Ser Ile Phe Ser Tyr Ala Thr Lys Arg Gln Asp Asn Glu
65                  70                  75                  80

Ile Leu Ile Phe Trp Ser Lys Asp Ile Gly Tyr Ser Phe Thr Val Gly
                85                  90                  95

Gly Ser Glu Ile Leu Phe Glu Val Pro Glu Val Thr Val Ala Pro Val
            100                 105                 110

His Ile Cys Thr Ser Trp Glu Ser Ala Ser Gly Ile Val Glu Phe Trp
        115                 120                 125

Val Asp Gly Lys Pro Arg Val Arg Lys Ser Leu Lys Lys Gly Tyr Thr
130                 135                 140
```

```
Val Gly Ala Glu Ala Ser Ile Ile Leu Gly Gln Gln Asp Ser Phe
145                 150                 155                 160

Gly Gly Asn Phe Glu Gly Ser Gln Ser Leu Val Gly Asp Ile Gly Asn
            165                 170                 175

Val Asn Met Trp Asp Phe Val Leu Ser Pro Asp Glu Ile Asn Thr Ile
            180                 185                 190

Tyr Leu Gly Gly Pro Phe Ser Pro Asn Val Leu Asn Trp Arg Ala Leu
            195                 200                 205

Lys Tyr Glu Val Gln Gly Glu Val Phe Thr Lys Pro Gln Leu Trp Pro
    210                 215                 220
```

<210> SEQ ID NO 59
<211> LENGTH: 418
<212> TYPE: PRT
<213> ORGANISM: Homo sapiens

<400> SEQUENCE: 59

```
Met Pro Ser Ser Val Ser Trp Gly Ile Leu Leu Leu Ala Gly Leu Cys
  1               5                  10                  15

Cys Leu Val Pro Val Ser Leu Ala Glu Asp Pro Gln Gly Asp Ala Ala
             20                  25                  30

Gln Lys Thr Asp Thr Ser His His Asp Gln Asp His Pro Thr Phe Asn
         35                  40                  45

Lys Ile Thr Pro Asn Leu Ala Glu Phe Ala Phe Ser Leu Tyr Arg Gln
     50                  55                  60

Leu Ala His Gln Ser Asn Ser Thr Asn Ile Phe Phe Ser Pro Val Ser
 65                  70                  75                  80

Ile Ala Thr Ala Phe Ala Met Leu Ser Leu Gly Thr Lys Ala Asp Thr
                 85                  90                  95

His Asp Glu Ile Leu Glu Gly Leu Asn Phe Asn Leu Thr Glu Ile Pro
            100                 105                 110

Glu Ala Gln Ile His Glu Gly Phe Gln Glu Leu Leu Arg Thr Leu Asn
        115                 120                 125

Gln Pro Asp Ser Gln Leu Gln Leu Thr Thr Gly Asn Gly Leu Phe Leu
    130                 135                 140

Ser Glu Gly Leu Lys Leu Val Asp Lys Phe Leu Glu Asp Val Lys Lys
145                 150                 155                 160

Leu Tyr His Ser Glu Ala Phe Thr Val Asn Phe Gly Asp Thr Glu Glu
                165                 170                 175

Ala Lys Lys Gln Ile Asn Asp Tyr Val Glu Lys Gly Thr Gln Gly Lys
            180                 185                 190

Ile Val Asp Leu Val Lys Glu Leu Asp Arg Asp Thr Val Phe Ala Leu
        195                 200                 205

Val Asn Tyr Ile Phe Phe Lys Gly Lys Trp Glu Arg Pro Phe Glu Val
    210                 215                 220

Lys Asp Thr Glu Glu Glu Asp Phe His Val Asp Gln Val Thr Thr Val
225                 230                 235                 240

Lys Val Pro Met Met Lys Arg Leu Gly Met Phe Asn Ile Gln His Cys
                245                 250                 255

Lys Lys Leu Ser Ser Trp Val Leu Leu Met Lys Tyr Leu Gly Asn Ala
            260                 265                 270

Thr Ala Ile Phe Phe Leu Pro Asp Glu Gly Lys Leu Gln His Leu Glu
        275                 280                 285

Asn Glu Leu Thr His Asp Ile Ile Thr Lys Phe Leu Glu Asn Glu Asp
```

```
                290                 295                 300
Arg Arg Ser Ala Ser Leu His Leu Pro Lys Leu Ser Ile Thr Gly Thr
305                 310                 315                 320

Tyr Asp Leu Lys Ser Val Leu Gly Gln Leu Gly Ile Thr Lys Val Phe
                325                 330                 335

Ser Asn Gly Ala Asp Leu Ser Gly Val Thr Glu Glu Ala Pro Leu Lys
                340                 345                 350

Leu Ser Lys Ala Val His Lys Ala Val Leu Thr Ile Asp Glu Lys Gly
                355                 360                 365

Thr Glu Ala Ala Gly Ala Met Phe Leu Glu Ala Ile Pro Met Ser Ile
                370                 375                 380

Pro Pro Glu Val Lys Phe Asn Lys Pro Phe Val Phe Leu Met Ile Glu
385                 390                 395                 400

Gln Asn Thr Lys Ser Pro Leu Phe Met Gly Lys Val Val Asn Pro Thr
                405                 410                 415

Gln Lys

<210> SEQ ID NO 60
<211> LENGTH: 531
<212> TYPE: PRT
<213> ORGANISM: Homo sapiens

<400> SEQUENCE: 60

Met Ser Lys Pro His Ser Glu Ala Gly Thr Ala Phe Ile Gln Thr Gln
1               5                   10                  15

Gln Leu His Ala Ala Met Ala Asp Thr Phe Leu Glu His Met Cys Arg
                20                  25                  30

Leu Asp Ile Asp Ser Pro Pro Ile Thr Ala Arg Asn Thr Gly Ile Ile
            35                  40                  45

Cys Thr Ile Gly Pro Ala Ser Arg Ser Val Glu Thr Leu Lys Glu Met
        50                  55                  60

Ile Lys Ser Gly Met Asn Val Ala Arg Leu Asn Phe Ser His Gly Thr
65                  70                  75                  80

His Glu Tyr His Ala Glu Thr Ile Lys Asn Val Arg Thr Ala Thr Glu
                85                  90                  95

Ser Phe Ala Ser Asp Pro Ile Leu Tyr Arg Pro Val Ala Val Ala Leu
                100                 105                 110

Asp Thr Lys Gly Pro Glu Ile Arg Thr Gly Leu Ile Lys Gly Ser Gly
            115                 120                 125

Thr Ala Glu Val Glu Leu Lys Lys Gly Ala Thr Leu Lys Ile Thr Leu
        130                 135                 140

Asp Asn Ala Tyr Met Glu Lys Cys Asp Glu Asn Ile Leu Trp Leu Asp
145                 150                 155                 160

Tyr Lys Asn Ile Cys Lys Val Val Glu Val Gly Ser Lys Ile Tyr Val
                165                 170                 175

Asp Asp Gly Leu Ile Ser Leu Gln Val Lys Gln Lys Gly Ala Asp Phe
            180                 185                 190

Leu Val Thr Glu Val Glu Asn Gly Gly Ser Leu Gly Ser Lys Lys Gly
        195                 200                 205

Val Asn Leu Pro Gly Ala Ala Val Asp Leu Pro Ala Val Ser Glu Lys
            210                 215                 220

Asp Ile Gln Asp Leu Lys Phe Gly Val Glu Gln Asp Val Asp Met Val
225                 230                 235                 240

Phe Ala Ser Phe Ile Arg Lys Ala Ser Asp Val His Glu Val Arg Lys
```

```
                    245                 250                 255
Val Leu Gly Glu Lys Gly Lys Asn Ile Lys Ile Ile Ser Lys Ile Glu
            260                 265                 270

Asn His Glu Gly Val Arg Arg Phe Asp Glu Ile Leu Glu Ala Ser Asp
        275                 280                 285

Gly Ile Met Val Ala Arg Gly Asp Leu Gly Ile Glu Ile Pro Ala Glu
    290                 295                 300

Lys Val Phe Leu Ala Gln Lys Met Met Ile Gly Arg Cys Asn Arg Ala
305                 310                 315                 320

Gly Lys Pro Val Ile Cys Ala Thr Gln Met Leu Glu Ser Met Ile Lys
            325                 330                 335

Lys Pro Arg Pro Thr Arg Ala Glu Gly Ser Asp Val Ala Asn Ala Val
        340                 345                 350

Leu Asp Gly Ala Asp Cys Ile Met Leu Ser Gly Glu Thr Ala Lys Gly
    355                 360                 365

Asp Tyr Pro Leu Glu Ala Val Arg Met Gln His Leu Ile Ala Arg Glu
    370                 375                 380

Ala Glu Ala Ala Ile Tyr His Leu Gln Leu Phe Glu Glu Leu Arg Arg
385                 390                 395                 400

Leu Ala Pro Ile Thr Ser Asp Pro Thr Glu Ala Thr Ala Val Gly Ala
            405                 410                 415

Val Glu Ala Ser Phe Lys Cys Cys Ser Gly Ala Ile Ile Val Leu Thr
        420                 425                 430

Lys Ser Gly Arg Ser Ala His Gln Val Ala Arg Tyr Arg Pro Arg Ala
    435                 440                 445

Pro Ile Ile Ala Val Thr Arg Asn Pro Gln Thr Ala Arg Gln Ala His
    450                 455                 460

Leu Tyr Arg Gly Ile Phe Pro Val Leu Cys Lys Asp Pro Val Gln Glu
465                 470                 475                 480

Ala Trp Ala Glu Asp Val Asp Leu Arg Val Asn Phe Ala Met Asn Val
            485                 490                 495

Gly Lys Ala Arg Gly Phe Phe Lys Lys Gly Asp Val Val Ile Val Leu
        500                 505                 510

Thr Gly Trp Arg Pro Gly Ser Gly Phe Thr Asn Thr Met Arg Val Val
    515                 520                 525

Pro Val Pro
    530

<210> SEQ ID NO 61
<211> LENGTH: 1257
<212> TYPE: PRT
<213> ORGANISM: Homo sapiens

<400> SEQUENCE: 61

Met Lys Ala Ala Asp Glu Pro Ala Tyr Leu Thr Val Gly Thr Asp Val
1               5                   10                  15

Ser Ala Lys Tyr Arg Gly Ala Phe Cys Glu Ala Lys Ile Lys Thr Val
            20                  25                  30

Lys Arg Leu Val Lys Val Lys Val Leu Leu Lys Gln Asp Asn Thr Thr
        35                  40                  45

Gln Leu Val Gln Asp Asp Gln Val Lys Gly Pro Leu Arg Val Gly Ala
    50                  55                  60

Ile Val Glu Thr Arg Thr Ser Asp Gly Ser Phe Gln Glu Ala Ile Ile
65                  70                  75                  80
```

```
Ser Lys Leu Thr Asp Ala Ser Trp Tyr Thr Val Phe Asp Asp Gly
            85              90              95

Asp Glu Arg Thr Leu Arg Arg Thr Ser Leu Cys Leu Lys Gly Glu Arg
            100             105             110

His Phe Ala Glu Ser Glu Thr Leu Asp Gln Leu Pro Leu Thr Asn Pro
            115             120             125

Glu His Phe Gly Thr Pro Val Ile Ala Lys Lys Thr Asn Arg Gly Arg
            130             135             140

Arg Ser Ser Leu Pro Val Thr Glu Asp Glu Lys Glu Glu Ser Ser
145             150             155             160

Glu Glu Glu Asp Glu Asp Lys Arg Arg Leu Asn Asp Glu Leu Leu Gly
            165             170             175

Lys Val Val Ser Val Val Ser Ala Thr Glu Arg Thr Glu Trp Tyr Pro
            180             185             190

Ala Leu Val Ile Ser Pro Ser Cys Asn Asp Asp Ile Thr Val Lys Lys
            195             200             205

Asp Gln Cys Leu Val Arg Ser Phe Ile Asp Ser Lys Phe Tyr Ser Ile
            210             215             220

Ala Arg Lys Asp Ile Lys Glu Val Asp Ile Leu Asn Leu Pro Glu Ser
225             230             235             240

Glu Leu Ser Thr Lys Pro Gly Leu Gln Lys Ala Ser Ile Phe Leu Lys
            245             250             255

Thr Arg Val Val Pro Asp Asn Trp Lys Met Asp Ile Ser Glu Ile Leu
            260             265             270

Glu Ser Ser Ser Asp Glu Asp Gly Pro Ala Glu Glu Asn Asp
            275             280             285

Glu Glu Lys Glu Lys Glu Ala Lys Lys Thr Glu Glu Val Pro Glu
            290             295             300

Glu Glu Leu Asp Pro Glu Glu Arg Asp Asn Phe Leu Gln Gln Leu Tyr
305             310             315             320

Lys Phe Met Glu Asp Arg Gly Thr Pro Ile Asn Lys Pro Pro Val Leu
            325             330             335

Gly Tyr Lys Asp Leu Asn Leu Phe Lys Leu Phe Arg Leu Val Tyr His
            340             345             350

Gln Gly Gly Cys Asp Asn Ile Asp Ser Gly Ala Val Trp Lys Gln Ile
            355             360             365

Tyr Met Asp Leu Gly Ile Pro Ile Leu Asn Ser Ala Ala Ser Tyr Asn
            370             375             380

Val Lys Thr Ala Tyr Arg Lys Tyr Leu Tyr Gly Phe Glu Glu Tyr Cys
385             390             395             400

Arg Ser Ala Asn Ile Gln Phe Arg Thr Val His His His Glu Pro Lys
            405             410             415

Val Lys Glu Glu Lys Lys Asp Leu Glu Glu Ser Met Glu Glu Ala Leu
            420             425             430

Lys Leu Asp Gln Glu Met Pro Leu Thr Glu Val Lys Ser Glu Pro Glu
            435             440             445

Glu Asn Ile Asp Ser Asn Ser Glu Ser Glu Arg Glu Glu Ile Glu Leu
            450             455             460

Lys Ser Pro Arg Gly Arg Arg Ile Ala Arg Asp Val Asn Ser Ile
465             470             475             480

Lys Lys Glu Ile Glu Glu Glu Lys Thr Glu Asp Lys Leu Lys Asp Asn
            485             490             495

Asp Thr Glu Asn Lys Asp Val Asp Asp Tyr Glu Thr Ala Glu Lys
```

```
                500                 505                 510
    Lys Glu Asn Glu Leu Leu Gly Arg Lys Asn Thr Pro Lys Gln Lys
                    515                 520                 525

Glu Lys Lys Ile Lys Lys Gln Glu Asp Ser Asp Lys Asp Ser Asp Glu
            530                 535                 540

Glu Glu Glu Lys Ser Gln Arg Glu Thr Glu Ser Lys Cys Asp
    545                 550                 555                 560

Ser Glu Gly Glu Asp Glu Glu Asp Met Glu Pro Cys Leu Thr Gly
                    565                 570                 575

Thr Lys Val Lys Val Lys Tyr Gly Arg Gly Lys Thr Gln Lys Ile Tyr
                580                 585                 590

Glu Ala Ser Ile Lys Ser Thr Glu Ile Asp Asp Gly Glu Val Leu Tyr
                595                 600                 605

Leu Val His Tyr Tyr Gly Trp Asn Val Arg Tyr Asp Glu Trp Val Lys
                610                 615                 620

Ala Asp Arg Ile Ile Trp Pro Leu Asp Lys Gly Gly Pro Lys Lys Lys
    625                 630                 635                 640

Gln Lys Lys Lys Ala Lys Asn Lys Glu Asp Ser Glu Lys Asp Glu Lys
                    645                 650                 655

Arg Asp Glu Glu Arg Gln Lys Ser Lys Arg Gly Arg Pro Pro Leu Lys
                    660                 665                 670

Ser Thr Leu Ser Ser Asn Met Pro Tyr Gly Leu Ser Lys Thr Ala Asn
                    675                 680                 685

Ser Glu Gly Lys Ser Asp Ser Cys Ser Ser Asp Ser Glu Thr Glu Asp
                690                 695                 700

Ala Leu Glu Lys Asn Leu Ile Asn Glu Glu Leu Ser Leu Lys Asp Glu
    705                 710                 715                 720

Leu Glu Lys Asn Glu Asn Leu Asn Asp Lys Leu Asp Glu Glu Asn
                    725                 730                 735

Pro Lys Ile Ser Ala His Ile Leu Lys Glu Asn Asp Arg Thr Gln Met
                    740                 745                 750

Gln Pro Leu Glu Thr Leu Lys Leu Glu Val Gly Glu Asn Glu Gln Ile
                755                 760                 765

Val Gln Ile Phe Gly Asn Lys Met Glu Lys Thr Glu Glu Val Lys Lys
                770                 775                 780

Glu Ala Glu Lys Ser Pro Lys Gly Lys Gly Arg Arg Ser Lys Thr Lys
    785                 790                 795                 800

Asp Leu Ser Leu Glu Ile Ile Lys Ile Ser Ser Phe Gly Gln Asn Glu
                    805                 810                 815

Ala Gly Ser Glu Pro His Ile Glu Ala His Ser Leu Glu Leu Ser Ser
                    820                 825                 830

Leu Asp Asn Lys Asn Phe Ser Ala Thr Glu Asp Glu Ile Asp Gln
                    835                 840                 845

Cys Val Lys Glu Lys Lys Leu Lys Arg Lys Ile Leu Gly Gln Ser Ser
                    850                 855                 860

Pro Glu Lys Lys Ile Arg Ile Glu Asn Gly Met Glu Met Thr Asn Thr
    865                 870                 875                 880

Val Ser Gln Glu Arg Thr Ser Asp Cys Ile Gly Ser Glu Gly Met Lys
                    885                 890                 895

Asn Leu Asn Phe Glu Gln His Phe Glu Arg Glu Asn Glu Gly Met Pro
                    900                 905                 910

Ser Leu Ile Ala Glu Ser Asn Gln Cys Ile Gln Gln Leu Thr Ser Glu
                    915                 920                 925
```

Arg Phe Asp Ser Pro Ala Glu Glu Thr Val Asn Ile Pro Leu Lys Glu
            930                 935                 940

Asp Glu Asp Ala Met Pro Leu Ile Gly Pro Glu Thr Leu Val Cys His
945                 950                 955                 960

Glu Val Asp Leu Asp Asp Leu Asp Glu Lys Asp Lys Thr Ser Ile Glu
                965                 970                 975

Asp Val Ala Val Glu Ser Ser Glu Ser Asn Ser Leu Val Ser Ile Pro
            980                 985                 990

Pro Ala Leu Pro Pro Val Val Gln His Asn Phe Ser Val Ala Ser Pro
        995                 1000                1005

Leu Thr Leu Ser Gln Asp Glu Ser Arg Ser Val Lys Ser Glu Ser Asp
    1010                1015                1020

Ile Thr Ile Glu Val Asp Ser Ile Ala Glu Glu Ser Gln Glu Gly Leu
1025                1030                1035                1040

Cys Glu Arg Glu Ser Ala Asn Gly Phe Glu Thr Asn Val Ala Ser Gly
                1045                1050                1055

Thr Cys Ser Ile Ile Val Gln Glu Arg Glu Ser Arg Glu Lys Gly Gln
            1060                1065                1070

Lys Arg Pro Ser Asp Gly Asn Ser Gly Leu Met Ala Lys Lys Gln Lys
        1075                1080                1085

Arg Thr Pro Lys Arg Thr Ser Ala Ala Ala Lys Asn Glu Lys Asn Gly
    1090                1095                1100

Thr Gly Gln Ser Ser Asp Ser Glu Asp Leu Pro Val Leu Asp Asn Ser
1105                1110                1115                1120

Ser Lys Cys Thr Pro Val Lys His Leu Asn Val Ser Lys Pro Gln Lys
                1125                1130                1135

Leu Ala Arg Ser Pro Ala Arg Ile Ser Pro His Ile Lys Asp Gly Glu
            1140                1145                1150

Lys Asp Lys His Arg Glu Lys His Pro Asn Ser Ser Pro Arg Thr Tyr
        1155                1160                1165

Lys Trp Ser Phe Gln Leu Asn Glu Leu Asp Asn Met Asn Ser Thr Glu
    1170                1175                1180

Arg Ile Ser Phe Leu Gln Glu Lys Leu Gln Glu Ile Arg Lys Tyr Tyr
1185                1190                1195                1200

Met Ser Leu Lys Ser Glu Val Ala Thr Ile Asp Arg Arg Arg Lys Arg
                1205                1210                1215

Leu Lys Lys Lys Asp Arg Glu Val Ser His Ala Gly Ala Ser Met Ser
            1220                1225                1230

Ser Ala Ser Ser Asp Thr Gly Met Ser Pro Ser Ser Ser Pro Pro
        1235                1240                1245

Gln Asn Val Leu Ala Val Glu Cys Arg
    1250                1255

<210> SEQ ID NO 62
<211> LENGTH: 282
<212> TYPE: PRT
<213> ORGANISM: Homo sapiens

<400> SEQUENCE: 62

Met Gln Arg Leu Arg Trp Leu Arg Asp Trp Lys Ser Ser Gly Arg Gly
1               5                   10                  15

Leu Thr Ala Ala Lys Glu Pro Gly Ala Arg Ser Ser Pro Leu Gln Ala
            20                  25                  30

Met Arg Ile Leu Gln Leu Ile Leu Leu Ala Leu Ala Thr Gly Leu Val

```
            35                   40                  45
Gly Gly Glu Thr Arg Ile Ile Lys Gly Phe Glu Cys Lys Pro His Ser
 50                  55                  60

Gln Pro Trp Gln Ala Ala Leu Phe Glu Lys Thr Arg Leu Leu Cys Gly
 65                  70                  75                  80

Ala Thr Leu Ile Ala Pro Arg Trp Leu Leu Thr Ala Ala His Cys Leu
                     85                  90                  95

Lys Pro Arg Tyr Ile Val His Leu Gly Gln His Asn Leu Gln Lys Glu
                    100                 105                 110

Glu Gly Cys Glu Gln Thr Arg Thr Ala Thr Glu Ser Phe Pro His Pro
                115                 120                 125

Gly Phe Asn Asn Ser Leu Pro Asn Lys Asp His Arg Asn Asp Ile Met
130                 135                 140

Leu Val Lys Met Ala Ser Pro Val Ser Ile Thr Trp Ala Val Arg Pro
145                 150                 155                 160

Leu Thr Leu Ser Ser Arg Cys Val Thr Ala Gly Thr Ser Cys Leu Ile
                    165                 170                 175

Ser Gly Trp Gly Ser Thr Ser Ser Pro Gln Leu Arg Leu Pro His Thr
                180                 185                 190

Leu Arg Cys Ala Asn Ile Thr Ile Ile Glu His Gln Lys Cys Glu Asn
                195                 200                 205

Ala Tyr Pro Gly Asn Ile Thr Asp Thr Met Val Cys Ala Ser Val Gln
210                 215                 220

Glu Gly Gly Lys Asp Ser Cys Gln Gly Asp Ser Gly Gly Pro Leu Val
225                 230                 235                 240

Cys Asn Gln Ser Leu Gln Gly Ile Ile Ser Trp Gly Gln Asp Pro Cys
                    245                 250                 255

Ala Ile Thr Arg Lys Pro Gly Val Tyr Thr Lys Val Cys Lys Tyr Val
                260                 265                 270

Asp Trp Ile Gln Glu Thr Met Lys Asn Asn
                275                 280

<210> SEQ ID NO 63
<211> LENGTH: 277
<212> TYPE: PRT
<213> ORGANISM: Homo sapiens

<400> SEQUENCE: 63

Met Trp Pro Leu Ala Leu Val Ile Ala Ser Leu Thr Leu Ala Leu Ser
  1               5                  10                  15

Gly Gly Val Ser Gln Glu Ser Ser Lys Val Leu Asn Thr Asn Gly Thr
                 20                  25                  30

Ser Gly Phe Leu Pro Gly Gly Tyr Thr Cys Phe Pro His Ser Gln Pro
             35                  40                  45

Trp Gln Ala Ala Leu Leu Val Gln Gly Arg Leu Leu Cys Gly Gly Val
 50                  55                  60

Leu Val His Pro Lys Trp Val Leu Thr Ala Ala His Cys Leu Lys Glu
 65                  70                  75                  80

Gly Leu Lys Val Tyr Leu Gly Lys His Ala Leu Gly Arg Val Glu Ala
                 85                  90                  95

Gly Glu Gln Val Arg Glu Val Val His Ser Ile Pro His Pro Glu Tyr
                100                 105                 110

Arg Arg Ser Pro Thr His Leu Asn His Asp His Asp Ile Met Leu Leu
                115                 120                 125
```

```
Glu Leu Gln Ser Pro Val Gln Leu Thr Gly Tyr Ile Gln Thr Leu Pro
    130                 135                 140

Leu Ser His Asn Asn Arg Leu Thr Pro Gly Thr Thr Cys Arg Val Ser
145                 150                 155                 160

Gly Trp Gly Thr Thr Thr Ser Pro Gln Val Asn Tyr Pro Lys Thr Leu
                165                 170                 175

Gln Cys Ala Asn Ile Gln Leu Arg Ser Asp Glu Glu Cys Arg Gln Val
            180                 185                 190

Tyr Pro Gly Lys Ile Thr Asp Asn Met Leu Cys Ala Gly Thr Lys Glu
            195                 200                 205

Gly Gly Lys Asp Ser Cys Glu Gly Asp Ser Gly Gly Pro Leu Val Cys
    210                 215                 220

Asn Arg Thr Leu Tyr Gly Ile Val Ser Trp Gly Asp Phe Pro Cys Gly
225                 230                 235                 240

Gln Pro Asp Arg Pro Gly Val Tyr Thr Arg Val Ser Arg Tyr Val Leu
                245                 250                 255

Trp Ile Arg Glu Thr Ile Arg Lys Tyr Glu Thr Gln Gln Lys Trp
            260                 265                 270

Leu Lys Gly Pro Gln
            275

<210> SEQ ID NO 64
<211> LENGTH: 122
<212> TYPE: PRT
<213> ORGANISM: Homo sapiens

<400> SEQUENCE: 64

Met Lys Leu Leu Thr Gly Leu Val Phe Cys Ser Leu Val Leu Gly Val
1               5                   10                  15

Ser Ser Arg Ser Phe Phe Ser Phe Leu Gly Glu Ala Phe Asp Gly Ala
            20                  25                  30

Arg Asp Met Trp Arg Ala Tyr Ser Asp Met Arg Glu Ala Asn Tyr Ile
        35                  40                  45

Gly Ser Asp Lys Tyr Phe His Ala Arg Gly Asn Tyr Asp Ala Ala Lys
    50                  55                  60

Arg Gly Pro Gly Gly Val Trp Ala Ala Glu Ala Ile Ser Asp Ala Arg
65                  70                  75                  80

Glu Asn Ile Gln Arg Phe Phe Gly His Gly Ala Glu Asp Ser Leu Ala
                85                  90                  95

Asp Gln Ala Ala Asn Glu Trp Gly Arg Ser Gly Lys Asp Pro Asn His
            100                 105                 110

Phe Arg Pro Ala Gly Leu Pro Glu Lys Tyr
        115                 120

<210> SEQ ID NO 65
<211> LENGTH: 99
<212> TYPE: PRT
<213> ORGANISM: Homo sapiens

<400> SEQUENCE: 65

Met Gln Pro Arg Val Leu Leu Val Val Ala Leu Leu Ala Leu Leu Ala
1               5                   10                  15
```

-continued

```
Ser Ala Arg Ala Ser Glu Ala Glu Asp Ala Ser Leu Leu Ser Phe Met
        20                  25                  30

Gln Gly Tyr Met Lys His Ala Thr Lys Thr Ala Lys Asp Ala Leu Ser
        35                  40                  45

Ser Val Gln Glu Ser Gln Val Ala Gln Gln Ala Arg Gly Trp Val Thr
        50                  55                  60

Asp Gly Phe Ser Ser Leu Lys Asp Tyr Trp Ser Thr Val Lys Asp Lys
65                      70                  75                  80

Phe Ser Glu Phe Trp Asp Leu Asp Pro Glu Val Arg Pro Thr Ser Ala
                85                  90                  95

Val Ala Ala
```